(12) United States Patent
Fujimoto et al.

(10) Patent No.: US 8,691,756 B2
(45) Date of Patent: Apr. 8, 2014

(54) MACROCYCLES AND THEIR USES

(71) Applicant: Novartis AG, Basel (CH)

(72) Inventors: Roger Aki Fujimoto, Winchester, MA (US); Philipp Krastel, Grenzach-Wyhlen (DE); Matthew J. LaMarche, Reading, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/900,866

(22) Filed: May 23, 2013

(65) Prior Publication Data

US 2013/0252883 A1     Sep. 26, 2013

Related U.S. Application Data

(62) Division of application No. 12/132,377, filed on Jun. 3, 2003, now Pat. No. 8,476,224.

(60) Provisional application No. 60/941,777, filed on Jun. 4, 2007.

(51) Int. Cl.
    *A61K 38/12* (2006.01)
(52) U.S. Cl.
    USPC .............. 514/3.6; 514/2.3; 514/21.1; 530/317
(58) Field of Classification Search
    None
    See application file for complete search history.

(56) References Cited

U.S. PATENT DOCUMENTS

| | | | |
|---|---|---|---|
| 5,514,649 A | 5/1996 | Selva | |
| 5,747,295 A | 5/1998 | Selva | |
| 5,843,890 A | 12/1998 | Selva | |
| 6,043,217 A | 3/2000 | Muraoka | |
| 2008/0131453 A1 | 6/2008 | Thompson | |
| 2010/0093615 A1* | 4/2010 | Lamarche et al. | 514/11 |

FOREIGN PATENT DOCUMENTS

| | | |
|---|---|---|
| EP | 451488 | 10/1991 |
| EP | 494078 | 7/1992 |
| EP | 529410 | 3/1993 |
| EP | 825194 | 2/1998 |
| WO | WO 92/12172 | 7/1992 |
| WO | WO 97/30078 | 8/1997 |
| WO | WO 03/105881 | 12/2003 |
| WO | WO 2007/142986 | 12/2007 |
| WO | WO 2008/082562 | 7/2008 |

OTHER PUBLICATIONS

Enrico Selva et al., "Components of the GE2270 Complex Produced by Planobispora rosea ATCC 53773" *Journal of Antibiotica* 48(9):1039-1042, Sep. 1, 1995.

* cited by examiner

*Primary Examiner* — Cecilia J Tsang
*Assistant Examiner* — Fred Reynolds
(74) *Attorney, Agent, or Firm* — Mark W. Milstead

(57) ABSTRACT

The present application describes a method of treating a bacterial infection comprising administering to a subject in need thereof a pharmaceutically acceptable amount of a defined macrocycle compound.

16 Claims, No Drawings

MACROCYCLES AND THEIR USES

CROSS-REFERENCE TO RELATED APPLICATIONS

This application is a divisional application of U.S. Ser. No. 12/132,377, filed Jun. 3, 2008, which claims priority to U.S. provisional application Ser. No. 60/941,777, filed Jun. 4, 2007, the contents of which are incorporated herein by reference in their entirety.

BACKGROUND

Since the discovery of penicillin, pharmaceutical companies have produced a number of antibacterial agents to combat a wide variety of bacterial infections. In the past several years, there has been rapid emergence of bacterial resistance to several of these antibiotics. The multidrug resistance among these bacterial pathogens may also be due to mutation leading to more virulent clinical isolation. Perhaps the most disturbing occurrence has been the acquisition of resistance to vancomycin, an antibiotic generally regarded as the agent of last resort for serious Gram-positive infections.

This is true especially of some Gram-positive pathogen groups, such as staphylococci, pneumococci and enterococci (S. Ewig et al.; Antibiotika-Resistenz bei Erregern ambulant erworbener Atemwegsinfektionen (Antibiotic resistance in pathogens of outpatient-acquired respiratory tract infections); Chemother. J. 2002, 11, 12-26; F. Tenover; Development and spread of bacterial resistance to antimicrobial agents: an overview; Clin. Infect. Dis. 2001 Sep. 15, 33 Suppl. 3, 108-115) as well as *Staphylococcus, Streptococcus, Mycobacterium, Enterococcus, Corynebacterium, Borrelia, Bacillus, Chlamydia, Mycoplasma*, and the like.

A problem of equally large dimension is the increasing incidence of the more virulent, methicillin-resistant *Staphylococcus aureas* (MRSA) among clinical isolates found worldwide. As with vancomycin resistant organisms, many MRSA strains are resistant to most of the known antibiotics, but MRSA strains have remained sensitive to vancomycin. However, in view of the increasing reports of vancomycin resistant clinical isolates and growing problem of bacterial resistance, there is an urgent need for new molecular entities effective against the emerging and currently problematic Gram-positive organisms.

This growing multidrug resistance has recently rekindled interest in the search for new structural classes of antibiotics that inhibit or kill these bacteria.

SUMMARY OF THE INVENTION

There remains a need for new treatments and therapies for bacterial infections. There is also a need for compounds useful in the treatment or prevention or amelioration of one or more symptoms of bacterial infections. Furthermore, there is a need for methods for modulating the activity of the elongation factor EF-Tu, using the compounds provided herein. In one aspect, the invention provides a compound of formula I:

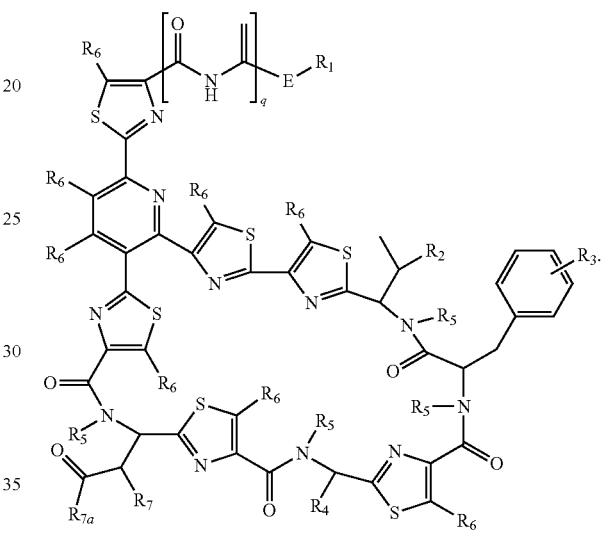

I

In another aspect, the invention provides a compound of formula II:

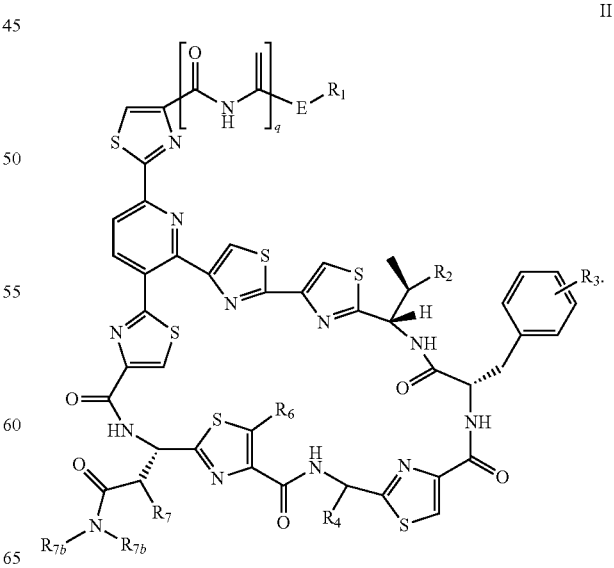

II

In yet another aspect, the invention provides a compound of formula III:

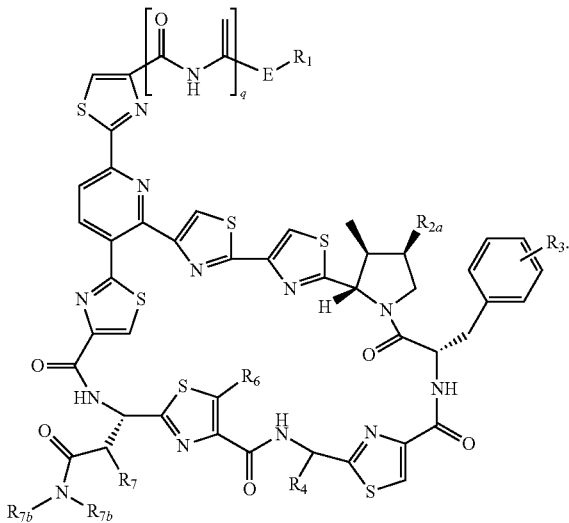

In yet another aspect, the invention provides a compound of formula IV:

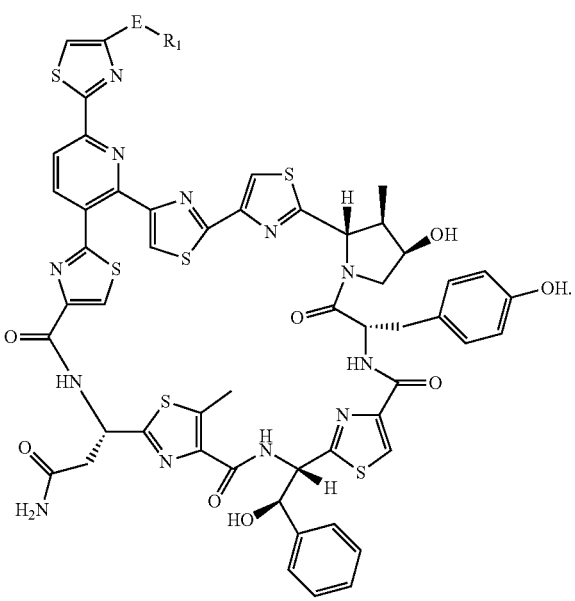

In another aspect, the invention provides a method of treating a bacterial infection wherein the treatment includes administering to a subject in need thereof a pharmaceutically acceptable amount of a compound of formula I, II, III, or IV (or any subformula thereof), such that the bacterial infection is treated.

In another aspect, the invention provides a method of treating an EF-Tu associated-state wherein the treatment includes administering to a subject in need thereof a pharmaceutically acceptable amount of a compound of formula I, II, III, or IV (or any subformula thereof), such that the EF-Tu associated state is treated.

In still another aspect, the invention provides a method of treating, inhibiting or preventing the activity of EF-Tu in a subject in need thereof, which includes administering to the subject a pharmaceutically acceptable amount of a compound of formula I, II, III, or IV (or any subformula thereof). In one embodiment, a bacterial infection is treated in a subject in need thereof.

In another aspect, the invention provides a method of treating, inhibiting or preventing the activity of bacteria in a subject in need thereof, which includes administering to the subject a pharmaceutically acceptable amount of a compound of formula I, II, III, or IV (or any subformula thereof), wherein the compound interacts with any target in the life cycle of the bacteria. In one embodiment, the target is EF-Tu.

In another aspect, the invention provides a method of treating a bacterial infection in a subject, wherein the treatment includes administering to a subject in need thereof a pharmaceutically acceptable amount of a compound of the formula I, II, III, or IV (or any subformula thereof), and a pharmaceutically acceptable carrier, such that the bacterial infection is treated.

In still another aspect, the invention provides a method of treating a bacterial infection wherein the treatment includes administering to a subject in need thereof a pharmaceutically effective amount of a compound of the formula I, II, III, or IV (or any subformula thereof), in combination with a pharmaceutically effective amount of an additional therapeutic agent, such that the bacterial infection is treated. In one embodiment, the compound of the formula I, II, III, or IV (or any subformula thereof) and the other pharmaceutical agent are administered as part of the same pharmaceutical composition. In another embodiment, the compound of the formula I, II, III, or IV (or any subformula thereof) and the other therapeutic agent are administered as separate pharmaceutical compositions, and the compound is administered prior to, at the same time as, or following administration of the other agent.

In another aspect, the invention provides a packaged bacterial infection treatment, comprised of formula I, II, III, or IV (or any subformula thereof), packaged with instructions for using an effective amount of the compound to treat a bacterial infection.

In another aspect, the invention provides a method of treating acne in subject in need thereof, wherein the treatment includes administering to the subject a pharmaceutically acceptable amount of a compound of formula I, II, III, or IV (or any subformula thereof).

In yet another aspect, the invention provides a pharmaceutical composition which includes a compound of formula I, II, III, or IV (or any subformula thereof), and at least one pharmaceutically acceptable carrier or diluent.

DETAILED DESCRIPTION OF THE INVENTION

This invention is directed to compounds, e.g., macrocyclic compounds, and intermediates thereto, as well as pharmaceutical compositions containing the compounds for use in treatment of bacterial infection. This invention is also directed to the compounds of the invention or compositions thereof as modulators of the elongation factor EF-Tu. The compounds are particularly useful in interfering with the life cycle of bacteria and in treating or preventing a bacterial infection or physiological conditions associated therewith. The present invention is also directed to methods of combination therapy for inhibiting EF-Tu activity in cells, or for treating or preventing a bacterial infection in patients using the compounds of the invention or pharmaceutical compositions, or kits thereof.

In one aspect, the invention provides compounds of the formula I:

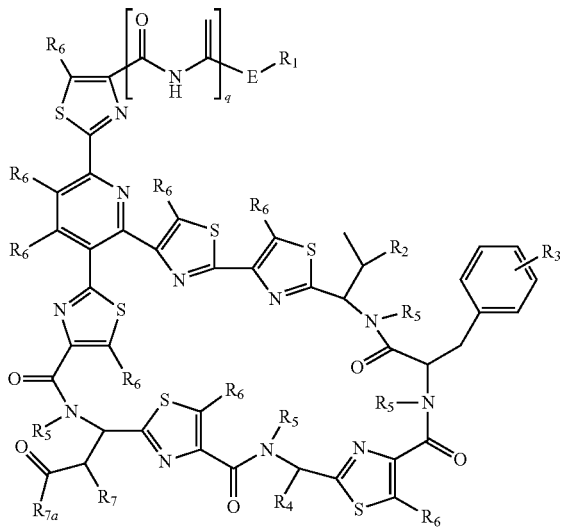

I and pharmaceutically acceptable salts, enantiomers, stereoisomers, rotamers, tautomers, diastereomers, atropisomers or racemates thereof, including pyridine N-oxides thereof;

wherein q is 0, 1, 2, or 3;

E is absent or a divalent residue selected from C(O), C(O)C(O), C(O)O, N($R_9$), C(O)N($R_9$), N($R_9$)C(O), N($R_9$)C(O)C(O), N($R_9$)C(O)O, N($R_9$)C(O)N($R_9$), C(N$R_9$)N($R_9$), N($R_9$)C(N$R_9$), N($R_9$)C(N$R_9$)N($R_9$), S(O)$_m$, S(O)$_m$N($R_9$), N($R_9$)S(O)$_m$ and N($R_9$)S(O)$_m$N($R_9$);

$R_1$ is hydrogen or is selected from the group consisting of $C_{1-8}$alkyl, $C_{2-8}$alkenyl, $C_{2-8}$alkynyl, $C_{1-8}$alkoxy, cycloalkyl$C_{0-6}$alkyl, heterocycloalkyl$C_{0-6}$alkyl, aryl$C_{0-6}$alkyl, heteroaryl$C_{0-6}$alkyl each of which is substituted with 0 to 6 residues independently selected at each occurrence from the group consisting of hydroxy, oxo, $C_{1-8}$alkyl (which may be further substituted with 0-3 residues independently selected from hydroxyl, halogen, amino, $C_{1-4}$alkoxy, COOH, CONH$_2$, or COOC$_{1-4}$alkyl), $C_{1-8}$alkoxy (which may be further substituted with 0-3 residues independently selected from hydroxyl, halogen, amino, $C_{1-4}$alkoxy, COOH, CONH$_2$, or COOC$_{1-4}$alkyl), $C_{3-7}$cycloalkyl$C_{0-6}$alkyl (which may be further substituted with 0-3 residues independently selected from hydroxyl, halogen, amino, $C_{1-4}$alkoxy, COOH, CONH$_2$, or COOC$_{1-4}$alkyl), COOH, NH$_2$, mono- and di-$C_{1-8}$alkylamino, tri-$C_{1-8}$alkylammonium, heterocycle$C_{0-6}$alkyl (which may be further substituted with 0-3 residues independently selected from hydroxyl, halogen, amino, $C_{1-4}$alkoxy, COOH, CONH$_2$, or COOC$_{1-4}$alkyl), heteroaryl$C_{0-6}$alkyl (which may be further substituted with 0-3 residues independently selected from hydroxyl, halogen, amino, $C_{1-4}$alkoxy, COOH, CONH$_2$, or COOC$_{1-4}$alkyl) and —(CH$_2$—CH$_2$—O—)$_n$—R$_9$;

$R_2$, $R_3$ and $R_6$ are each independently selected, at each occurrence from the group consisting of hydrogen, halogen, hydroxy, or oxo, or are independently selected from the group consisting of $C_{1-8}$alkyl, $C_{2-8}$alkenyl, $C_{2-8}$alkynyl, $C_{1-8}$alkoxy, amino, mono- and di-$C_{1-8}$alkylamino, $C_{3-7}$cycloalkyl$C_{0-6}$alkyl, heterocycloalkyl$C_{0-6}$alkyl, aryl$C_{0-6}$alkyl, or heteroaryl$C_{0-6}$alkyl, each of which is substituted with hydroxy, oxo, halo, $C_{1-8}$alkyl, halo$C_{1-8}$alkyl, $C_{1-8}$alkoxy, halo$C_{1-8}$alkoxy, $C_{3-7}$cycloalkyl$C_{0-6}$alkyl, COOH, NH$_2$, mono- and di-$C_{1-8}$alkylamino, tri-$C_{1-8}$alkylammonium, heterocycle$C_{0-6}$alkyl, heteroaryl$C_{0-6}$alkyl and —(CH$_2$—CH$_2$—O—)$_n$—R$_8$;

or $R_2$ and $R_5$, taken in combination, form a 4 to 7 membered heterocyclic ring which is saturated or partially unsaturated and is further substituted with 0-4 residues, each independently selected from $R_{2a}$;

$R_4$ is hydrogen, oxo or NH or is selected from the group consisting of COOH, CONH$_2$, $C_{1-8}$alkyl, $C_{2-8}$alkenyl, $C_{2-8}$alkynyl, aryl(CR$_{10}$R$_{11}$)$_q$, heteroaryl(CR$_{10}$R$_{11}$)$_q$, $C_{3-7}$cycloalkyl(CR$_{10}$R$_{11}$)$_q$, each of which is substituted with 0-3 $R_{4a}$ residues;

$R_{2a}$ and $R_{4a}$ are each independently selected at each occurrence from hydrogen or from the group consisting of $C_{1-8}$alkyl, $C_{2-8}$alkenyl, $C_{2-8}$alkynyl, $C_{1-8}$alkoxy, amino, mono- and di-$C_{1-8}$alkylamino, $C_{3-7}$cycloalkyl$C_{0-6}$alkyl, C(O)(CH$_2$)$_z$R$_{4b}$, C(O)N(H)(CH$_2$)$_z$R$_{4b}$, or heterocycloalkyl$C_{0-6}$alkyl, each of which is substituted with 0 to 4 substituents independently selected at each occurrence from hydroxy, oxo, halo, $C_{1-8}$alkyl, halo$C_{1-8}$alkyl, $C_{1-8}$alkoxy, halo$C_{1-8}$alkoxy, $C_{3-7}$cycloalkyl$C_{0-6}$alkyl, COOH, NH$_2$, mono- and di-$C_{1-8}$alkylamino, tri-$C_{1-8}$alkylammonium, heterocycle$C_{0-6}$alkyl, heteroaryl$C_{0-6}$alkyl, or —(CH$_2$—CH$_2$—O—)$_n$—R$_8$;

$R_{4b}$ is selected from the group consisting of H, OH, NH$_2$, $C_{1-8}$alkyl, $C_{1-8}$alkoxy, mono- and di-$C_{1-8}$alkylamino, heterocycle, cycloalkyl, and -E-R$_1$;

$R_5$ is independently selected at each occurrence from the group consisting of H, $C_{1-8}$alkyl, and —(CH$_2$—CH$_2$—O—)$_n$—R$_8$;

$R_7$ is selected from the group consisting of H, OH, NH$_2$, $C_{1-8}$alkyl, $C_{1-8}$alkoxy, mono- and di-$C_{1-8}$alkylamino, heterocycle, cycloalkyl, and -E-R$_1$;

$R_{7a}$ is OR$_{7b}$ or N(R$_{7b}$)$_2$;

$R_{7b}$ is independently selected, at each occurrence, from hydrogen or from the group consisting of $C_{1-8}$alkyl, $C_{2-8}$alkenyl, $C_{2-8}$alkynyl, $C_{1-8}$alkoxy, amino, mono- and di-$C_{1-8}$alkylamino, $C_{3-7}$cycloalkyl$C_{0-6}$alkyl, heterocycloalkyl$C_{0-6}$alkyl, aryl$C_{0-6}$alkyl, or heteroaryl$C_{0-6}$alkyl, each of which is substituted with hydroxy, oxo, halo, $C_{1-8}$alkyl, halo$C_{1-8}$alkyl, $C_{1-8}$alkoxy, halo$C_{1-8}$alkoxy, $C_{3-7}$cycloalkyl$C_{0-6}$alkyl, COOH, NH$_2$, mono- and di-$C_{1-8}$alkylamino, tri-$C_{1-8}$alkylammonium, heterocycle$C_{0-6}$alkyl, heteroaryl$C_{0-6}$alkyl and —(CH$_2$—CH$_2$—O—)$_n$—R$_8$;

n is an integer of between 1-60,000 or is a mean of a plurality of integers having a value of between 1-60,000;

$R_8$ is independently selected at each occurrence from the group consisting of H, $C_{1-8}$alkyl and CH$_2$CO$_2$H;

$R_9$ is hydrogen or is selected from the group consisting of $C_{1-8}$alkyl, $C_{2-8}$alkenyl, $C_{2-8}$alkynyl, $C_{1-8}$alkoxy, cycloalkyl$C_{0-6}$alkyl, heterocycloalkyl$C_{0-6}$alkyl, aryl$C_{0-6}$alkyl, heteroaryl$C_{0-6}$alkyl each of which is substituted with 0 to 6 residues independently selected at each occurrence from the group consisting of hydroxy, oxo, $C_{1-8}$alkyl (which may be further substituted with 0-3 residues independently selected from hydroxyl, halogen, amino, $C_{1-4}$alkoxy, COOH, CONH$_2$, or COOC$_{1-4}$alkyl), $C_{1-8}$alkoxy (which may be further substituted with 0-3 residues independently selected from hydroxyl, halogen, amino, $C_{1-4}$alkoxy, COOH, CONH$_2$, or COOC$_{1-4}$alkyl), $C_{3-7}$cycloalkyl$C_{0-6}$alkyl (which may be further substituted with 0-3 residues independently selected from hydroxyl, halogen, amino, $C_{1-4}$alkoxy, COOH, CONH$_2$, or COOC$_{1-4}$alkyl), COOH, NH$_2$, mono- and di-$C_{1-8}$ alkylamino, tri-$C_{1-8}$alkylammonium, heterocycle$C_{0-6}$alkyl (which may be further substituted with 0-3 residues independently selected from hydroxyl, halogen, amino, $C_{1-4}$alkoxy, COOH, CONH$_2$, or COOC$_{1-4}$alkyl), heteroaryl$C_{0-6}$alkyl (which may be further substituted with 0-3 residues independently selected from hydroxyl, halogen, amino, $C_{1-4}$alkoxy, COOH, CONH$_2$, or COOC$_{1-4}$alkyl) and —(CH$_2$—CH$_2$—O—)$_n$—R$_8$;

q is 0, 1, 2, or 3;

z is an integer of from 0 to 6;

R$_{10}$ is absent, hydrogen, or $C_{1-8}$alkyl; and

R$_{11}$ is hydrogen, hydroxy, OR$_{4a}$, C(O)R$_{4a}$, C(O)OR$_{4a}$, C(O)N(R$_{4a}$)$_2$, OC(O)N(R$_{4a}$)$_2$, oxo, amino, NHR$_{4a}$, N(R$_{4a}$)$_2$, =NR$_{4a}$, C(NR$_{4a}$)N(R$_{4a}$)$_2$ or N(R$_{4a}$)C(NR$_{4a}$)N(R$_{4a}$)$_2$.

In certain aspects, compounds of Formula I include those compounds in which each occurrence of R$_5$ is hydrogen. Certain other compounds of Formula I include those compounds in which R$_6$ is independently selected at each occurrence from the group consisting of H, halogen, $C_{1-8}$alkyl, $C_{1-8}$alkoxy, mono- and di-$C_{1-8}$alkylamino, heterocycle and —O—(CH$_2$—CH$_2$—O—)$_n$—R$_8$. In yet other compounds, R$_6$ is hydrogen or methyl. Still other compounds of Formula I include those compounds in which R$_7$ and each occurrence of R$_{7b}$ are hydrogen.

In other aspects, compounds of Formula I include those compounds in which q is 0, 1, or 2; and E is a divalent residue selected from C(O), C(O)C(O), C(O)O, N(R$_9$), C(O)N(R$_9$), N(R$_9$)C(O), N(R$_9$)C(O)C(O), N(R$_9$)C(O)O, N(R$_9$)C(O)N(R$_9$), S(O)$_2$, S(O)$_2$N(R$_9$), N(R$_9$)S(O)$_2$, and N(R$_9$)S(O)$_2$N(R$_9$) or E is selected from the group consisting of C(O), C(O)C(O), C(O)O, N(H), C(O)N(H), N(H)C(O), N(H)C(O)C(O), N(H)C(O)O, N(H)C(O)N(H), S(O)$_2$, S(O)$_2$N(H), N(H)S(O)$_2$, and N(H)S(O)$_2$N(H). In certain other compounds of Formula I, q is 0, 1 or 2 and E is a divalent residue selected from C(O), C(O)O, N(R$_9$), C(O)N(R$_9$), N(R$_9$)C(O), N(R$_9$)C(O)O, and N(R$_9$)C(O)N(R$_9$).

In still other aspects, compounds of Formula I include those compounds in which q is 0, 1, or 2; E is a divalent residue selected from N(R$_9$), C(O)N(R$_9$), N(R$_9$)C(O), N(R$_9$)C(O)O, N(R$_9$)C(O)N(R$_9$); and R$_9$ is selected from hydrogen and $C_{1-8}$alkyl groups substituted by 0, 1, or 2 COOH groups. In certain compounds of Formula I, q is 0; E is a divalent residue selected from N(R$_9$), C(O)N(R$_9$), N(R$_9$)C(O), N(R$_9$)C(O)O, N(R$_9$)C(O)N(R$_9$); and R$_9$ is selected from hydrogen and $C_{1-8}$alkyl groups substituted by 0, 1, or 2 COOH groups.

In certain aspects, compounds of Formula I include those compounds in which R$_1$ and R$_9$ are independently selected at each occurrence from the group consisting of H, $C_{1-8}$alkyl, $C_{3-8}$cycloalkyl, and R$_{12}$, wherein the $C_{1-8}$alkyl and $C_{3-8}$cycloalkyl groups are unsubstituted or substituted with 1 or 2 groups selected from halogen, hydroxyl, or COOH.

In certain other aspects, compounds of Formula I include those compounds in which the fragment:

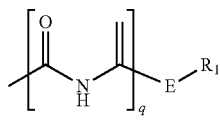

is selected from groups in which q is 0, E is N(R$_9$), N(R$_9$)C(O), or N(R$_9$)C(O)O; R$_9$ is hydrogen or Z—CO$_2$H; R$_1$ is Z—CO$_2$H; and Z is $C_1$-$C_8$alkylene, $C_3$-$C_8$cycloalkylene, $C_3$-$C_8$heterocycloalkylene, phenylene, or 5-6 membered heteroarylene, each of which is optionally substituted with one or more groups independently selected from $C_1$-$C_4$alkyl, $C_1$-$C_4$alkoxy, hydroxy, amino, mono- and di-$C_1$-$C_6$alkylamino, C(O)OH, or halogen.

In still other aspects, compounds of Formula I include those compounds in which the fragment:

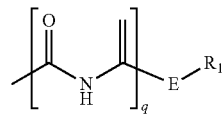

is selected from the group consisting of:

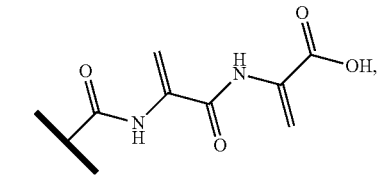

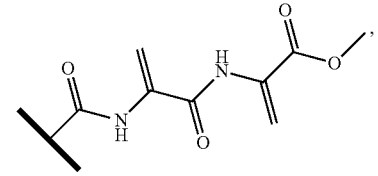

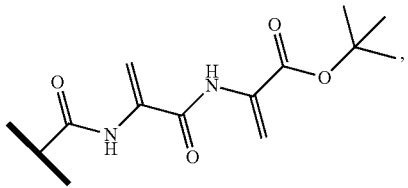

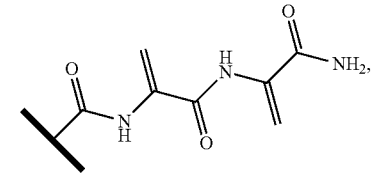

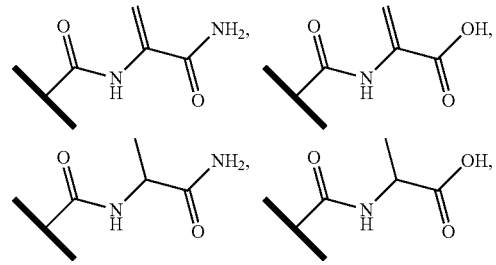

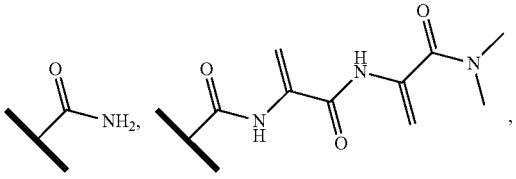

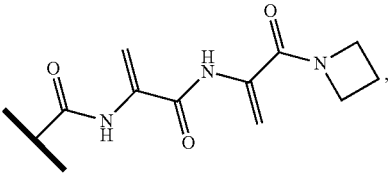

-continued

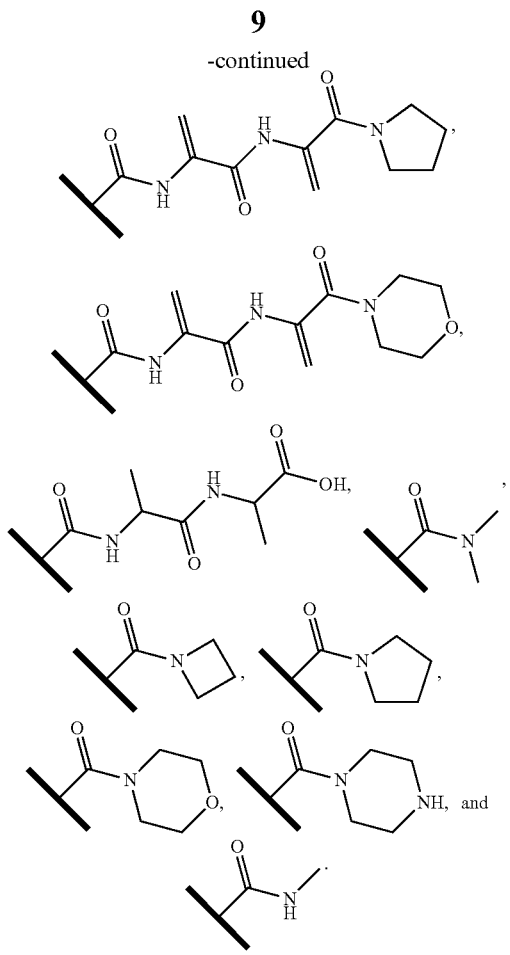

Certain other compounds of Formula I include those compounds in which q is 0; E-R₁ is selected from the group consisting of:

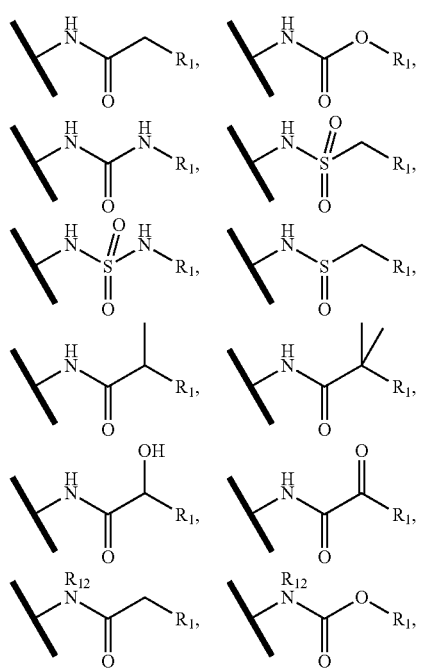

-continued

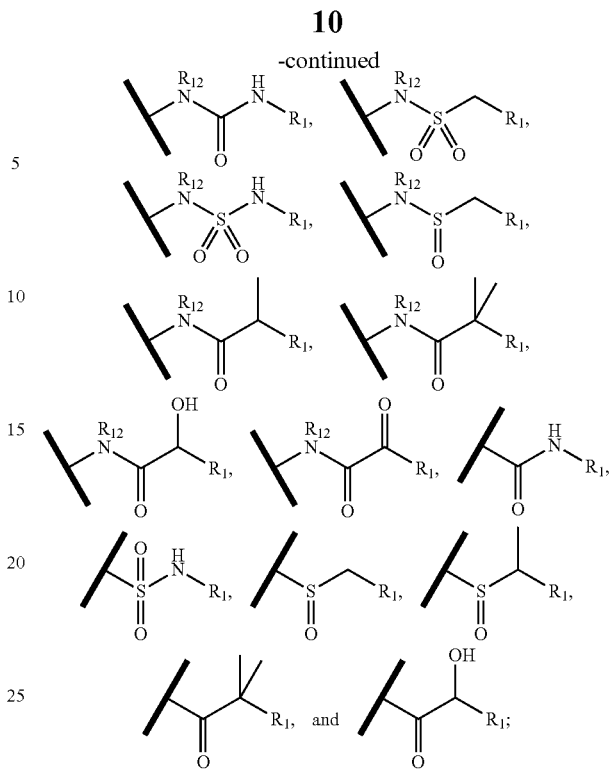

and R₁ is selected from the group consisting of hydrogen, hydroxymethyl, aminomethyl and $R_{12}$; and pharmaceutically acceptable salts thereof.

In yet other aspects, compounds of Formula I include those compounds in which q is 0; E-R₁ is selected from the group consisting of

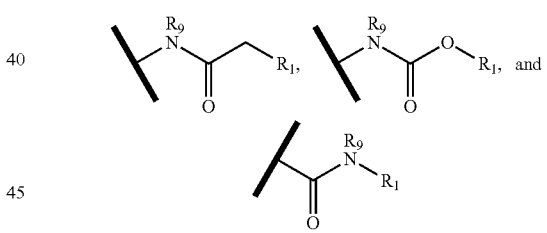

and R₁ and R₉ are independently selected from the group consisting of hydrogen, hydroxymethyl, aminomethyl and $R_{12}$; and pharmaceutically acceptable salts thereof.

Yet other compound of Formula I include those compounds in which R₂ is oxo or hydroxy or R₂ is selected from the group consisting of:

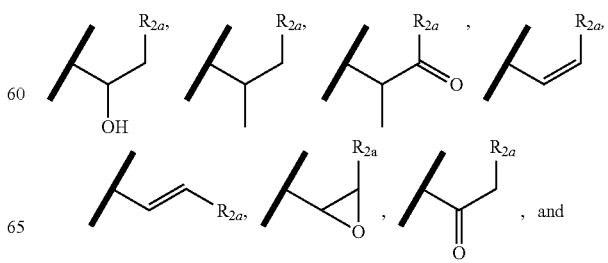

-continued

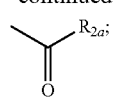

and

R$_{2a}$ is selected from hydrogen, amino, hydroxy, or R$_{13}$; and p is 0, 1, 2, 3, or 4.

Still other compounds of Formula I include those compounds in which R$_3$ is selected from R$_{3a}$, OR$_{3a}$, N(R$_{3a}$)$_2$ or R$_{13}$;

p is 0, 1, 2, 3, or 4; and

R$_{3a}$ is independently selected, at each occurrence from hydrogen, hydroxymethyl, aminomethyl or R$_{12}$; and pharmaceutically acceptable salts thereof.

Yet other compounds of Formula I include those compounds in which R$_4$ is selected from hydrogen, CO$_2$R$_{4a}$, C(O)N(R$_{4a}$)$_2$, N(R$_{3a}$)$_2$, or C(R$_{10}$)(R$_{11}$)phenyl;

R$_{10}$ is absent or hydrogen;

R$_{11}$ is hydrogen, oxo, R$_{4a}$, OR$_{4a}$, N(R$_{4a}$)$_2$, or =NR$_{4a}$;

R$_{4a}$ is independently selected at each occurrence from hydrogen, hydroxymethyl, aminomethyl and R$_{12}$; and pharmaceutically acceptable salts thereof.

Still other compounds of Formula I include those compounds in which R$_7$ is selected from the group consisting of H, OH, NH$_2$, C$_{1-8}$alkyl, C$_{1-8}$alkoxy, and mono- and di-C$_{1-8}$alkylamino and R$_{7b}$ is independently selected at each occurrence from hydrogen and C$_{1-4}$alkyl.

In other aspects, the invention provides compounds of Formula II:

II

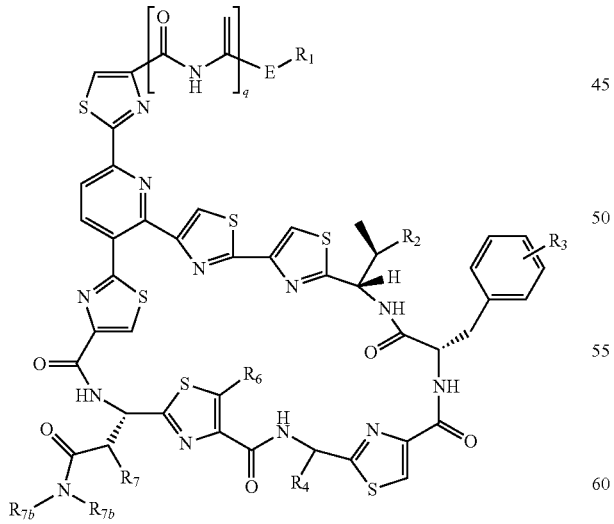

and pharmaceutically acceptable salts, enantiomers, stereoisomers, rotamers, tautomers, diastereomers, atropisomers or racemates thereof, including pyridine N-oxides thereof; wherein q is 1, or 2 and the fragment

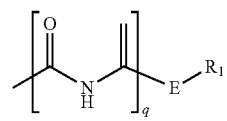

is selected from the group consisting of:

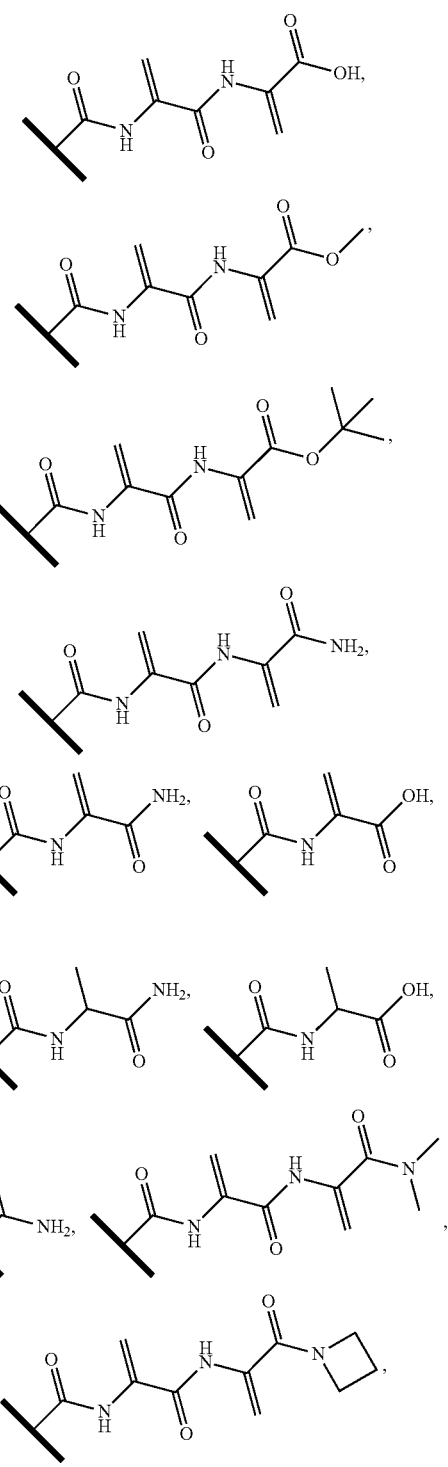

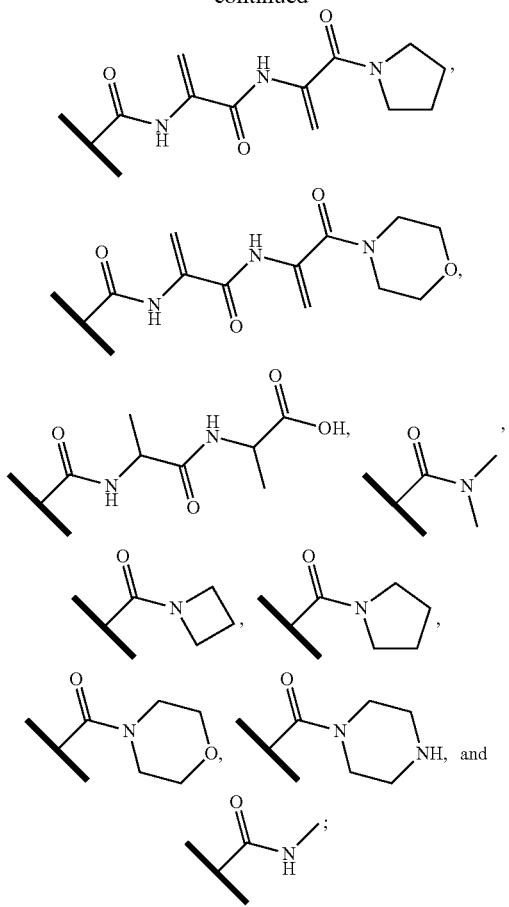

or q is 0 and E-R$_1$ is selected from the group consisting of:

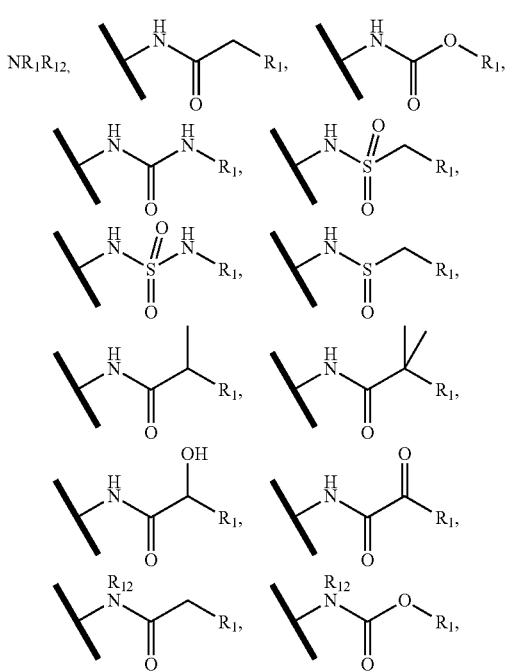

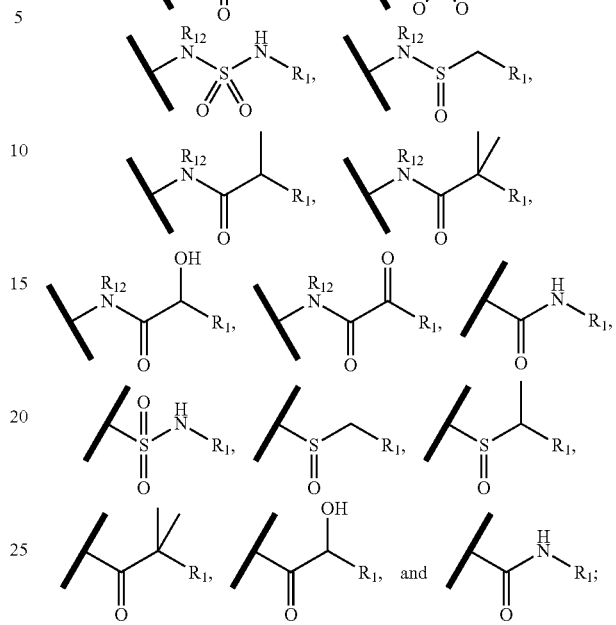

R$_1$ is selected from the group consisting of hydrogen, hydroxymethyl, and aminomethyl and R$_{12}$:

R$_2$ is oxo or hydroxy or R$_2$ is selected from the group consisting of:

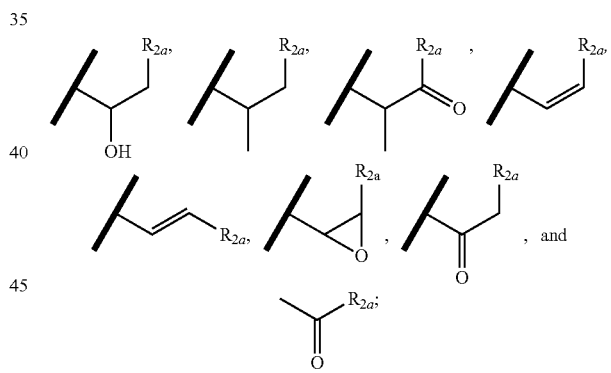

and

R$_{2a}$ is selected from hydrogen, amino, hydroxy or R$_{13}$;
R$_3$ is selected from R$_{12}$, OR$_{12}$, N(R$_{12}$)$_2$ or R$_{13}$;
R$_4$ is selected from hydrogen, CO$_2$R$_{4a}$, C(O)N(R$_{4a}$)$_2$, OR$_{3a}$, N(R$_{3a}$)$_2$, or C(R$_{10}$)(R$_{11}$)phenyl;
R$_{4a}$ is independently selected at each occurrence from hydrogen, hydroxymethyl, aminomethyl or R$_{12}$;
R$_6$ is hydrogen or C$_{1-4}$alkyl;
R$_7$ is selected from the group consisting of H, OH, NH$_2$, C$_{1-8}$alkyl, C$_{1-8}$alkoxy, and mono- and di-C$_{1-8}$alkylamino;
R$_{7a}$ is OR$_{7b}$ or N(R$_{7b}$)$_2$;
R$_{7b}$ is independently selected at each occurrence from the group consisting of H, C$_{1-8}$alkyl and —(CH$_2$—CH$_2$—O—)$_n$—R$_8$;
R$_8$ is independently selected at each occurrence from the group consisting of H, C$_{1-8}$alkyl and CH$_2$CO$_2$H;
R$_9$ is selected from R$_{12}$;

$R_{10}$ is absent or hydrogen; and $R_{11}$ is oxo, $OR_{4a}$, $N(R_{4a})_2$, or $=NR_{4a}$; and pharmaceutically acceptable salts thereof.

Certain other compounds of Formula I include those compounds represented by Formula III:

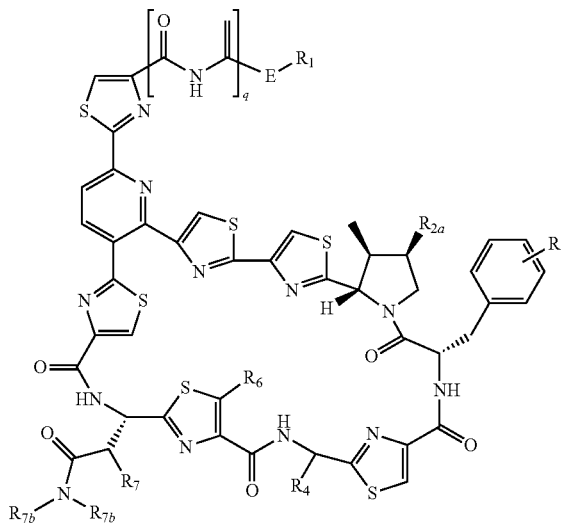

III and pharmaceutically acceptable salts, enantiomers, stereoisomers, rotamers, tautomers, diastereomers, atropisomers or racemates thereof, including pyridine N-oxides thereof; wherein q is 1, or 2 and the fragment

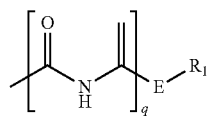

is selected from the group consisting of:

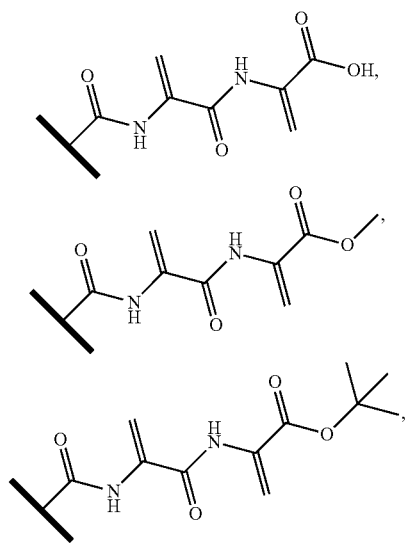

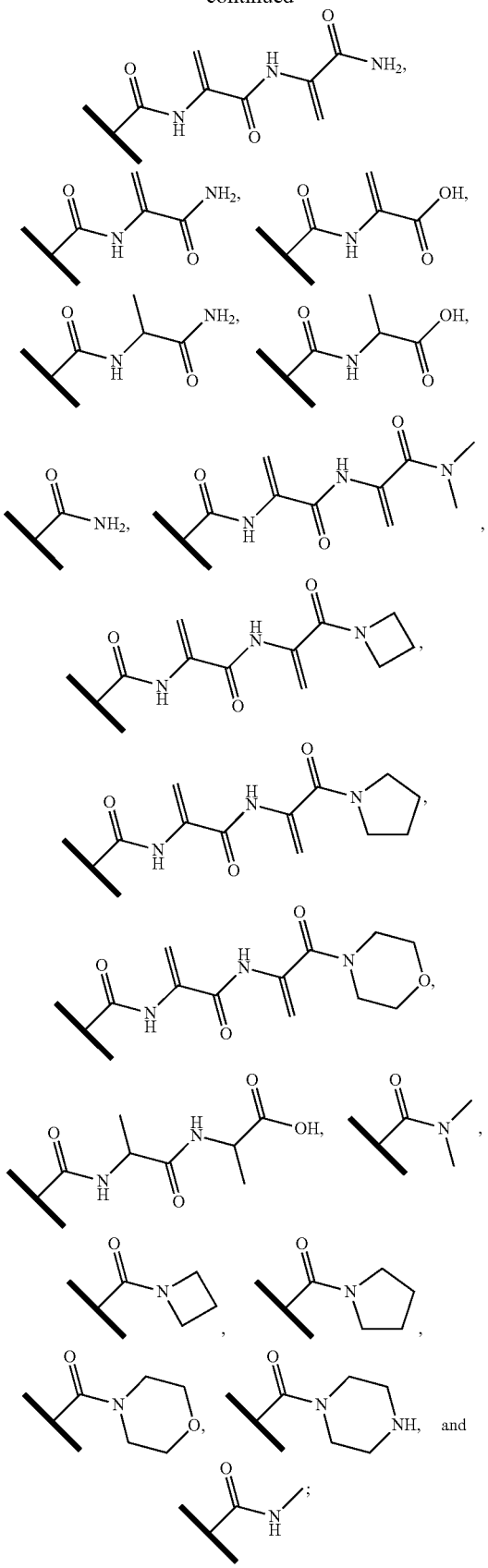

or q is 0 and E-R$_1$ is selected from the group consisting of:

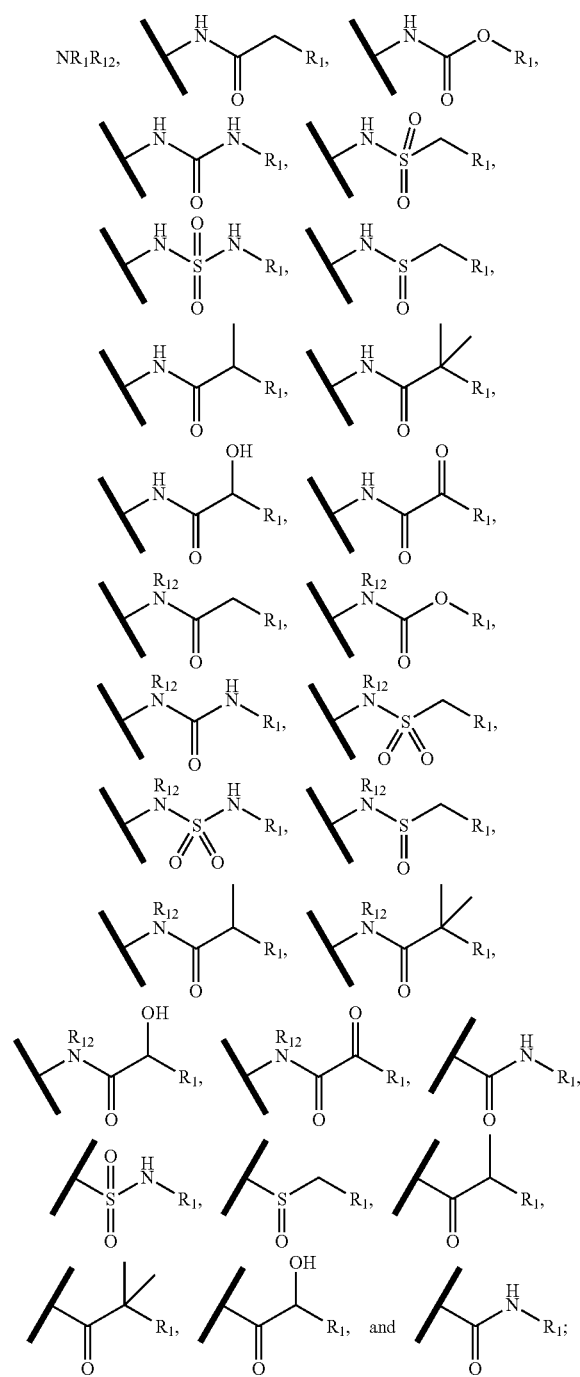

and R$_1$ is selected from the group consisting of hydrogen, hydroxymethyl, and aminomethyl and R$_{12}$:

R$_{2a}$ is hydrogen, hydroxy or amino, or is selected from the group consisting of C$_{1-8}$alkoxy, amino, mono- and di-C$_{1-8}$alkylamino, C$_{3-7}$cycloalkylC$_{0-6}$alkoxy, each of which is substituted with hydroxy, oxo, halo, C$_{1-8}$alkyl, haloC$_{1-8}$alkyl, C$_{1-8}$alkoxy, haloC$_{1-8}$alkoxy, C$_{3-7}$cycloalkylC$_{0-6}$alkyl, COOH, NH$_2$, mono- and di-C$_{1-8}$alkylamino, tri-C$_{1-8}$alkylammonium, heterocycleC$_{0-6}$alkyl, heteroarylC$_{0-6}$alkyl, or —(CH$_2$—CH$_2$—O—)$_n$—R$_8$;

R$_3$ is selected from R$_{12}$, OR$_{12}$, N(R$_{12}$)$_2$ or R$_{13}$;
R$_4$ is selected from hydrogen, CO$_2$R$_{4a}$, C(O)N(R$_{4a}$)$_2$, OR$_{3a}$, N(R$_{3a}$)$_2$, or C(R$_{10}$)(R$_{11}$)phenyl;
R$_{4a}$ is independently selected at each occurrence from hydrogen, hydroxymethyl, aminomethyl or R$_{12}$;
R$_6$ is hydrogen or C$_{1-4}$alkyl;
R$_7$ is selected from the group consisting of H, OH, NH$_2$, C$_{1-8}$alkyl, C$_{1-8}$alkoxy, and mono- and di-C$_{1-8}$alkylamino;
R$_{7a}$ is selected from the group consisting of H and C$_{1-8}$alkyl; and
R$_{7b}$ is independently selected at each occurrence from the group consisting of H, C$_{1-8}$alkyl and —(CH$_2$—CH$_2$—O—)$_n$—R$_8$, wherein R$_8$ is independently selected at each occurrence from the group consisting of H, C$_{1-8}$alkyl and CH$_2$CO$_2$H;
R$_9$ is selected from R$_{12}$;
R$_{10}$ is absent or hydrogen;
R$_{11}$ is oxo, OR$_{4a}$, N(R$_{4a}$)$_2$, or =NR$_{4a}$;
n is an integer of between 1-60,000 or is a mean of a plurality of integers having a value of between 1-60,000;
p is 0, 1, 2, 3, or 4;
and pharmaceutically acceptable salts thereof.

Certain compounds of Formula II or Formula III include those compounds in which R$_7$ and each occurrence of R$_{7b}$ are hydrogen.

In still other aspects, compounds of Formula II or Formula III include those compounds in which the fragment:

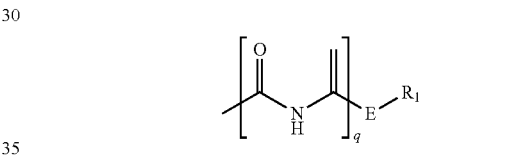

is selected from the group consisting of:

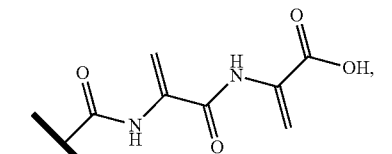

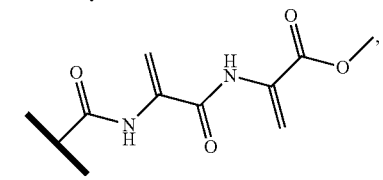

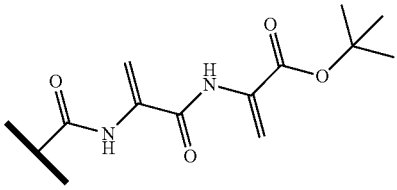

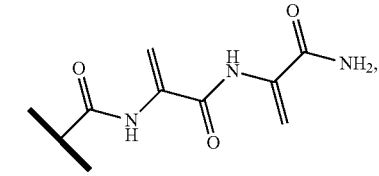

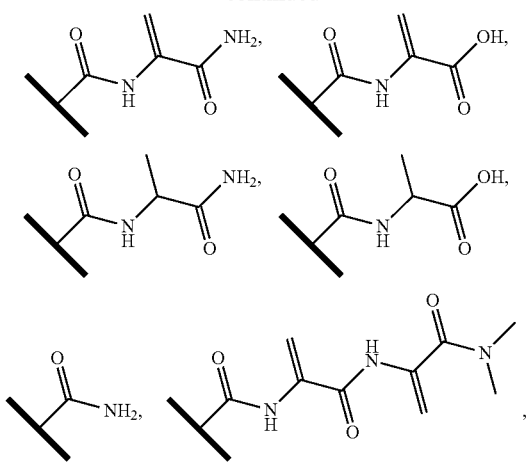
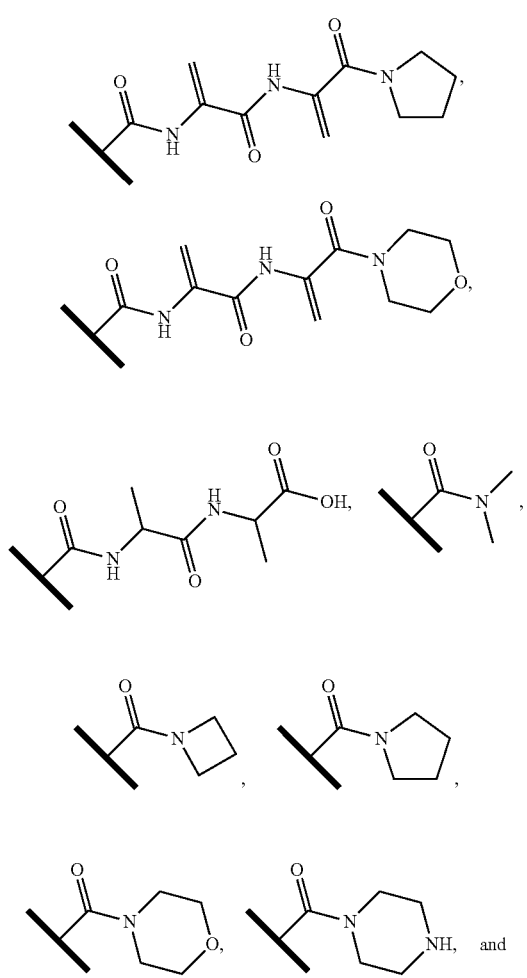

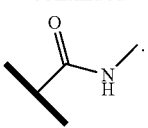

In certain other aspects, compounds of Formula II and III include those compounds in which the fragment:

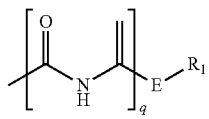

is selected from groups in which q is 0, E is $N(R_9)$, $N(R_9)C(O)$, or $N(R_9)C(O)O$; $R_9$ is hydrogen or $Z-CO_2H$; $R_1$ is $Z-CO_2H$; and Z is $C_1$-$C_8$alkylene, $C_3$-$C_8$cycloalkylene, $C_3$-$C_8$heterocycloalkylene, phenylene, or 5-6 membered heteroarylene, each of which is optionally substituted with one or more groups independently selected from $C_1$-$C_4$alkyl, $C_1$-$C_4$alkoxy, hydroxy, amino, mono- and di-$C_1$-$C_6$alkylamino, C(O)OH, or halogen.

Certain other compounds of Formula II and III include those compounds in which q is 0; E-$R_1$ is selected from the group consisting of:

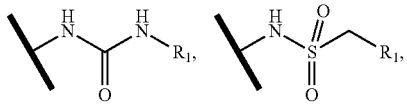
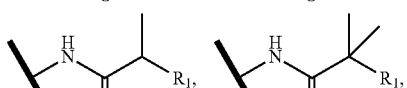
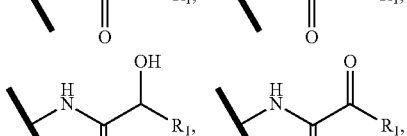
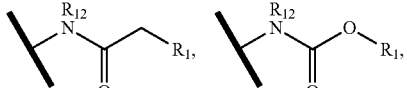
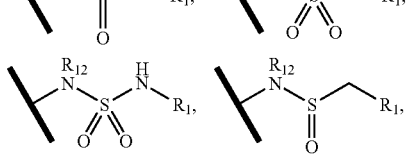

-continued

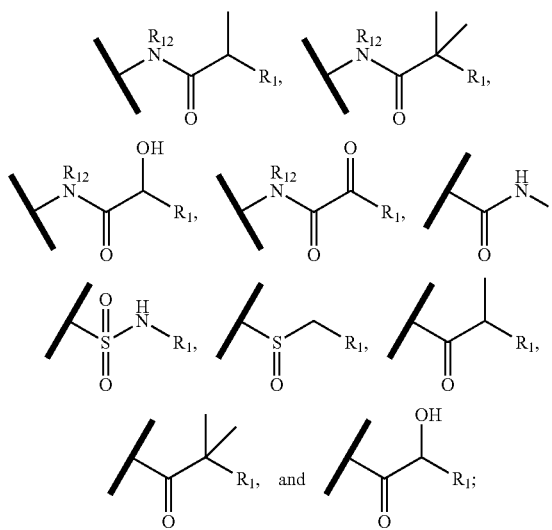

and $R_1$ is selected from the group consisting of hydrogen, hydroxymethyl, aminomethyl and $R_{12}$; and pharmaceutically acceptable salts thereof.

In yet other aspects, compounds of Formula II and III include those compounds in which q is 0; E-$R_1$ is selected from the group consisting of

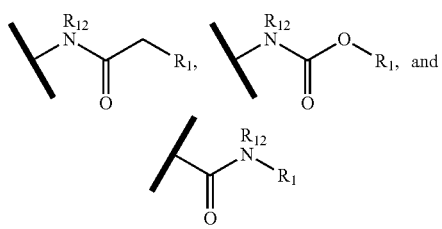

and $R_1$ is selected from the group consisting of hydrogen, hydroxymethyl, aminomethyl and $R_{12}$; and pharmaceutically acceptable salts thereof.

Certain other compounds of Formula II or Formula III include those compounds in which q is 0; E-$R_1$ is selected from the group consisting of:

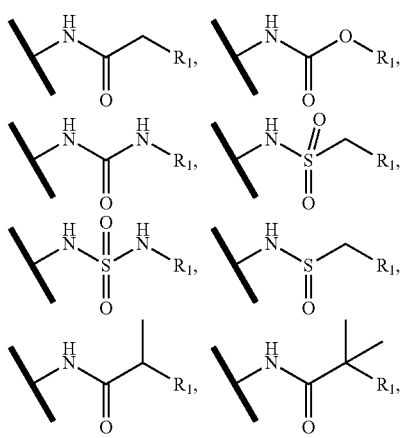

-continued

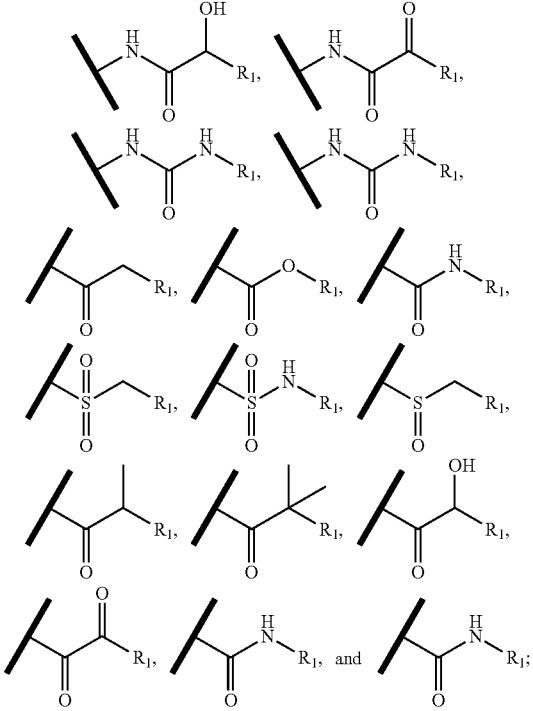

and $R_1$ is selected from the group consisting of hydrogen, hydroxymethyl, aminomethyl and $R_{12}$; and pharmaceutically acceptable salts thereof.

Yet other compound of Formula II or Formula III include those compounds in which $R_2$ is oxo or hydroxy or $R_2$ is selected from the group consisting of:

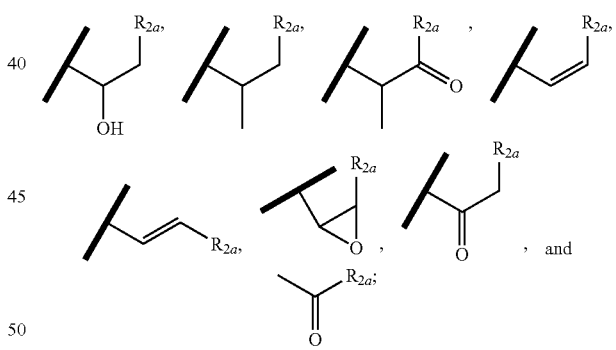

and
$R_{2a}$ is selected from hydrogen, amino, hydroxy, or $R_{13}$; and
p is 0, 1, 2, 3, or 4.
Still other compounds of Formula II or Formula III include those compounds in which $R_3$ is selected from $R_{3a}$, $OR_{3a}$, $N(R_{3a})_2$ or $R_{13}$;
p is 0, 1, 2, 3, or 4; and
$R_{3a}$ is independently selected, at each occurrence from hydrogen, hydroxymethyl, aminomethyl or
$R_{12}$; and pharmaceutically acceptable salts thereof.
Yet other compounds of Formula II or Formula III include those compounds in which $R_4$ is selected from hydrogen, $CO_2R_{4a}$, $C(O)N(R_{4a})_2$, $N(R_{4a})_2$, or $C(R_{10})(R_{11})$phenyl;
$R_{10}$ is absent or hydrogen;
$R_{11}$ is hydrogen, oxo, $R_{4a}$, $OR_{4a}$, $N(R_{4a})_2$, or =$NR_{4a}$;

$R_{4a}$ is independently selected at each occurrence from hydrogen, hydroxymethyl, aminomethyl and
$R_{12}$; and pharmaceutically acceptable salts thereof.

Still other compounds of Formula II or Formula III include those compounds in which $R_7$ is selected from the group consisting of H, OH, $NH_2$, $C_{1-8}$alkyl, $C_{1-8}$alkoxy, and mono- and di-$C_{1-8}$alkylamino and $R_{7b}$ is independently selected at each occurrence from hydrogen and $C_{1-4}$alkyl. In other compounds $R_7$ is selected from the group consisting of H, OH, $NH_2$, $C_{1-8}$alkyl, $C_{1-8}$alkoxy, and mono- and di-$C_{1-8}$alkylamino; and $R_{7a}$ and $R_{7b}$ are hydrogen.

In certain aspects, the invention provides compounds represented by Formula IV:

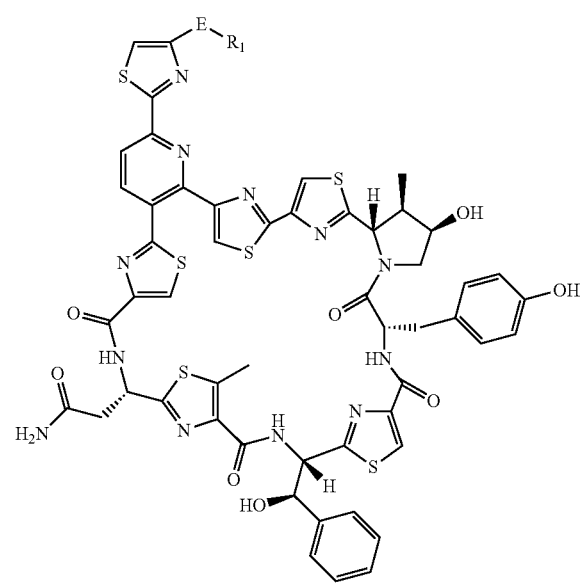

IV and pharmaceutically acceptable salts, enantiomers, stereoisomers, rotamers, tautomers, diastereomers, atropisomers or racemates thereof, including pyridine N-oxides thereof; wherein E is selected from the group consisting of C(O), C(O)C(O), C(O)O, N($R_9$), C(O)N($R_9$), N($R_9$)C(O), N($R_9$)C(O)C(O), N($R_9$)C(O)O, N($R_9$)C(O)N($R_9$), S(O)$_2$, S(O)$_2$N($R_9$), N($R_9$)S(O)$_2$, and N($R_9$)S(O)$_2$N($R_9$);

$R_1$ is hydrogen or is selected from the group consisting of $C_{1-8}$alkyl, $C_{2-8}$alkenyl, $C_{2-8}$alkynyl, $C_{1-8}$alkoxy, cycloalkyl$C_{0-6}$alkyl, heterocycloalkyl$C_{0-6}$alkyl, aryl$C_{0-6}$alkyl, heteroaryl$C_{0-6}$alkyl each of which is substituted with 0 to 6 residues independently selected at each occurrence from the group consisting of hydroxy, oxo, $C_{1-8}$alkyl, $C_{1-8}$alkoxy, $C_{3-7}$cycloalkyl$C_{0-6}$alkyl, COOH, $NH_2$, mono- and di-$C_{1-8}$ alkylamino, tri-$C_{1-8}$alkylammonium, heterocycle$C_{0-6}$alkyl, heteroaryl$C_{0-6}$alkyl and —(CH$_2$—CH$_2$—O—)$_n$—$R_8$;

$R_8$ is independently selected at each occurrence from the group consisting of H, $C_{1-8}$alkyl and CH$_2$CO$_2$H; and $R_9$ is hydrogen or is selected from the group consisting of $C_{1-8}$alkyl, $C_{2-8}$alkenyl, $C_{2-8}$alkynyl, $C_{1-8}$alkoxy, cycloalkyl$C_{0-6}$alkyl, heterocycloalkyl$C_{0-6}$alkyl, aryl$C_{0-6}$alkyl, heteroaryl$C_{0-6}$alkyl each of which is substituted with 0 to 6 residues independently selected at each occurrence from the group consisting of hydroxy, oxo, $C_{1-8}$alkyl, $C_{1-8}$alkoxy, $C_{3-7}$cycloalkyl$C_{0-6}$alkyl, COOH, $NH_2$, mono- and di-$C_{1-8}$ alkylamino, tri-$C_{1-8}$alkylammonium, heterocycle$C_{0-6}$alkyl, heteroaryl$C_{0-6}$alkyl and —(CH$_2$—CH$_2$—O—)$_n$—$R_8$.

In certain aspects, compounds of Formula IV include those compounds in which $R_1$ and $R_9$ are independently selected at each occurrence from the group consisting of H, $C_{1-8}$alkyl, $C_{3-8}$cycloalkyl, and $R_{12}$, wherein the $C_{1-8}$alkyl and $C_{3-8}$cycloalkyl groups are unsubstituted or substituted with 1 or 2 groups selected from halogen, hydroxyl, or COOH.

In yet other aspects, compounds of Formula IV include those compounds in which E is N($R_9$), N($R_9$)C(O), or N($R_9$) C(O)O; $R_9$ is hydrogen or Z—CO$_2$H; $R_1$ is Z—CO$_2$H; and Z is $C_1$-$C_8$alkylene, $C_3$-$C_8$cycloalkylene, $C_3$-$C_8$heterocycloalkylene, phenylene, or 5-6 membered heteroarylene, each of which is optionally substituted with one or more groups independently selected from $C_1$-$C_4$alkyl, $C_1$-$C_4$alkoxy, hydroxy, amino, mono- and di-$C_1$-$C_6$alkylamino, C(O)OH, or halogen.

In still other aspects, compounds of Formula IV include those compounds in which E-$R_1$ is selected from the group consisting of

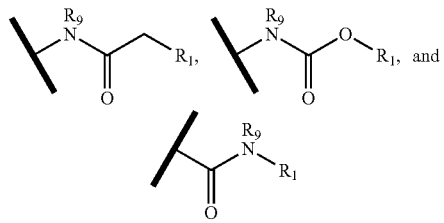

and $R_1$ and $R_9$ are independently selected from the group consisting of hydrogen, hydroxymethyl, aminomethyl and $R_{12}$; and pharmaceutically acceptable salts thereof.

In other aspects, compounds of Formula IV include those compounds in which E-$R_1$ is selected from the group consisting of

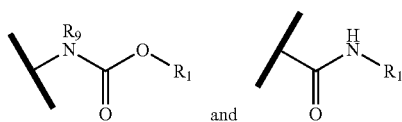

and $R_1$ and $R_9$ are independently selected from the group consisting of hydrogen, hydroxymethyl, aminomethyl and $R_{12}$; and pharmaceutically acceptable salts thereof.

In certain compounds of Formula IV, $R_1$ and $R_9$ are selected from the group consisting of —(CH$_2$)$_s$CO$_2$H and —C$_{4-7}$cycloalkyl-CO$_2$H, wherein s is 2, 3, 4, 5 or 6.

$R_{12}$ in compounds of Formula I, Formula II, Formula III, Formula IV and subformulae thereof is a residue independently selected at each occurrence from the group consisting of

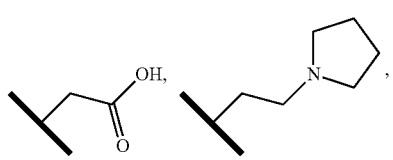

25
-continued
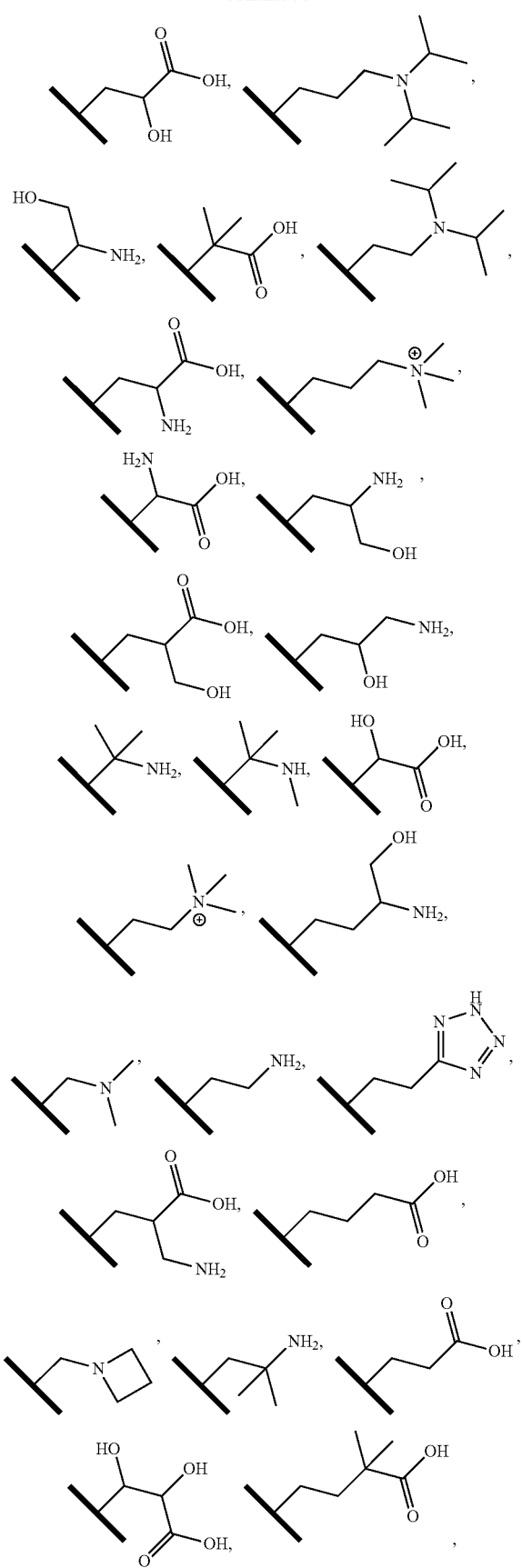
26
-continued
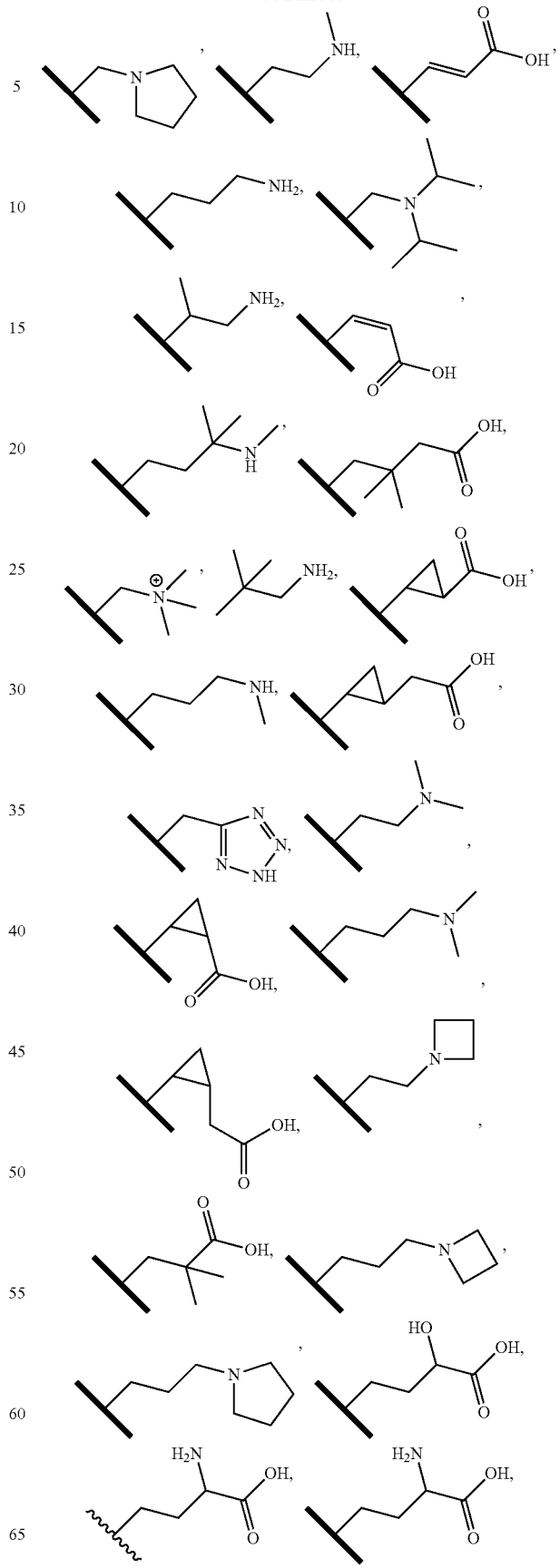

27
-continued
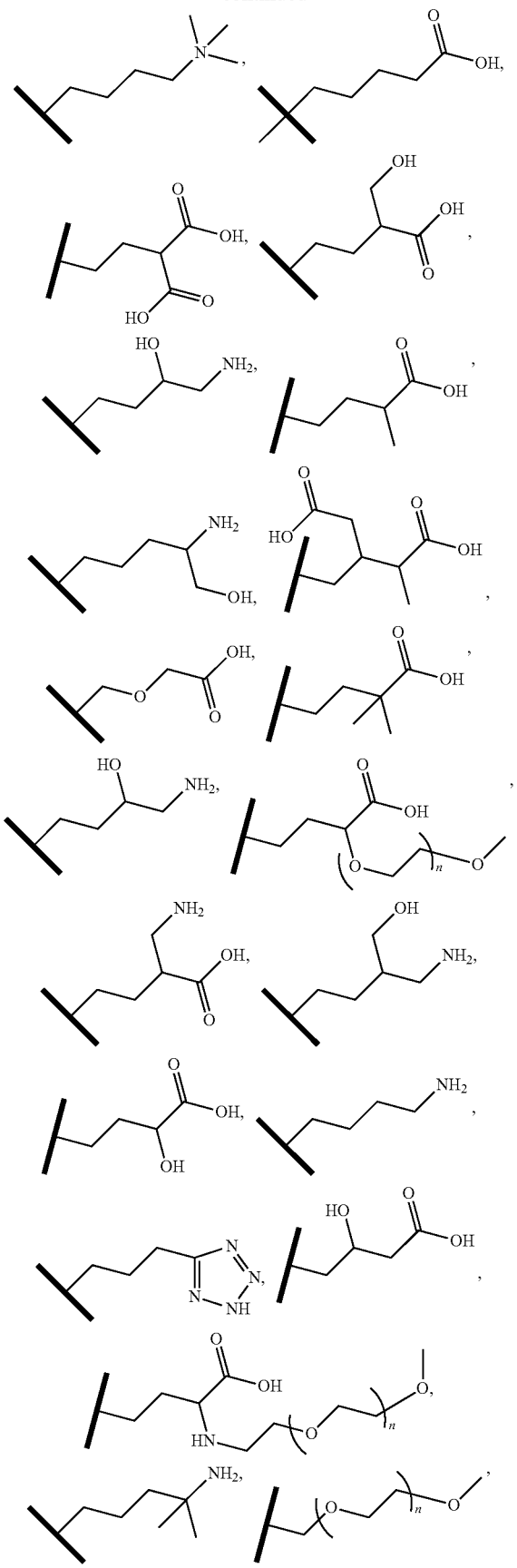
28
-continued
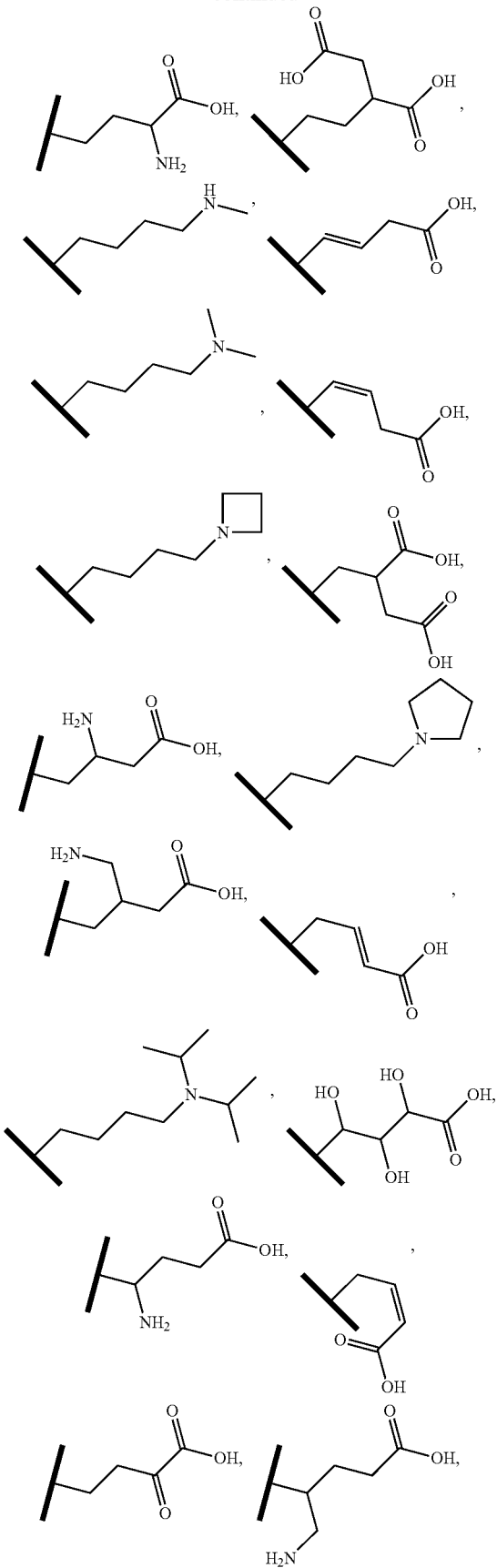

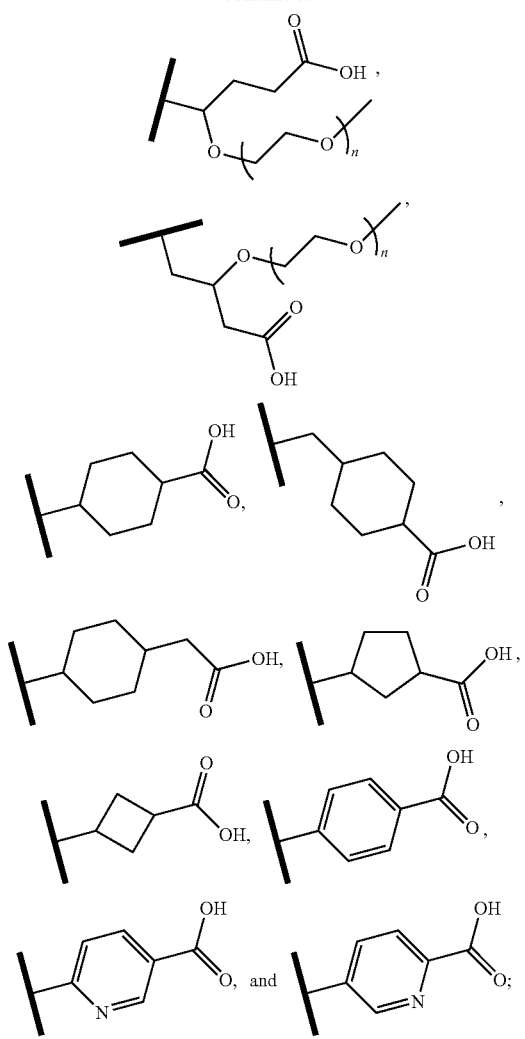
and
n is an integer of between 1-60,000 or is a mean of a plurality of integers having a value of between 1-60,000.
In certain compounds of Formula I, Formula II, Formula III, and subformulae thereof, $R_{13}$ is independently selected at each occurrence, from the group consisting of
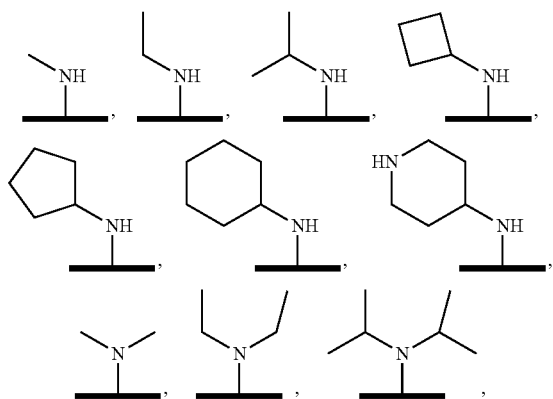
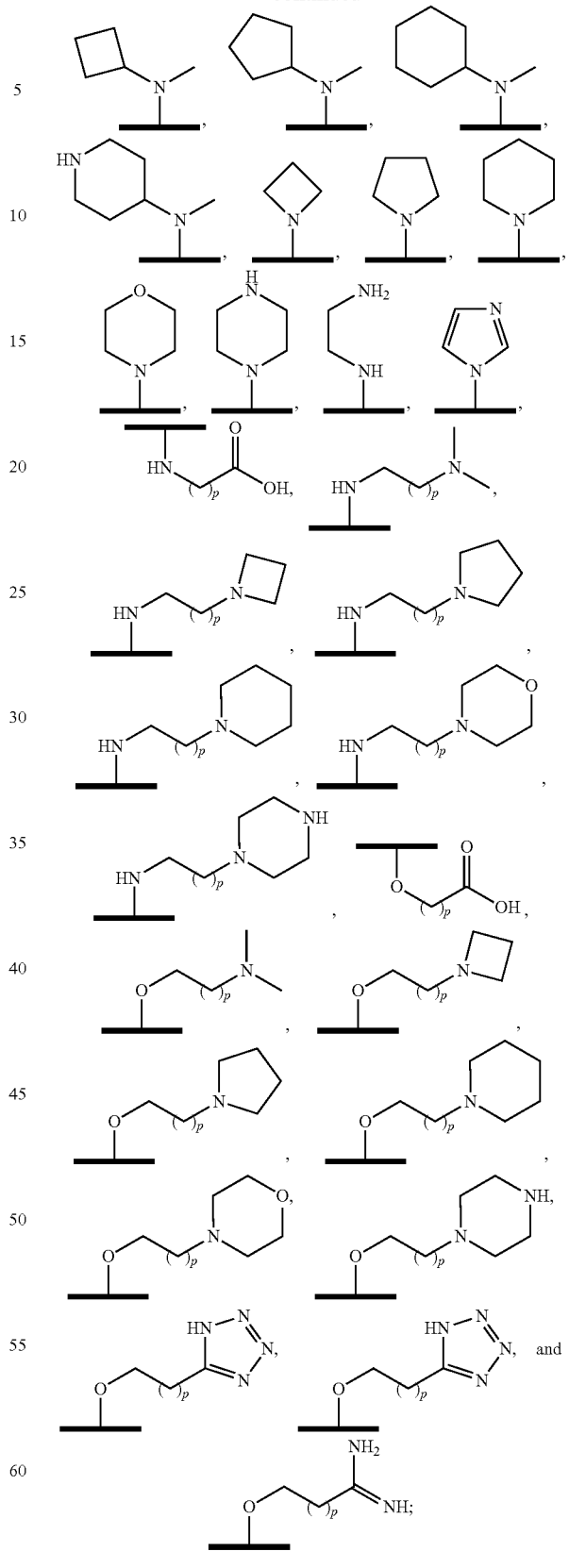
and
p is 0, 1, 2, 3, or 4.

Preferred embodiments of Formula I, II, III, IV or any subformulae thereof (including pharmaceutically acceptable salts thereof, as well as enantiomers, stereoisomers, rotamers, tautomers, diastereomers, atropisomers or racemates thereof, including N-pyridine-oxides thereof) include the compounds of Examples 1-143 infra, and are also considered to be "compounds of the invention." The compounds of the invention are also referred to herein as "antibiotics" and "EF-Tu inhibitors."

In certain embodiments, the compound of the present invention is further characterized as a modulator of EF-Tu, including a prokaryotic EF-Tu, and especially including a bacterial EF-Tu. In a preferred embodiment, the compound of the invention is an EF-Tu inhibitor.

As used herein, the term "bacterial infection(s)" includes, but is not limited to, bacterial infections that occur in mammals, fish and birds as well as disorders related to bacterial infections that may be treated or prevented by administering antibiotics such as the compounds of the present invention. In addition to treating infections caused by multi-drug resistant strains of *Staphyloccocus aureus, Streptococcus pneumoniae, Mycobacterium tuberculosis* and *Enterococci*, the compounds of the present invention are useful in treating infections caused by other bacteria including, but not limited to, *Clostridium difficile, Propionibacterium acnes, Bacteroides fagiles, Neisseria gonorrhoeae, Branhamella catarrhalis, Haemophilus influenzae, E. coli, Pseudomonas aeruginosa, Proteus vulgaris, Klebsiella pneumonia,* and *Chlamydia trachomatis*.

Such bacterial infections and disorders related to such infections include, but are not limited to, the following: acne, rosacea, skin infection, pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Peptostreptococcus* spp. or *Pseudomonas* spp.; pharynigitis, rheumatic fever, and glomerulonephritis related to infection by *Streptococcus pyogenes*, Groups C and G streptococci, *Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus,* etc.), *S. pyogenes, S. agalactiae*, Streptococcal groups C—F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Nesseria gonorrheae*; toxin diseases related to infection by *S. aureus* (food poisoning and Toxic shock syndrome), or Groups A, S, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp., odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium acne*; atherosclerosis related to infection by *Helicobacter pylori* or *Chlamydia pneumoniae*; or the like.

Further bacterial infections and disorders related to such infections that may be treated or prevented in animals include, but are not limited to, the following: bovine respiratory disease related to infection by *P. haemolytica., P. multocida, Mycoplasma bovis,* or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium,* or *Enterococcus* spp.; swine respiratory disease related to infection by *A. pleuropneumoniae., P. multocida,* or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis,* cow premature abortion related to infection by protozoa (i.e., neosporium); urinary tract infection in dogs and cats related to infection by *E. coli*; skin and soft tissue infections in dogs and cats related to infection by *S. epidermidis, S. intermedius,* coagulase neg. *Staphylococcus* or *P. multocida*; dental or mouth infections in dogs and goats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., *Trichomonas* spp. or *Prevotella* spp. Other bacterial infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Further bacterial infections and disorders related to such infections that may be treated or prevented in animals include, but are not limited to, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, antibacterial prophylaxis in immunosuppressed patients, such as patients receiving cancer chemotherapy, or organ transplant patients and chronic diseases caused by infectious organisms, e.g., arteriosclerosis.

Bacterial protein synthesis requires EF-Tu chaperone proteins. EF-Tu is one of the most abundant proteins in bacteria, as well as one of the most highly conserved, and in a number of species the gene is duplicated with identical function. When bound to GTP, EF-Tu can form a complex with most aminoacylated tRNAs, loading the tRNA onto the ribosome. In one embodiment, the bacterial infection is associated with the activity of EF-Tu. Without being bound by theory, it is believed that the disruption of EF-Tu protein activity by the compounds of the invention will interfere with protein synthesis and thus bacterial function and/or proliferation. Because EF-Tu is highly conserved across Gram-positive and Gram-negative bacteria, the compounds of the present invention are useful for treating infections of both classes of bacteria.

As used herein, the term "EF-Tu-associated state" or "EF-Tu-associated disorder" include disorders and states (e.g., a disease state) that are associated with the activity of EF-Tu. A non-limiting example of an EF-Tu associated disorder is a bacterial infection in a subject.

The present invention includes treatment of bacterial infections, as well as EF-Tu-associated disorders, as described above, but the invention is not intended to be limited to the manner by which the compound performs its intended function of treatment of a disease. The present invention includes treatment of diseases described herein in any manner that allows treatment to occur, e.g., bacterial infection.

In certain embodiments, the invention provides a pharmaceutical composition of any of the compounds of the present invention. In a related embodiment, the invention provides a pharmaceutical composition of any of the compounds of the present invention and a pharmaceutically acceptable carrier or excipient of any of these compounds. In certain embodiments, the invention includes the compounds as novel chemical entities.

In one embodiment, the invention includes a packaged bacterial infection treatment. The packaged treatment includes a compound of the invention packaged with instructions for using an effective amount of the compound of the invention for an intended use.

The compounds of the present invention are suitable as active agents in pharmaceutical compositions that are efficacious particularly for treating bacterial infections. The pharmaceutical composition in various embodiments has a pharmaceutically effective amount of the present active agent along with other pharmaceutically acceptable excipients, carriers, fillers, diluents and the like. The phrase, "pharmaceutically effective amount" as used herein indicates an amount necessary to administer to a host, or to a cell, issue, or organ of a host, to achieve a therapeutic result, especially an antibacterial infection effect, e.g., inhibition of proliferation of a bacterium, or of any other bacterial infection.

In other embodiments, the present invention provides a method for inhibiting the activity of an EF-Tu protein. The method includes contacting a cell with any of the compounds of the present invention. In a related embodiment, the method further provides that the compound is present in an amount effective to selectively inhibit the activity of an EF-Tu protein.

In other embodiments, the present invention provides a use of any of the compounds of the invention for manufacture of a medicament to treat a bacterial infection in a subject.

In other embodiments, the invention provides a method of manufacture of a medicament, including formulating any of the compounds of the present invention for treatment of a subject.

DEFINITIONS

The term "treat," "treated," "treating" or "treatment" includes the diminishment or alleviation of at least one symptom associated or caused by the state, disorder or disease being treated. In certain embodiments, the treatment comprises the induction of a bacterial infection, followed by the activation of the compound of the invention, which would in turn diminish or alleviate at least one symptom associated or caused by the bacterial infection being treated. For example, treatment can be diminishment of one or several symptoms of a disorder or complete eradication of a disorder.

The term "subject" is intended to include organisms, e.g., prokaryotes and eukaryotes, which are capable of suffering from or afflicted with a bacterial infection. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a bacterial infection, and for diseases or conditions described herein. In another embodiment, the subject is a cell.

The language "EF-Tu-modulating compound," "modulator of EF-Tu" or "EF-Tu inhibitor" refers to compounds that modulate, e.g., inhibit, or otherwise alter, the activity of EF-Tu. Examples of EF-Tu-modulating compounds include compounds of formula I, formula II, subformulae thereof, as well as compounds of Examples 1-143 (including pharmaceutically acceptable salts thereof, as well as enantiomers, stereoisomers, rotamers, tautomers, diastereomers, atropisomers or racemates thereof).

Additionally, a method of the invention includes administering to a subject an effective amount of an EF-Tu-modulating compound of the invention, e.g., EF-Tu-modulating compounds of formula I, formula II, subformulae thereof, as well as compounds of Examples 1-143 (including pharmaceutically acceptable salts thereof, as well as enantiomers, stereoisomers, rotamers, tautomers, diastereomers, atropisomers or racemates thereof).

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term "alkyl" also includes alkenyl groups and alkynyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl. Moreover, the term $C_{3-6}$-cycloalkyl includes, but is not limited to, cyclopropyl, cyclopentyl, and cyclohexyl. As discussed below, these alkyl groups, as well as cycloalkyl groups, may be further substituted.

The term alkyl further includes alkyl groups which can further include oxygen, nitrogen, sulfur or phosphorous atoms replacing one or more carbons of the hydrocarbon backbone. In an embodiment, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer carbons. Likewise, preferred cycloalkyls have from 4-7 carbon atoms in their ring structure, and more preferably have 5 or 6 carbons in the ring structure.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function.

The term "substituted" is intended to describe moieties having substituents replacing a hydrogen on one or more atoms, e.g. C, O or N, of a molecule. Such substituents can include, for example, oxo, alkyl, alkoxy, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperizine, cyclopentane, cyclohexane, pyridine, 5H-tetrazole, triazole, piperidine, or an aromatic or heteroaromatic moiety, and any combination thereof.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$, $-OSO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$ (e.g., $-CO_2H$), or $(CR'R'')_{0-3}OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety, and any combination thereof. In certain embodiments, a carbonyl moiety (C=O) may be further derivatized with an oxime moiety, e.g., an aldehyde moiety may be derivatized as its oxime (—C=N—OH) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkylamino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "carbonyl" or "carboxy" includes compounds and moieties which contain a carbon connected with a double bond to an oxygen atom, and tautomeric forms thereof. Examples of moieties that contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., —$CH_3$ and —$CH_2CH_2CH_2$—) can be combined to form a 3-methoxy-4-propoxybenzoic acid substituent. It is to be understood that when combining functional groups and molecules to create a larger molecular architecture, hydrogens can be removed or added, as required to satisfy the valence of each atom.

It is to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

It will be noted that the structures of some of the compounds of this invention include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

Use in Bacterial Infection

The compounds of the present invention have valuable pharmacological properties and are useful in the treatment of diseases. In certain embodiments, compounds of the invention are useful in the treatment of bacterial infections.

The term "use" includes any one or more of the following embodiments of the invention, respectively: the use in the treatment of bacterial infections; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from bacterial infections, as well as those diseases that depend on the activity of EF-Tu. The term "use" further includes embodiments of compositions herein which bind to an EF-Tu protein sufficiently to serve as tracers or labels, so that when coupled to a fluor or tag, or made radioactive, can be used as a research reagent or as a diagnostic or an imaging agent.

In certain embodiments, a compound of the present invention is used for treating EF-Tu-associated diseases, and use of the compound of the present invention as an inhibitor of any one or more EF-Tu proteins. It is envisioned that a use can be a treatment of inhibiting one or more isoforms of EF-Tu.

Assays

The inhibition of antibacterial activity by the compounds of the invention may be measured using a number of assays available in the art. An example of such an assay is the standard minimum inhibitory concentration (MIC) test conducted according to CSLI guidelines.

Pharmaceutical Compositions

The language "effective amount" of the compound is that amount necessary or sufficient to treat or prevent a bacterial infection, e.g. prevent the various morphological and somatic symptoms of a bacterial infection, and/or a disease or condition described herein. In an example, an effective amount of the compound of the invention is the amount sufficient to treat a bacterial infection in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a bacterial infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Synthetic Procedure

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

General Process Conditions

The following applies in general to all processes mentioned throughout this disclosure.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the H$^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Prodrugs

This invention also encompasses pharmaceutical compositions containing, and methods of treating bacterial infections through administering, pharmaceutically acceptable prodrugs of compounds of the compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Any reference to a compound of the present invention is therefore to be understood as referring also to the corresponding pro-drugs of the compound of the present invention, as appropriate and expedient.

Combinations

A compound of the present invention may also be used in combination with other agents, e.g., an additional antibacterial compound that is or is not a compound of the invention, for treatment of a bacterial infection in a subject.

By the term "combination" is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

A compound of the present invention may be used in combination with another antibacterial agent. The term "antibacterial agent" refers to any substance that is either bactericidal or bacteriostatic, i.e., capable of killing or inhibiting the growth of bacterial cells. Antibacterial agents include antibiotics, biocides, antimicrobials, and bacteriostatic agents. The known types of antibiotics include, e.g., cell wall synthesis inhibitors, cell membrane inhibitors, protein synthesis inhibitors and inhibitors that bind to or affect the synthesis of DNA or RNA. Numerous antibiotic agents suitable for use in the treatment of bacteria-related diseases and disorders, are known and disclosed, e.g. in The Physician's Desk Reference (PDR), Medical Economics Company (Montvale, N.J.), (53.sup.rd Ed.), 1999; Mayo Medical Center Formulary, Unabridged Version, Mayo Clinic (Rochester, Minn.), January 1998; Merck Index: An Encyclopedia of Chemicals, Drugs and Biologicals, (11.sup.th Ed.), Merck & Co., Inc. (Rahway, N.J.), 1989; University of Wisconsin Antimicrobial Use Guide, http://www.medsch.wisc.edu/clinsci/5amcg/amcg.html; Introduction on the Use of the Antibiotics Guideline, of Specific Antibiotic Classes, Thomas Jefferson University, http://jeffiine.tju.edu/CWIS/OAC/antibiotics_guide/intro.html; and references cited therein.

Examples of antibiotics for use in combination with the compounds of the invention include, but are not limited to, quinolone, macrolide, glycopeptide, oxazolidinone, β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), daptomycin, cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoxime, cefprozil, ceftazidime, ceftibuten, ceftizoxime, ceftriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol, and combinations thereof.

Examples of anti-viral agents for use in combination with the compounds of the invention include, but are not limited to, zidovudine, lamivudine, didanosine, zalcitabine, stavudine, abacavir, nevirapine, delavirdine, emtricitabine, efavirenz, saquinavir, ritonavir, indinavir, nelfinavir, amprenavir, tenofovir, adefovir, atazanavir, fosamprenavir, hydroxyurea, AL-721, ampligen, butylated hydroxytoluene; polymannoacetate, castanospermine; contracan; creme pharmatex, CS-87, penciclovir, famciclovir, acyclovir, cytofovir, ganciclovir, dextran sulfate, D-penicillamine trisodium phosphonoformate, fusidic acid, HPA-23, eflornithine, nonoxynol, pentamidine isethionate, peptide T, phenyloin, isoniazid, ribavirin, rifabutin, ansamycin, trimetrexate, SK-818, suramin, UA001, enfuvirtide, gp41-derived peptides, antibodies to CD4, soluble CD4, CD4-containing molecules, CD4-IgG2, and combinations thereof.

Further examples of agents the compounds of the present invention can be used in combination with include, but are not limited to, free radical scavengers, ascorbic acid, Vitamin C, anti-cancer agents, chemotherapeutic agents, non-steroidal anti-inflammatory drugs, steroidal anti-inflammatory drugs, anti-fungal agents, detoxifying agents, analgesics, bronchodilators, drugs for the treatment of vascular ischemia antibody monoclonal agent, minoxidil for topical application for hair growth, diuretics, immunosuppressants, lymphokynes, α-and-β-interferon and combinations thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

EXEMPLIFICATION OF THE INVENTION

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

General Synthesis Methods

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

EXAMPLES

| Definitions | |
|---|---|
| AcOH | acetic acid |
| aq | aqueous |
| boc | tert-butoxycarbonyl |
| C | Celsius |
| cat. | catalyst |
| CDI | cabonyldiimidazole |
| conc. | concentrated |
| $C_2CO_3$ | cesium carbonate |
| deg. | degrees |
| DIPEA | diisopropylethylamine |
| DIPC | N,N'-diisopropylcarbodiimide |
| DMF | N,N-dimethylformamide |
| DCC | N,N-dicyclohexylcarbodiimide |
| DCE | dichloroethane |
| DCM | dichloromethane |
| DMAP | 4-dimethylaminopyridine |
| DMSO | dimethylsulfoxide |
| EtOAc | ethyl acetate |
| EtOH | ethanol |
| eq | equivalents |
| HATU | O-(7-azabenzotriazol-1-yl)-N,N,N',N'-tetramethyluronium hexafluorophosphate |

-continued

| Definitions | |
|---|---|
| Hep | heptane |
| HCl | hydrochloric acid |
| $K_2CO_3$ | potassium carbonate |
| $LiBH_4$ | lithium borohydride |
| LC | liquid chromatography |
| LCMS | liquid chromatography mass spectrum |
| MeOH | methanol |
| $MgSO_4$ | magnesium sulfate |
| MHz | megahertz |
| $NaBH_4$ | sodium borohydride |
| Pd/C | palladium on carbon |
| PEG(750) | O-(2-aminoethyl)-O'-methyl polyethylene glycol 750; $NH_2(CH_2CH_2O)_nCH_3$; CAS# [80506-64-5]; Fluka 07964; AVERAGE MW = 750 |
| PS | polystyrene |
| Py | pyridine |
| RP | reverse phase |
| RT | room temperature |
| $R_t$ | retention time |
| s | solid |
| sat. | saturated |
| TBTU | O-benzotriazol-1-yl-N,N,N',N'-tetramethyluronium tetrafluoroborate |
| TLC | thin-layer chromatography |
| TEA | triethylamine |
| TFA | trifluoroacetic acid |
| THF | tetrahydrofuran |
| h | hours |
| min | minutes |
| m/z | mass to charge |
| MS | mass spectrum |
| HRMS | high resolution mass spectrum |
| NMR | nuclear magnetic resonance |

Analytical Methods

NMR: proton spectra are recorded on a Bruker 400 MHz ultrashield spectrometer. Chemical shifts are reported relative to methanol (δ 3.31), dimethyl sulfoxide (δ 2.50), or chloroform (δ 7.26).

LC/MS:

Method 1: compounds are analyzed on an Inertsil ODS-3 column (C18, 50×4.6 mm, 3 µm) with a 2 min gradient elution (20-80% acetonitrile/$H_2O$/5 mM ammonium formate) and a flow rate of 4 ml/min.

Method 5: GENERAL LC-MS method with acid mobile phase (0.1% formic acid) and fast gradient. Electrospray mass spectra (+) and (−), DAD-UV chromatogram 200-400 nm, scan range 120-1500 Da. Gradient: 20-80% MeCN/$H_2O$ in 2 min (2 mL/min), 2 µL injection. Column: Inertsil ODS3 C-18, 3 cm×33 mm×3.0 µm, 40 deg C.

Method 6: GENERAL LC-MS method with neutral mobile phase (5 mM $NH_4$+HCOO—) and fast (20-80%) gradient. Electrospray mass spectra (+) and (−), DAD-UV chromatogram 200-400 nm, scan range 120-1500 Da. Gradient: 20-80% MeCN/$H_2O$ in 2 min (2 mL/min), 2 µL injection. Column: Inertsil ODS3 C-18, 3 cm×33 mm×3.0 µm, 40 deg C.

Method 7: LC-MS method for NON-POLAR (greasy) compounds with acid mobile phase (0.1% formic acid) and fast (40-90%) gradient. Electrospray mass spectra (+) and (−), DAD-UV chromatogram 200-400 nm, scan range 120-1500 Da. Gradient: 40-90% MeCN/$H_2O$ in 2 min (2 mL/min), 2 µL injection. Column: Inertsil $C_{8-3, 3}$ cm×33 mm×3.0 µm, 40 deg C.

Method 8: LC-MS method for NON-POLAR (greasy) compounds with neutral mobile phase (5 mM $NH_4$+HCOO—) and fast (40-90%) gradient. Electrospray mass spectra (+) and (−), DAD-UV chromatogram 200-400 nm, scan range 120-

1500 Da. Gradient: 40-90% MeCN/H$_2$O in 2 min (2 mL/min), 2 μL injection. Column: Inertsil C8-3, 3.0 cm×33 mm×3.0 μm, 40 deg C.

Method 9: LC-MS method with broad range (5-95%) gradient with acid mobile phase (0.1% Formic Acid). Electrospray mass spectra (+) and (−), DAD-UV chromatogram 200-400 nm, scan range 120-1500 Da. Gradient: 5-95% MeCN/H$_2$O in 2 min (2 mL/min), 2 μL injection. Column: Inertsil C8-3, 3.0 cm×33 mm×3.0 μm, 40 deg C.

Method 10: LC-MS method with broad range (5-95%) gradient with neutral mobile phase (5 mM NH$_4$+HCOO—). Electrospray mass spectra (+) and (−), DAD-UV chromatogram 200-400 nm, scan range 120-1500 Da. Gradient: 5-95% MeCN/H$_2$O in 2 min (2 mL/min), 2 μL injection. Column: Inertsil C$_{8-3, 3}$ cm×433 mm×3.0 μm, 40 deg C.

Method 11: LC-MS method for POLAR compounds with acid mobile phase (0.1% formic acid) and slow (0-100%) gradient. Electrospray mass spectra (+) and (−), DAD-UV chromatogram 200-400 nm, scan range 120-1500 Da. Gradient: 0-100% MeCN/H$_2$O in 2 min (2 mL/min), 2 μL injection. Column: Inertsil ODS3 (C-18, 3 cm×33 mm×3.0 μm, 40 degree C.)

Method 12: LC-MS method for POLAR compounds with neutral mobile phase (5 mM NH$_4$+HCOO—) and slow (0-100%) gradient. Electrospray mass spectra (+) and (−), DAD-UV chromatogram 200-400 nm, scan range 120-1500 Da. Gradient: 0-100% MeCN/H$_2$O in 2 min (2 mL/min), 2 μL injection. Column: Inertsil ODS-3 (C-18, 3 cm×33 mm×3.0 μm, 40 deg C.

Method 13: Compounds are analyzed on an Inertsil ODS-3 column (C8, 30 mm×3.0 mm, 3.0 μm) with a 2 min gradient elution (5-90% acetonitrile/H$_2$O/5 mM ammonium formate) and a flow rate of 2 ml/min.

Method 14: Compounds are analyzed on an Inertsil ODS-3 column (C8, 30 mm×3.0 mm, 3.0 μm) with a 2 min gradient elution (5-90% acetonitrile/H$_2$O/0.1% formic acid) and a flow rate of 2 ml/min.

HPLC purification utilizes a C8 or C18 column (30×100 mm, 5 μm, brand: Sunfire or XTerra) and is performed with an appropriate gradient according to two methods (unless otherwise noted). Method 1 consists of 0.1% TFA in 5%-95% ACN in H$_2$O. Method 2 consists of 10 mM NH$_4$OH in 5%-95% ACN in H$_2$O.

LC analysis utilizes a liquid chromatography-UV detection (LC-UV) using a Agilent 1100 liquid chromatograph. LC conditions were as follows:

Column: Atlantis C18 (Waters, Inc.), 15 cm×4.6 mm×5 μm; column temperature: ambient; flow rate: 1.4 mL/min; injection volume: 3.0 μL; gradient: A=0.1% trifluoroacetic acid (TFA) in water, B=0.05% trifluoroacetic Acid (TFA) in acetonitrile, 0-95% B in 19.0 min, 1.8 min hold.

General Scheme 1:

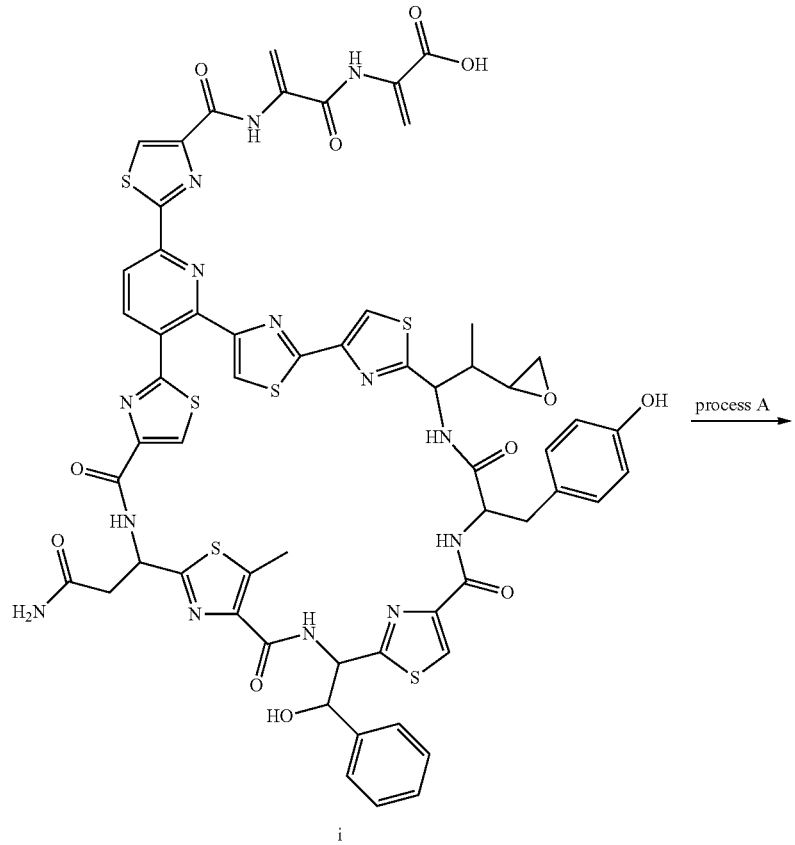

i

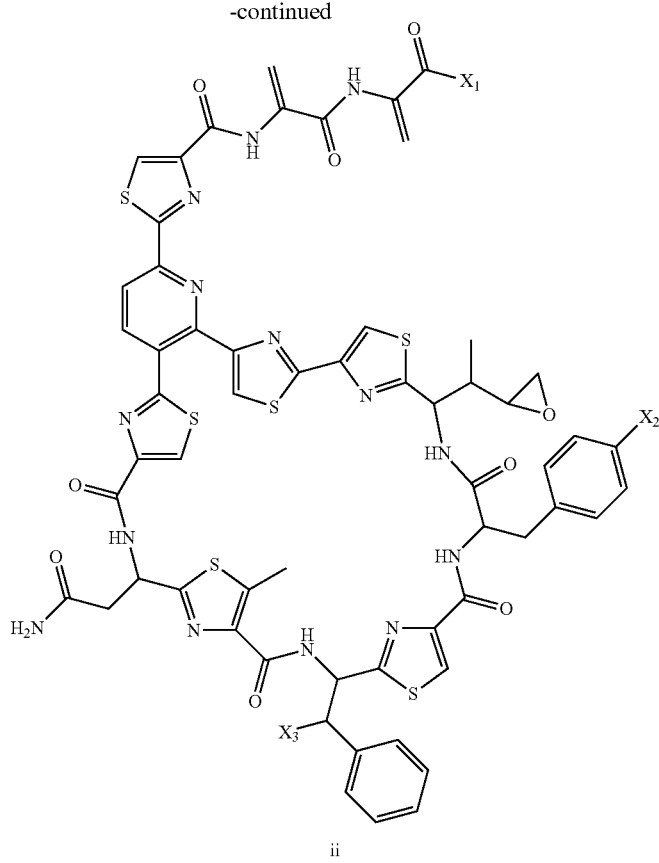
ii
General Scheme 2:
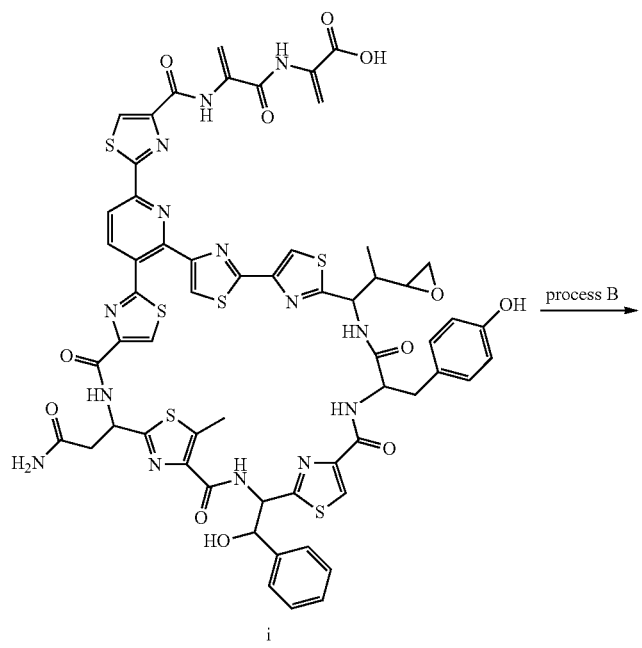
i → process B

-continued
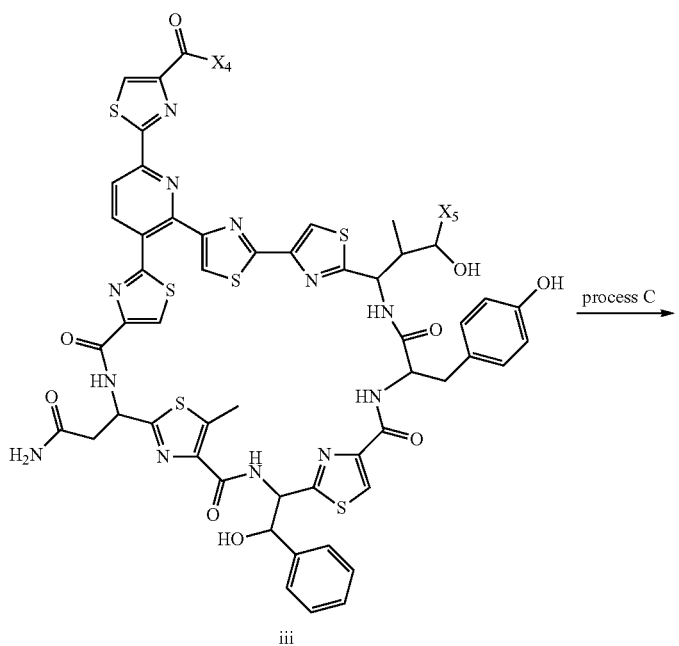
iii
process C →
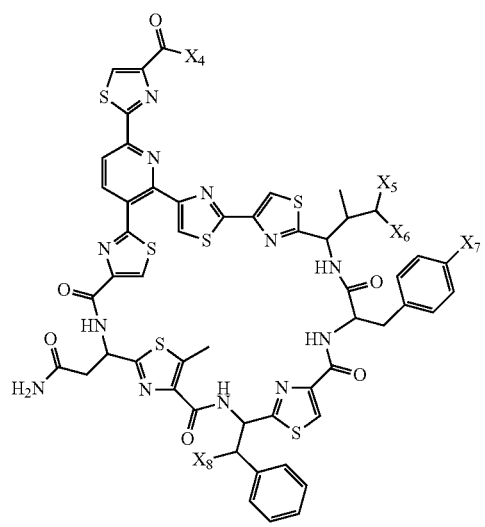
iv

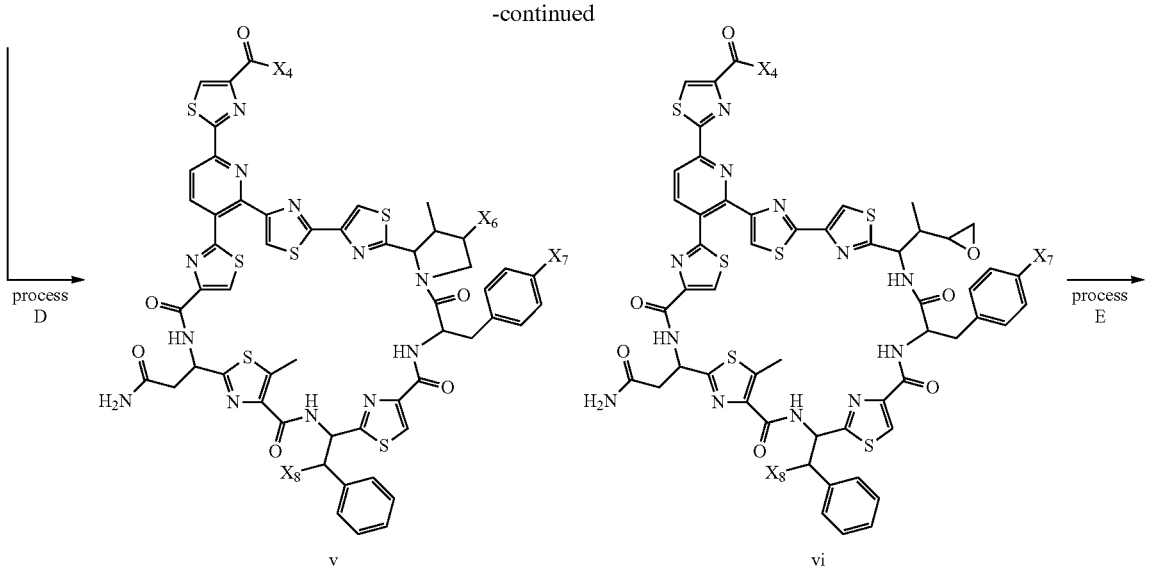

The compound of general formula (i) may be prepared via synthetic methods known to those skilled in the art, or alternatively isolated from a fermentation broth. The compound of general structural formula (ii) may be prepared by process A by the acid or base mediated alkylation of compound (i) in the presence of an electrophile.

The compound of general formula (iii) may be prepared in process B from (i) via an acid or base catalyzed reaction which removes the dehydroalanine sidechain or part thereof. This process may or may not concomitantly open the epoxide to provide iii. The compounds of general formulae iv may be prepared from compound iii via acid or base catalyzed alkylation, oxidation, reduction, amidation, or protection according to process C. Compounds of general formulae v and vi may be prepared via acid or base mediated ring closure according to process D. Compounds vii, viii may be prepared from compounds v, vi in process E via an acid or base mediated alkylation, acylation, retroaldol trapping, amination, amidation, oxidation, reduction, protection, or deprotection. A suitable protecting group can be selected by those skilled in the art. Protecting groups are selected so that they are suitable for the depicted transformations and can be removed following the synthesis with little or no loss of yield. The introduction and selective removal of protecting groups are taught in Greene and Wuts, "Protective Groups in Organic Synthesis", John Wiley & Sons (1991). Alternatively, any of these steps (A-E) may be performed in a different order, or with some steps removed or slightly altered.

Scheme 1: Preparation of Esters (2-4):
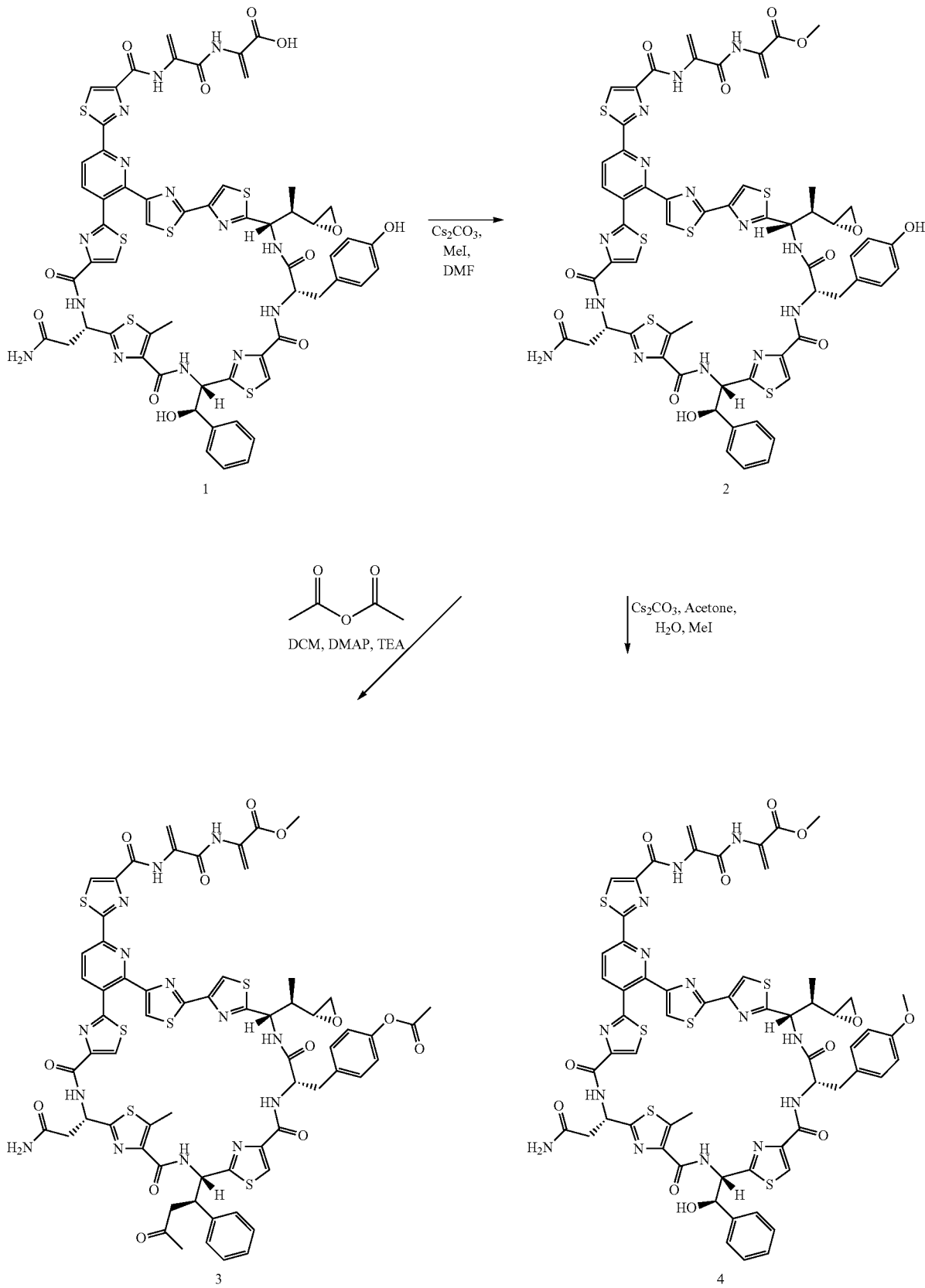

Example 1

Preparation of Methylester (2)

(2)

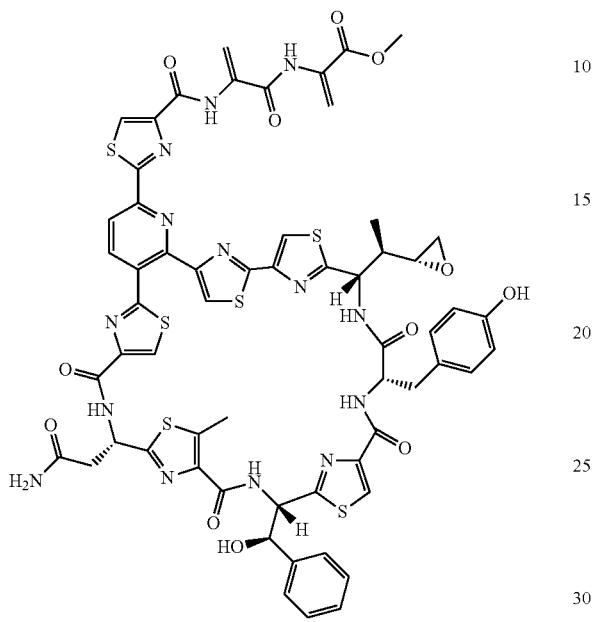

To a solution of acid (1, 45 mg, 0.747 mmol) in DMF (1 mL) is added Cs$_2$CO$_3$ (10 mg) and iodomethane (30 uL, 1.5 M solution in DMF). The solution is stirred at RT for 1 h, MeOH is added (3 mL) and the reaction is concentrated. The crude residue is purified by preparative TLC (5% MeOH/DCM) to furnish 5.5 mg of ester 2. LC/MS: [M+H]$^+$ 1353, R$_t$=1.49 min (method 1).

Example 2

Preparation of Methylester (3)

(3)

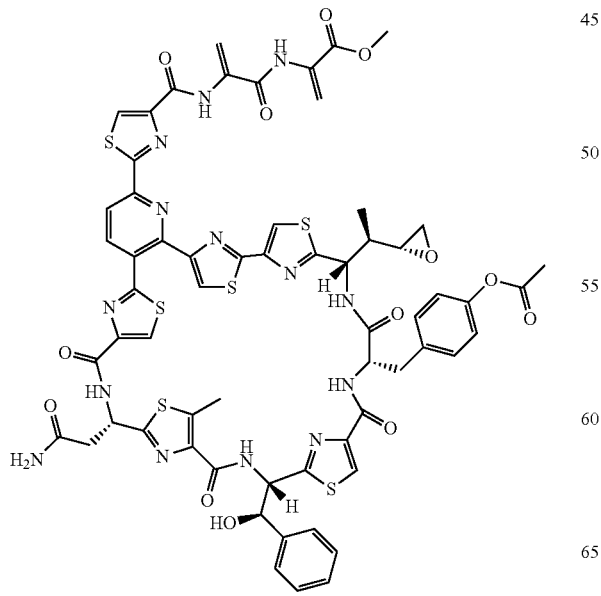

To a solution of methylester (2, 16 mg, 0.0111 mmol) in DCM (10 mL) is added triethylamine (10 uL), DMAP (cat.) and acetic anhydride (30 uL). The solution is stirred at RT for 2 h and concentrated. The crude residue is purified by preparative TLC (5% MeOH/DCM) to afford 10 mg of product (3). LC/MS: [M+2H]$^+$ 1438, R$_t$=1.64 min (method 1).

Example 3

Preparation of Methylester (4)

(4)

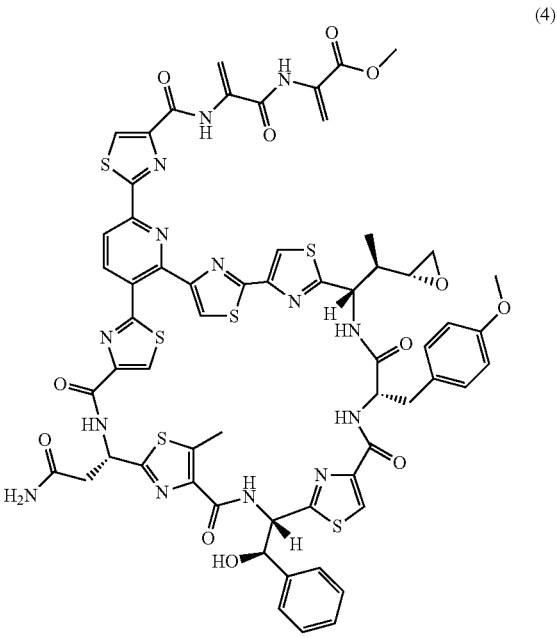 [SMILES: C=C(NC(=O)c1csc(-c2ccc3c(n2)-c2csc(n2)-c2csc(n2)[C@H]([C@@H](C)[C@@H]2CO2)NC(=O)[C@H](Cc2ccc(OC)cc2)NC(=O)c2csc(n2)[C@H]([C@H](O)c2ccccc2)NC(=O)c2nc(sc2C)[C@H](CC(N)=O)NC(=O)c2csc-3n2)n1)C(=O)NC(=C)C(=O)OC]

To a solution of acid (1, 200 mg, 0.149 mmol) in acetone (50 mL), and H$_2$O (10 mL) is added cesium carbonate (50 mg) and iodomethane (10 uL). The reaction is stirred for 12 h at RT and iodomethane (10 uL) is added, and the reaction is stirred for 12 h further. The reaction is concentrated and purified by flash chromatography (gradient elution: 0-10% MeOH/DCM) then preparative thin layer chromagraphy (5% MeOH/DCM) which affords 5 mg of 4. LC/MS [M+2H]$^+$ 1368, R$_t$=1.58 min, (method 1).

Scheme 2, Preparation of Amides (5, 6):
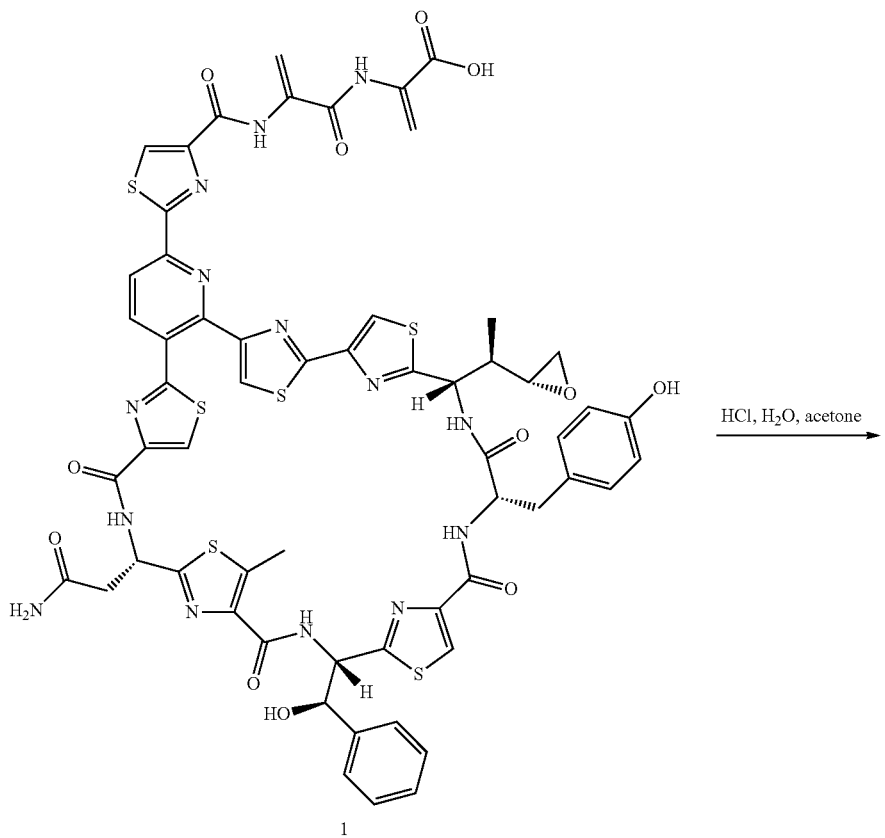
HCl, H₂O, acetone →
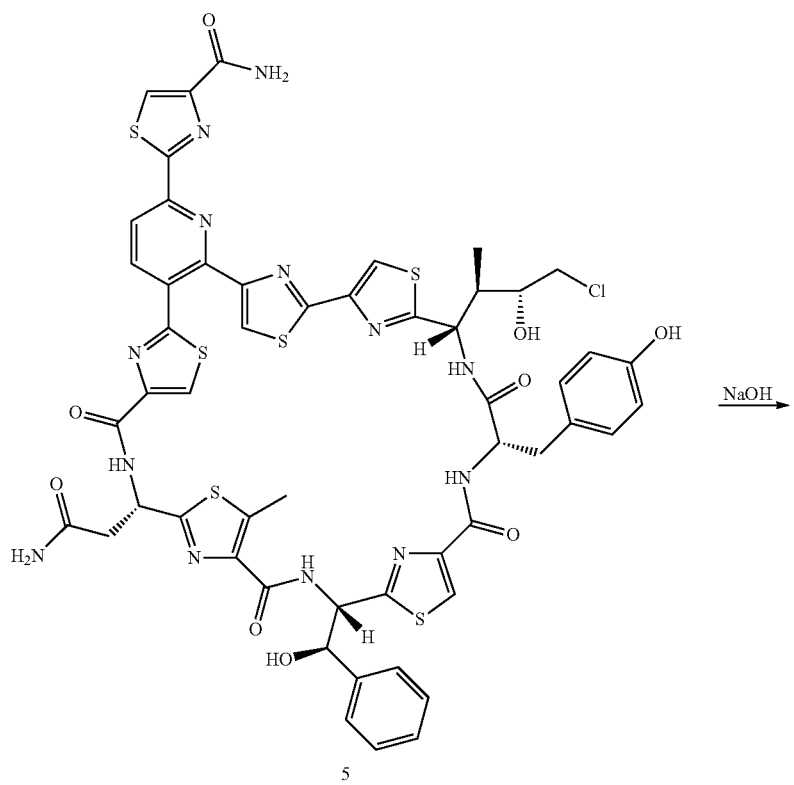
NaOH →

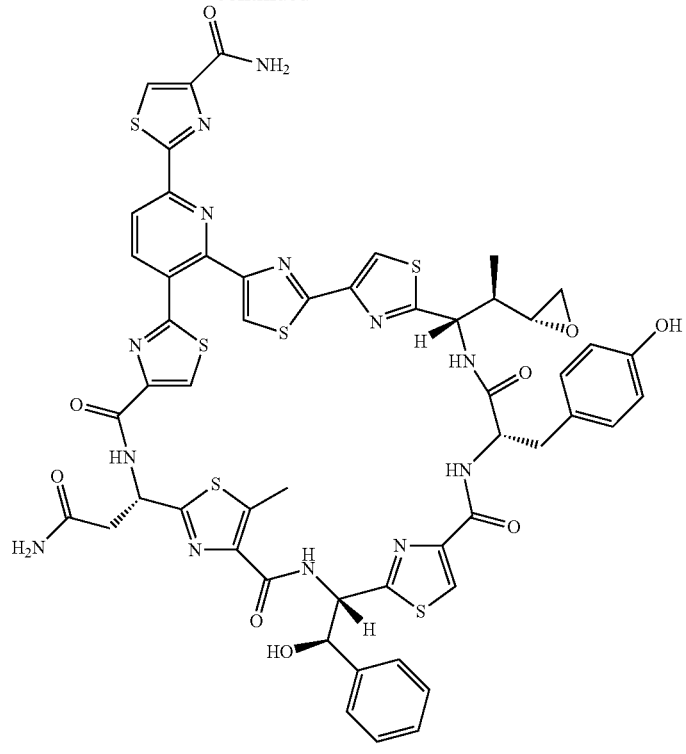
6
Example 4
Preparation of Chlorohydrin (5)
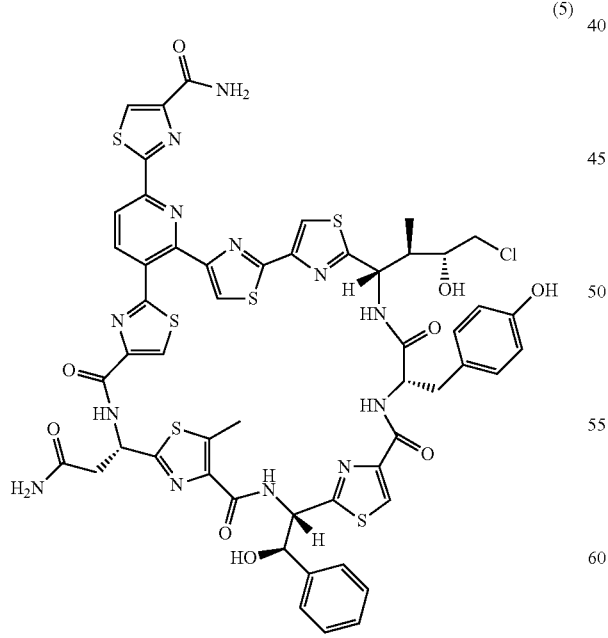
(5)
To a solution of acid (1, 145 mg, 0.1083 mmol) is added 50 uL of concentrated aq HCl (12 M). The flask is sealed, heated to 50° C., and stirred for 1 h. The reaction is concentrated and purified by preparative TLC (10% MeOH/EtOAc) which affords 5 mg of chlorohydrin 5. LC/MS: [M+H]⁺ 1236, $R_t$=1.17 min, (method 1).
Example 5
Preparation of Epoxide (6)
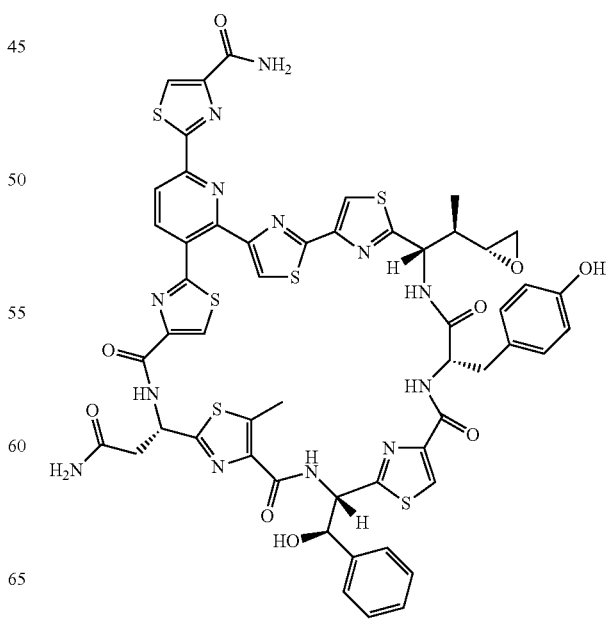
(6)

To a solution of chlorohydrin (5, 100 mg, 0.0809 mmol) in MeOH (50 mL) is added sodium hydroxide (s, 50 mg) and H₂O (20 mL). The reaction is stirred at RT for 1 h and then concentrated. The crude residue is purified by preparative TLC (10% MeOH/DCM) which affords 10 mg of epoxide 6. LC/MS: [M+2H]⁺ 1201, $R_t$=1.10 min (method 1).
Scheme 3, Preparation of Amines (7-10):
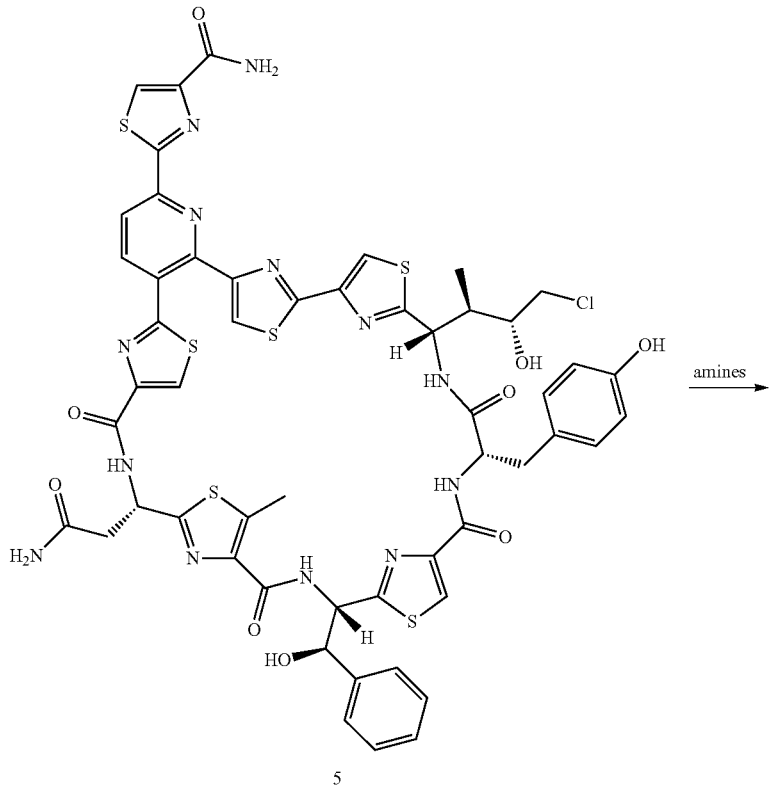
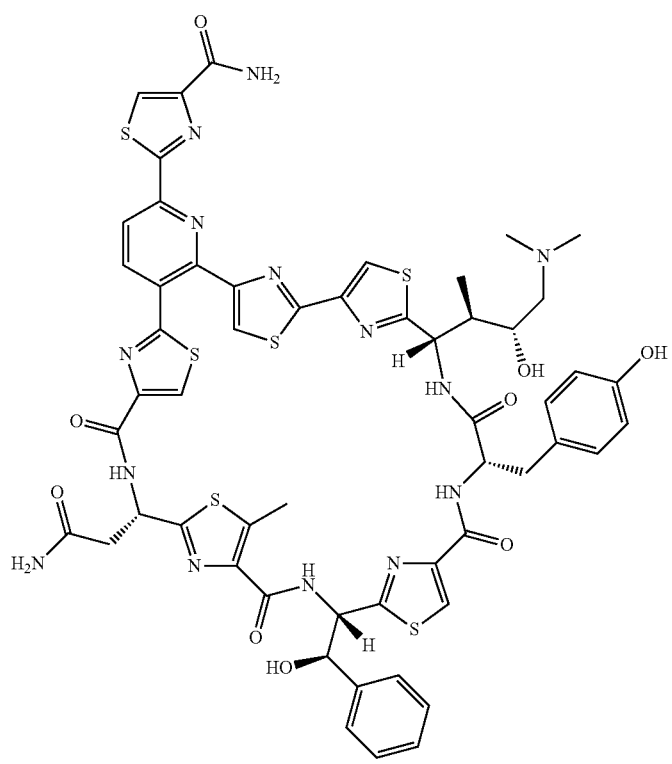

8
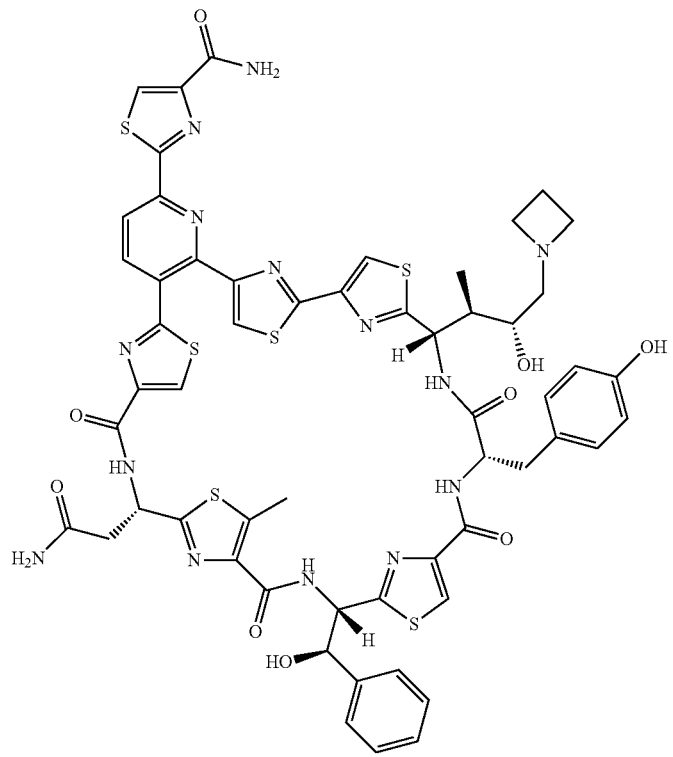
9
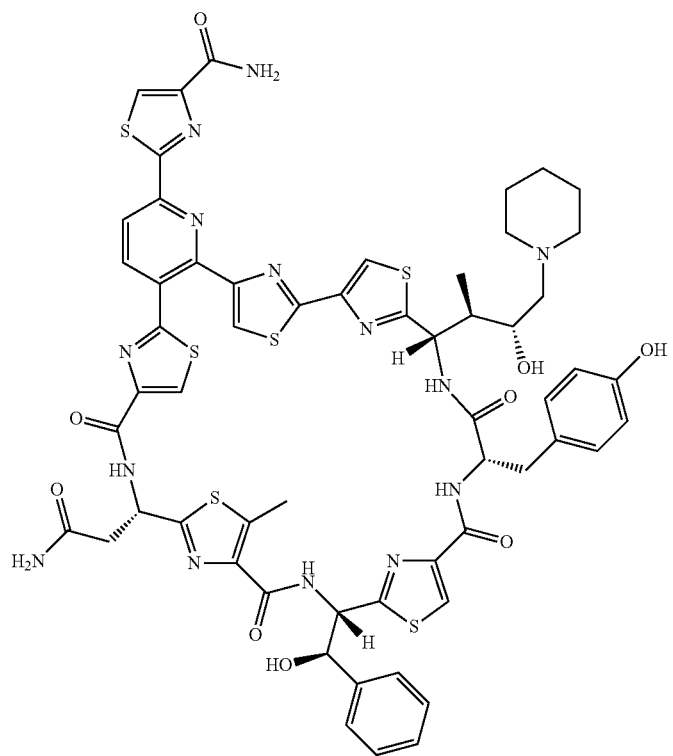

10

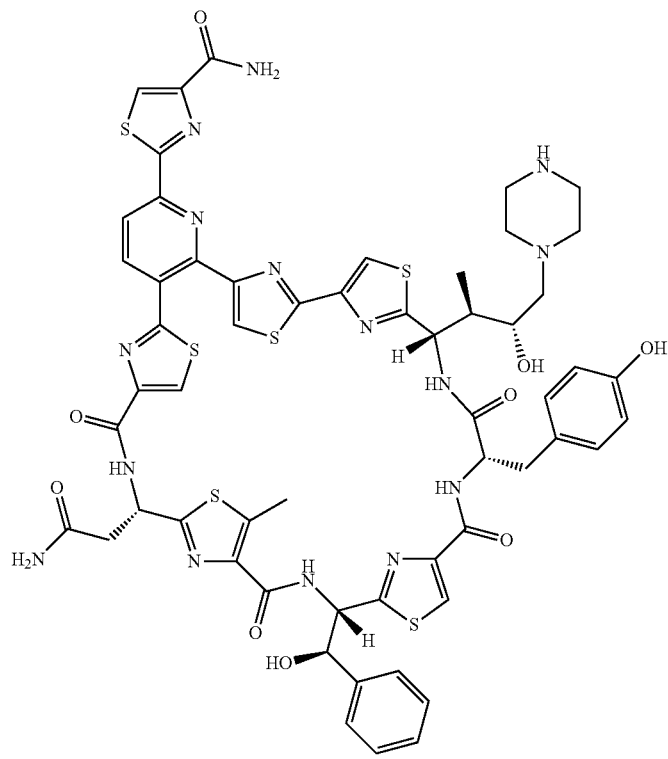

Example 6

Preparation of Amine (7)

(7)

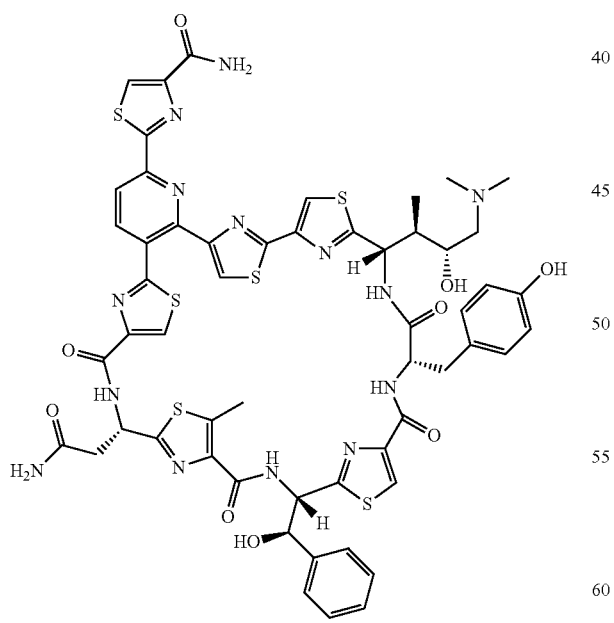

To a suspension of chlorohydrin (5, 105 mg, 0.0848 mmol) in THF (10 mL) is added sodium perchlorate (8 mg, 0.0848 mmol) and dimethylamine (212 uL, 2.0 M solution in THF, 0.424 mmol). The reaction is heated to 50° C. After 2 h, 1 eq of perchlorate and 5 eq of amine are added. The reaction is stirred for 12 h and is concentrated onto SiO$_2$. The crude material is purified via flash chromatography (gradient elution: 0-10% MeOH/DCM, then 0-10% MeOH/DCM+0.1% NH$_4$OH) which affords 29 mg of amine 7. LC/MS: [M+H]$^+$ 1245, R$_t$=0.69 min (method 1).

Example 7

Preparation of Amine (8)

(8)

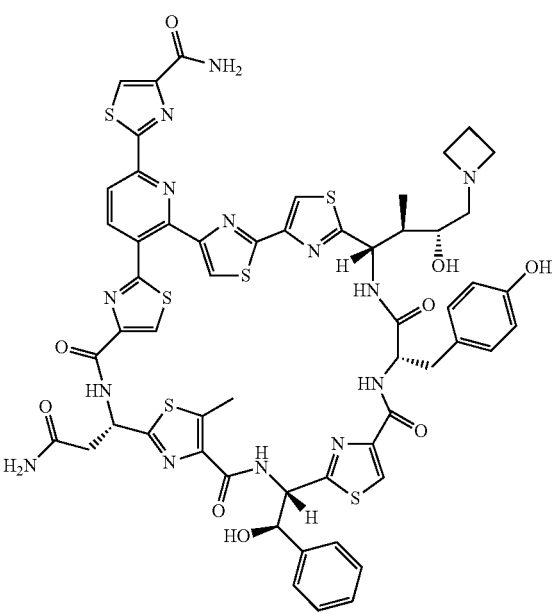

Compound 8 is prepared as described in example 6. LC/MS: [M+H]+ 1257, $R_t$=0.82 min (method 1).

Example 8

Preparation of Amine (9)

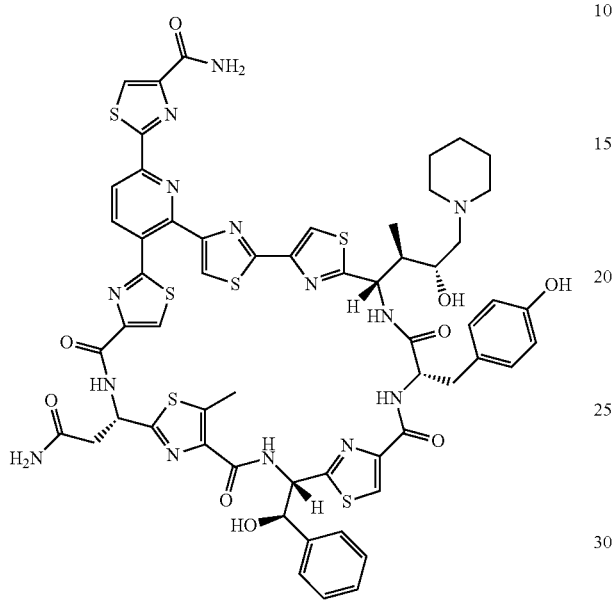

(9)

Compound 9 is prepared as described in example 6. LC/MS: [M+H]+ 1285, $R_t$=0.87 min (method 1).

Example 9

Preparation of Amine (10)

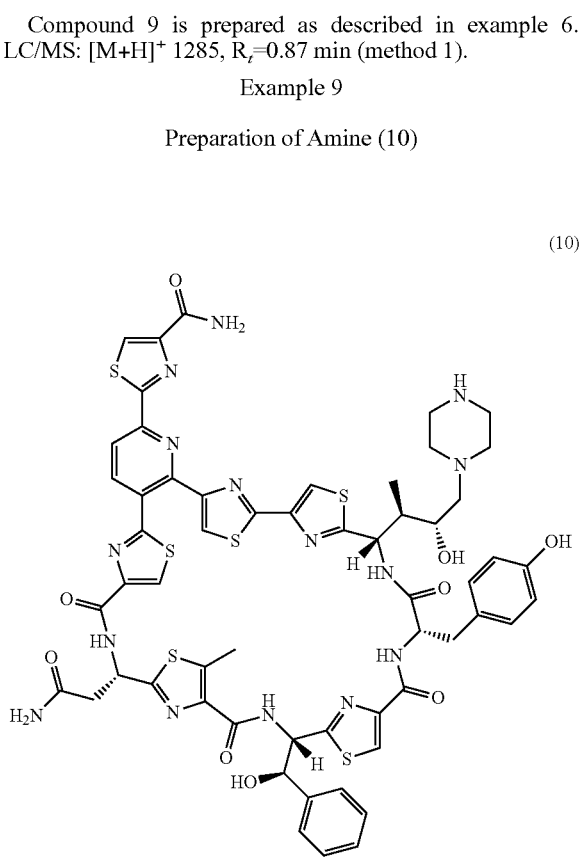

(10)

Compound 10 is prepared as described in example 6. LC/MS: [M+H]+ 1286, $R_t$=0.79 min (method 1).

Example 10

Preparation of Pyrrolidine (11)

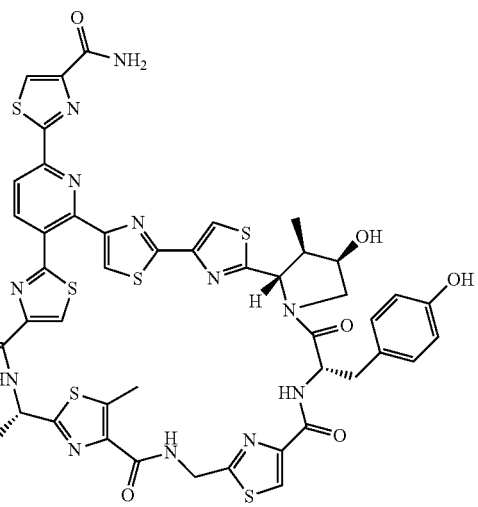

(11)

To a suspension of the chlorohydrin (100 mg, 0.0808 mmol) in acetone (5 mL) is added ammonium hydroxide (500 uL, sat. aq). The reaction is sealed and stirred for 12 h at 65° C. The reaction is concentrated and purified by HPLC (method 1) which affords 20 mg compound 11. LC/MS: [M+H]+ 1094, $R_t$=0.99 min (method 1).

Example 11

Preparation of Carboxylic acid (12)

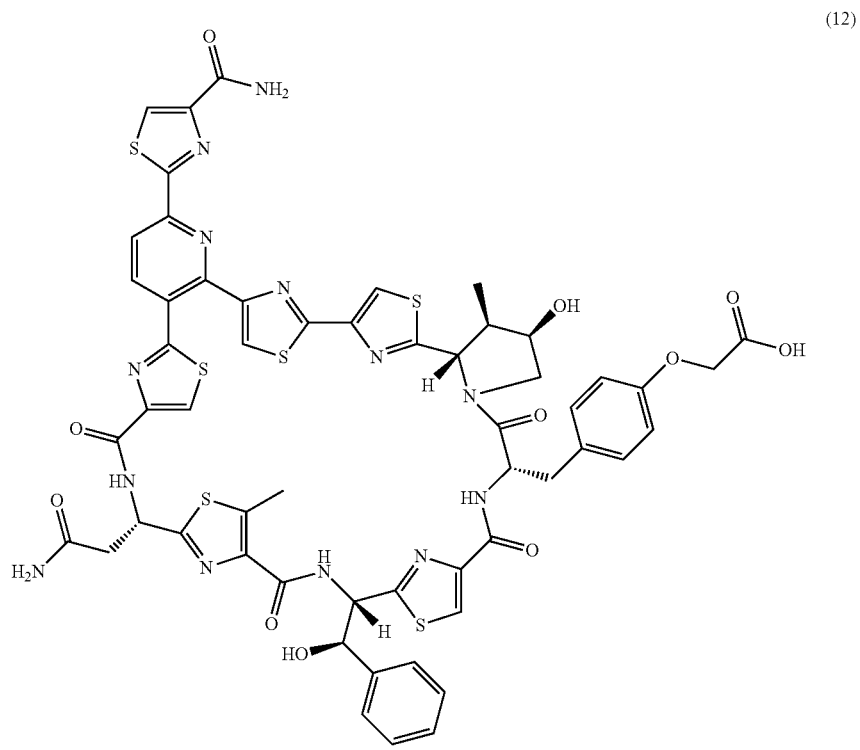 [SMILES: Cc1sc2nc1C(=O)N[C@@H]([C@H](O)c1ccccc1)c1nc(cs1)C(=O)N[C@@H](Cc1ccc(OCC(=O)O)cc1)C(=O)N1C[C@H](O)[C@H](C)[C@H]1c1nc(cs1)-c1nc(cs1)-c1nc(-c3nc(C(N)=O)cs3)ccc1-c1nc(cs1)C(=O)N[C@H]2CC(N)=O]

(12)

To a suspension of the chlorohydrin (5, 115 mg, 0.0929 mmol) in THF (50 mL) is added sodium hydride (50 mg, 60% dispersion, 1.25 mmol) then t-butylbromoacetate (50 uL, 0.197 mmol). The reaction is stirred at RT for 8 h and concentrated onto $SiO_2$. Purification by flash chromatography (gradient elution: 0-10% MeOH/DCM, then 0-10% MeOH/DCM+1% AcOH) then HPLC (method 1) affords 10 mg compound 12. LC/MS: $[M+H]^+$ 1258, $R_t$=0.81 min (method 1).

Example 12
Preparation of Pyrrolidine (13)
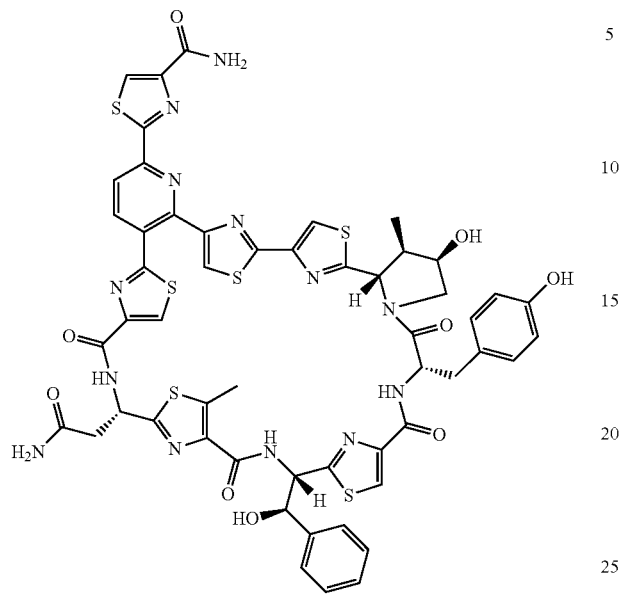
(13)
To a suspension of the chlorohydrin (5, 100 mg, 0.808 mmol) in THF (50 mL) is added DBU (30 uL, 0.197 mmol). The reaction is stirred at RT for 3 h while dissolution occurs and then is concentrated onto $SiO_2$. Purification by flash chromatography (gradient elution: 0-10% MeOH/DCM) affords 70 mg compound 13. LC/MS: $[M+2H]^+$ 1201, $R_t$=1.10 min (method 1).
Scheme 4, Preparation of Acid (14):
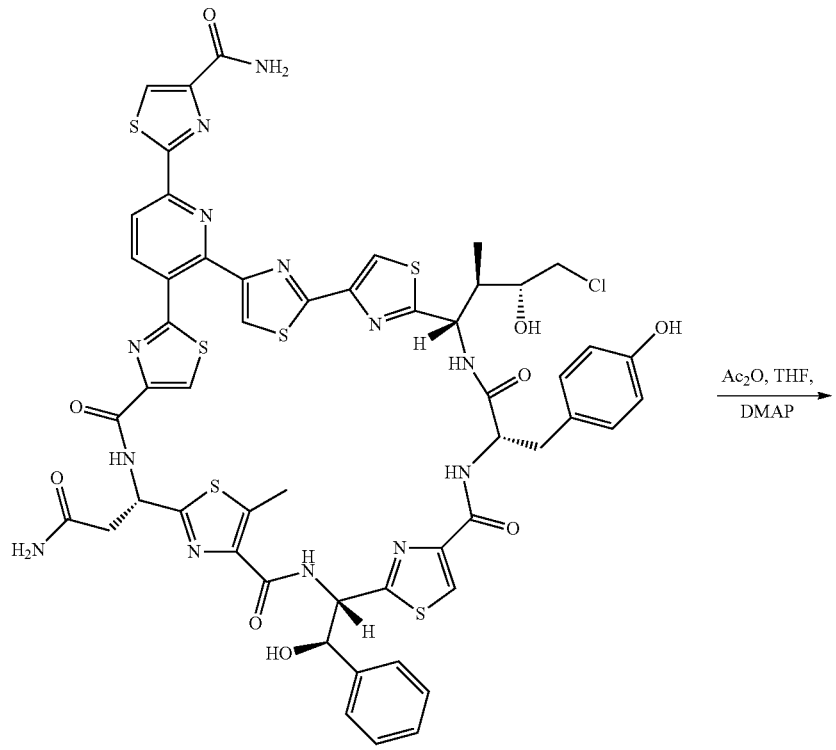

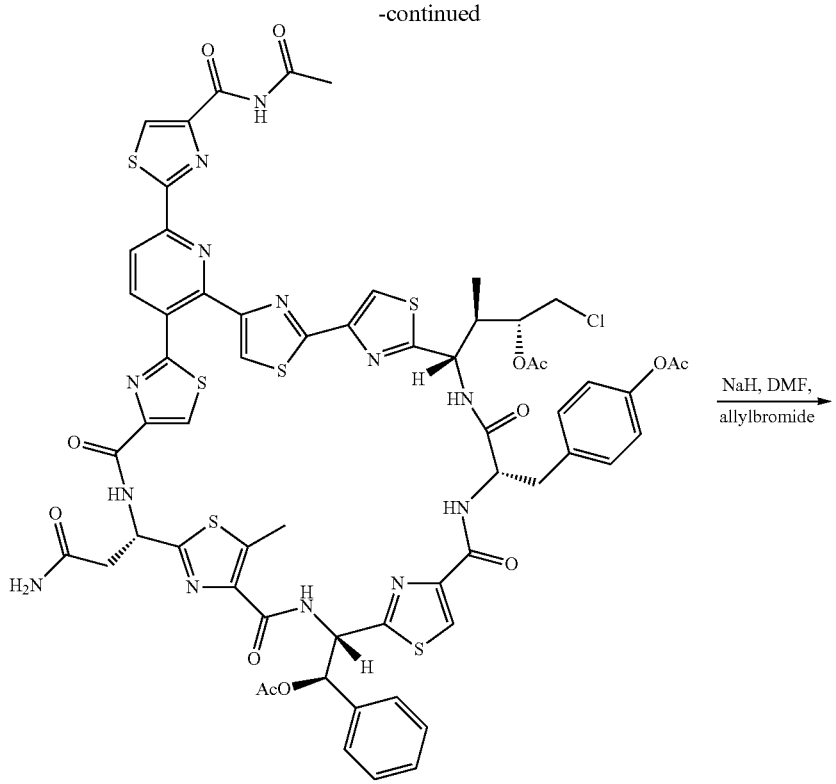
NaH, DMF,
allylbromide
→
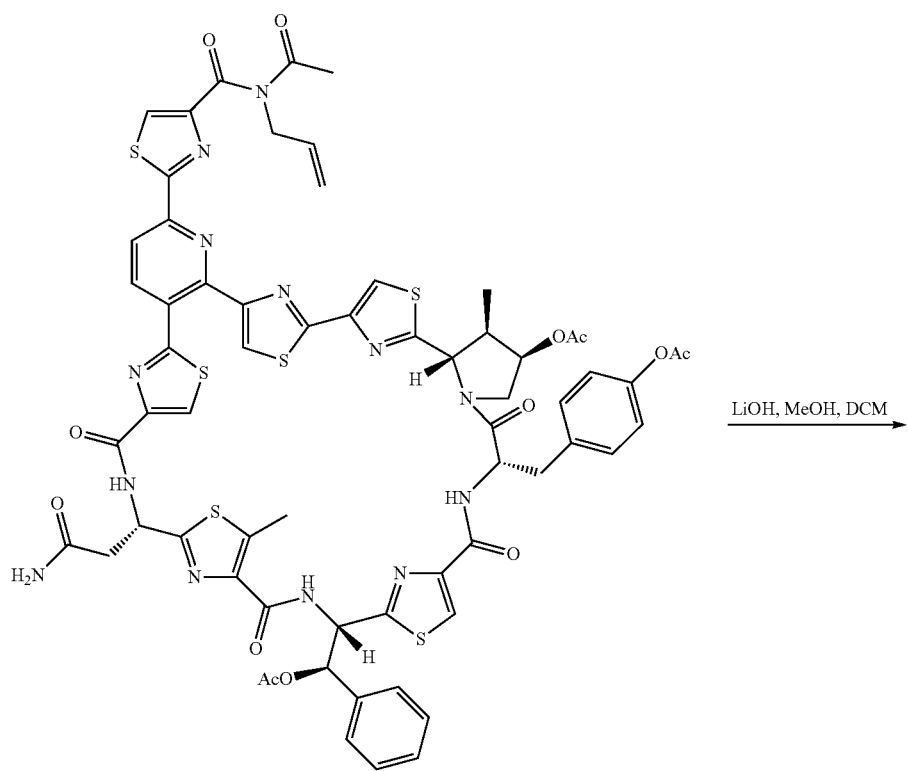
LiOH, MeOH, DCM
→

-continued

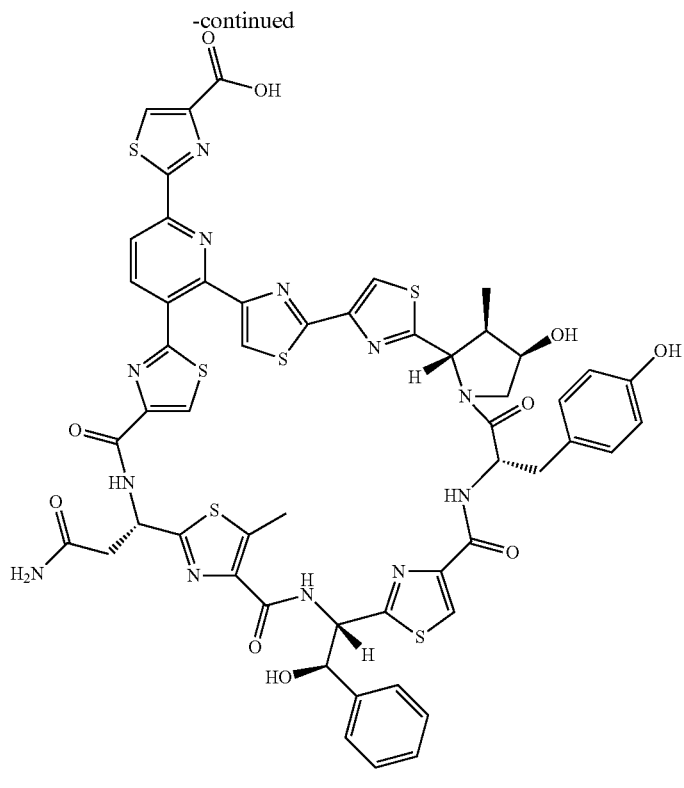

14

Example 13

Preparation of Acid (14)

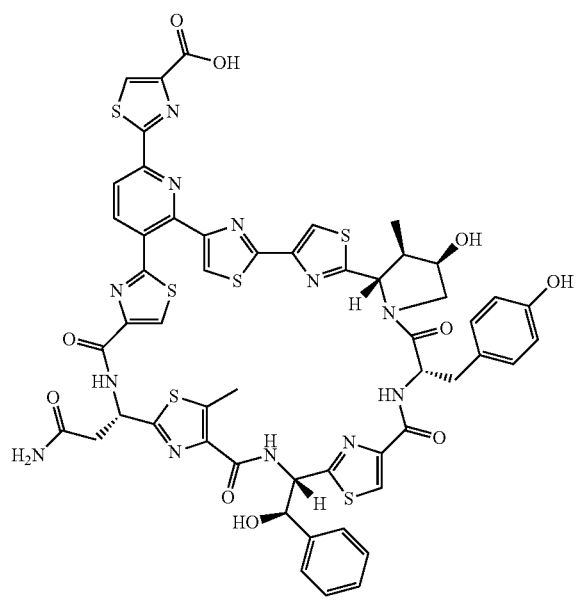

(14)

Step 1:

To a solution of the chlorohydrin (5, 200 mg, 0.162 mmol) in THF (10 mL) is added DMAP (50 mg, 0.410 mmol) and acetic anhydride (200 uL, 1.96 mmol). The solution is stirred at 60° C. for 72 h and concentrated onto $SiO_2$. Flash chromatography (gradient elution: 0-10% MeOH/DCM) affords 70 mg of the imide triacetate. LC/MS: $[M+2H]^+$ 1405, $R_t$=1.56 min. (method 1).

Step 2:

To a solution of the imide-triacetate (175 mg, 0.125 mmol) in DMF (2 mL) is added allylbromide (100 uL). The reaction is cooled to −10° C. and sodium hydride is added (50 mg, 1.25 mmol). The reaction is warmed to 0° C. and the reaction stirs for 12 h at 0° C. The reaction is diluted with $H_2O$ and ethyl acetate. The aq. layer is extracted 3× with ethyl acetate and the combined organic extracts are washed with $H_2O$ (5×). The organics are dried under $MgSO_4$, filtered, and concentrated which affords the crude allylimide. LC/MS: $[M+2H]^+$ 1409, $R_t$=1.66 min (method 1).

Step 3:

To a solution of the crude allylimide in MeOH/DCM (50 mL, 10:1) is added 50 uL of saturated aq LiOH. The reaction stirs at RT for 12 h and is concentrated onto $SiO_2$. Flash chromatography (gradient elution: 0-10% MeOH/DCM+ 0.1% AcOH) followed by reverse phase flash chromatography (gradient elution: 20-60% MeCN/$H_2O$) affords 13 mg of compound 14. LC/MS: $[M+H]^+$ 1201, $R_t$=1.01 min. (method 1).

Scheme 4a:
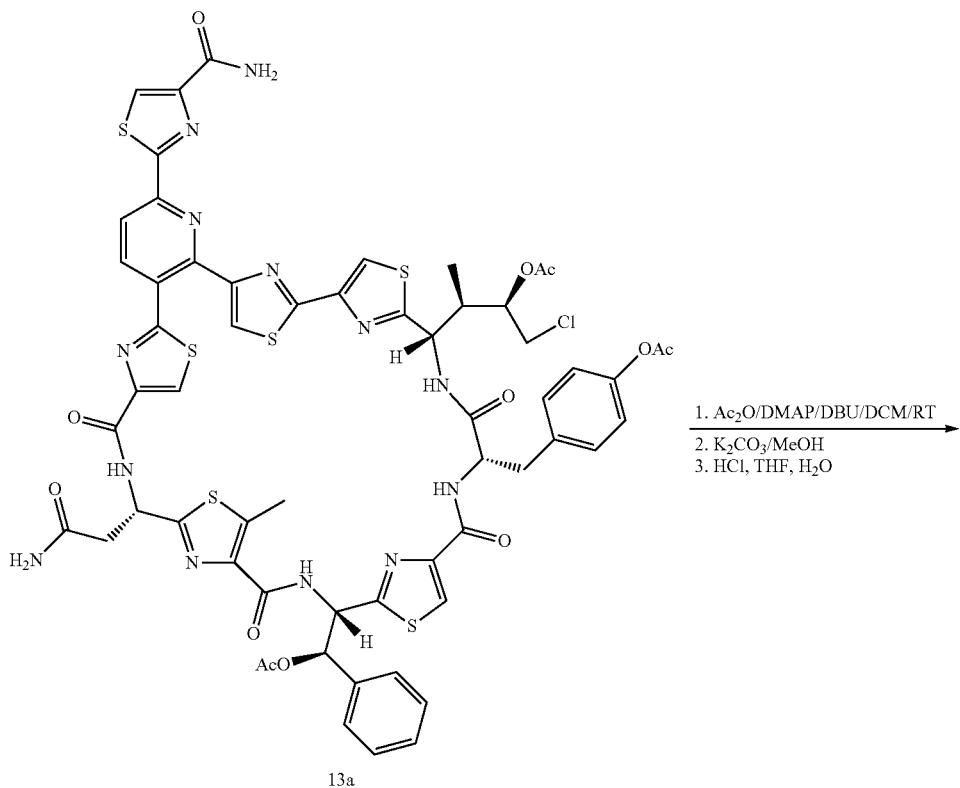
13a
1. Ac$_2$O/DMAP/DBU/DCM/RT
2. K$_2$CO$_3$/MeOH
3. HCl, THF, H$_2$O
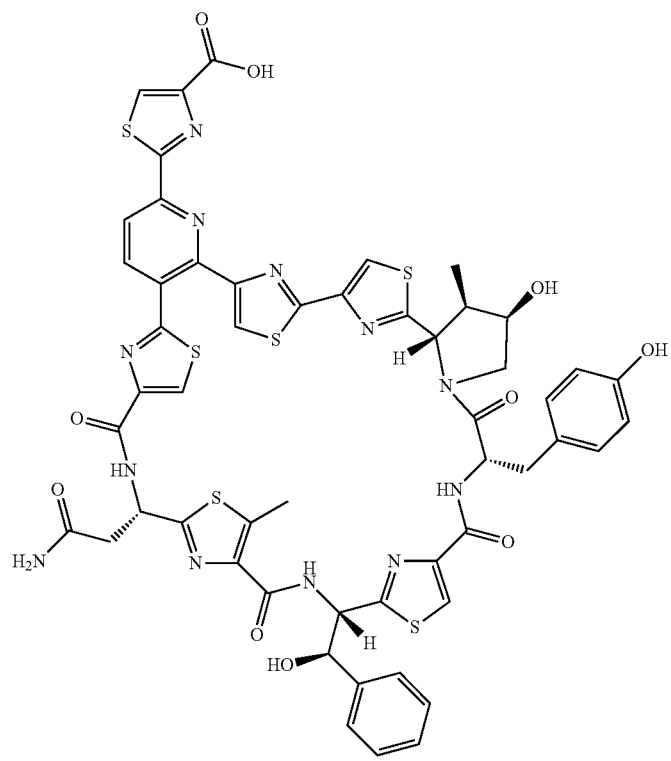
14

Alternative Synthesis (Scheme 4a):

Steps 1, 2:

To a mixture of compound 13a (9.5 g), DMAP (0.35 g), Ac₂O (7.2 mL) in DCM (300 mL) is added DBU (8.6 mL) and stirred at RT. When the reaction is finished (~8 h, LC/MS), K₂CO₃ (10 g) and MeOH (300 mL) are added to the reaction mixture. When the reaction is finished (~16 h, LC/MS), the mixture is concentrated in vacuo to dryness (bath temp <25° C.). Water (400 mL) is added and the resulting solid is filtered through a fritted glass funnel and washed with water. The filtercake is dried in vacuo for 12 h to provide 9.2 g of compound 13. LC/MS: [M+H]⁺ 1200, R$_t$=1.22 min (method 13).

Step 3: Preparation of Acid (14):

To 18 g of 13 is added 94 mL of THF and 3 mL of conc. HCl in pressure bottle. The sealed bottle is heated to 100° C. and stirred for 3 days. After cooling to below 35° C., additional 2 mL of conc. HCl is added. The sealed bottle is heated to 100° C. for another two days and cooled to room temperature. The mixture is transferred into 500 mL round-bottomed-flask and 40 g of silica gel is added. After concentration, the residue is divided into four portions. Flash chromatography (gradient elution: 0-20% MeOH/DCM with 1% acetic acid) affords 12 g of 14. LC/MS: [M+H]⁺ 1201, R$_t$=1.14 min (method 13).

Example 14

Preparation of Pyrrolidine (15)

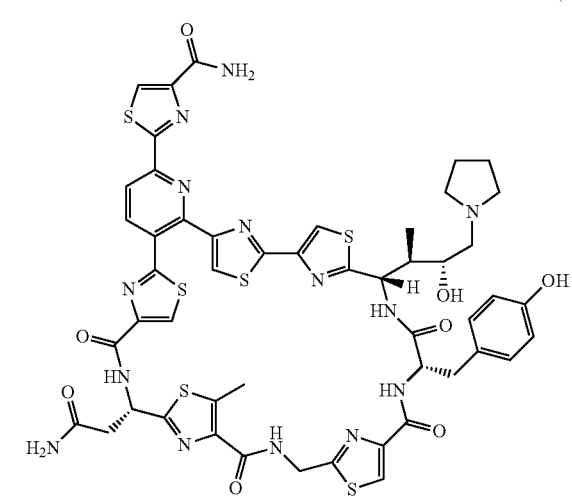

(15)

To a suspension of chlorohydrin (5, 100 mg, 0.081 mmol) in THF (15 mL) is added LiClO₄ (26 mg, 0.243 mmol) and pyrrolidine (34 uL, 0.405 mmol). The reaction is stirred at 50° C. for 12 h. The reaction is cooled to RT and concentrated onto silica gel for purification by flash chromatography (gradient elution: 0-10% MeOH/DCM+0.1% AcOH) then by HPLC (30-60% acetonitrile in H₂O+0.1% TFA) furnishing 2.7 mg compound 15 as the TFA salt. LC/MS: [M+H]⁺ 1165, R$_t$=0.67 min (method 1).

Example 15

Preparation of Piperidine (16)

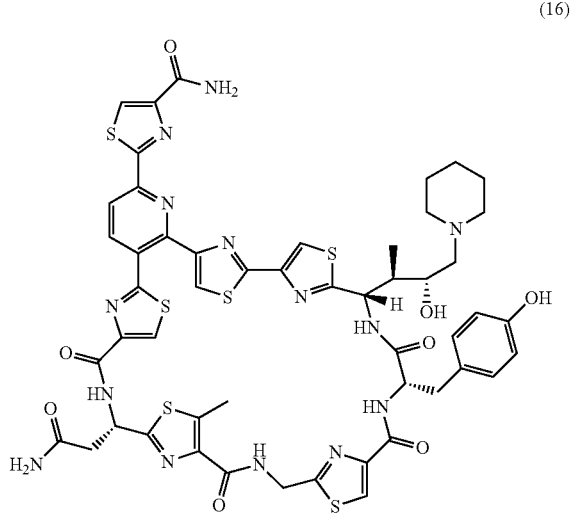 [SMILES: Cc1sc2nc1C(=O)NCc1nc(cs1)C(=O)N[C@@H](Cc1ccc(O)cc1)C(=O)N[C@@H]([C@@H](C)[C@@H](O)CN1CCCCC1)c1nc(cs1)-c1nc(cs1)-c1nc(-c3nc(C(N)=O)cs3)ccc1-c1nc(cs1)C(=O)N[C@H]2CC(N)=O]

(16)

Compound 16 is prepared as described in example 14. LC/MS: [M+H]⁺ 1179, R$_t$=0.74 min (method 1).

Example 16

Preparation of Aminoacid (17)

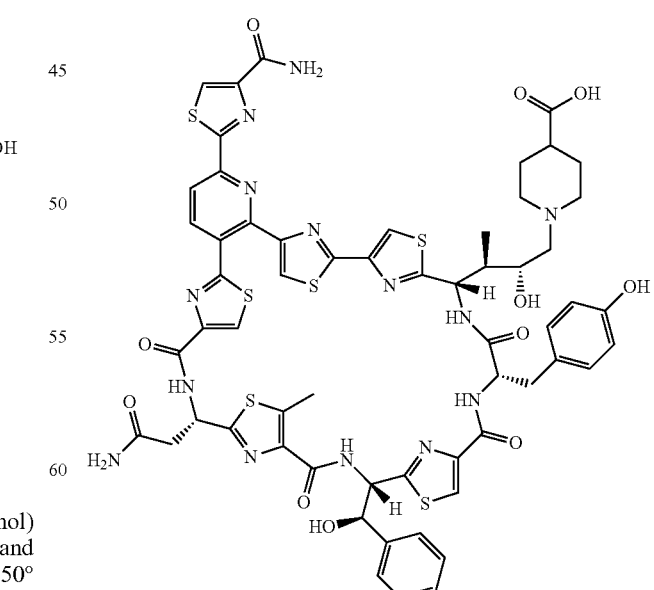

(17)

Step 1:

To a suspension of chlorohydrin (5, 100 mg, 0.081 mmol) in THF (15 mL) are added LiClO$_4$ (26 mg, 0.243 mmol) and methyl isonipecotate (12.7 mg, 0.089 mmol). The reaction is stirred at 50° C. for 12 h. Additional methyl isonipecotate (11.6 mg, 0.081 mmol) is added to the reaction and stirring continues for 48 h. The reaction is cooled to RT and concentrated onto silica gel for purification by flash chromatography (gradient elution: 0-10% MeOH/DCM). LC/MS: [M+H]$^+$ 1343, R$_t$=0.96 min (method 1).

Step 2:

The crude material is dissolved in MeOH (8 mL) and DCM (5 mL) and NaOH (s, 10 mg, 0.243 mmol) is added. The reaction is stirred at 30° C. for 12 h and is cooled to RT and concentrated onto silica gel for purification by flash chromatography (gradient elution: 0-10% MeOH/DCM+1% AcOH) followed by HPLC (30-70% acetonitrile in H$_2$O+0.1% TFA) to afford 3.5 mg compound 17. LC/MS: [M+H]$^+$ 1329, R$_t$=0.78 min (method 1).

Example 17

Preparation of Amino-Acid (18)

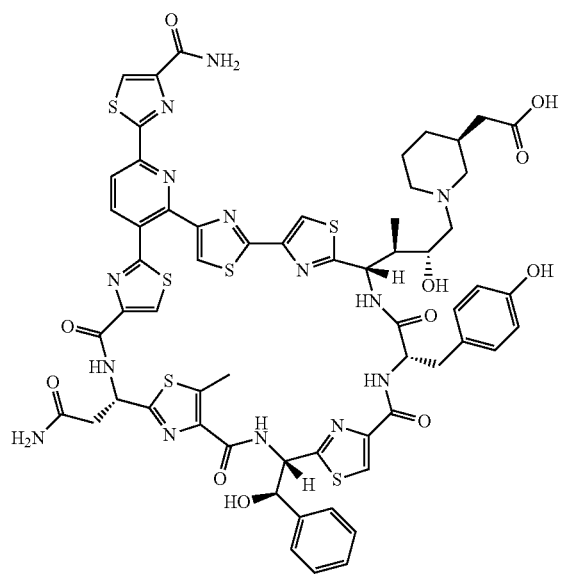

(18)

Compound 18 is prepared as described in example 16. LC/MS: [M+H]$^+$ 1343, R$_t$=0.79 min (method 1).

Example 18

Preparation of Amino-Piperidine (19)

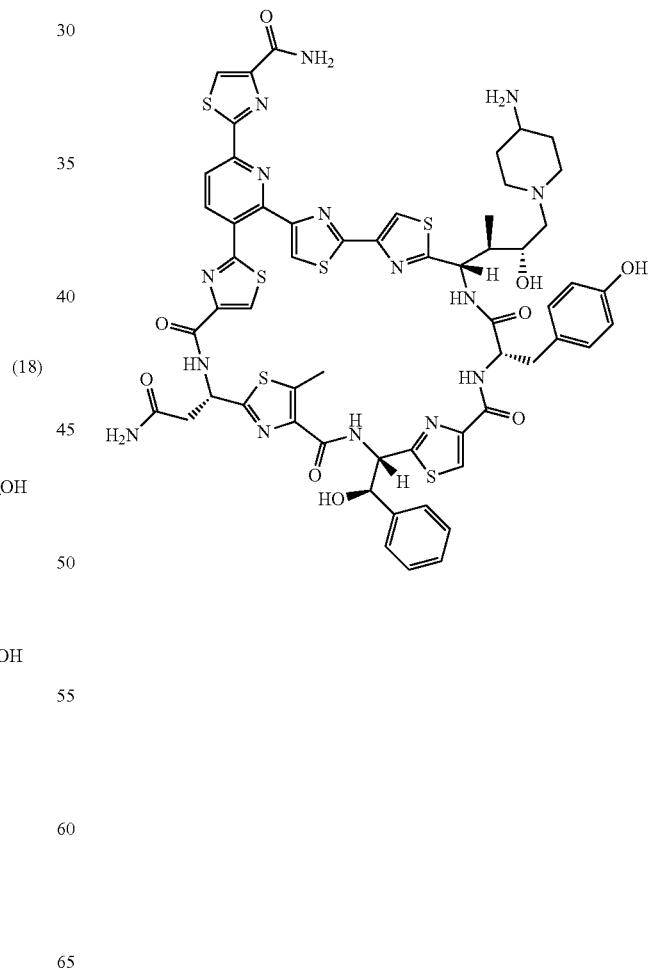

(19)

Compound 19 is prepared as described in example 14. LC/MS: [M+H]$^+$ 1300, R$_t$=0.71 min (method 1).

Example 19

Preparation of Pyrrolidine Acid (20)

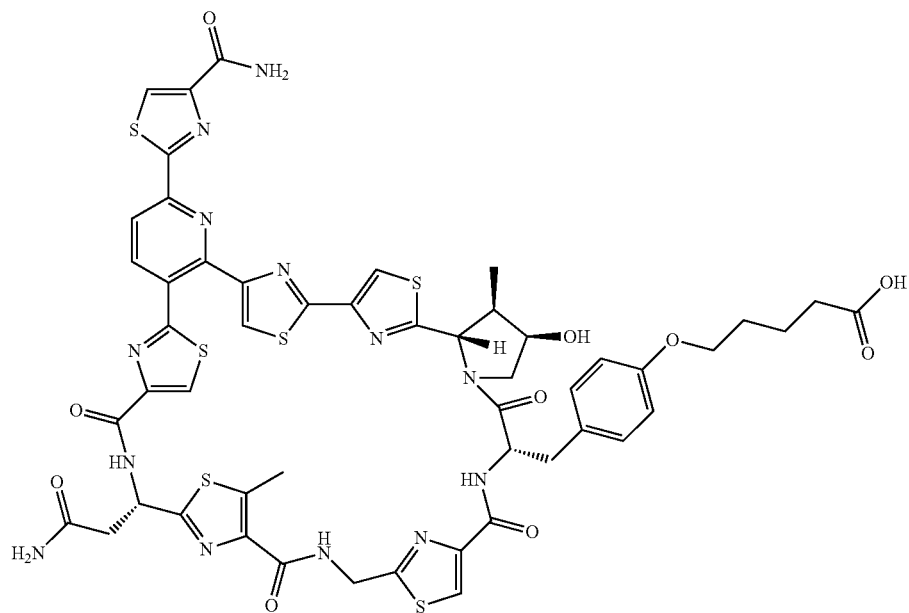

(20)

To a solution of chlorohydrin (5, 150 mg, 0.121 mmol) in DMF (10 mL) is added $K_2CO_3$ (25.1 mg, 0.182 mmol). The reaction is stirred at RT for 1 h, then methyl-5-bromovalerate (47.2 uL, 0.242 mmol) is added and the reaction is heated to 35° C. for 2 h. Additional $K_2CO_3$ (0.242 mmol) and methyl-5-bromovalerate (47.2 uL, 0.242 mmol) is added and the reaction is stirred for 16 h. The reaction is cooled to RT and $H_2O$ (60 mL) is added. The resulting precipitate is filtered and dried in vacuo. The crude material is dissolved in MeOH (16 mL) and $H_2O$ (4 mL). NaOH (s, 19.3 mg, 0.484 mmol) is added and the reaction is stirred at RT for 12 h. The reaction is concentrated onto silica gel for purification by flash chromatography (gradient elution: 0-10% MeOH/DCM+0.1% AcOH) followed by HPLC (35-70% acetonitrile in $H_2O$+ 0.1% TFA) to afford 11 mg compound 20. LC/MS: $[M+H]^+$ 1194, $R_t$=0.97 min (method 1).

Example 20

Preparation of Pyrrolidine (21)

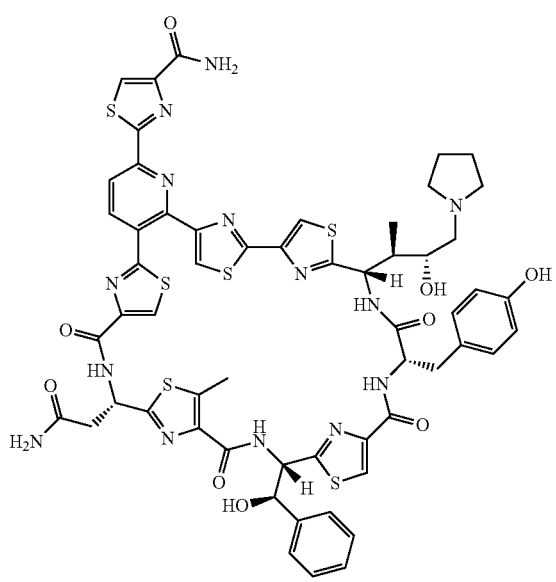 [SMILES: Cc1sc2nc1C(=O)N[C@@H]([C@H](O)c1ccccc1)c1nc(cs1)C(=O)N[C@@H](Cc1ccc(O)cc1)C(=O)N[C@@H]([C@@H](C)[C@@H](O)CN1CCCC1)c1nc(cs1)-c1nc(cs1)-c1nc(-c3nc(C(N)=O)cs3)ccc1-c1nc(cs1)C(=O)N[C@H]2CC(N)=O]

Step 1:

To a suspension of chlorohydrin (5, 500 mg, 0.404 mmol) in MeOH (50 mL) is added excess of saturated aq LiOH (1 mL) and reaction is stirred for 2 h at RT. The reaction is concentrated onto silica gel and purified by flash chromatography (gradient elution: 0-10% MeOH/DCM) to furnish 450 mg of epoxide 6. LC/MS: [M+H]$^+$ 1200, R$_t$ 1.12 min (method 1).

Step 2:

To a suspension of the epoxide (6, 150 mg, 0.125 mmol) in EtOH (20 mL) is added excess pyrrolidine (>10 eq) and the reaction is heated to 70° C. for 16 h. The reaction is cooled to RT and concentrated onto silica gel. Purification by flash chromatography (gradient elution: 0-10% MeOH/DCM) followed by reversed phase chromatography (C18 column, 30-70% acetonitrile in H$_2$O with 0.1% NH$_4$OH) furnishes 120 mg compound 21. LC/MS: [M+H]$^+$ 1271, R$_t$=0.77 min (method 1).

Example 21

Preparation of Triacetate (22)

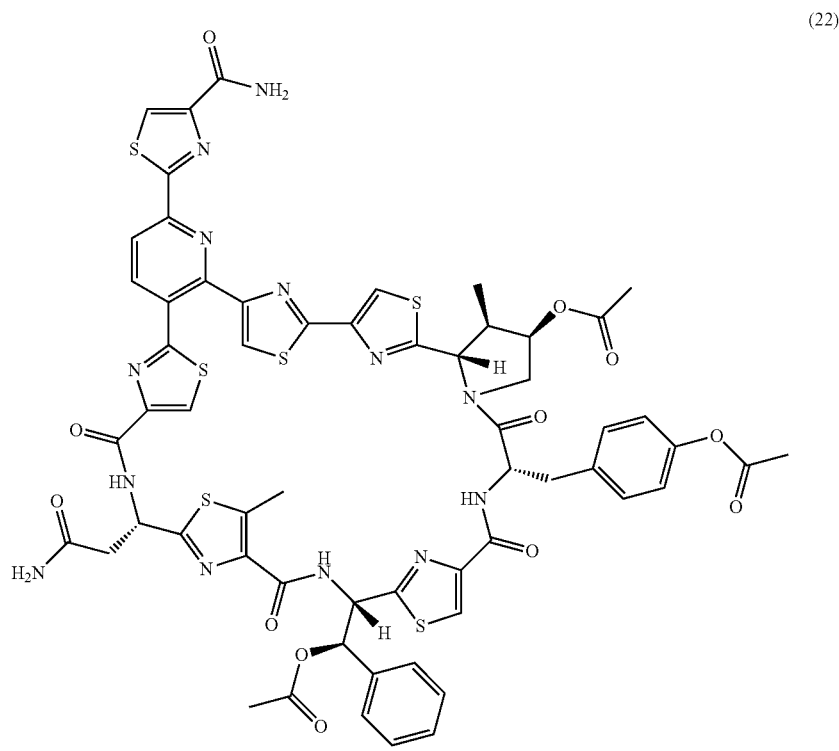

(22)

To a solution of chlorohydrin (5, 70 mg, 0.057 mmol) in THF (10 mL) is added acetic anhydride (100 uL) and DMAP (20 mg). The reaction is stirred at RT for 2 h and is concentrated onto silica gel and purified by flash chromatography (gradient elution: 0-5% MeOH/DCM) to furnish 6.6 mg compound 22. LC/MS: [M+2H]+ 1327, $R_t$=1.36 min (method 1).

Example 22

Preparation of Pyrrolidine-Alcohol (23)

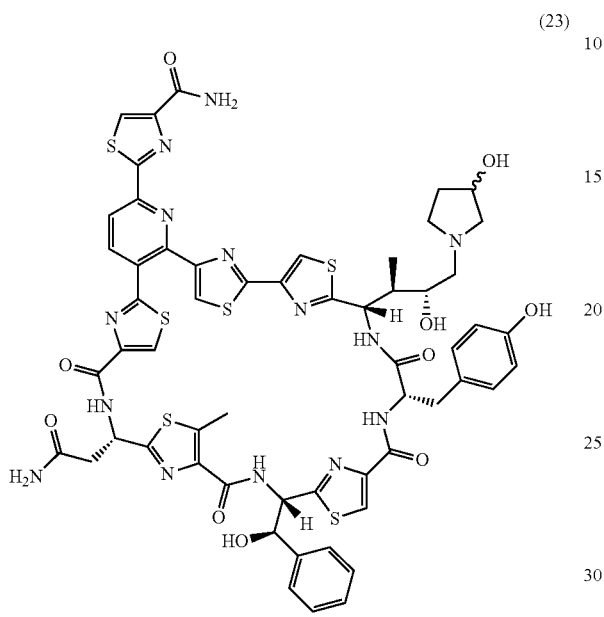
(23)

Compound 23 is prepared as described in example 16. LC/MS: [M+H]+ 1287, $R_t$=0.69 min (method 1).

Example 23

Preparation of Propylamine (24)

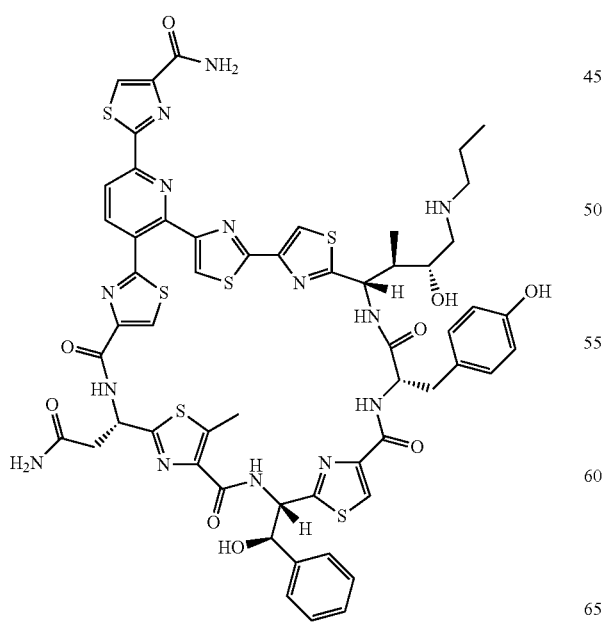
(24)

To a suspension of epoxide (6, 120 mg, 0.100 mmol) in EtOH (20 mL) is added an excess of propylamine. The reaction is heated to 70° C. in a sealed tube for 16 h. The reaction is cooled to RT and concentrated onto silica gel. Purification by flash chromatography (gradient elution: 0-10% MeOH/DCM+0.1% NH$_4$OH) followed by HPLC (30-60% acetonitrile in H$_2$O with 0.1% TFA) furnishes 5.4 mg compound 24. LC/MS: [M+H]+ 1259, $R_t$=0.72 min (method 1).

Example 24

Preparation of Diol (25)

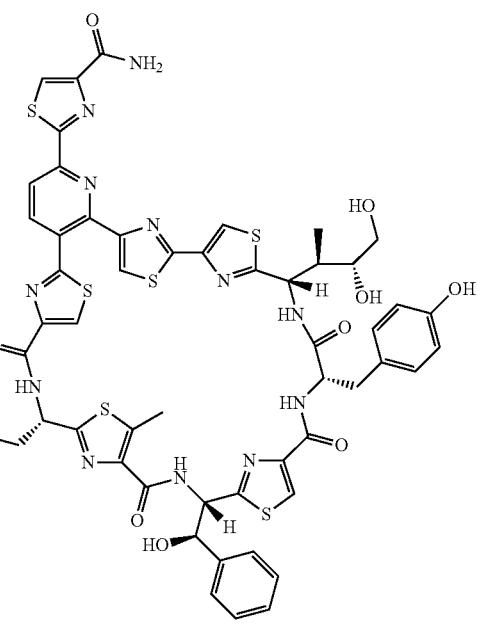
(25)

To a suspension of epoxide (6, 200 mg, 0.167 mmol) in MeOH (10 mL) and DCM (20 mL) is added TFA (5 mL). The reaction is sealed and stirred at RT for 16 h. The reaction is concentrated and purified by HPLC (20-60% acetonitrile in H$_2$O with 0.1% TFA) to furnish 20 mg compound 25. LC/MS: [M+H]+ 1218, $R_t$=0.89 min (method 1).

Example 25
Preparation of Diamine (26)
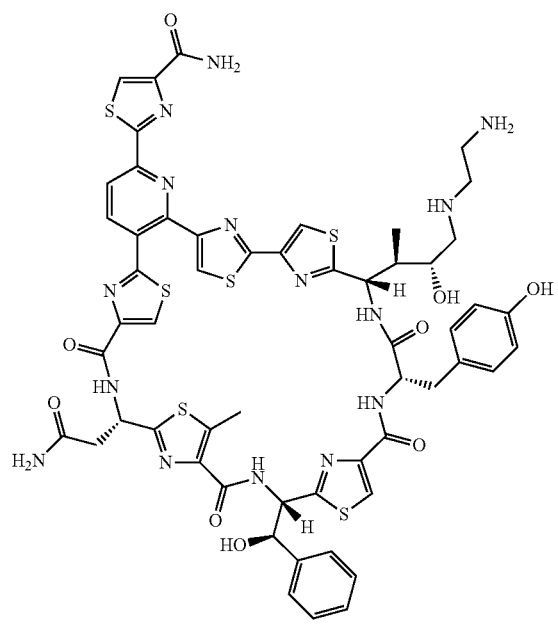
(26)
Compound 26 is prepared as described in example 23.
LC/MS: [M+H]+ 1260, $R_t$=0.67 min (method 1).
Example 26
Preparation of Amine (27)
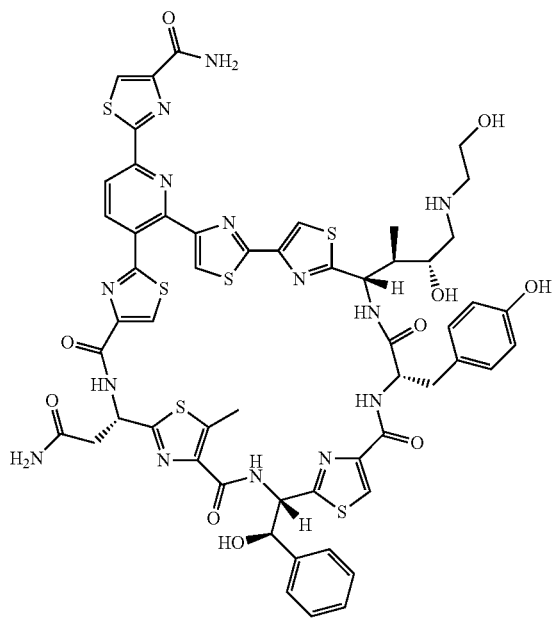
(27)
Compound 27 is prepared as described in example 23.
LC/MS: [M+H]+ 1261, $R_t$=0.69 min (method 1).
Example 27
Preparation of Amine (28)
(28)
Compound 28 is prepared as described in example 23.
LC/MS: [M] 1230, $R_t$=0.53 min (method 1).
Example 28
Preparation of Amine (29)
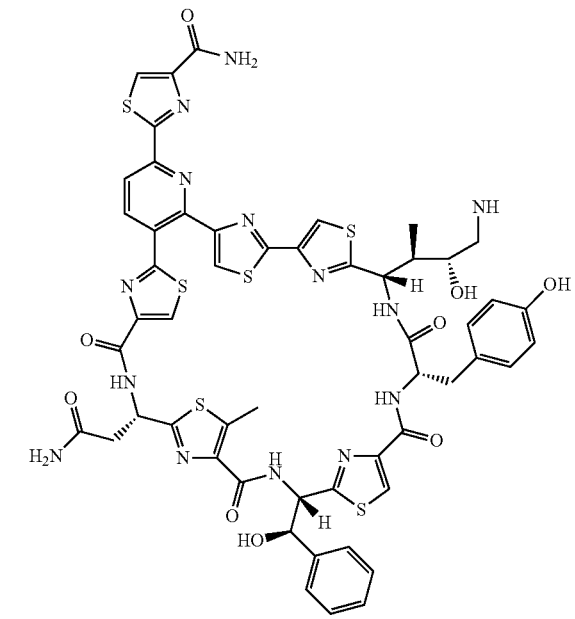
(29)

To a suspension of epoxide (6, 200 mg, 0.167 mmol) in EtOH (20 mL) is added ammonium hydroxide solution in $H_2O$ (1:1, 1.2 mL). The reaction is heated to 60° C. in a sealed tube for 18 h. Additional ammonium hydroxide solution (2 mL) is added and the reaction is heated to 70° C. for 12 h. The reaction is cooled to RT and concentrated onto silica gel. Purification by flash chromatography (gradient elution: 0-10% MeOH/DCM+0.1% $NH_4OH$) followed by HPLC (25-60% acetonitrile in $H_2O$ with 0.1% $NH_4OH$) furnishes 21 mg compound 29. LC/MS: $[M+H]^+$ 1217, $R_t$=0.66 min (method 1).

Example 29

Preparation of Methylethers (30, 31)

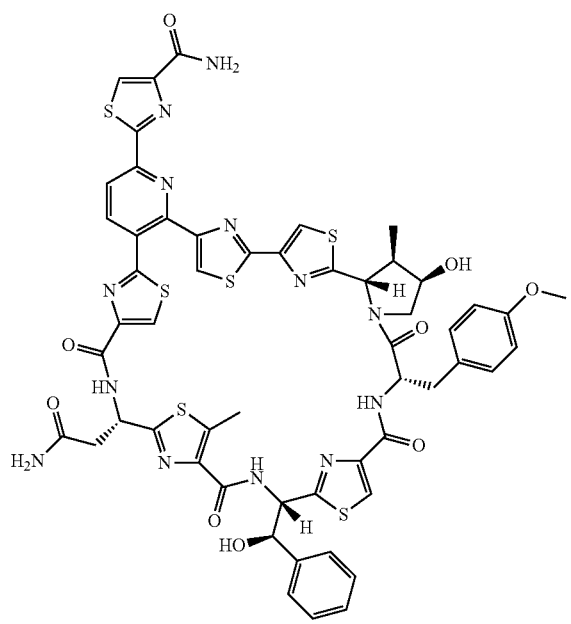

(30)

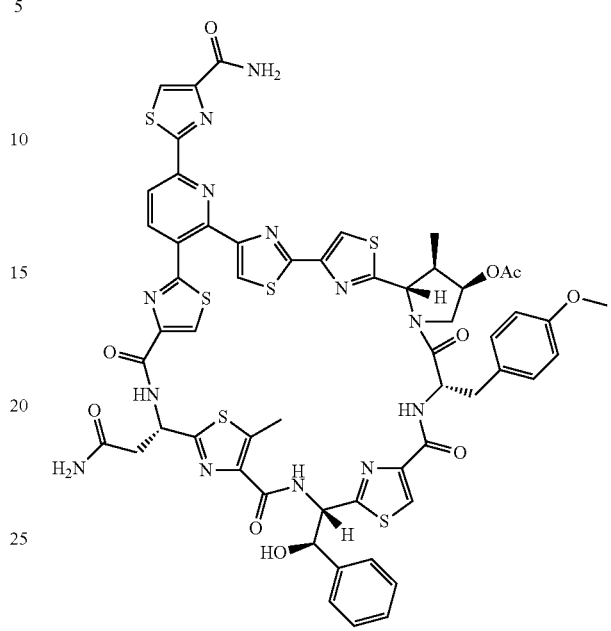

(31)

To a solution of pyrrolidine (13, 214 mg) in DMF (7 mL) is added cesium bicarbonate (103 mg, 0.316 mmol), and MeI (10 μL, 0.16 mmol). The reaction slowly progresses to 50% completion (LC/MS), and is cooled to 0° C. and stored for 12 h. Upon warming to 40° C. no further reaction is observed. Water (20 mL) is added and the resulting white precipitate is filtered. The crude white solid is then resubjected to the above conditions (85% completion via LC/MS). Water (20 mL) is added to the reaction mixture, and the resulting precipitate is filtered. Excess iodomethane is removed from the crude mixture in vacuo. To a solution of the crude methylether in DMF (7 mL) is added acetic anhydride (200 μL, >100 eq) and DMAP (cat). The reaction mixture stirs for 12 h. Pyridine (2 mL) is added to the reaction mixture, and the reaction is stirred 1 h. Water (20 mL) is added, and the resulting white precipitate is filtered. The product is purified via flash chromatography (gradient elution: 0-10% MeOH/DCM) then HPLC (40-70% acetonitrile/water+0.1% $NH_4OH$) to separately furnish compounds 30 and 31. Compound 30, LC/MS: $[M+H]^+$ 1214, $R_t$=1.2 min (method 1). Compound 31, LC/MS: $[M+H]^+$ 1256, $R_t$=1.3 min (method 1).

Example 31
Preparation of Acids (32, 33)
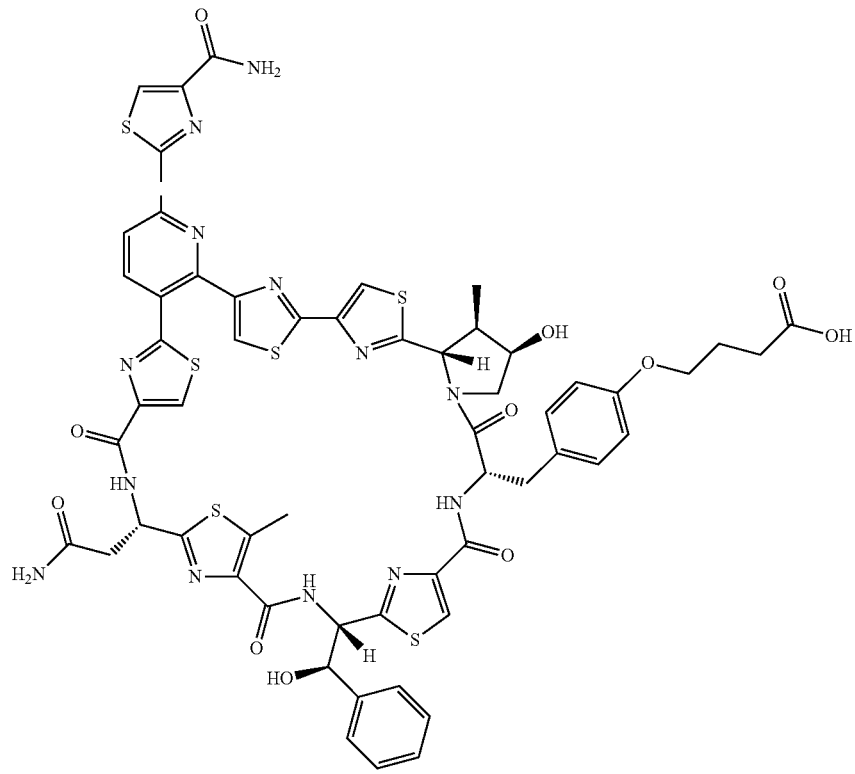
(32)
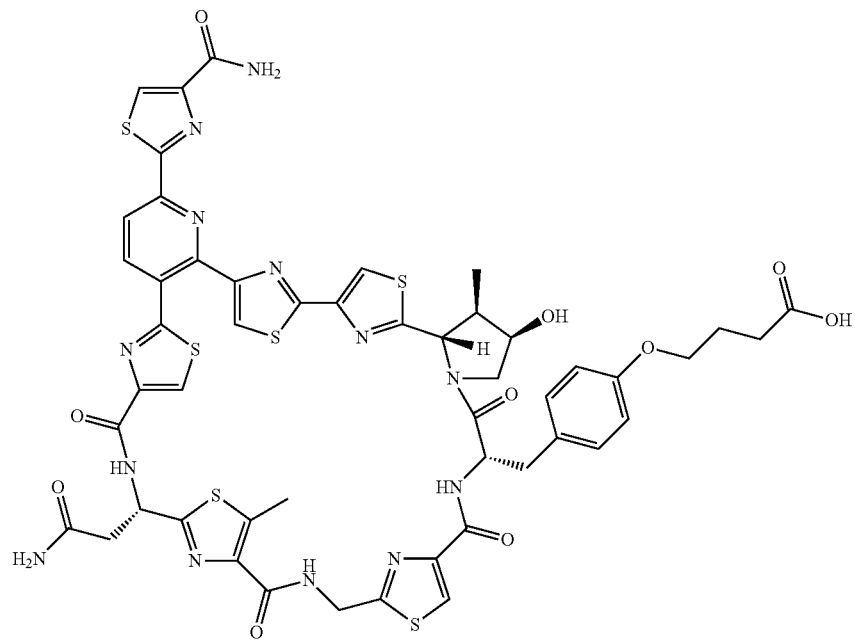
(33)

Step 1:
To a solution of pyrrolidine (13, 150 mg, 0.125 mmol) in DMF (2 mL) is added cesium carbonate (50 mg, >100 eq) and 4-bromobutyric acid methyl ester (10 μL, >10 eq). The reaction is stirred at 35° C. for 48 h. Water (20 mL) is added and the precipitate is filtered.

Step 2:
To a solution of the ether precipitate from step 1 in a 1:1:1 solution of THF/MeOH/water (40 mL) is added aq LiOH (4 N, 0.5 mL, >100 eq) Ammonium chloride (2 mL, saturated aq) is added to quench the reaction, and the mixture is concentrated onto silica gel. The crude mixture is purified via flash chromatography (gradient elution: 0-10% MeOH/DCM) to separately afford compounds 32 and 33. Compound 32 is then further purified via HPLC (method 6) to furnish a white solid. LC/MS: [M+H]$^+$ 1286, $R_t$=0.99 min (method 1). Compound 33 is further purified via HPLC (method 1) to afford a white solid. LC/MS: [M] 1179, $R_t$=0.95 min (method 1).

Scheme 5, Preparation of Amides 34, 35

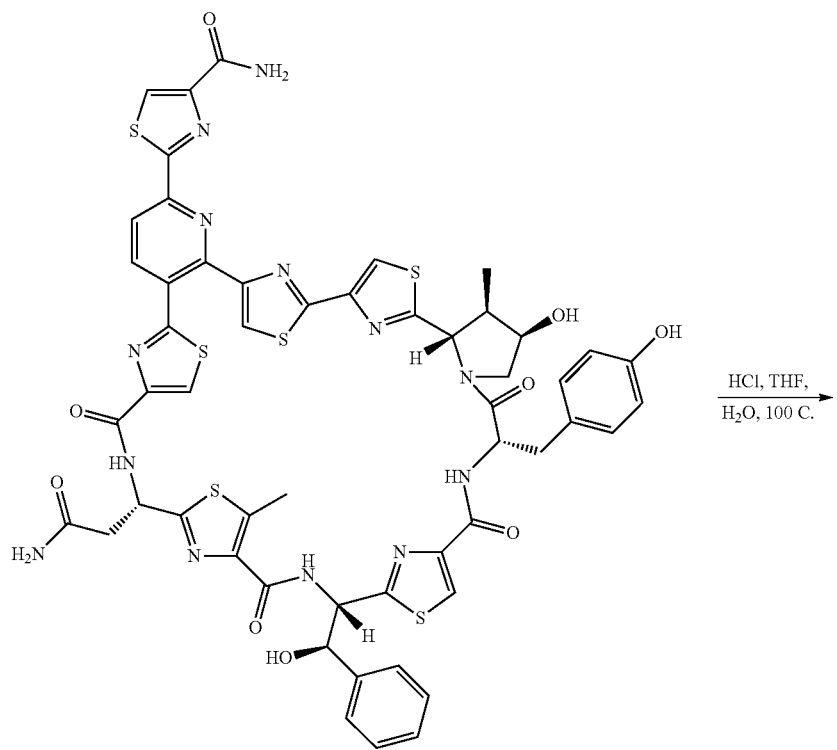

13

-continued
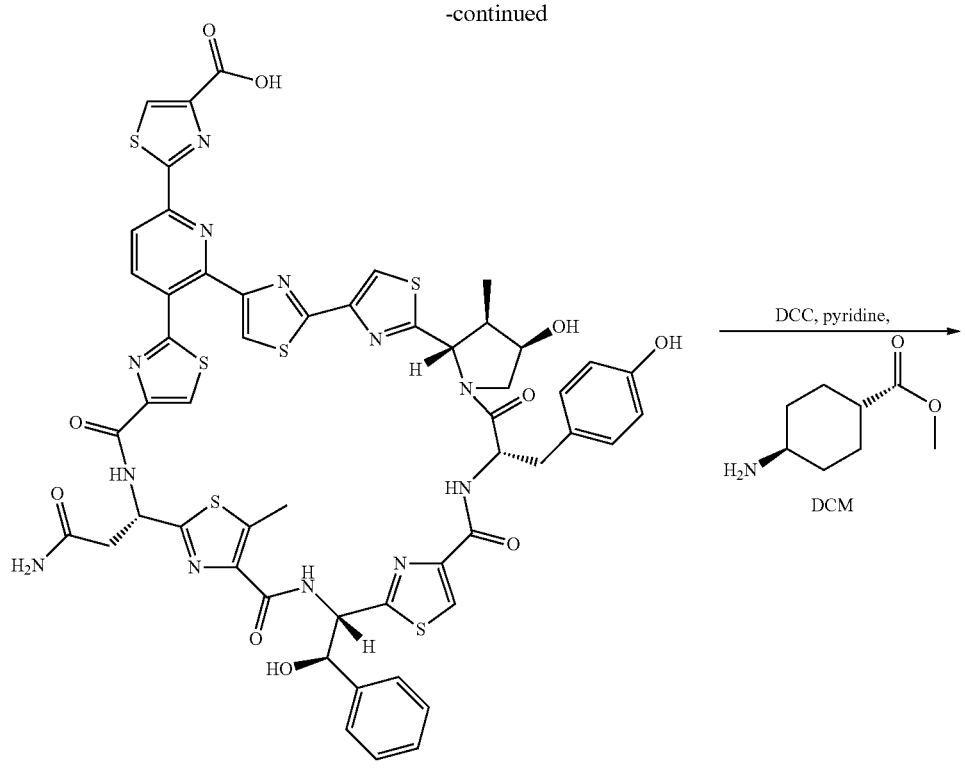
14
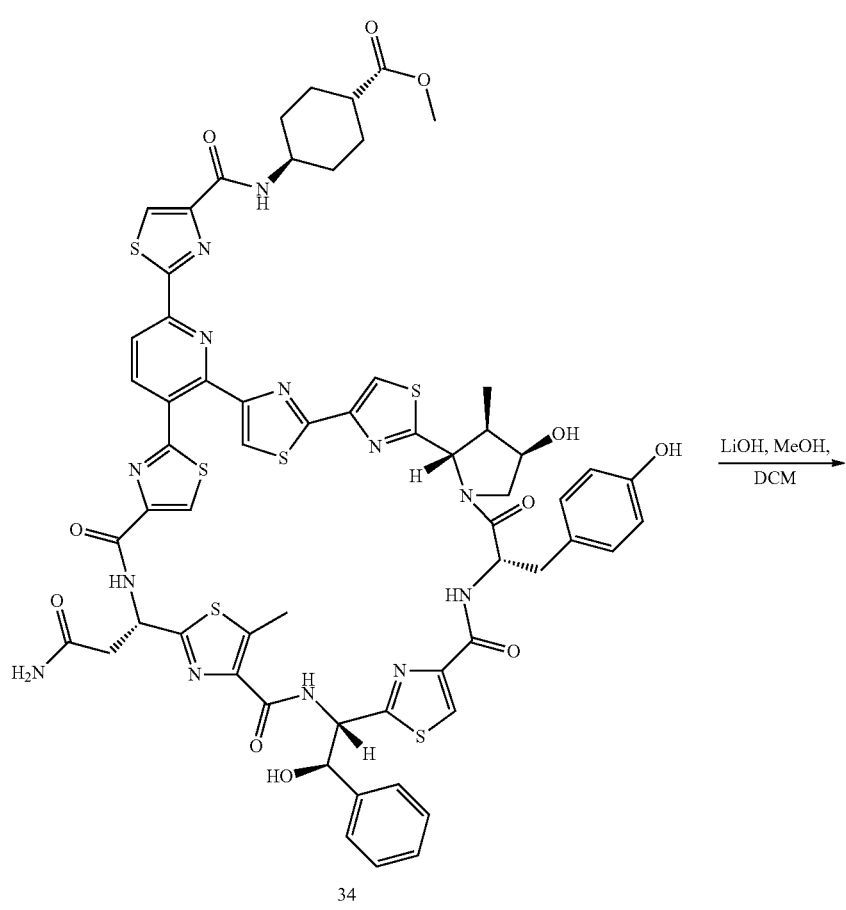
34

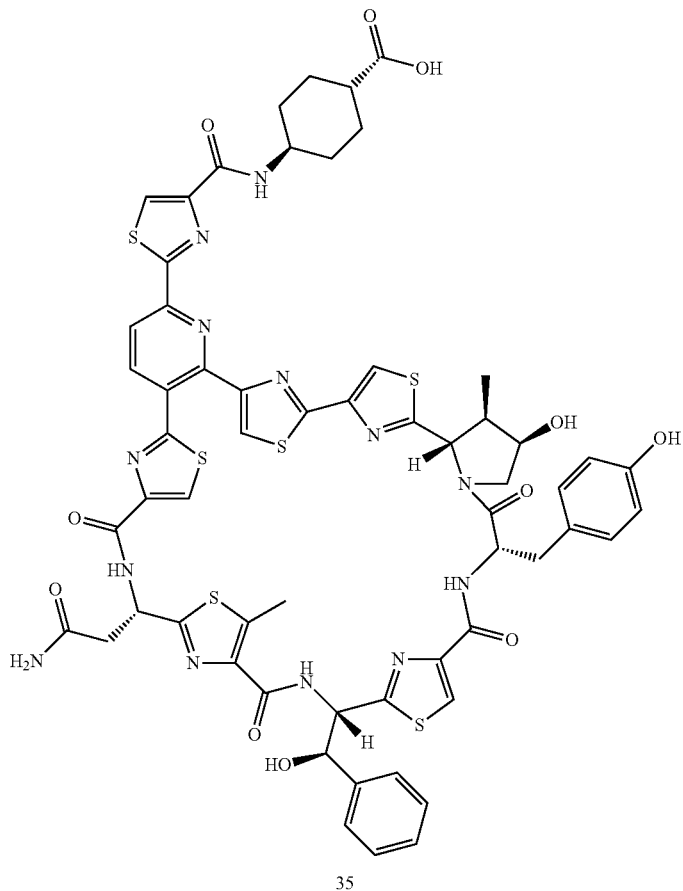

35

Step 1:

To a suspension of pyrrolidine 13 (100 mg, 0.0833 mmol) in THF (5 mL) in a glass reinforced sealed tube is added concentrated aq HCl (12 M, 100 uL). The suspension is sonicated for 5 min and sealed. The mixture is heated to 100° C. and stirs for 12 h. The mixture is mounted onto $SiO_2$ and purified by flash chromatography (gradient elution: 0-10% MeOH/DCM) which affords 70 mg of acid 14.

Step 2:

To a solution of acid 14 (70 mg, 0.0583) in DCM (10 mL) is added N,N'-dicyclohexylcarbodiimide (92 mg, 0.1746 mmol, immobilized on polystyrene, 1.9 mmol/g), trans-4-amino-cyclohexylcarboxylic acid methyl ester hydrochloride (14 mg, 0.0873 mmol), and pyridine (30 uL). Alternatively, TBTU, HATU and other amino-acid coupling conditions may be used in the coupling reaction. The reaction is stirred for 12 h and is mounted onto $SiO_2$. Flash chromatography (gradient elution: 0-10% MeOH/DCM) affords 25 mg of the amide 34. LC/MS: $[M+H]^+$ 1340, $R_t$=1.43 min (method 1).

Step 3:

To a solution of amide 34 (25 mg, 0.0089 mmol) in DCM (10 mL) and MeOH (5 mL) is added LiOH (50 uL, saturated aq solution). The reaction stirs at RT for 6 h and is mounted onto $SiO_2$ and filtered through a $SiO_2$ plug (10% MeOH/DCM+0.1% AcOH) which results in the recovery of 18 mg of crude acid. The crude acid is then purified via preparatory TLC (10% MeOH/DCM) which affords 8 mg of acid 35.
LC/MS: [M+H]$^+$=1326, $R_t$=1.17 min (method 1).
Example 33
Preparation of Acid (36)
(36)
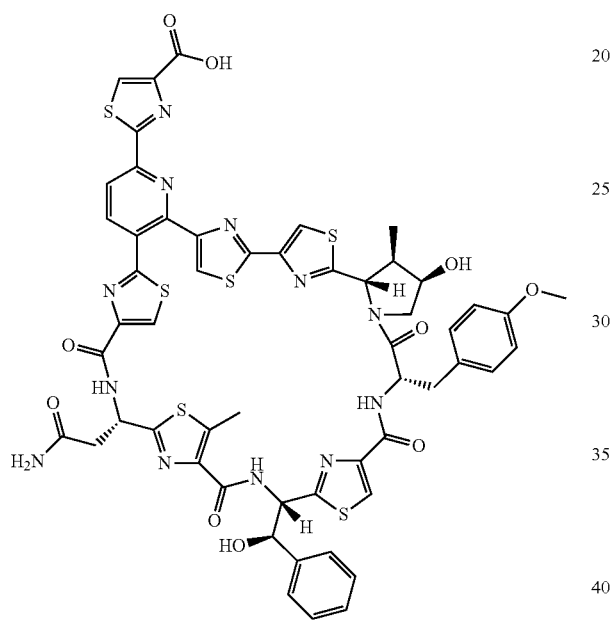
Compound 36 is prepared as described in scheme 5 and example 29. LC/MS: [M+H]$^+$ 1215, $R_t$=1.24 min (method 1).
Example 34
Preparation of Amines (37, 38)
(37)
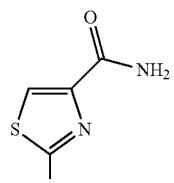

-continued

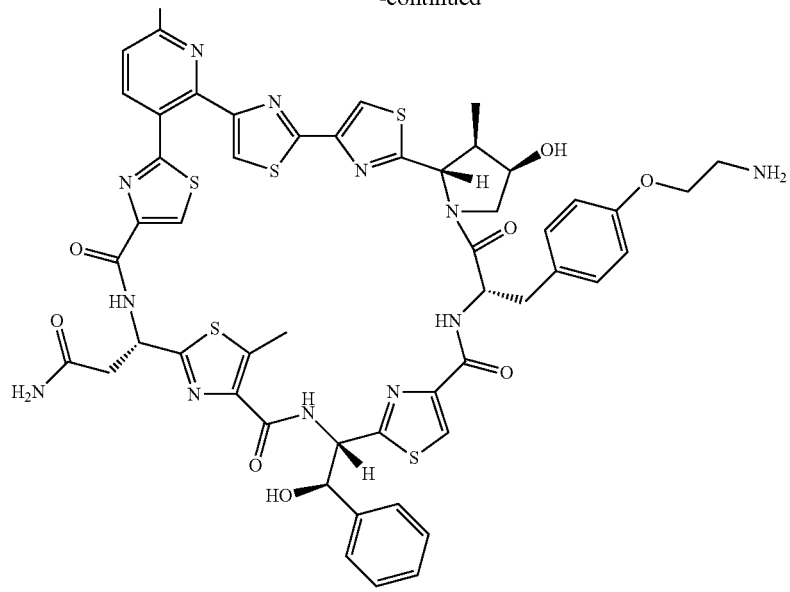

(38)

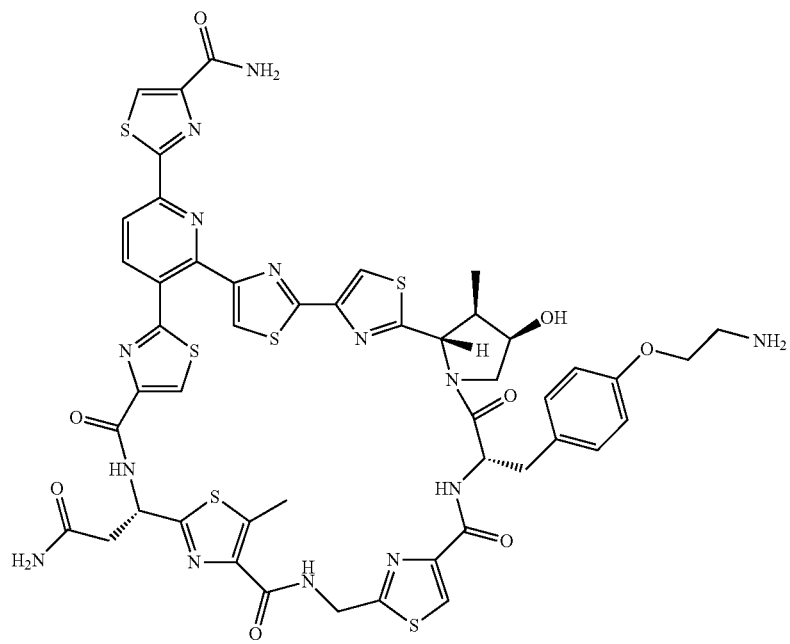

Step 1:

To a solution of the pyrrolidine (13, 300 mg, 0.20 mmol) in DMF (10 mL) at 0° C. is added 2-(boc-amino) ethyl bromide (224 mg, 1.0 mmol) then Cs$_2$CO$_3$ (800 mg, 2.5 mmol). The reaction is allowed to warm to RT. Excess Cs$_2$CO$_3$ (800 mg, 2.5 mmol) and 2-(boc-amino) ethyl bromide (224 mg, 1.0 mmol) are added. Water (100 mL) is added and the products are collected via filtration.

Step 2:

To a solution of the crude boc protected amine (contaminated with the benzaldehyde elimination byproduct) in DCM (30 mL) is added TFA (5 mL). Upon completion of the deprotection, the mixture is concentrated onto silica gel and purified via flash chromatography (gradient elution 0-10% MeOH/DCM, then 2% NH$_4$OH, in 15% MeOH/DCM.). Final purification is performed via HPLC yielding 37, LC/MS: [M+H]$^+$ 1243, R$_t$=0.8 min (method 1), and 38, LC/MS [M+H]$^+$ 1137, R$_t$=0.7 min (method 1).

Example 35
Preparation of Acid (39)
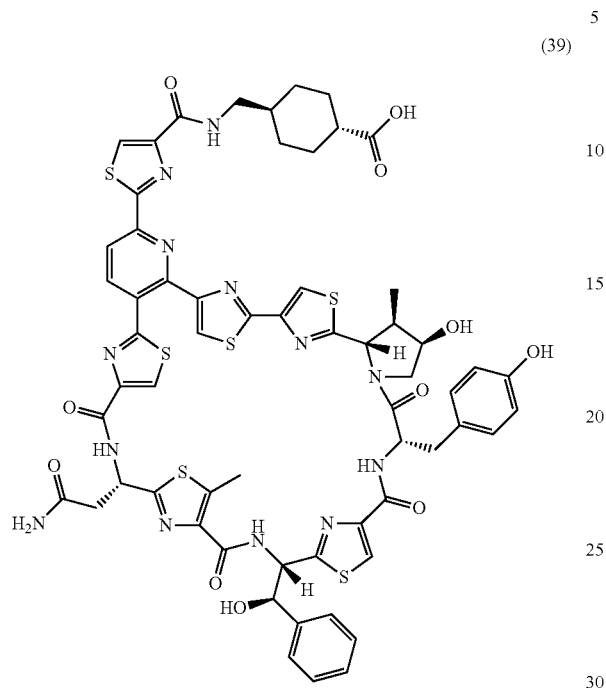
Compound 39 is prepared as described in scheme 5. LC/MS: [M+2H]$^+$ 1341, R$_t$=1.1 min (method 1).
Example 36
Preparation of Amino-Ester (40)
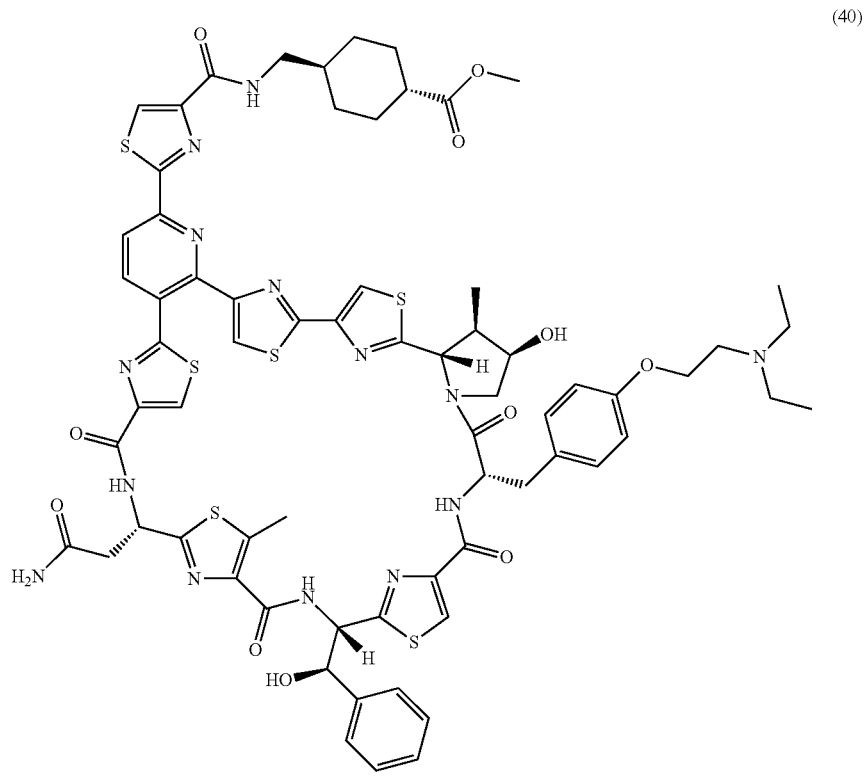

Compound 40 is prepared as described in scheme 5 and example 34. LC/MS: [M+2H]+ 1454, R$_t$=1.1 min (method 1).

Example 37

Preparation of Ester (41)

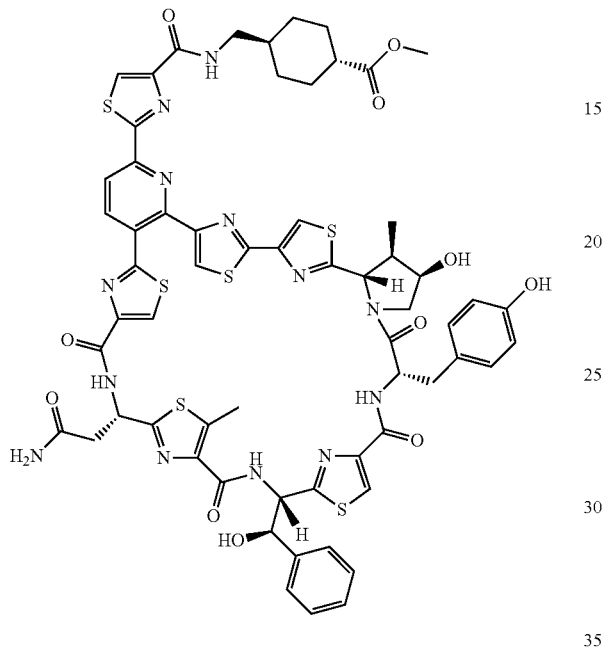

(41)

Compound 41 is prepared as described in scheme 5. LC/MS: [M+2H]+ 1355, R$_t$=1.3 min (method 1).

Example 38

Preparation of Acid (42)

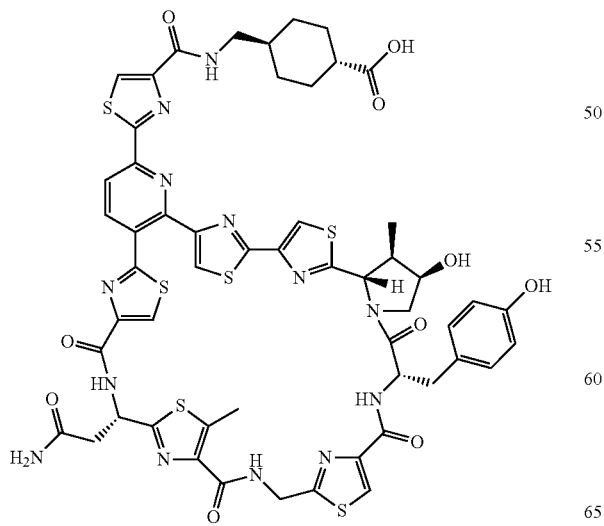

(42)

Compound 42 is prepared as described in scheme 5. LC/MS: [M+H]+ 1234, R$_t$=1.05 min (method 1).

Example 39

Preparation of Acid (43)

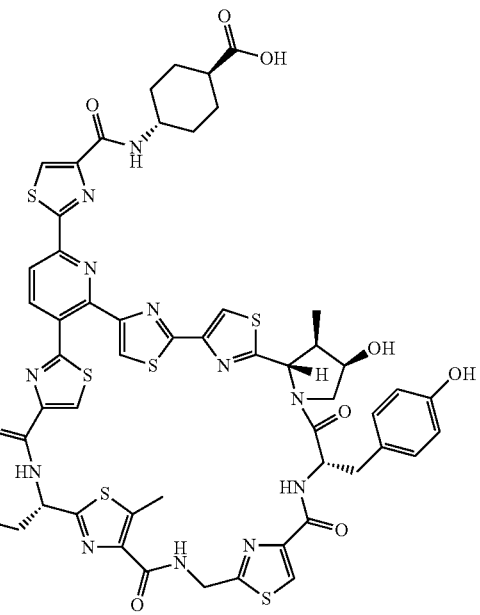

(43)

Compound 43 is prepared as described in scheme 5. LC/MS: [M+H]+ 1220, R$_t$=0.98 min (method 1).

Example 40
Preparation of amines (44, 45)
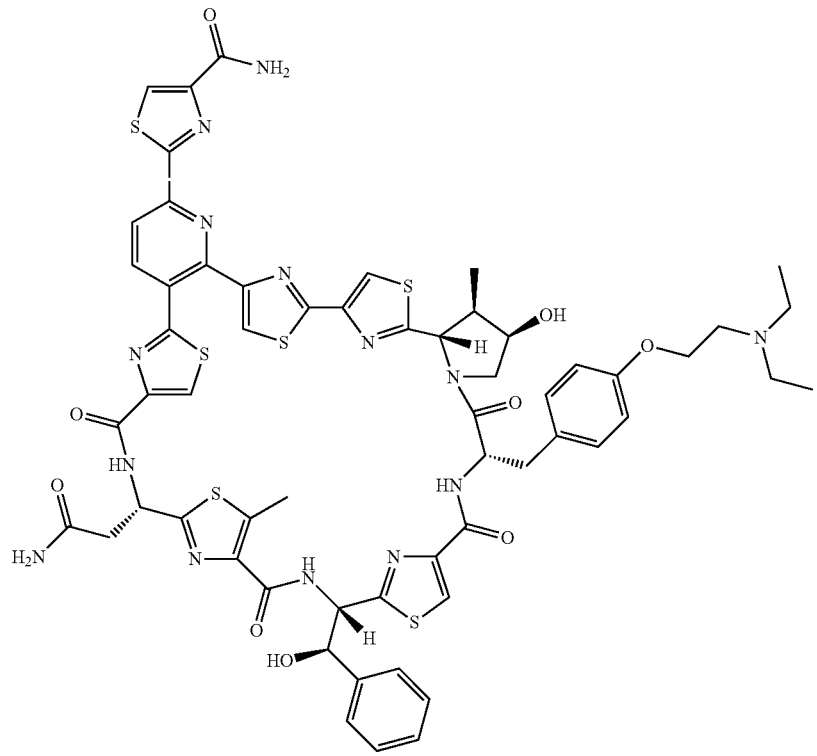
(44)
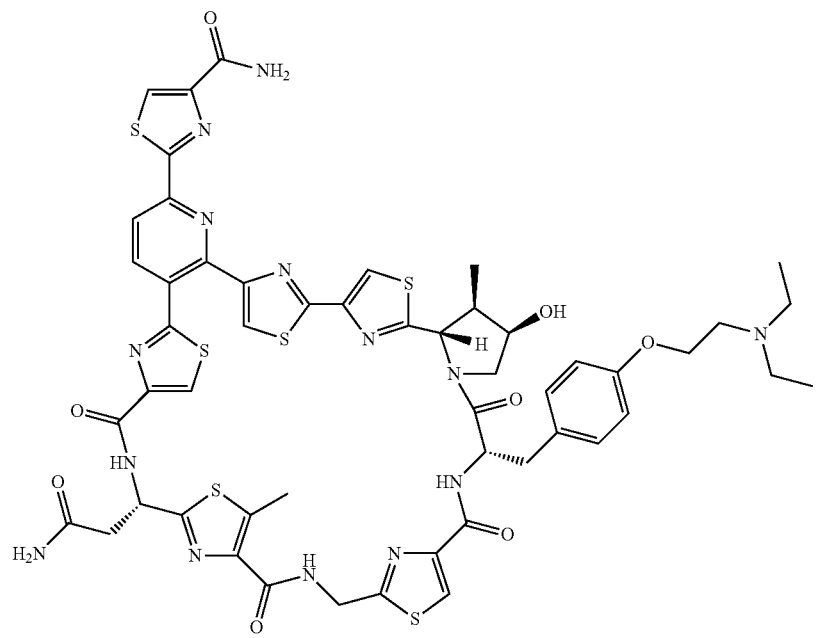
(45)
Compounds 44, 45 are prepared as described in example 34. Compound 44: LC/MS [M+H]$^+$ 1299, $R_t$=0.9 min (method 1) Compound 45: LC/MS [M+H]$^+$ 1193, $R_t$=0.8 min (method 1).

Example 41
Preparation of Amino-Acid (46)
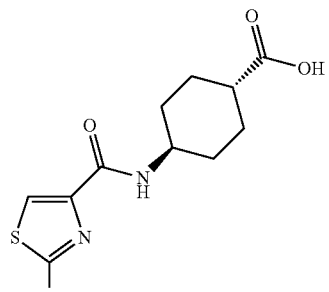
(46)
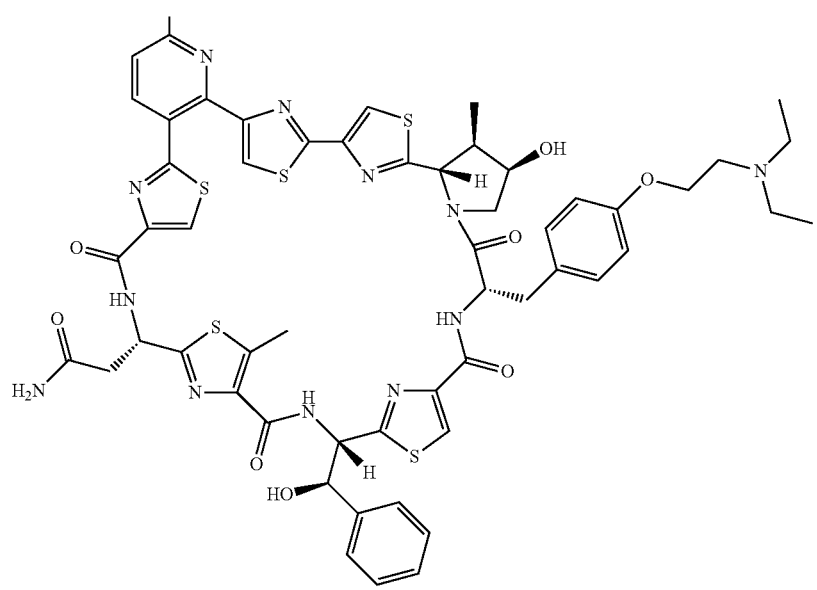
Compound 46 is prepared as described in scheme 5 and in example 34. LC/MS: [M+H]$^+$ 1425, R$_t$=0.94 min (method 1).
Example 42
Preparation of Amino-Acid (47)
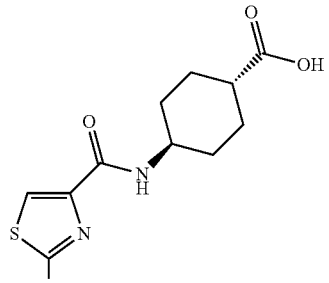
(47)

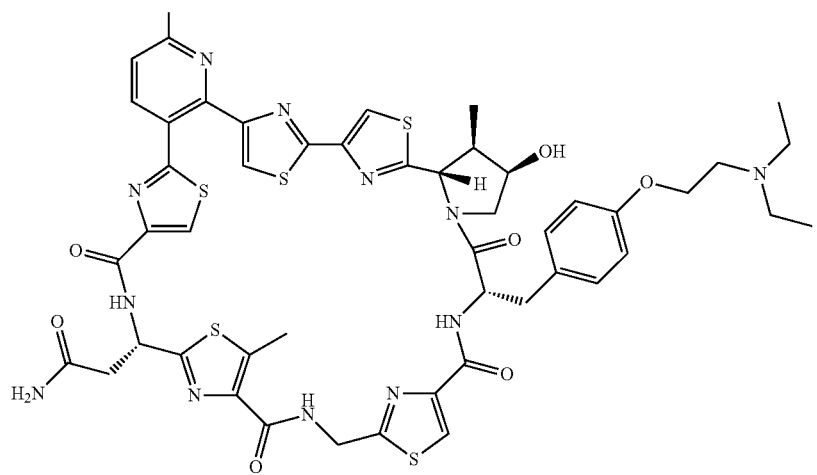
Compound 47 is prepared as described in scheme 5 and in example 34. LC/MS: [M+H]$^+$ 1319, $R_t$=0.92 min (method 1).
Example 43
Preparation of Amino-Acid (48)
(48)
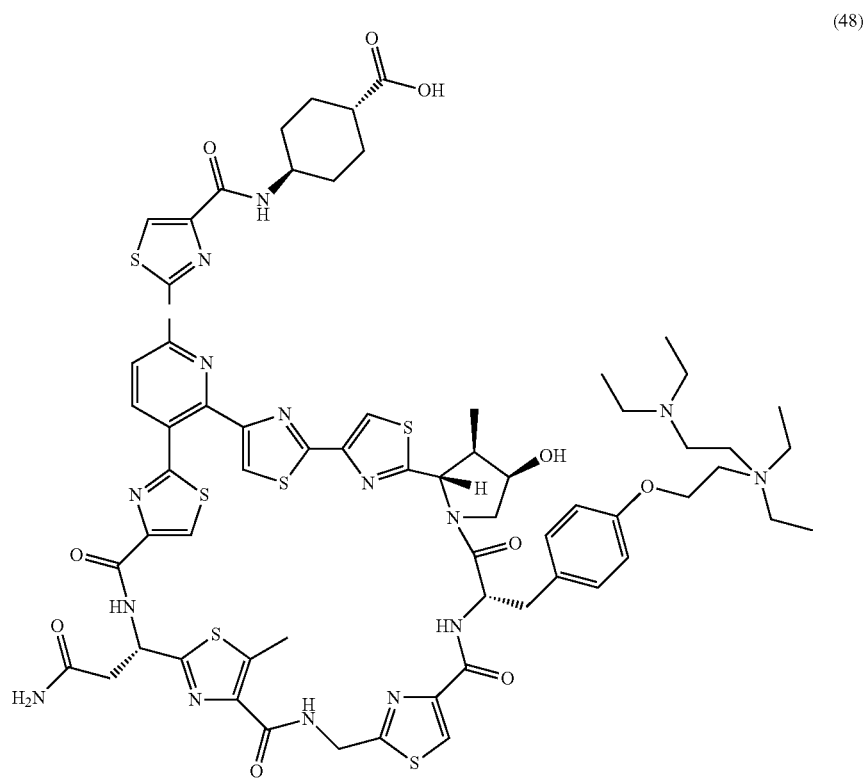

Compound 48 is prepared as described in scheme 5 and in example 34. LC/MS: [M] 1418, $R_t$=0.96 min (method 1).

Example 44

Preparation of Bromoacids (49, 50)

(49)

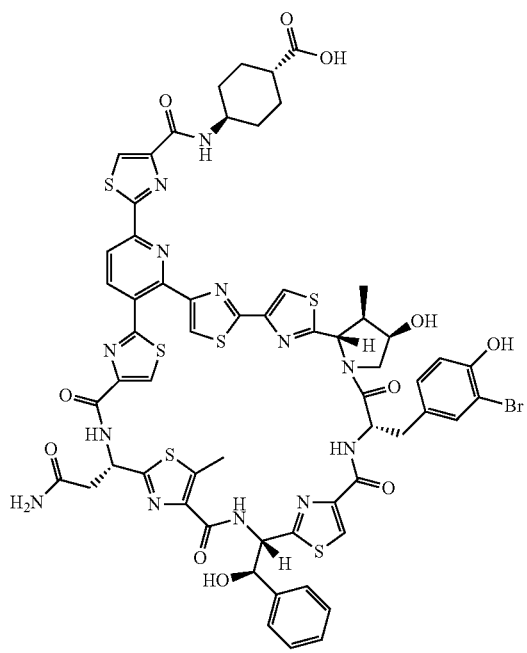

(50)

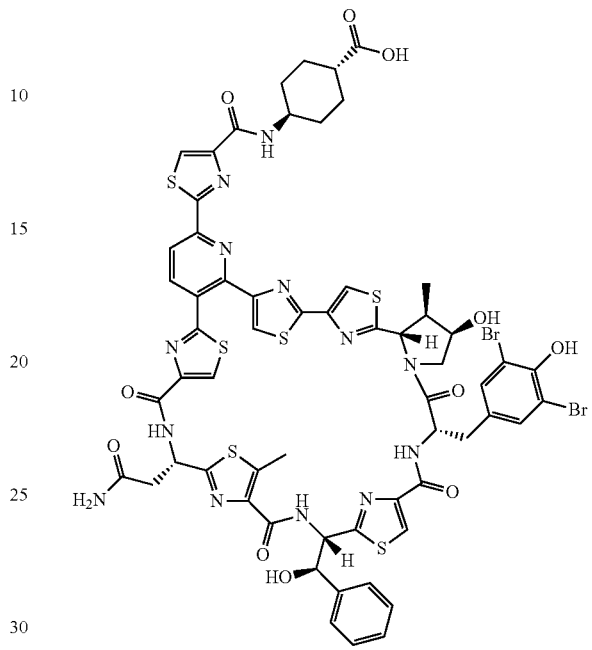

Step 1:

To a sonicated, −78° C. THF suspension of ester (100 mg compound 34 in 10 mL THF) is added 100 uL of bromine solution (prepared by adding 20 uL bromine to 1 mL DCM). The reaction is monitored by LC/MS and is quenched at −78° C. by adding 1 g of $SiO_2$. The solvents are removed in vacuo and the crude material is eluted with 10% MeOH in DCM. The crude material (a mixture of mono and di-brominated products) is carried on with no further purification.

Step 2:

To a solution of the crude bromination products (20 mL, 1:1 DCM/MeOH) is added LiOH (1 mL sat'd aq solution). The reaction stirs at RT for 6 h and is concentrated onto $SiO_2$ and is eluted with 10% MeOH in DCM+1% AcOH. The products are purified via HPLC (gradient elution: 55%-65% MeCN/$H_2O$+0.1% TFA). Compound 49: LC/MS: [M+3H]$^+$ 1406, $R_t$=1.17 min (method 1). Compound 50: LC/MS: [M+5H]$^+$ 1486, $R_t$=1.22 min (method 1).

Example 45
Preparation of Tetrazole (51)
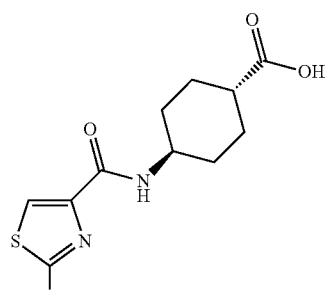
(51)
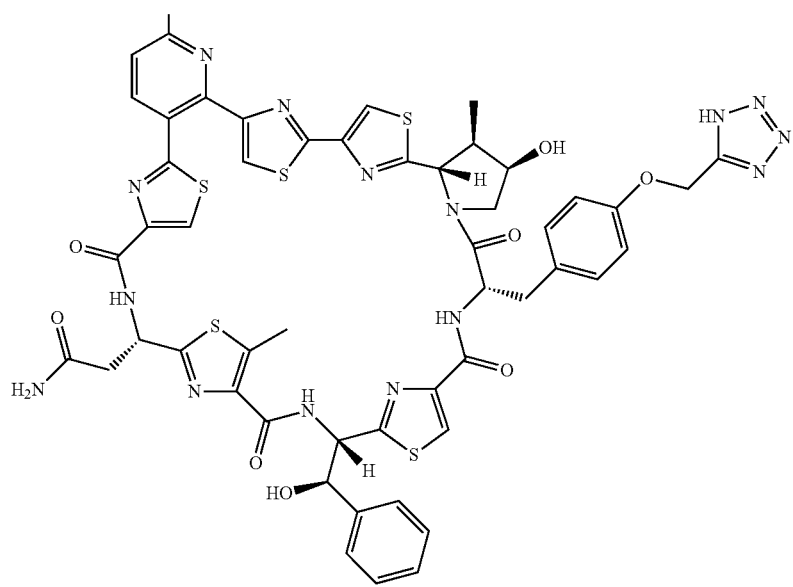
Compound 51 is prepared as described in scheme 5 and in example 34. LC/MS: [M+3H]$^+$ 1410, $R_t$=0.86 min (method 1).

Example 46

Preparation of Nitroacid (52)

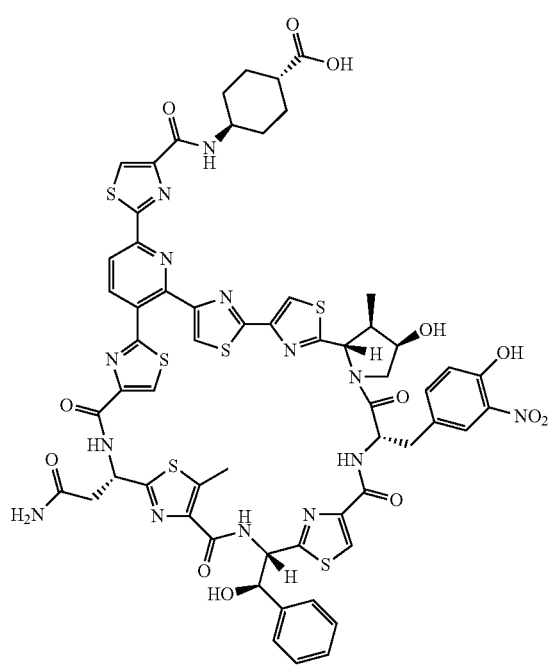

(52)

Step 1:
To a solution of the ester (34, 200 mg) in AcOH (5 mL) is added 300 uL of 60% nitric acid. The reaction stirs for 20 min, 1 mL of sat'd aq bicarbonate solution is added, and 1 g of $SiO_2$. The solvents are removed in vacuo and the crude product is eluted through a short silica plug with 10% MeOH in DCM. The sovents are removed in vacuo and the crude nitro-ester is taken on with no further purification.

Step 2:
100 mg of the crude nitro ester is dissolved in MeOH/DCM (5 mL, 1:1) and LiOH sat'd aq solution is added (150 uL). After 5 h, 1 g $SiO_2$ is added and the solvents are removed in vacuo. The crude mixture is eluted through a short silica plug with 10% MeOH in DCM+1% AcOH. The solvents are removed in vacuo and the crude nitro-acid is purified via HPLC (gradient elution: 55%-80% MeCN/$H_2O$+0.1% TFA). LC/MS: $[M+2H]^+$ 1372, $R_t$=1.16 min (method 1).

Example 47

Preparation of Aniline-Acid (53)

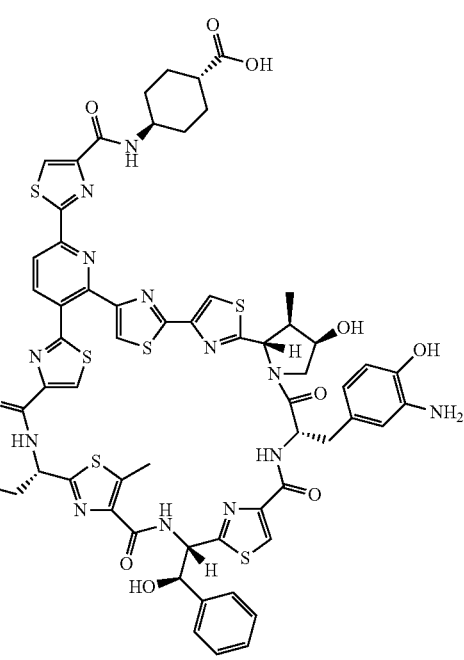

(53)

Step 1:
To a solution (10 mL DCM/MeOH, 1:1) of the nitro-ester (as prepared in example 46) is added 100 mg of Pd/C (10%). The suspension is evacuated of dissolved gases and backfilled with hydrogen via balloon (3×). The reaction is stirred at RT for 48 h and monitored by LC/MS. The mixture is then filtered though a pad of Celite (10% MeOH/DCM) and the resulting white solid is taken on to the next step with no further purification.

Step 2:
The crude ester is dissolved in 10 mL MeOH/DCM (2:1) and LiOH is added (150 uL sat'd aq solution). After 5 h of stirring at RT, the reaction is concentrated onto $SiO_2$ and eluted through a short silica plug with 10% MeOH/DCM+1% AcOH. The crude material is then purified by HPLC (gradient elution: 20-60% MeCN/H₂O+0.1% TFA). LC/MS: [M+3H]⁺ 1343 (method 1), $R_t$=11.86 min (LC).

Example 48

Preparation of Aniline (54)

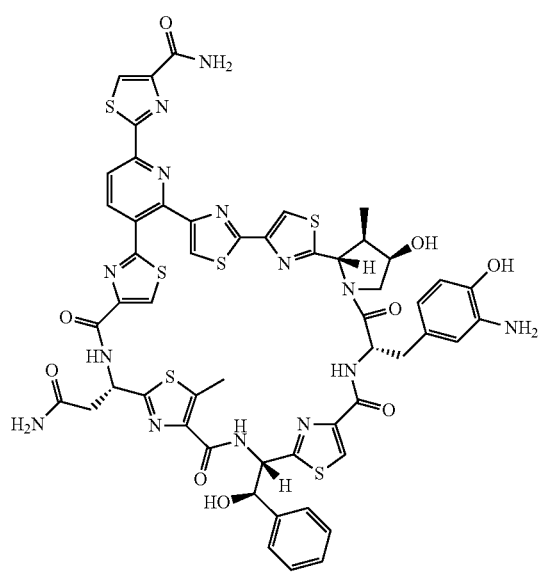

Compound 54 is prepared from pyrrolidine 13 according to the procedures described in example 47. LC/MS: [M+H]⁺ 1215, $R_t$=1.07 min (method 1).

Example 49

Preparation of Alcohol (55)

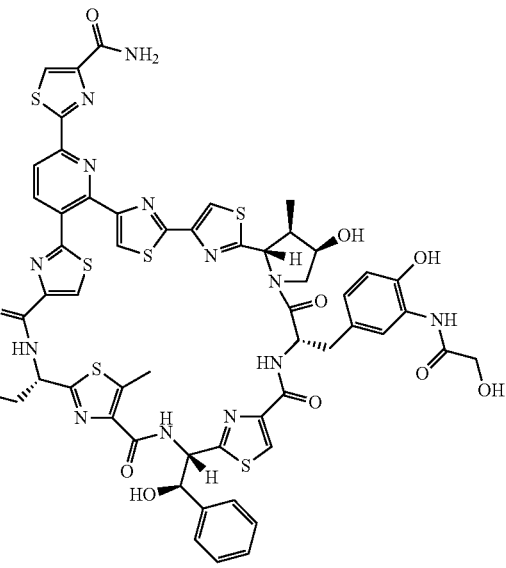

Compound 55 is prepared from compound 54 by dissolving the aniline in pyridine (200 mg in 10 mL) and adding 100 mg of TBTU and 25 mg of glycolic acid. The reaction stirs for 3 h at RT and is concentrated onto SiO₂. The crude alcohol is purified by flash chromatography (gradient elution 0-10% MeOH in DCM) and then HPLC (gradient elution: 35-55% MeCN in H₂O+0.1% TFA). LC/MS: [M+H]⁺ 1273, $R_t$=1.02 min (method 1).

Example 50

Preparation of Guanidine-Acid (56)

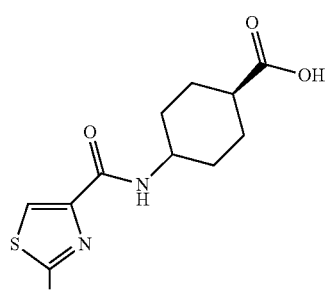

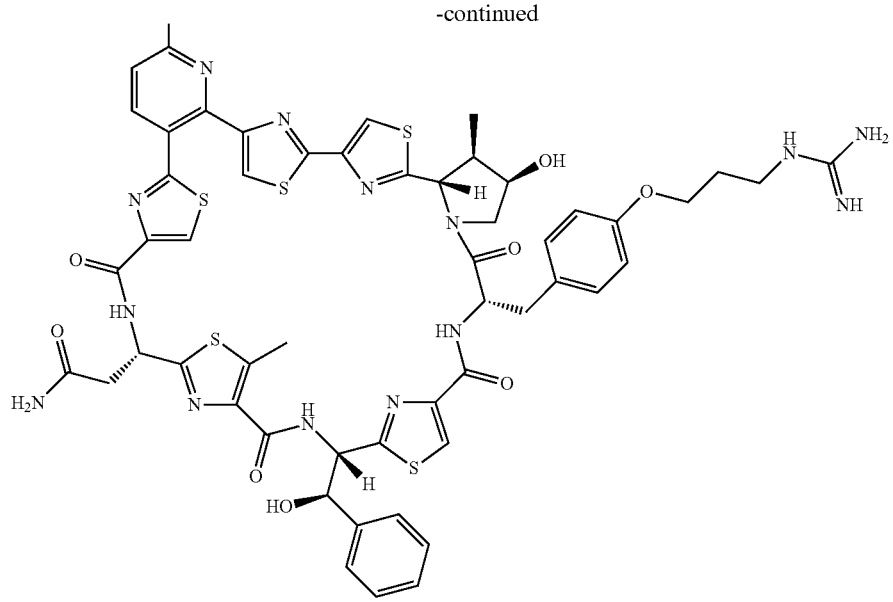

Step 1:

To a solution of compound 34 (1.0 g, 0.75 mmol) in DCM/DMF (5:1, 120 mL) is added acetic anhydride (0.5 mL, 10 eq) and DMAP (cat.). The DCM is removed under vacuum, and the product is precipitated upon addition of water (400 mL) to give the intermediate triacetate as an orange solid (780 mg). The triacetate is dissolved in DCM (2 mL). MeOH is added (20 mL), followed by HCl (conc. 100 μL). The reaction is concentrated onto silica gel, and purified via flash chromatography (gradient elution 0-5% MeOH/DCM) to provide a mixture of diacetate and starting material (1:1, 400 mg). [M+H]$^+$ 1424, R$_t$=1.44 (method 1).

Step 2:

To a solution of the diacetate (600 mg, 0.42 mmol) in DMF is added 3-(boc-amino)propyl bromide (1.0 g, 4.22 mmol) and cesium carbonate (1.4 g, 4.22 mmol). The reaction is stirred for 12 h. The mixture is concentrated onto silica gel and purified via flash chromatography (gradient elution 0-10% MeOH/DCM). To a solution of this crude mixture in DCM (20 mL) is added acetic anhydride (0.5 mL, >100 eq) and DMAP (cat). The solution is concentrated and placed under vacuum providing the boc-amino-diacetate.

Step 3:

To a solution of the intermediate boc-amino-diacetate in DCM (10 mL) is added TFA (1 mL). After 1 hr the solution is concentrated onto silica gel and purified via flash chromatography (gradient elution 0-10% MeOH/DCM) to provide amino-diacetate (200 mg).

Step 4:

To a solution of amino-diacetate (200 mg, 0.14 mmol) in DCM (10 mL) is added DIEA (0.5 mL) and 1-amidinopyrazol monohydrochloride (120 mg, 1.1 mmol). After the reaction is complete, DCM (10 mL), MeOH (10 mL), water (3 mL) and LiOH (4 mL) are added. The solution is concentrated onto silica gel and purified via flash chromatography (gradient elution 0-10% MeOH/DCM), HPLC, then preparative TLC (10% MeOH/DCM). LC/MS: [M+H]$^+$ 1425, R$_t$=0.82 (method 1).

Example 51

Preparation of Tetrazole (57)

(57)

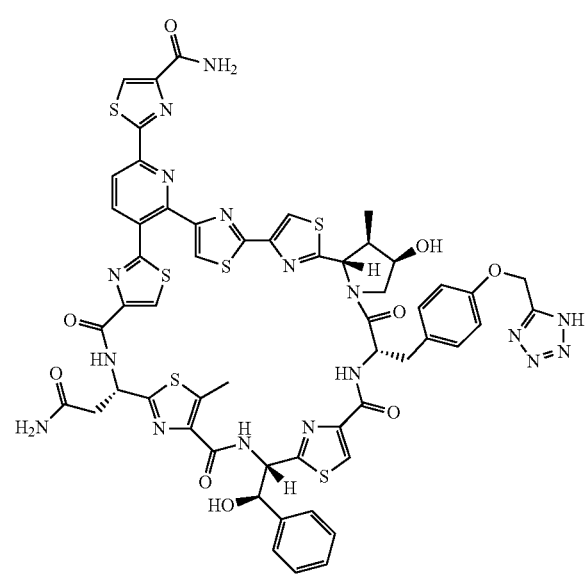

Compound 57 is prepared according to the procedures described in example 34. LC/MS: [M+H]$^+$ 1282, R$_t$=0.84 (method 1).

Example 52
Preparation of Morpholine (58)
(58)
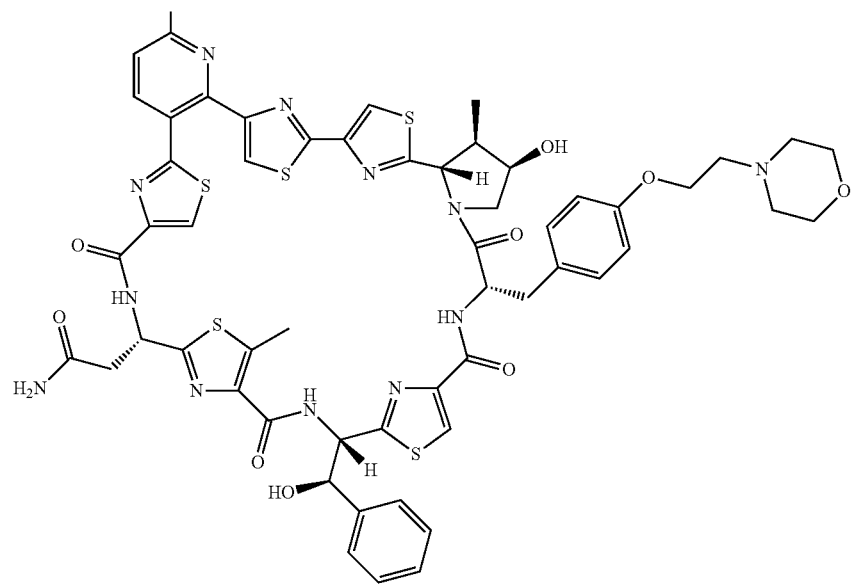
Compound 58 is prepared according to the procedures described in example 34. LC/MS: [M+H]$^+$ 1313, $R_f$=1.00 (method 1).
Example 53
Preparation of Imidazole (59)
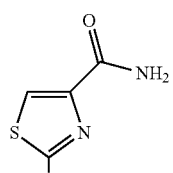
(59)

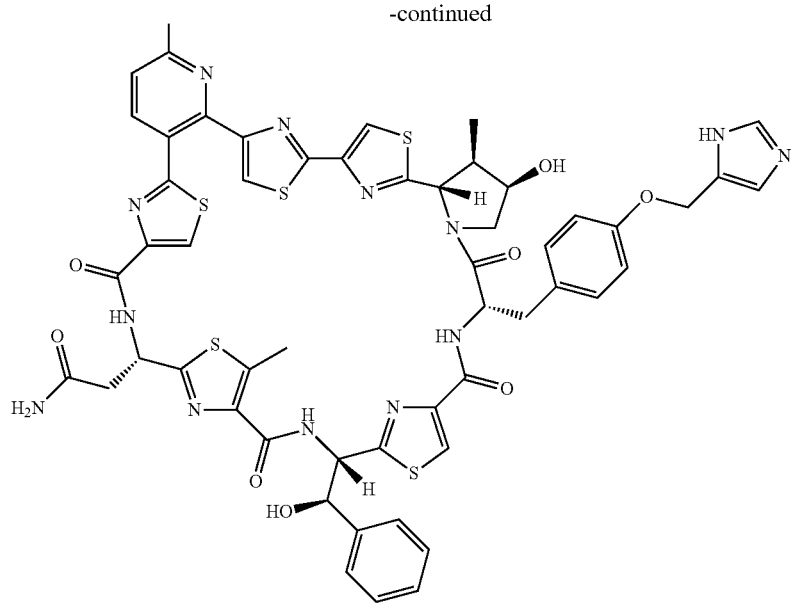
Compound 59 is prepared according to the procedures described in example 34. LC/MS: [M+H]$^+$ 1280, $R_f$=0.92 (method 1).
Example 54
Preparation of Pyrrolidine (60)
(60)
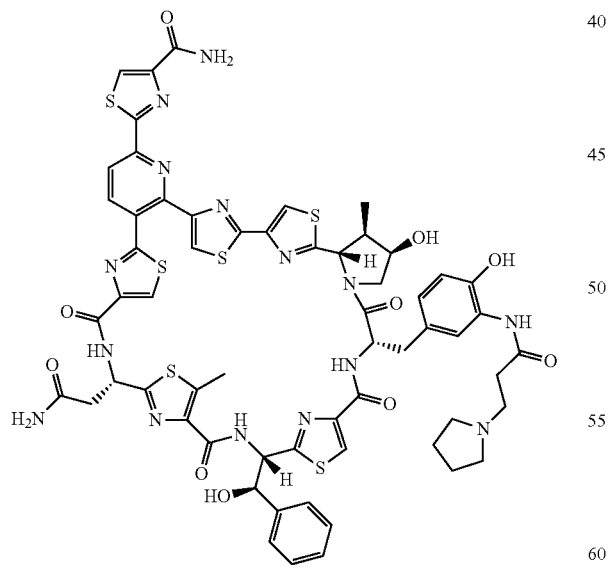
Compound 60 is prepared according to the procedures described in example 49. LC/MS: [M+2H]$^+$ 1341, $R_f$=0.91 (method 1).

Example 55
Preparation of Piperidine (61)
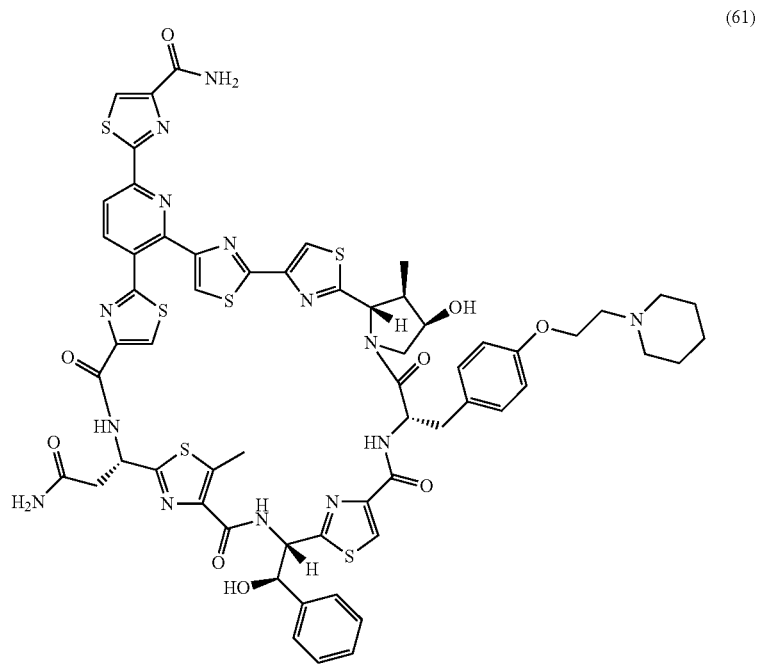
Compound 61 is prepared according to the procedures described in example 34. LC/MS: [M+H]$^+$ 1311, R$_t$=0.90 (method 1).
Example 56
Preparation of Amine (62)
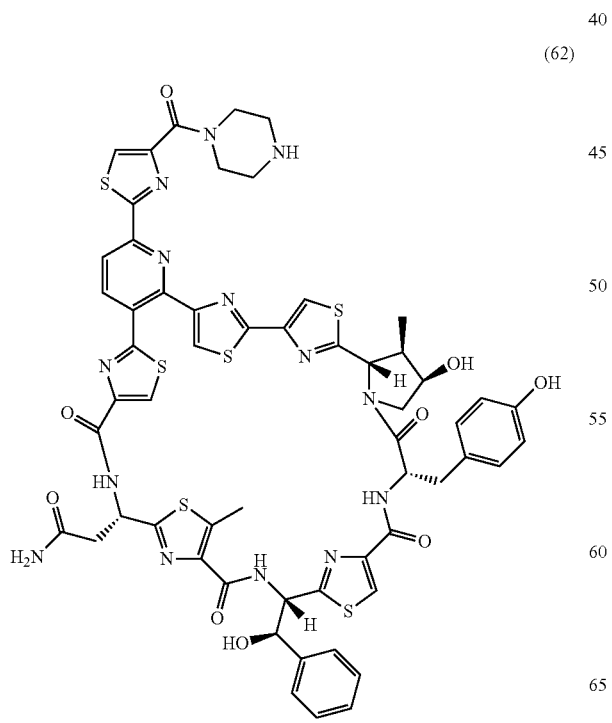

To a solution of compound 14 (300 mg, 0.25 mmol) in pyridine (10 mL) is added piperazine hydrochloride (108 mg, 1.25 mmol) and TBTU (160 mg, 0.50 mmol). The solution is stirred for 12 h, then concentrated onto silica gel and purified via flash chromatography (gradient elution 0-20% MeOH/DCM with 1% NH₄OH). Final purification via HPLC provides compound 62. LC/MS: [M+2H]⁺ 1270, $R_t$=0.85 min (method 1).

Example 57

Preparation of Amine (63)

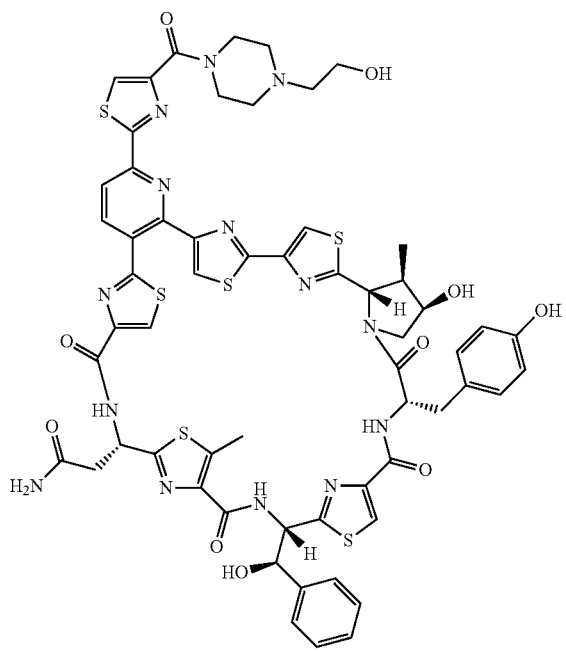

(63)

Compound 63 is prepared as described in example 56. LC/MS: [M+2H]⁺ 1314, $R_t$=0.92 min (method 1).

Example 58

Preparation of Amine (64)

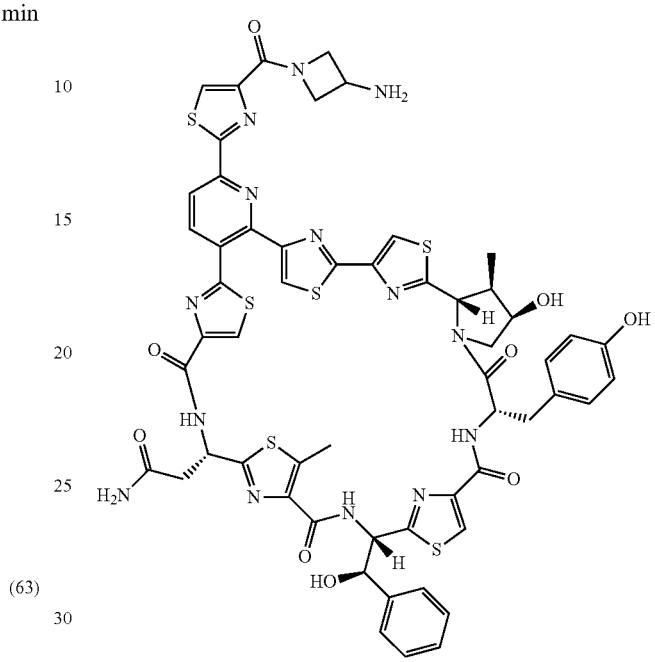

(64)

Compound 64 is prepared as described in example 56. LC/MS: [M+2H]⁺ 1256, $R_t$=1.1 min (method 1).

Example 59

Preparation of Amine (65)

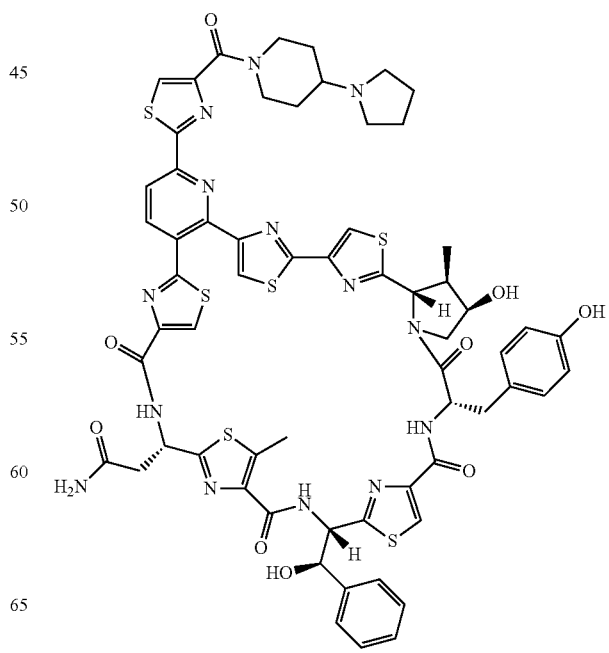

(65)

Compound 65 is prepared as described in example 56. LC/MS: [M+2H]$^+$ 1338, $R_t$=1.0 min (method 1).

Example 60

Preparation of Acid (66)

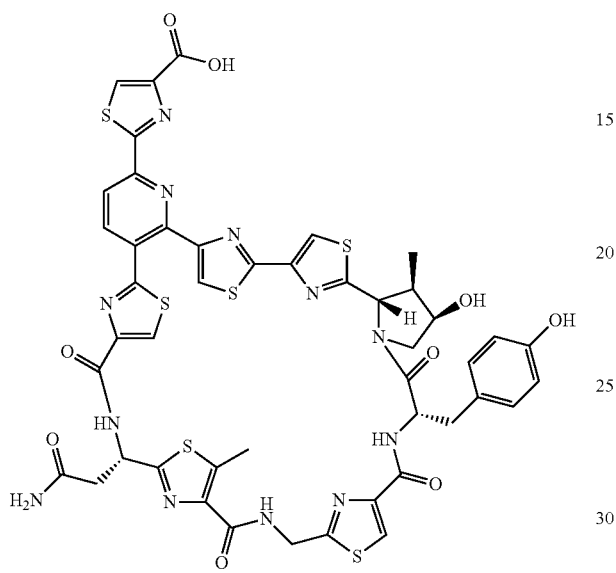
(66)

To a solution of pyrrolidine 13 (100 mg in 80 mL DCM, 20 mL MeOH, 5 mL H$_2$O) is added 2 mL of saturated aq LiOH. The reaction is stirred at RT for 4 h. NaOH is added (50 mg, s), and the reaction stirs 12 h. The reaction is heated to 40° C. for 3 h and is concentrated onto SiO$_2$ and purified by flash chromatography (gradient elution: 0-10% MeOH/DCM+ 0.1% AcOH) then HPLC (gradient elution: 30-60% MeCN in H$_2$O+0.1% TFA). LC/MS: [M+H]$^+$ 1095, $R_t$=0.94 min (method 1).

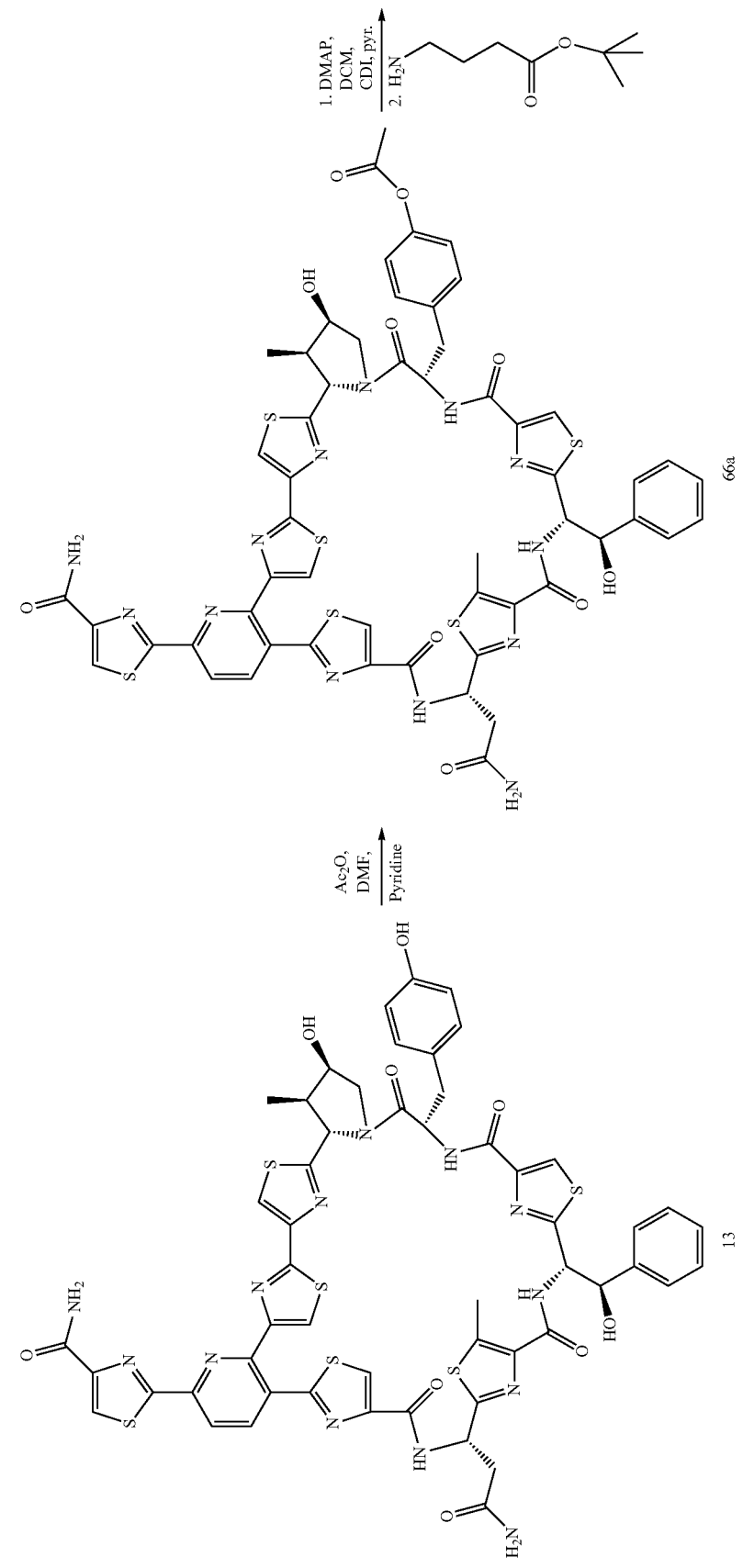

-continued
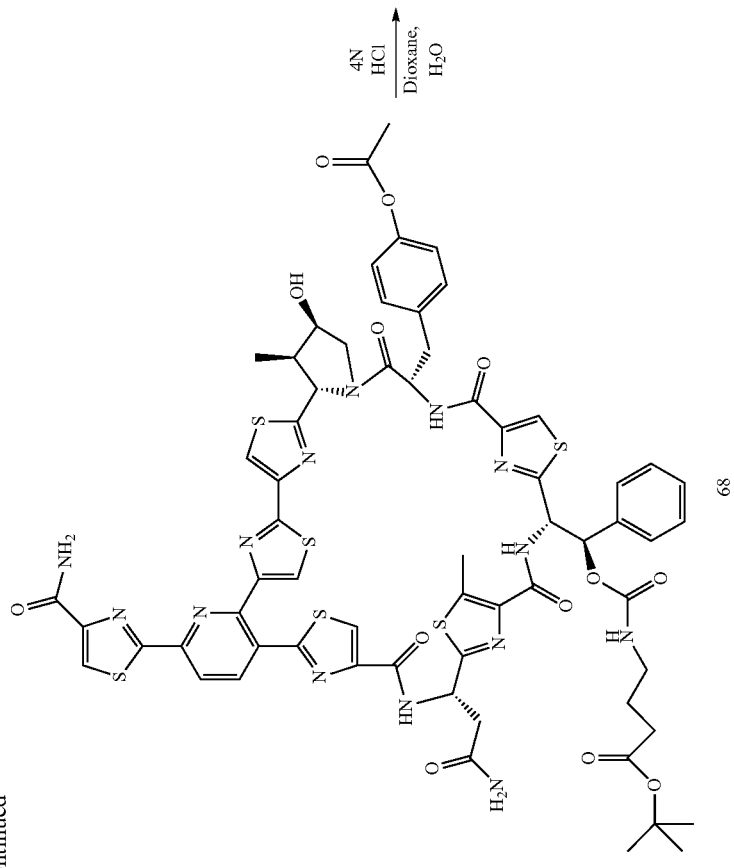
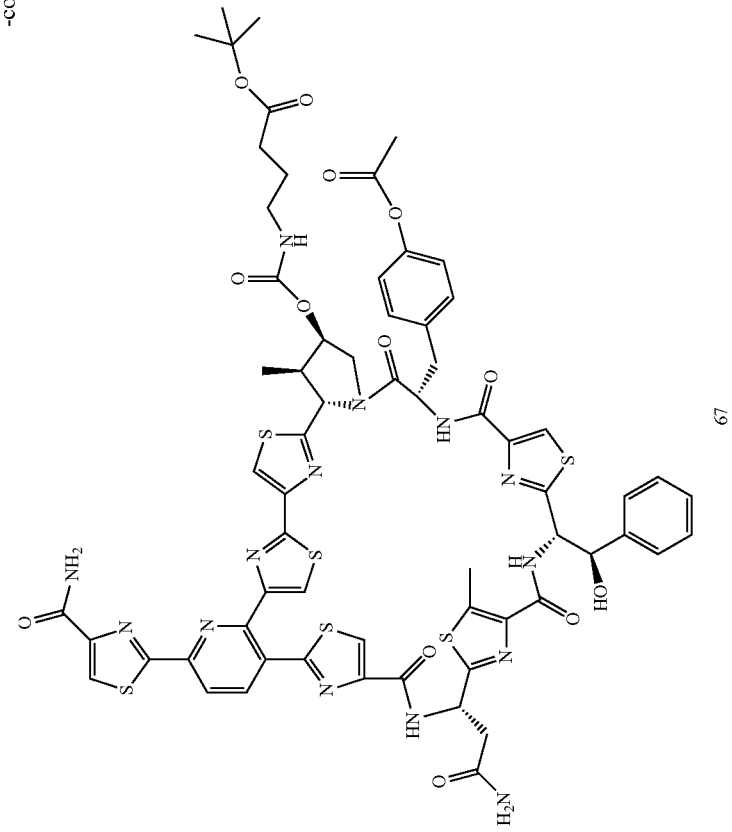

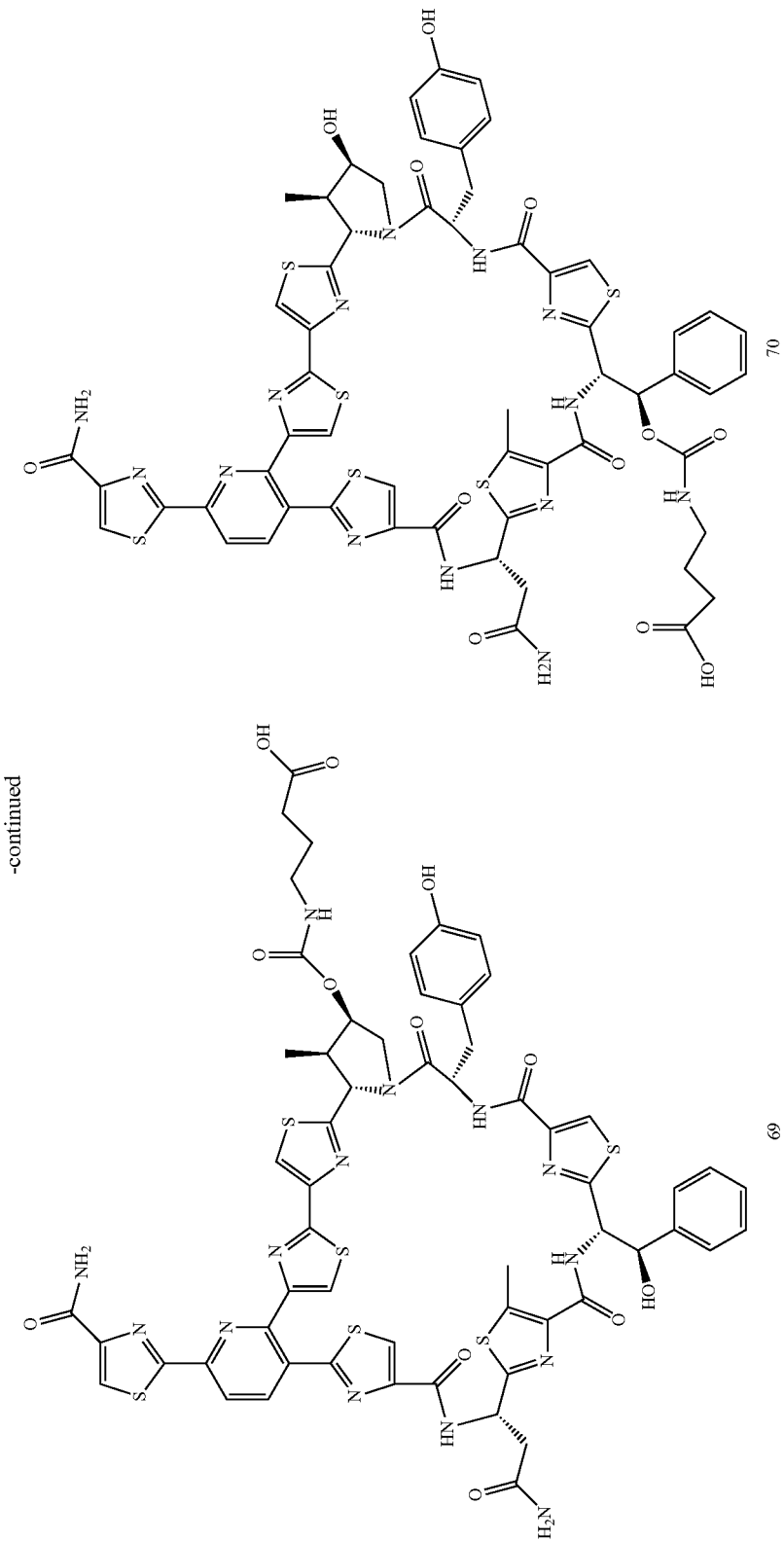

Example 61

Preparation of Acids (69, 70)

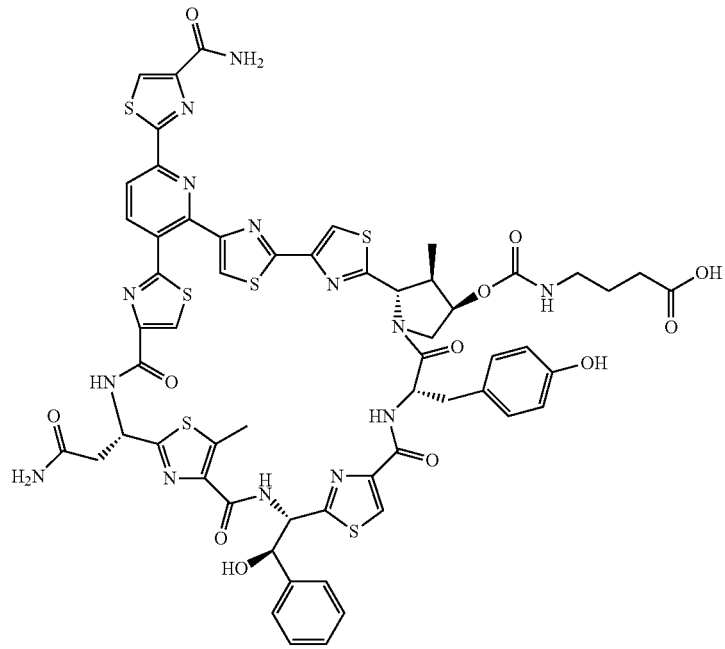

(69)

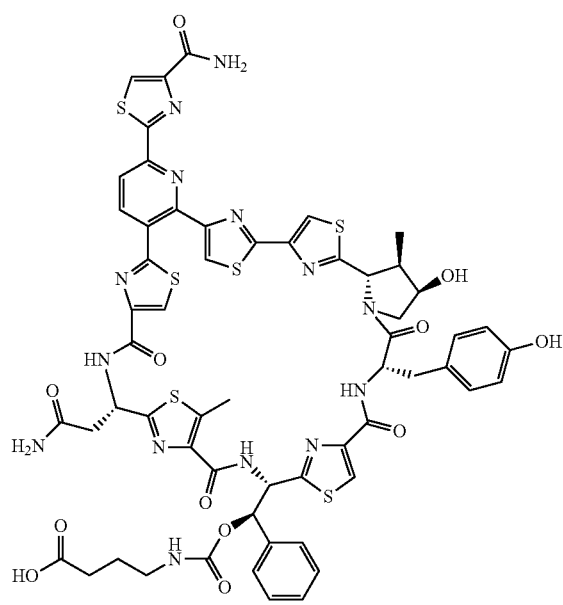

(70)

Step 1:

To a solution of compound 13 (400 mg, 0.333 mmol) in pyridine (0.54 mL) and DMF (40 mL), is added acetic anhydride (34.6 uL, 0.366 mmol). The reaction mixture is stirred at 0° C. for 3 h, and the reaction is quenched by MeOH. The reaction mixture is concentrated and the residue is purified by flash chromatography, (gradient elution: 0-10% MeOH/DCM) to provide the desired monoacetate 66a. LC/MS: $[M+2H]^+$ 1243, $R_t$=0.61 (method 14).

Step 2:

To a solution of compound 66a (100 mg, 0.08 mmol) in DMF (0.7 mL), is added DMAP (19.7 mg, 0.161 mmol) and CDI (39 mg, 0.24 mmol). The reaction mixture is stirred at RT for 3 h. Pyridine is then added (0.08 mL) followed by the amine (47.5 mg, 0.24 mmol). The reaction is stirred at RT for 12 h. The reaction mixture is concentrated, the residue is purified by flash chromatography, eluting with MeOH/DCM (0-10%) to provide compound 67 and compound 68. 67: LC/MS: $[M+NH_4]^+$ 1445, $R_t$=1.43 min. 68: LC/MS: $[M+NH_4]^+$ 1445, $R_t$=1.41 min (method 14).

Step 3:

To a solution of compound 67 (100 mg, 0.070 mmol) in DMF (3 mL), is added concentrated HCl (4 mL) and 4N HCl/dioxane (4 mL). The reaction is stirred at RT for 12 h.

The reaction mixture is concentrated, and the residue is purified by HPLC (neutral conditions) to provide compound 69. LC/MS: [M+2H]$^+$ 1330, $R_t$=1.21 min. Compound 68 (80 mg, 0.056 mmol) is dissolved in DMF (2 mL) and concentrated HCl (1.5 mL), 4N HCl/Dioxane (3 mL) and 3 drops of H$_2$O. The reaction is stirred at RT for 12 h. The reaction mixture is concentrated, and the residue is purified by HPLC (neutral condition) to provide compound 70. LC/MS: [M+2H]$^+$ 1330, $R_t$=1.19 min (method 14).

Example 62

Preparation of Urethanes (71, 72)

(71)

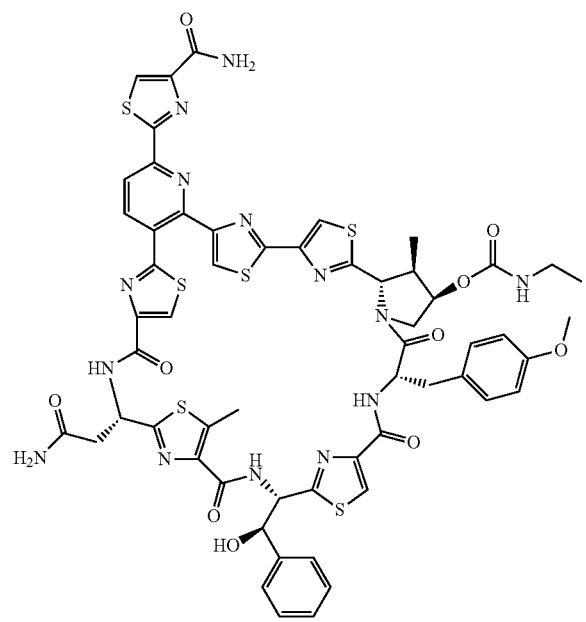

(72)

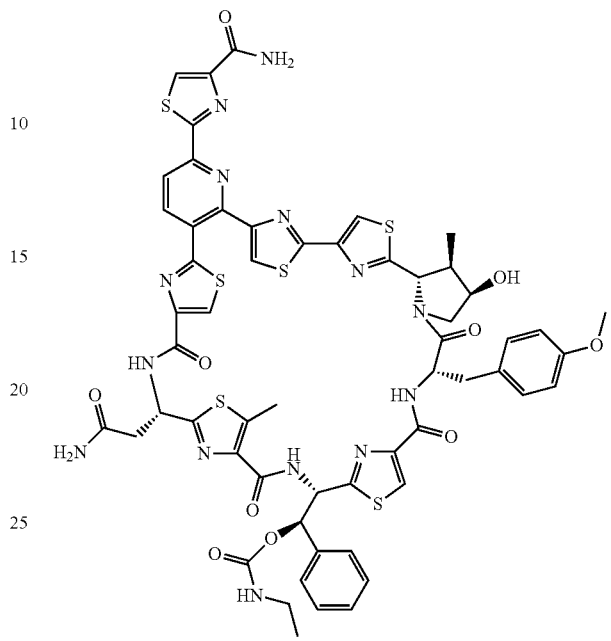

Step 1:

To a solution of the amide (13, 716 mg, 0.596 mmol) in methanol (6.4 mL) and dichloromethane (57 mL) are added N,N-diisopropylethylamine (1.04 mL, 5.96 mmol) and trimethylsilyldiazomethane (2 M in ether, 3.00 mL, 5.96 mmol) dropwise. The resulting mixture is stirred at RT for 12 h and then concentrated under reduced pressure. The resulting residue is treated with dichloromethane (100 mL) and filtered to provide a white solid of the methyl ether (720 mg). LC/MS: [M+H]$^+$ 1214, $R_t$=1.28 min (method 13).

Step 2:

To a solution of the methyl ether (106 mg, 0.0873 mmol) in N,N-dimethyl formamide (1 mL), N,N-diisopropylethylamine (76 uL, 0.437 mmol) and ethyl isocyanate (10 uL, 0.131 mmol) is added 1,8-diazabicyclo[5.4.0]undec-7-ene (13 uL, 0.0873 mmol) dropwise at 0° C. After 30 min at 0° C., methanol (0.5 mL) is added and then concentrated under reduced pressure. The residue is purified via prep-TLC (10% MeOH/DCM) and HPLC to provide compound 71 and compound 72. Compound 71: LC/MS: [M+H]$^+$ 1285, $R_t$=1.32 min (method 13). Compound 72: LC/MS: [M+H]$^+$ 1285, $R_t$=1.31 min (method 13).

Example 63
Preparation of Acids (73, 74)
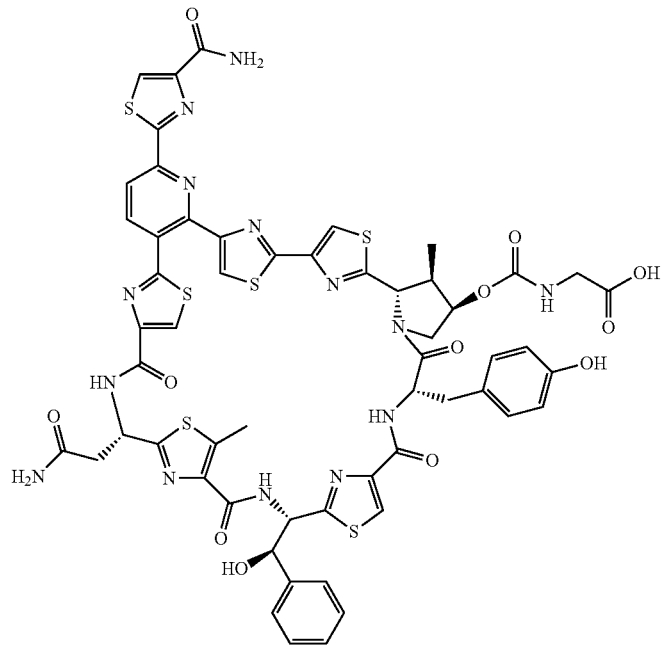
(73)
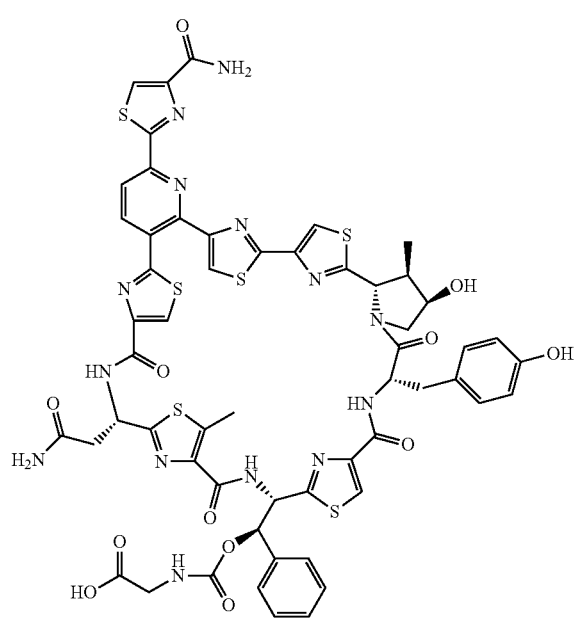
(74)
Compounds 73 and 74 are prepared as described in example 61. Compound 73: LC/MS: [M+2H]$^+$ 1302, R$_t$=1.19 min (method 14). Compound 74: LC/MS: [M+2H]$^+$ 1302, R$_t$=1.17 min (method 14).

Example 64
Preparation of Amine (75)
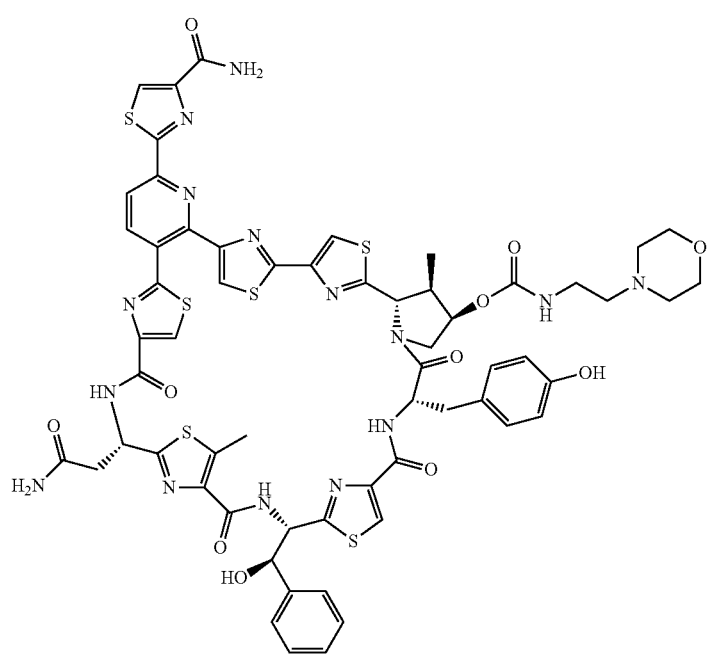
(75)
Compound 75 is prepared as described in example 61. LC/MS: [M+H]+ 1356, R$_t$=1.22 min (method 13).
Example 65
Preparation of Amines (76, 77)
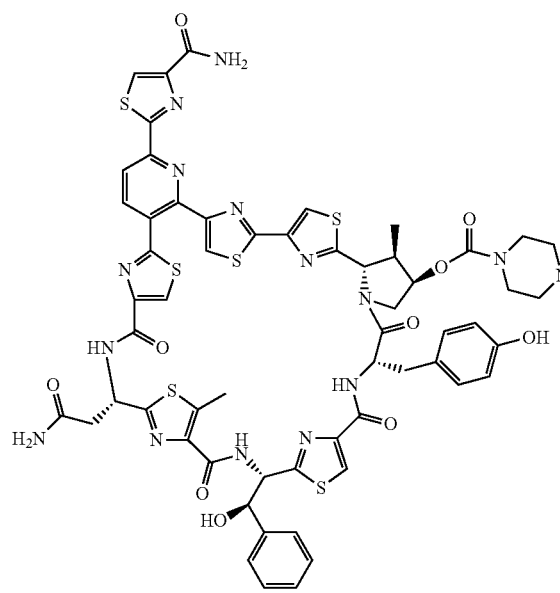
(76)
-continued
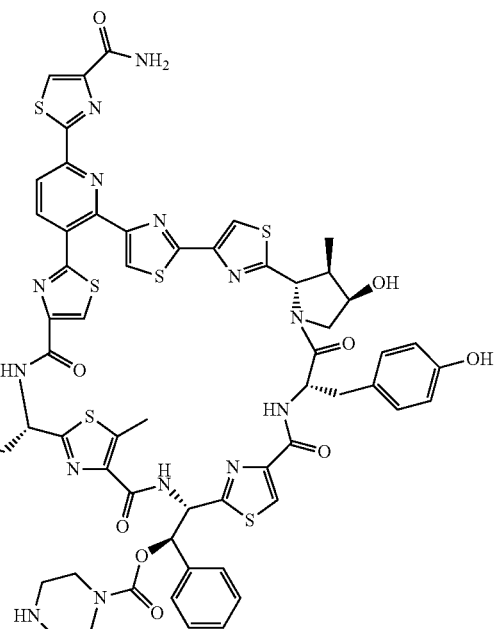
(77)
Compounds 76, 77 are prepared as described in example 61. Compound 76: LC/MS: [M+2H]+ 1313, R$_t$=1.10 min (method 13). Compound 77: LC/MS: [M+H]+ 1312, R$_t$=1.04 min (method 13).

Example 66
Preparation of Urethane (78)
(78)
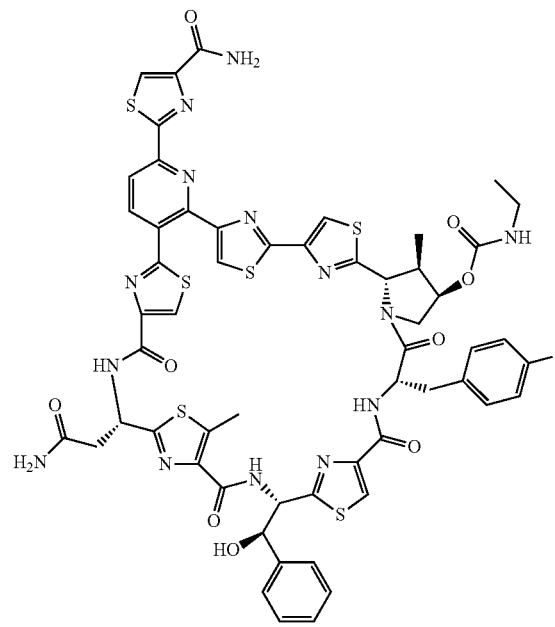
Compound 78 is prepared as described in example 61. Compound 78: LC/MS: [M+H]$^+$ 1271, R$_t$=1.11 min (method 13).
Example 67
Preparation of Acid (79)
(79)
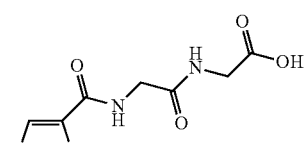
Compound 79 is prepared according to scheme 5. LC/MS: [M+2H]$^+$ 1287, R$_t$=1.20 min (method 14).
Example 68
Preparation of Acid (80)
(80)
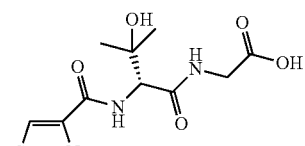
Compound 80 is prepared according to scheme 5. LC/MS: [M+2H]$^+$ 1316, R$_t$=1.15 min (method 14).
Example 69
Preparation of Acid (81)
(81)
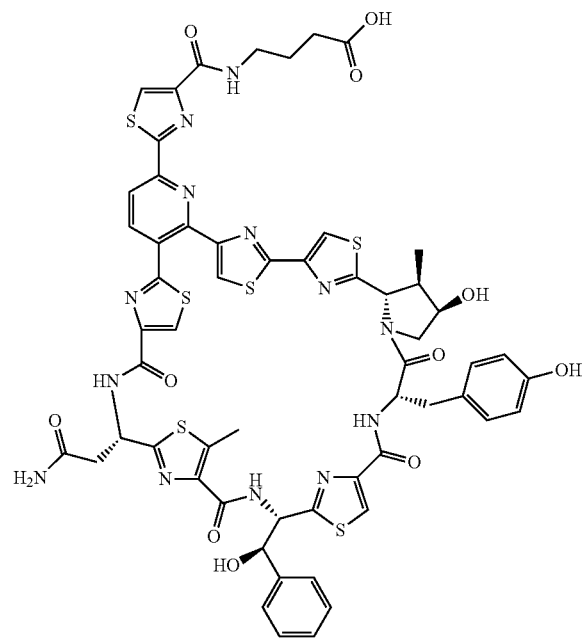

Compound 81 is prepared according to scheme 5. LC/MS: [M+2H]+ 1374, R$_t$=1.17 min (method 14).

Example 70

Preparation of Acid (82)

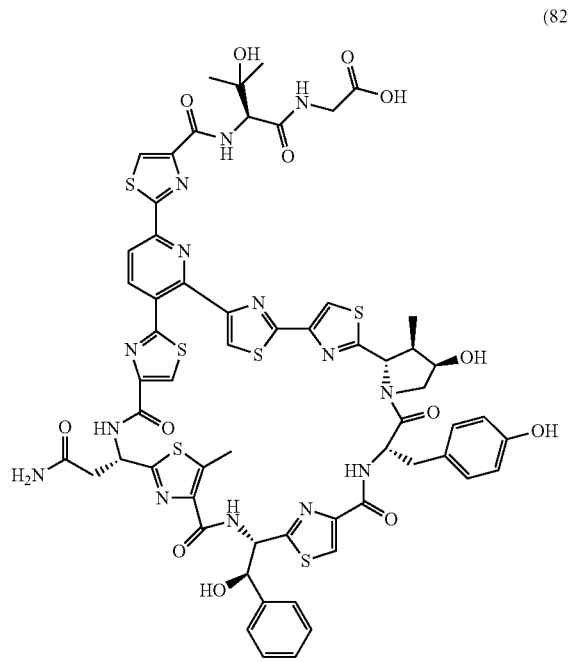 [SMILES: Cc1sc2nc1C(=O)N[C@@H]([C@H](O)c1ccccc1)c1nc(cs1)C(=O)N[C@@H](Cc1ccc(O)cc1)C(=O)N1C[C@H](O)[C@H](C)[C@H]1c1nc(cs1)-c1nc(cs1)-c1nc(-c3nc(C(=O)N[C@H](C(=O)NCC(=O)O)C(C)(C)O)cs3)ccc1-c1nc(cs1)C(=O)N[C@H]2CC(N)=O]
(82)

Compound 82 is prepared according to scheme 5. LC/MS: [M+2H]+ 1374, R$_t$=1.17 min (method 14).

Example 71

Preparation of Acid (83)

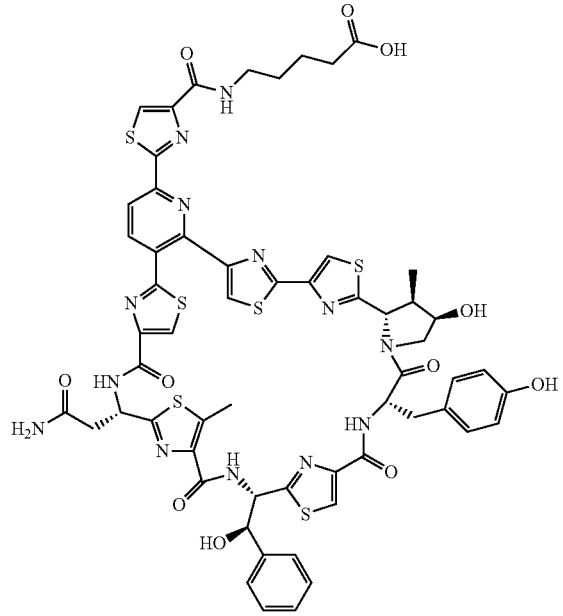
(83)

Compound 83 is prepared according to scheme 5. LC/MS: [M+H]+ 1300, R$_t$=1.24 min (method 14).

Example 72

Preparation of Acid (84)

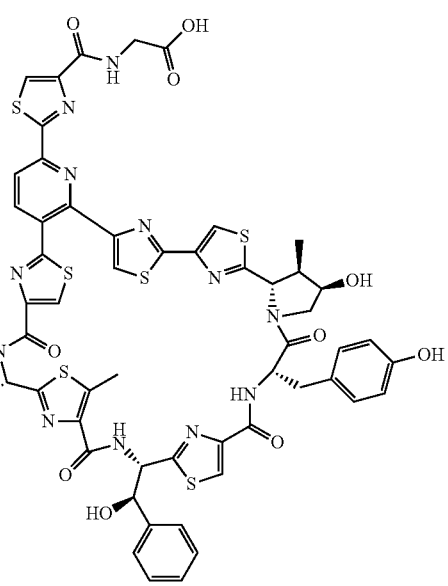
(84)

Compound 84 is prepared according to scheme 5. LC/MS: [M+2H]+ 1259, R$_t$=1.20 min (method 14).

Example 73

Preparation of Acid (85)

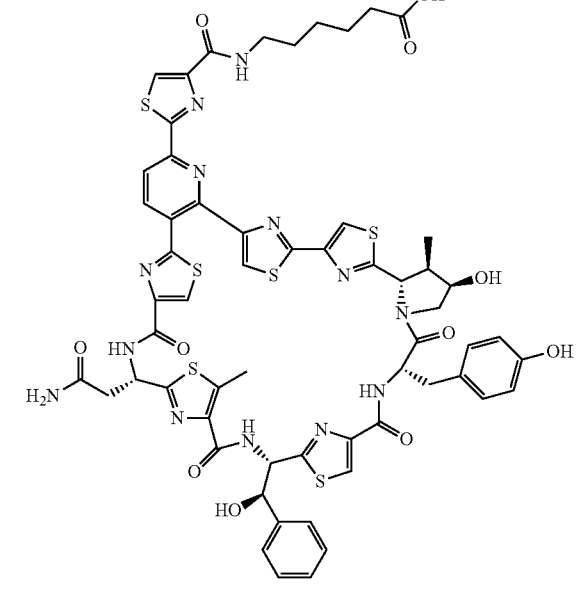
(85)

161
Compound 85 is prepared according to scheme 5. LC/MS: [M+2H]+ 1315, $R_t$=1.27 min (method 14).
Example 74
Preparation of Acid (86)
162
Compound 86 is prepared according to scheme 5. LC/MS: [M+2H]+ 1327, $R_t$=1.27 min (method 14).
Example 75
Preparation of Amine (87)
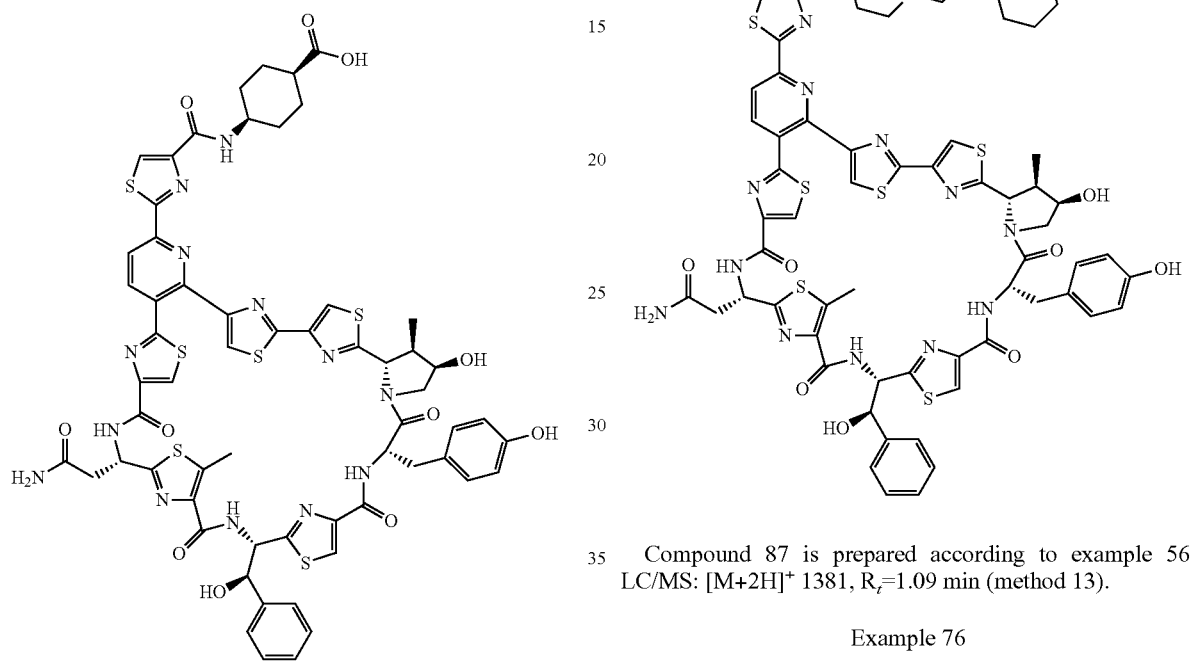
Compound 87 is prepared according to example 56. LC/MS: [M+2H]+ 1381, $R_t$=1.09 min (method 13).
Example 76
Preparation of Amine (88)
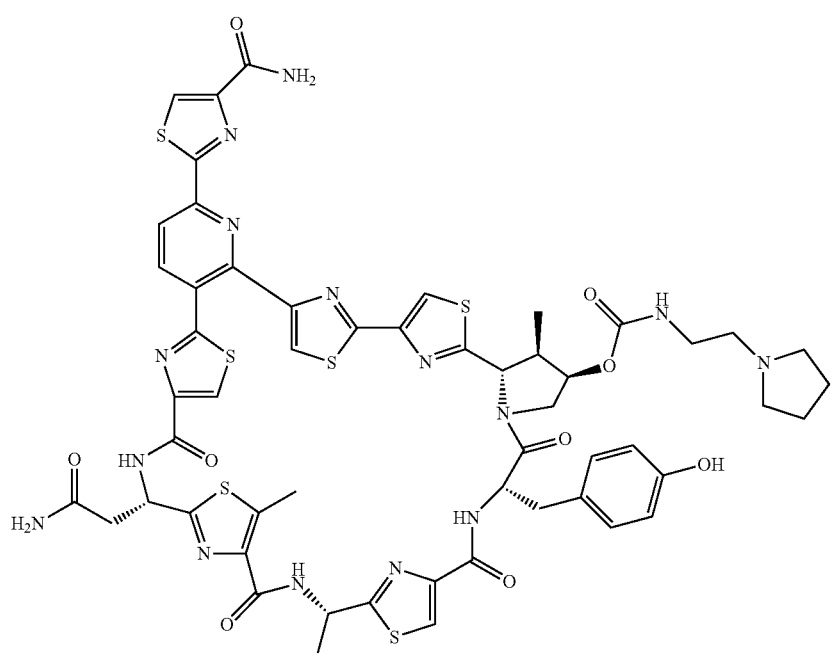

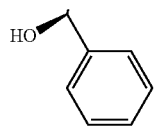
Compound 88 is prepared according to example 61.
LC/MS: [M+H]$^+$ 1340, R$_t$=0.99 min (method 14).
Example 77
Preparation of Amine (89)
(89)
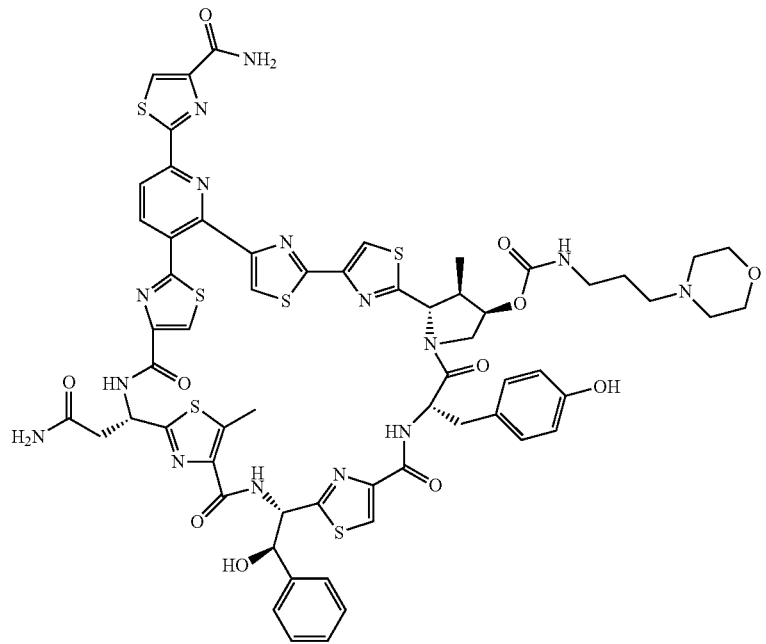

Compound 89 is prepared according to example 61.
LC/MS: [M+2H]+ 1371, $R_t$=1.00 min (method 14).
Example 78
Preparation of Amine (90)
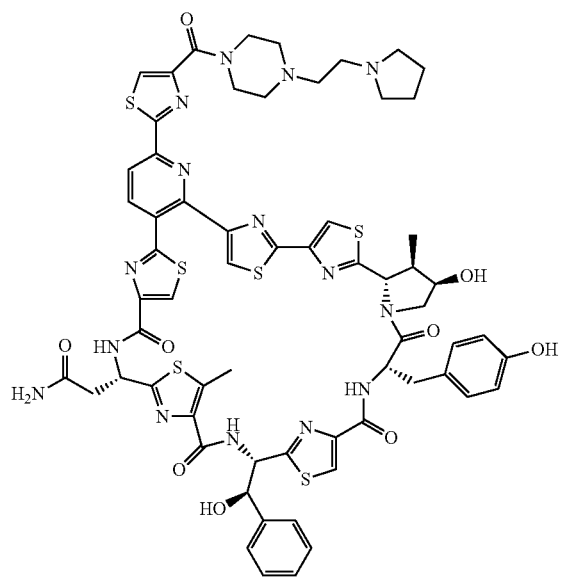
(90)
Compound 90 is prepared according to example 56.
LC/MS: [M+3H]+ 1368, $R_t$=1.07 min (method 13).
Example 79
Preparation of Amine (91)
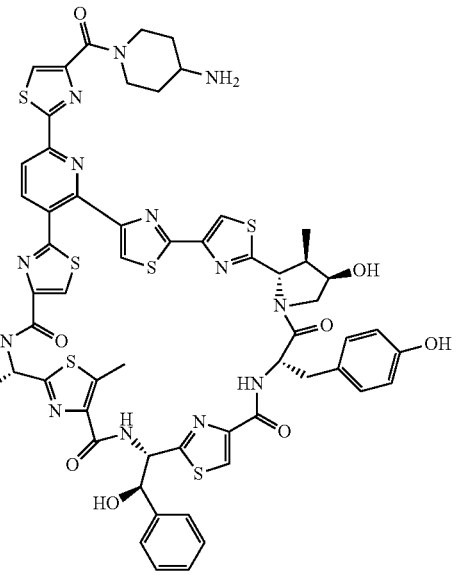
(91)
Compound 91 is prepared according to example 56.
LC/MS: [M+3H]+ 1385, $R_t$=0.99 min (method 13).
Example 80
Preparation of Amine (92)
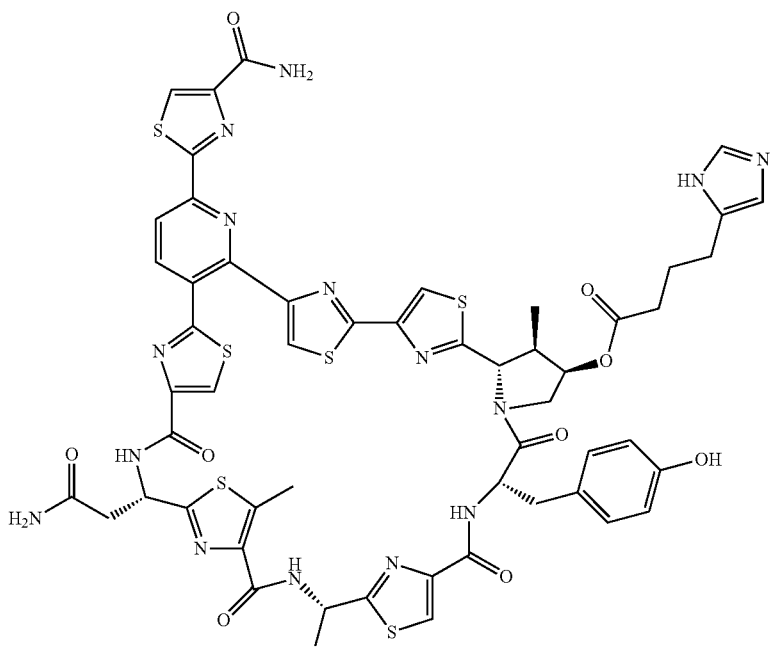
(92)

-continued
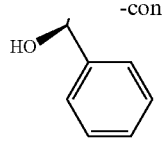
Compound 92 is prepared according to example 61.
LC/MS: [M+H]+ 1337, $R_t$=1.00 min (method 14).
Example 81
Preparation of Amine (93)
(93)
Compound 93 is prepared according to example 61.
LC/MS: [M+2H]+ 1287, $R_t$=0.96 min (method 14).

Example 82
Preparation of Diamine (94)
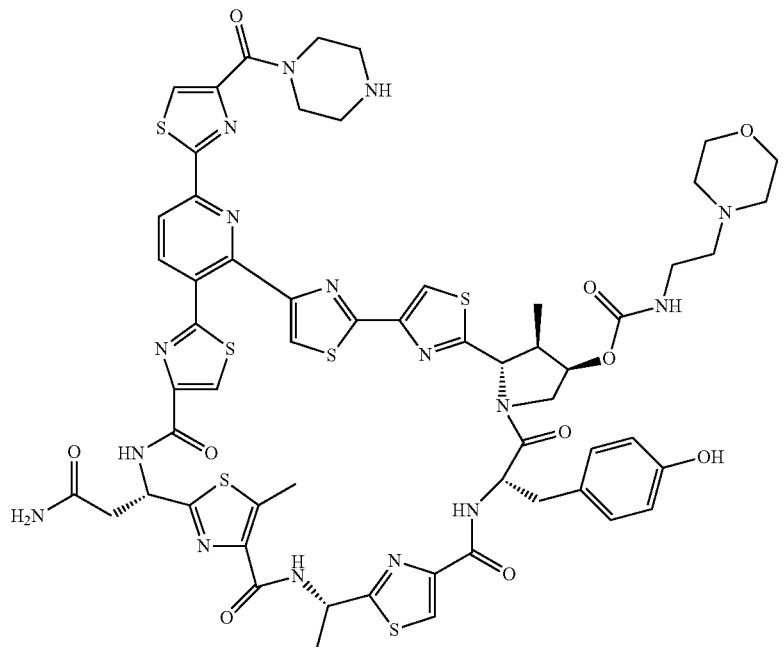
(94)
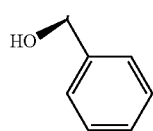
Compound 94 is prepared according to the procedures described in examples 56 and 61. LC/MS: [M+3H]$^+$ 1427, $R_t$=0.80 min (method 14).

Example 83
Preparation of Diol (95)
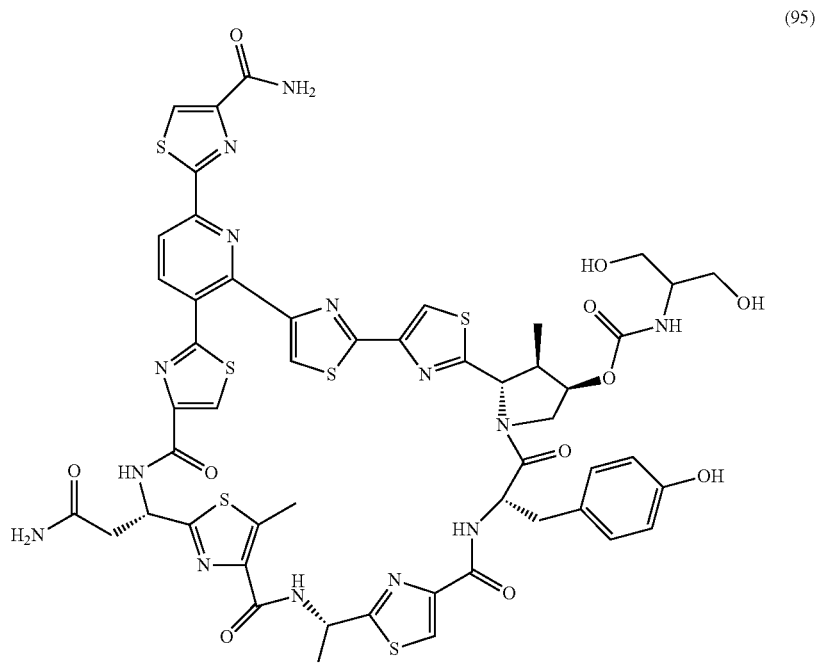
(95)
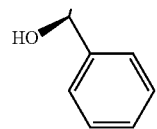
Compound 95 is prepared according to the procedures described in example 61. LC/MS: [M+H]$^+$ 1317, R$_t$=1.15 min (method 14).

Example 84

Preparation of Diamine (96)

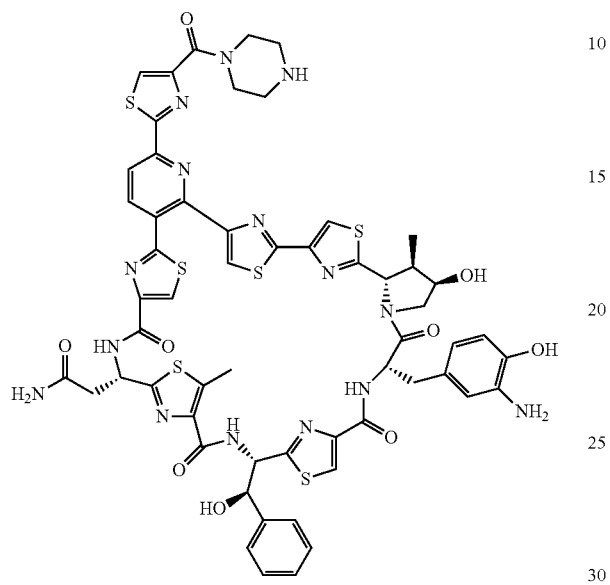

(96)

Compound 96 is prepared according to the procedures described in examples 56 and 47. LC/MS: [M+3H]⁺ 1286, $R_t$=0.85 min (method 14).

Example 85

Preparation of Diamine (97)

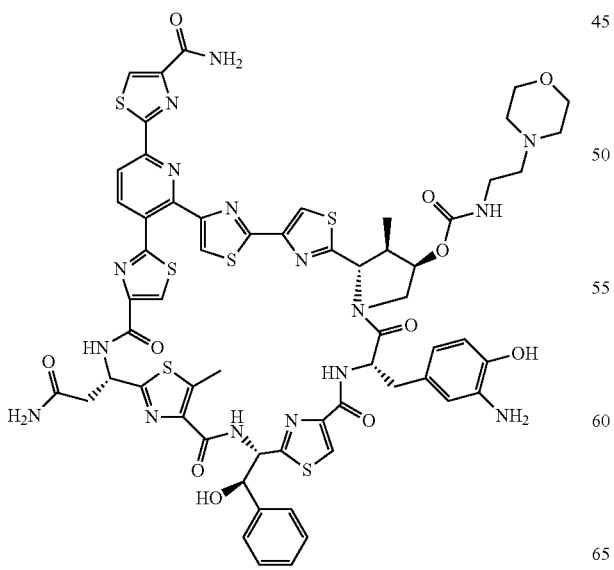

(97)

Compound 97 is prepared according to the procedures described in examples 61 and 47. LC/MS: [M+3H]⁺ 1373, $R_t$=0.93 min (method 14).

Example 86

Preparation of Polyol (98)

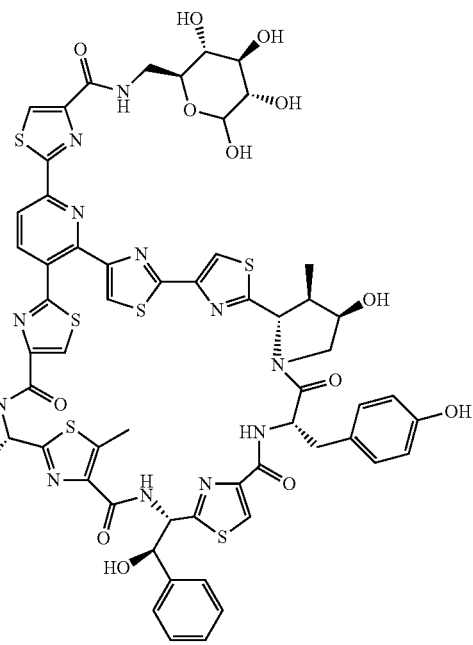

(98)

Compound 98 is prepared according to the procedures described in example 56. LC/MS: [M+3H]⁺ 1364, $R_t$=1.07 min (method 13).

Scheme 7:
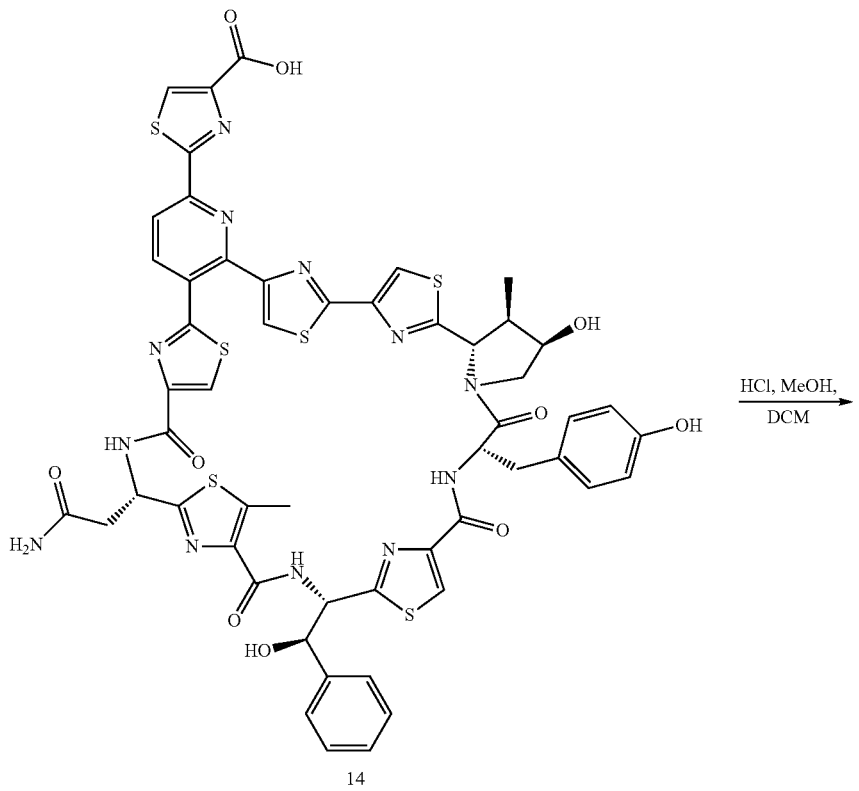
14
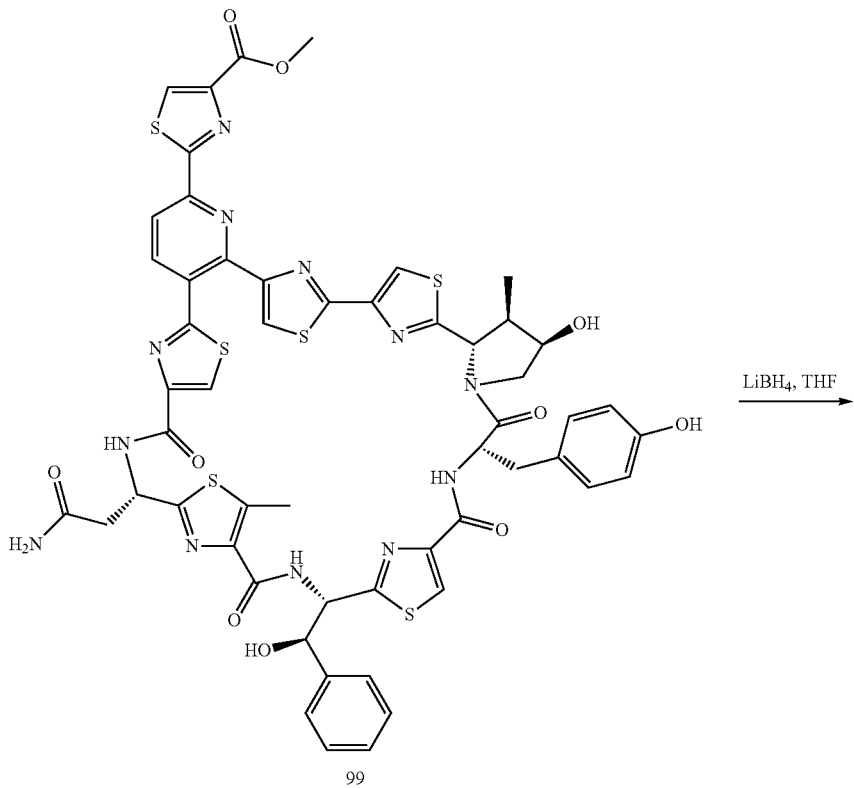
99

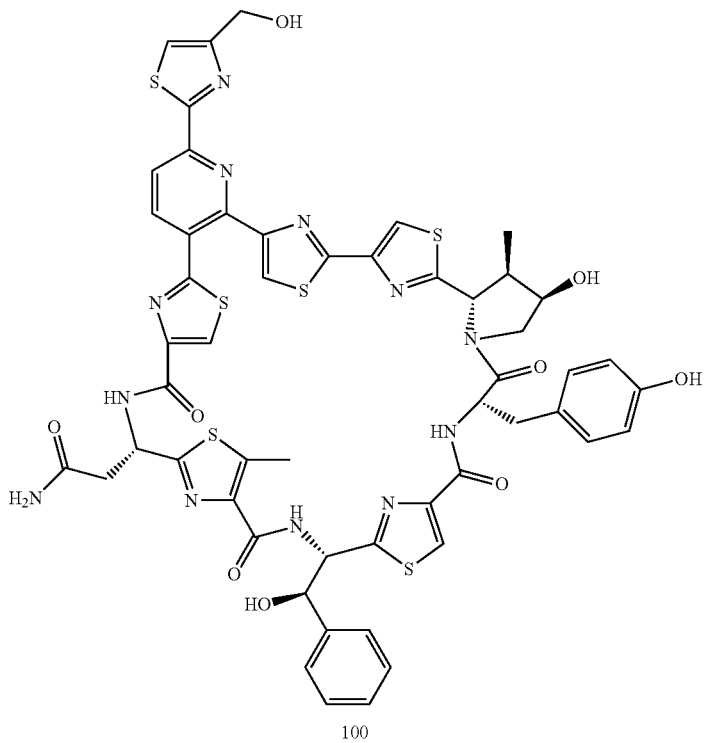 [SMILES: Cc1sc2nc1C(=O)N[C@@H]([C@H](O)c1ccccc1)c1nc(cs1)C(=O)N[C@@H](Cc1ccc(O)cc1)C(=O)N1C[C@H](O)[C@H](C)[C@H]1c1nc(cs1)-c1nc(cs1)-c1nc(-c3nc(CO)cs3)ccc1-c1nc(cs1)C(=O)N[C@H]2CC(N)=O]

100

Example 87

Preparation of Alcohol (100)

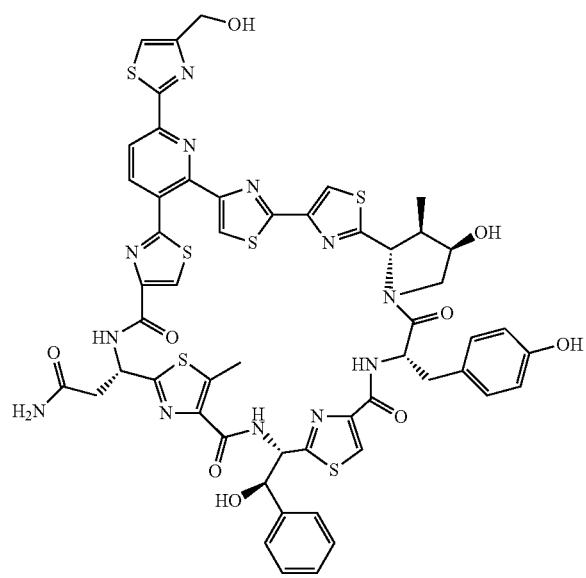

(100)

Step 1:

To a solution of acid 14 (650 mg, 0.5410 mmol) in DCM (50 mL) and MeOH (50 mL) is added 12N HCl (aq) (3.0 mL). The mixture stirs at ambient temperature 12 h. The mixture is mounted onto $SiO_2$ and purified by flash chromatography (gradient elution: 0-100% Acetone/DCM) which affords 410 mg of methyl ester 99. LC/MS: $[M+2H]^+$ 1216, $R_t$=1.34 min (method 13).

Step 2:

To a solution of methyl ester 99 (410 mg, 0.3373 mmol) in anhydrous THF (50 mL) at 0° C. is added $LiBH_4$ (73 mg, 3.373 mmol). The reaction stirs at RT for 12 h and is mounted onto $SiO_2$ and purified (10% MeOH/DCM) which affords 550 mg of alcohol 100. LC/MS: $[M+2H]^+$ 1188, $R_t$=1.22 min (method 13).

Example 88

Preparation of Amine (101)

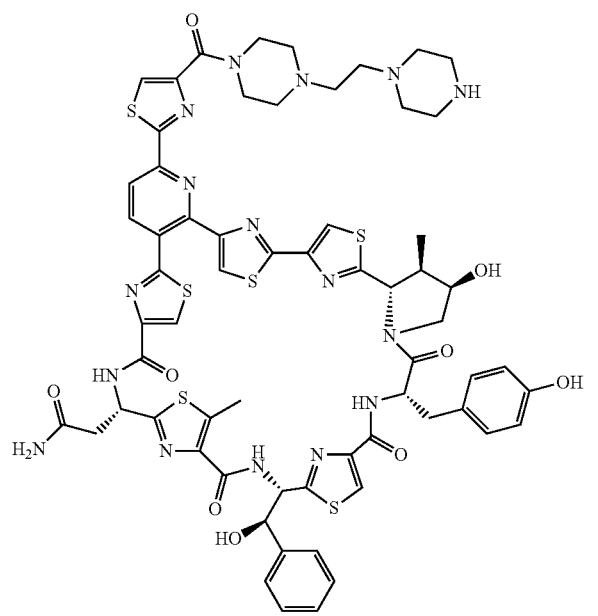 [SMILES: Cc1sc2nc1C(=O)N[C@@H]([C@H](O)c1ccccc1)c1nc(cs1)C(=O)N[C@@H](Cc1ccc(O)cc1)C(=O)N1C[C@H](O)[C@H](C)[C@H]1c1nc(cs1)-c1nc(cs1)-c1nc(-c3nc(CO)cs3)ccc1-c1nc(cs1)C(=O)N[C@H]2CC(N)=O]

(101)

Compound 101 is prepared according to the procedures described in example 56. LC/MS: [M+3H]+ 1383, $R_t$=1.03 min (method 13).

Example 89

Preparation of Amide (102)

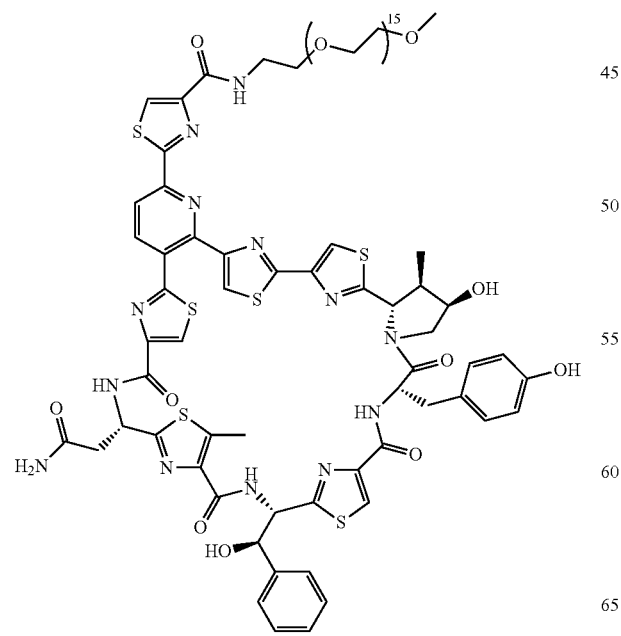

(102)

Compound 102 is prepared according to the procedures described in example 56. $^1$H NMR (400 MHz, DMSO-D6) δ ppm 1.08 (m, 4H) 1.59 (m, 1H) 1.89 (m, 1H) 2.19 (m, 1H) 2.33 (m, 1H) 2.56 (m, 2H) 2.70 (m, 5H) 2.95 (m, 2H) 3.23 (m, 4H) 3.51 (m, 93H) 3.78 (m, 1H) 3.88 (m, 1H) 4.17 (m, 1H) 4.69 (m, 1H) 5.02 (m, 1H) 5.16 (m, 1H) 5.31 (m, 1H) 5.45 (m, 1H) 6.35 (m, 1H) 6.60 (m, 2H) 6.69 (m, 1H) 6.92 (m, 2H) 7.03 (m, 2H) 7.23 (m, 4H) 7.36 (m, 1H) 7.62 (m, 1H) 8.22 (m, 1H) 8.27 (m, 1H) 8.43 (m, 2H) 8.50 (m, 2H) 8.62 (m, 2H) 8.81 (m, 1H) 9.16 (m, 1H).

Example 90

Preparation of Amine (103)

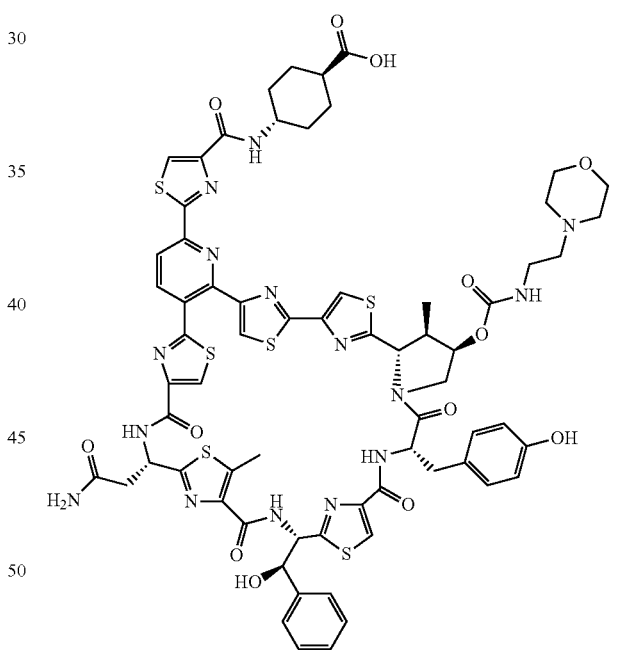

(103)

Compound 103 is prepared according to the procedures described in example 61 and scheme 5. LC/MS: [M+3H]+ 1484, $R_t$=0.96 min (method 14).

Example 91

Preparation of Polyol (104)

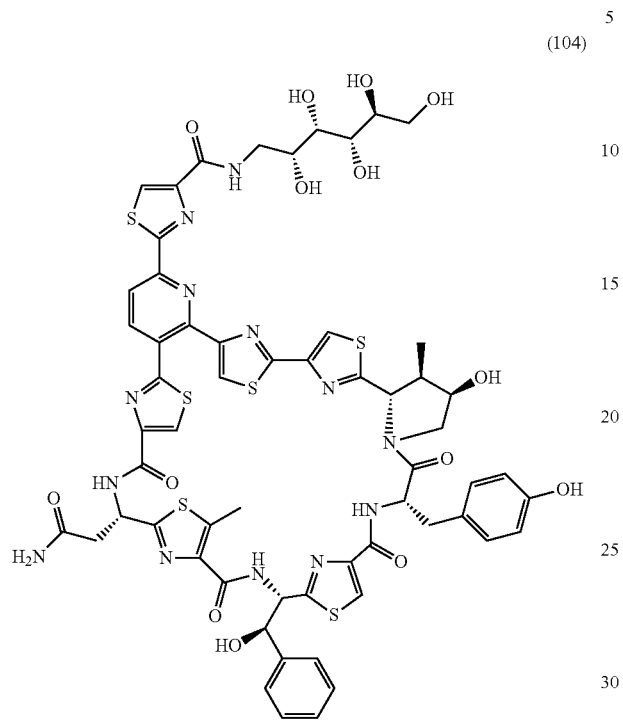

(104)

Compound 104 is prepared according to the procedures described in example 56. LC/MS: [M+2H]$^+$ 1365, R$_t$=1.10 min (method 13).

Example 92

Preparation of Polyol (105)

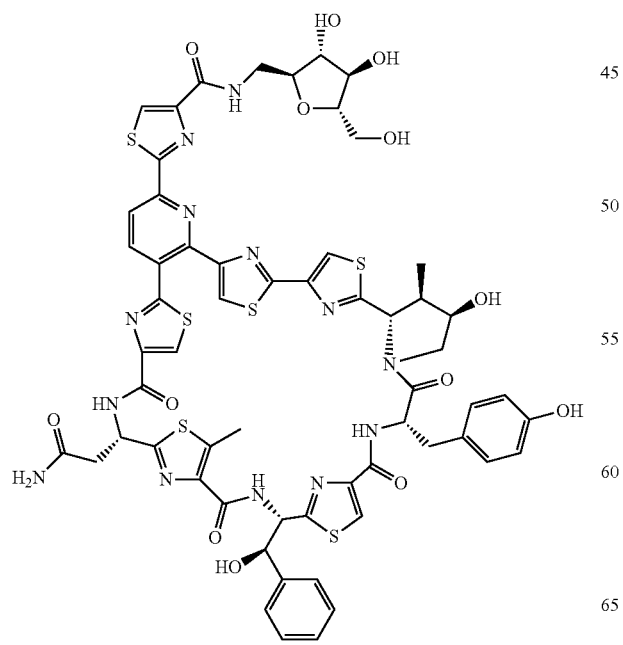

(105)

Compound 105 is prepared according to the procedures described in example 56. LC/MS: [M+3H]$^+$ 1348, R$_t$=1.10 min (method 14).

Example 93

Preparation of Aminoacid (106)

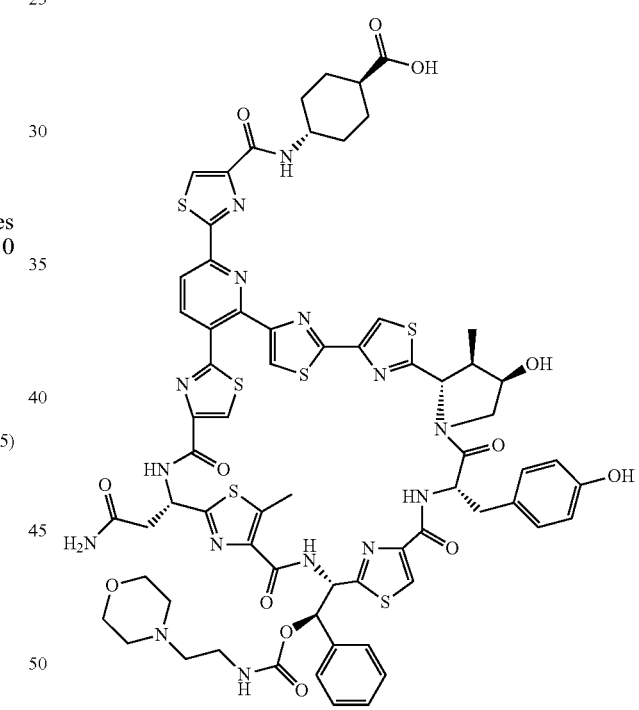

(106)

Compound 106 is prepared according to the procedures described in example 61 and scheme 5. LC/MS: [M+3H]$^+$ 1484, R$_t$=1.04 min (method 14).

Example 94
Preparation of Acid (107)

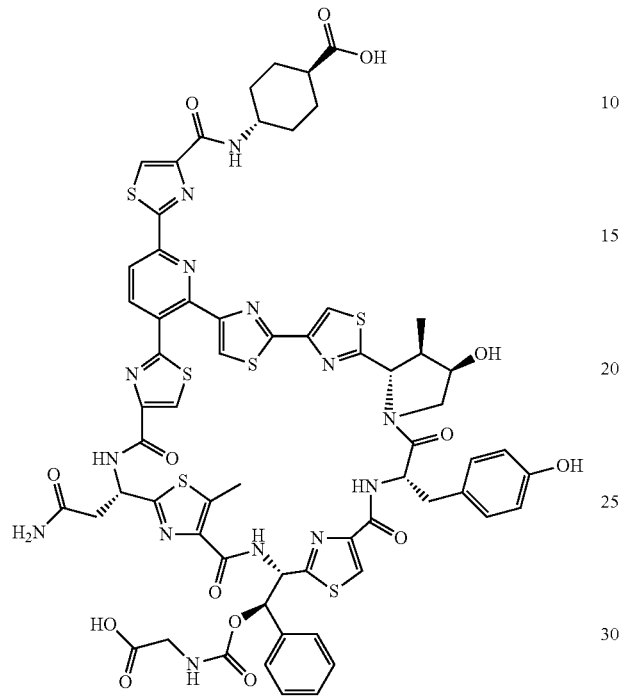
(107)

Compound 107 is prepared according to the procedures described in example 61 and scheme 5. LC/MS: [M+2H]$^+$ 1428, R$_t$=1.24 min (method 14).

Example 95
Preparation of Acid (108)

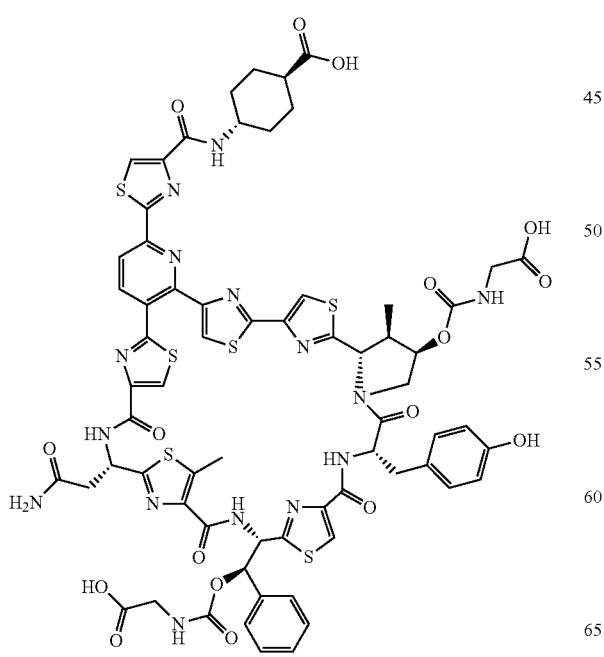
(108)

Compound 108 is prepared according to the procedures described in example 61 and scheme 5. LC/MS: [M+H]$^+$ 1528, R$_t$=1.22 min (method 14).

Example 96
Preparation of Diacid (109)

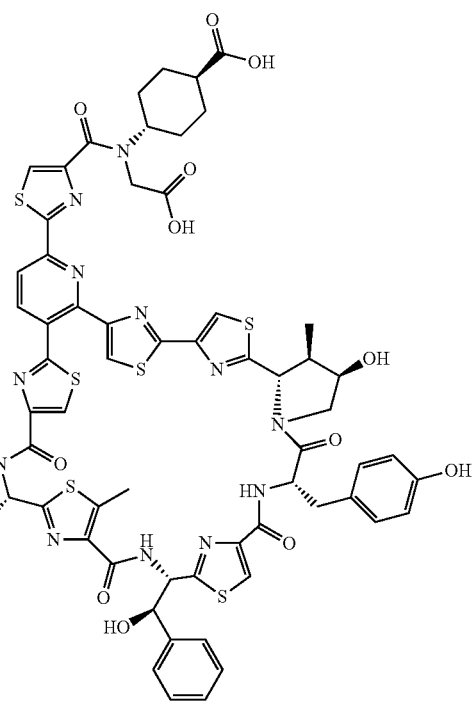
(109)

Step 1:
To a solution of trans-4-aminocyclohexane carboxylic acid hydrochloride (5.0 g, 34.92 mmol) in aqueous 2.0N NaOH (35 mL) is added benzyl chloroformate (5.0 mL, 34.92 mmol). The mixture stirs for 1.5 h. Then the suspension is acidified with 12N HCl (aq) to pH=1. H$_2$O is added (100 mL) and the precipitate is filtered off. The filter cake is dried to afford 8.2 g of 4-benzyloxycarbonylamino-cyclohexanecarboxylic acid. LC/MS: [M+H]$^{30}$ =278, R$_t$=0.85 min (method 6)

Step 2:

To a solution of 4-benzyloxycarbonylamino-cyclohexanecarboxylic acid (8.0 g, 28.78 mmol) in DCM (35 mL) and DMF (35 mL) is added t-butanol (10 mL, 105.4 mmol) and DMAP (1.4 g, 11.50 mmol). DIPC (10 mL) is added portionwise over 1 h. The resulting mixtures stirs 18 h. The mixture is mounted onto SiO$_2$ and purified by flash chromatography (gradient elution: 0-60% EtOAc/Hep) which affords 5.2 g of 4-benzyloxycarbonylamino-cyclohexanecarboxylic acid tert-butyl ester. $^1$H NMR (400 MHz, DMSO-D6) δ ppm 1.14 (m, 2H) 1.30 (m, 2H) 1.38 (m, 9H) 1.82 (m, 4H) 2.07 (m, 1H) 3.20 (m, 1H) 3.47 (m, 3H) 4.99 (m, 2H) 7.27 (m, 5H).

Step 3:

To a solution of 4-benzyloxycarbonylamino-cyclohexanecarboxylic acid tert-butyl ester (3.0 g, 9.009 mmol) in THF (80 mL) is added TEA (0.24 mL, 1.724 mmol) and 10% Pd/C (wet) (420 mg). The mixture stirs under a blanket of hydrogen gas at atmospheric pressure for 12 h. The mixture is then filtered though celite. The celite is washed with MeOH (50 mL). The filtrated is concentrated to afford 1.8 g of 4-amino-cyclohexanecarboxylic acid tert-butyl ester. LC/MS: [M+H]$^+$ 200, R$_t$=0.39 min (method 6).

Step 4:

To a solution of 4-amino-cyclohexanecarboxylic acid tert-butyl ester (500 mg, 2.500 mmol) in MeOH (3 mL) is added TEA (140 uL, 1.000 mmol), MgSO$_4$ (452 mg, 3.750 mmol), and benzaldehyde (278 uL, 2.750 mmol). The mixture stirs 1 h. The mixture is then cooled to 0° C. and NaBH$_4$ (568 mg, 15.00 mmol) is added portionwise over 10 min. The mixture stirs 1 h at ambient temperature. Then H$_2$O (20 mL) is added and the mixture is extracted with EtOAc (2×50 mL), dried and concentrated to affords 730 mg of 4-benzylamino-cyclohexanecarboxylic acid tert-butyl ester. LC/MS: [M+H]$^+$ 290, R$_t$=0.80 min (method 6).

Step 5:

To a solution of 4-benzylamino-cyclohexanecarboxylic acid tert-butyl ester (630 mg, 2.180 mmol) in DMF (20 mL) is added t-butyl bromoacetate (1 mL, 6.856 mmol) and Cs$_2$CO$_3$ (1.0 g, 3.069 mmol). The mixture stirs for 2 h. Then H$_2$O (50 mL) is added the mixture is extracted with EtOAc (2×100 mL), dried with sodium sulfate and concentrated. The resulting solid is purified by flash chromatography (gradient elution: 0-20% EtOAc/Hep) which affords 300 mg of 4-(benzyl-tert-butoxycarbonylmethyl-amino)-cyclohexanecarboxylic acid tert-butyl ester. $^1$H NMR (400 MHz, DMSO-D6) δ ppm 1.24 (m, 5H), 1.38 (m, 18H), 1.86 (m, 4H), 2.09 (m, 1H), 3.14 (m, 2H), 3.71 (m, 2H), 7.29 (m, 5H).

Step 6:

To a solution of 4-(benzyl-tert-butoxycarbonylmethyl-amino)-cyclohexanecarboxylic acid tert-butyl ester (300 mg, 0.7433 mmol) in EtOH (10 mL) is added 10% Pd/C (wet) (40 mg). The mixture stirs under a blanket of hydrogen gas at atmospheric pressure for 12 h. The mixture is then filtered though celite. The celite is washed with MeOH (50 mL). The filtrated is concentrated to afford 243 mg of 4-(tert-butoxycarbonylmethyl-amino)-cyclohexanecarboxylic acid tert-butyl ester. $^1$H NMR (400 MHz, DMSO-D6) δ ppm 0.98 (m, 2H), 1.25 (m, 2H), 1.36 (m, 9H), 1.41 (m, 9H), 1.81 (m, 4H), 2.05 (m, 1H), 2.28 (m, 1H), 3.20 (m, 2H).

Step 7:

To a solution of acid 14 (100 mg, 0.083 mmol) in DMF (10 mL) is added 4-(tert-butoxycarbonylmethyl-amino)-cyclohexanecarboxylic acid tert-butyl ester (40 mg, 0.125 mmol), DIPEA (45 uL, 0.250 mmol), and HATU (63 mg, 0.166 mmol). The mixture stirs 12 h. The mixture is mounted onto SiO$_2$ and purified by flash chromatography (gradient elution: 0-7% MeOH/DCM) which affords 75 mg of the diester. LC/MS: [M+H]$^+$ 1498, R$_t$=1.64 min (method 13).

Step 8:

To a solution of the diester (75 mg, 0.0501 mmol) in DCM (2 mL) is added TFA (2 mL). The mixture stirs 1 h. Then DCM is removed under reduced pressure and the resulting oil is purified via HPLC (method 1) to afford 25.6 mg of compound 109. LC/MS: [M+2H]$^+$ 1385, R$_t$=1.08 min (method 13).

Example 97

Preparation of Diacid (110)

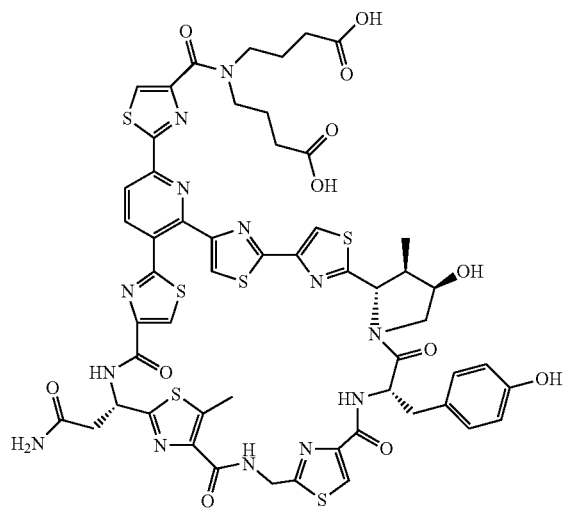

(110)

Compound 110 is prepared according to the procedures described in example 96. LC/MS: [M+2H]$^+$ 1267, R$_t$=1.00 min (method 13).

Example 98

Preparation of Diacid (111)

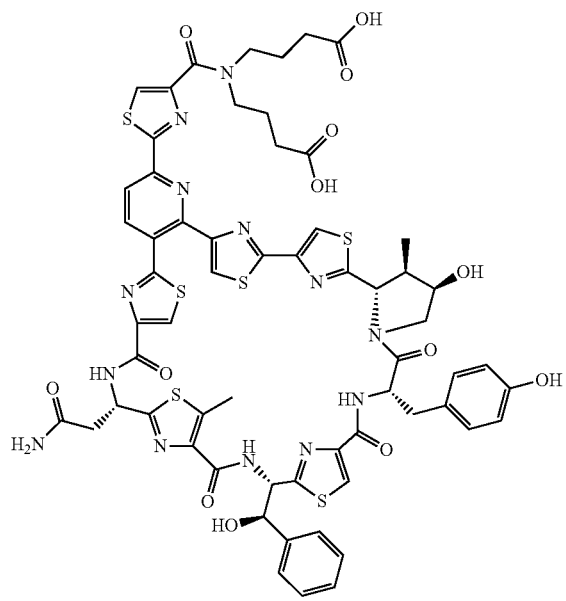

(111)

Compound 111 is prepared according to the procedures described in example 96. LC/MS: [M+3H]$^+$ 1374, R$_t$=1.21 min (method 14).

Example 99

Preparation of Diacid (112)

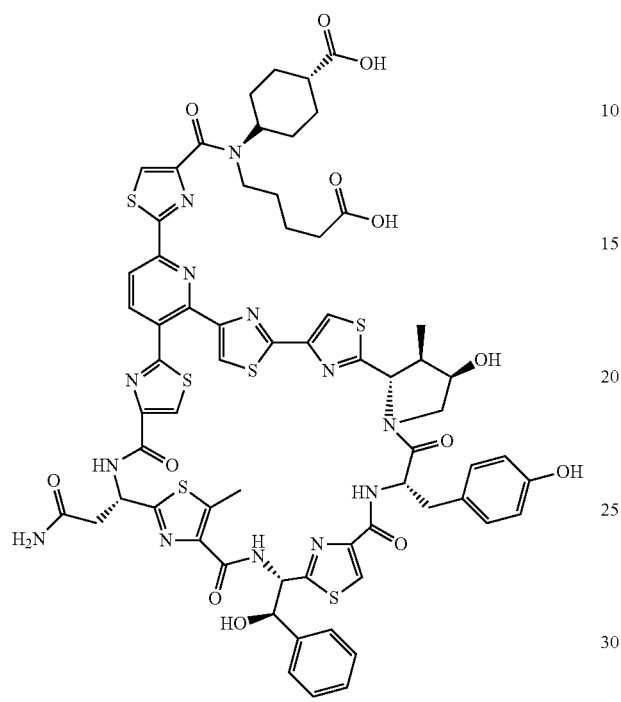

(112)

Compound 112 is prepared according to the procedures described in example 96. LC/MS: [M+2H]$^+$ 1427, $R_t$=1.10 min (method 13).

Example 100

Preparation of Diacid (113)

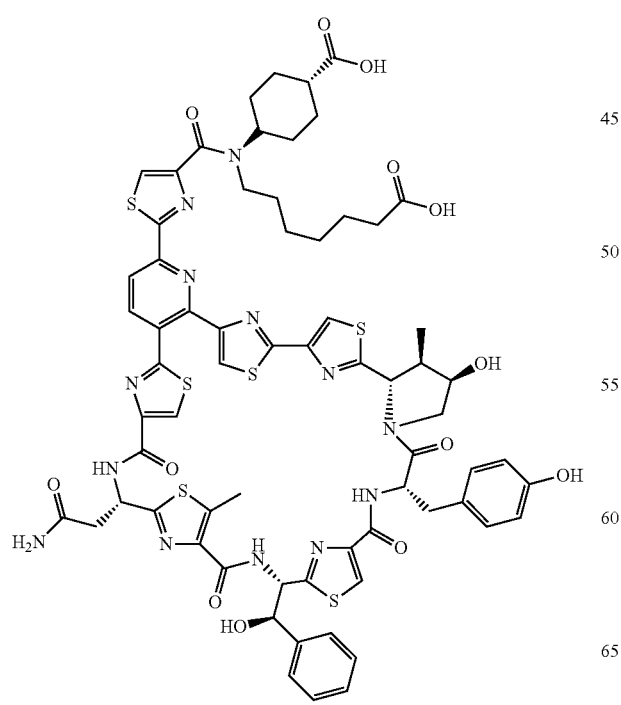

(113)

Compound 113 is prepared according to the procedures described in example 96. LC/MS: [M+3H]$^+$ 1456, $R_t$=1.18 min (method 13).

Example 101

Preparation of Diacid (114)

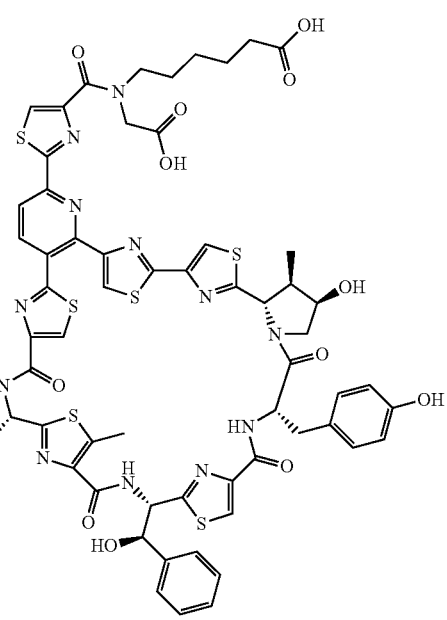

(114)

Compound 114 is prepared according to the procedures described in example 96. LC/MS: [M+H$_3$O]$^+$ 1390, $R_t$=1.14 min (method 13).

Example 102
Preparation of Diacid (115)
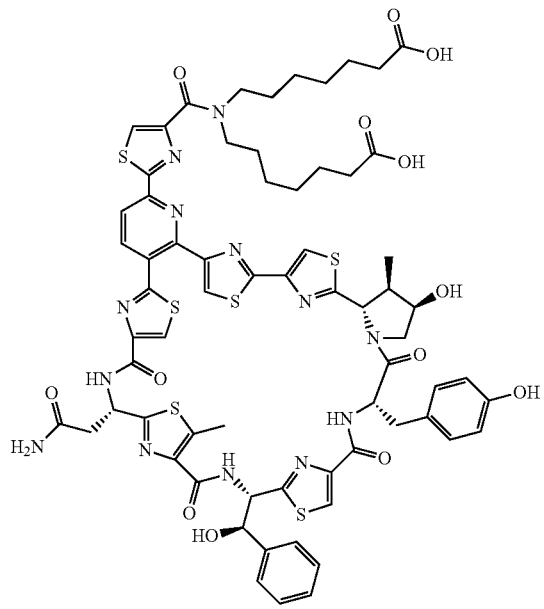
(115)
Compound 115 is prepared according to the procedures described in example 96. LC/MS: [M+3H]$^+$ 1458, R$_t$=1.30 min (method 13).
Example 103
Preparation of Diacid (116)
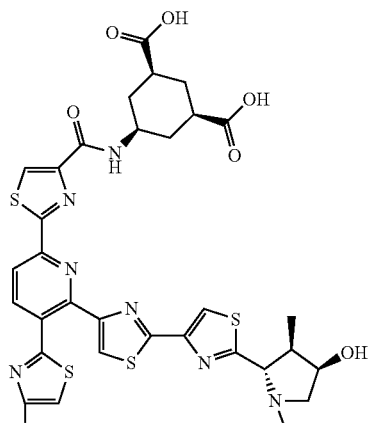
(116)
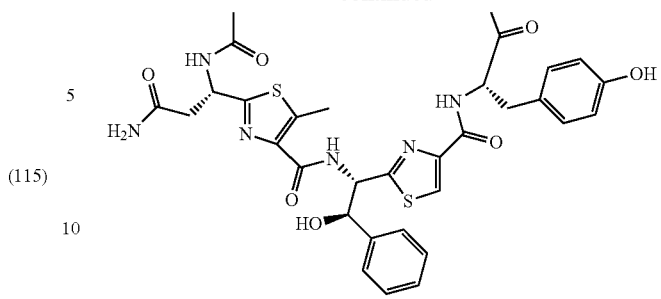
Compound 116 is prepared according to the procedures described in example 96. LC/MS: [M+2H]$^+$ 1371, R$_t$=1.13 min (method 13).
Example 104
Preparation of Diacid (117)
(117)
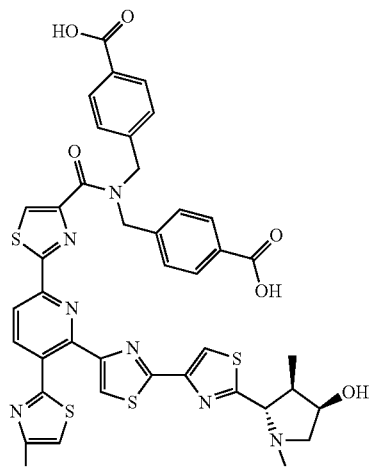
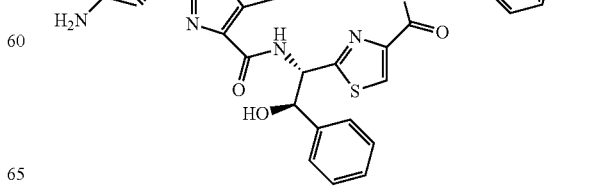

Compound 117 is prepared according to the procedures described in example 96. LC/MS: [M+2H]+ 1469, $R_t$=1.07 min (method 13).

Example 105

Preparation of Diacid (118)

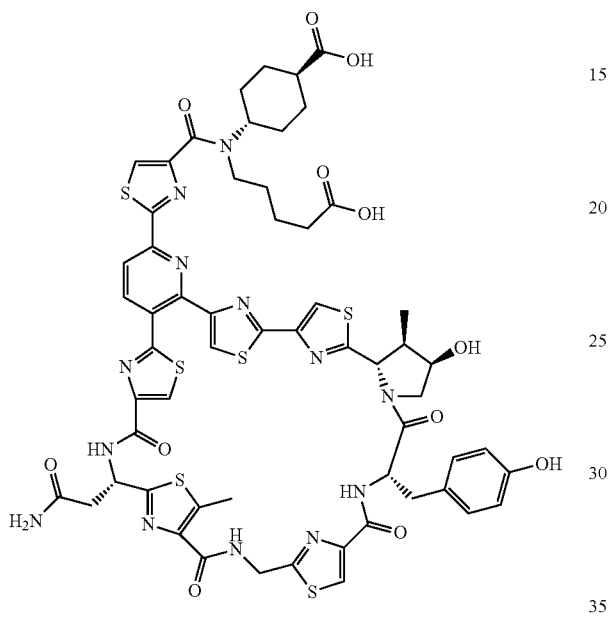

(118)

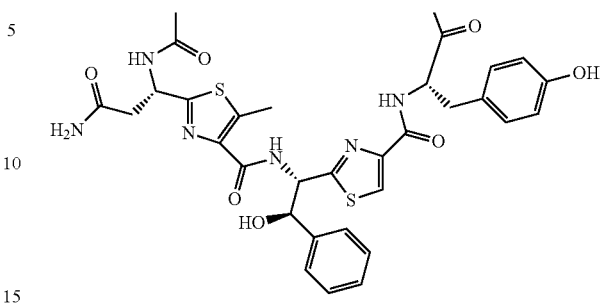

Compound 118 is prepared according to the procedures described in example 96. LC/MS: [M+2H]+ 1321, $R_t$=1.06 min (method 13).

Example 106

Preparation of Diacid (119)

(119)

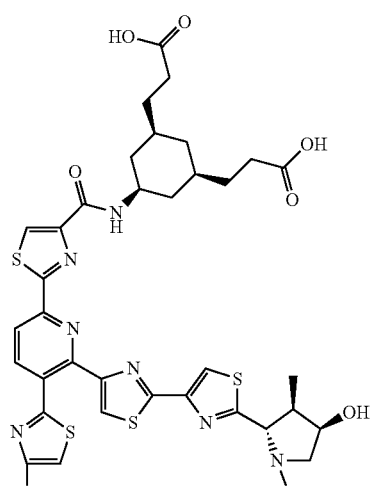

Compound 119 is prepared according to the procedures described in example 96. LC/MS: [M+2H]+ 1427, $R_t$=1.21 min (method 13).

Example 107

Preparation of Diacid (120)

(120)

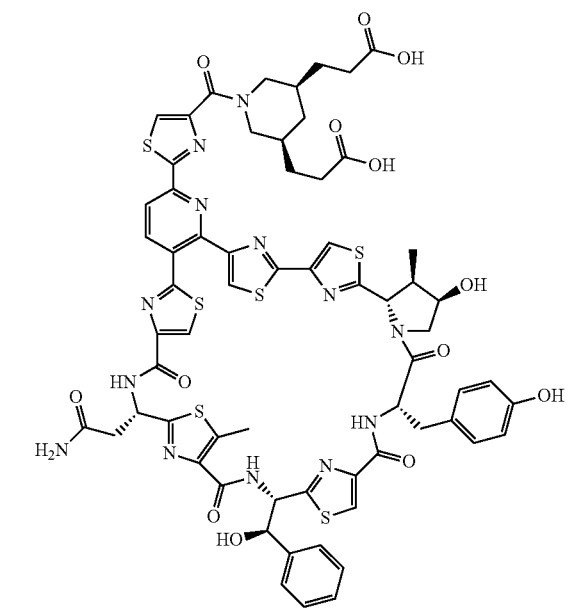

Compound 120 is prepared according to the procedures described in example 96. LC/MS: [M+2H]+ 1413, $R_t$=1.12 min (method 13).

Example 108

Preparation of Diacid (121)

(121)

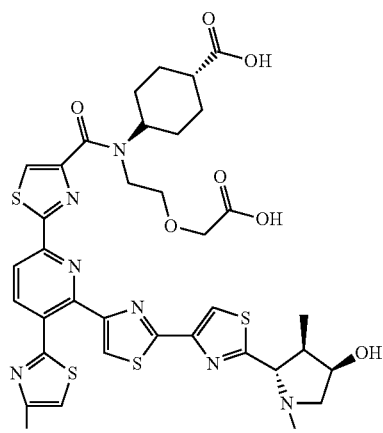

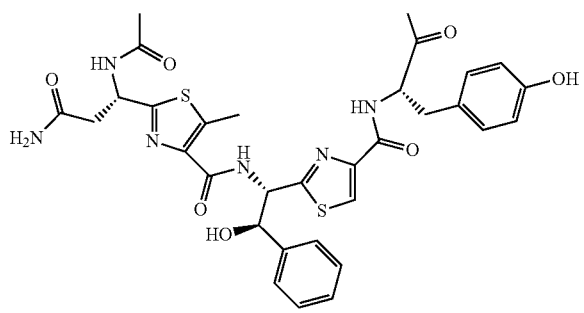

Compound 121 is prepared according to the procedures described in example 96. LC/MS: [M+2H]+ 1429, $R_t$=1.09 min (method 13).

Example 109

Preparation of Diacid (122)

(122)

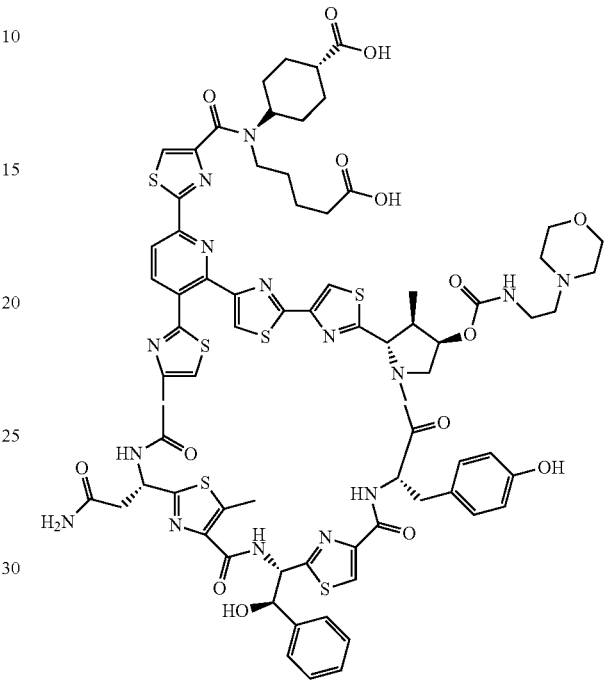

Step 1:

To a solution of trans-4-amino-cyclohexylcarboxylic acid methyl ester hydrochloride (4.5 g, 23.24 mmol) in MeOH (30 mL) is added TEA (1.3 mL, 9.339 mmol), MgSO$_4$ (4.2 g, 34.88 mmol), and benzaldehyde (2.5 mL, 24.74 mmol). The mixture stirs 1 h. The mixture is then cooled to 0° C. and NaBH$_4$ (5.0 g, 132.2 mmol) is added portionwise over 0.5 h. The mixture stirs 1 h at ambient temperature. Then H$_2$O (200 mL) is added and the mixture is extracted with EtOAc (2×500 mL), dried and concentrated. The resulting solid is purified by flash chromatography (gradient elution: 0-100% EtOAc/Hep) which affords 2.7 g of 4-benzylamino-cyclohexanecarboxylic acid methyl ester. LC/MS: [M+H]+ 248, $R_t$=0.82 min (method 11).

Step 2:

To a solution of amine 4-benzylamino-cyclohexanecarboxylic acid methyl ester (1.4 g, 5.645 mmol) in DMSO (3 mL) is added K$_2$CO$_3$ (1.5 g, 11.29 mmol) and methyl 5-bromovalerate (1.6 mL, 11.29 mmol). The mixture stirs 24 h, then H$_2$O (20 mL) is added and the mixture is extracted with EtOAc (2×100 mL). The organic solution is washed with aqueous sat. sodium chloride solution (100 mL), dried and concentrated. The resulting solid is purified by flash chromatography (gradient elution: 0-5% MeOH/DCM) which affords 960 mg of 4-[benzyl-(4-methoxycarbonyl-butyl)-amino]-cyclohexanecarboxylic acid methyl ester. LC/MS: [M+H]+ 362, $R_t$=0.78 min (method 9).

Step 3:

To a solution of amine 4-[benzyl-(4-methoxycarbonyl-butyl)-amino]-cyclohexanecarboxylic acid methyl ester (950 mg, 2.628 mmol) in MeOH (40 mL) is added 10% Pd/C (wet) (135 mg). The mixture stirs under a blanket of hydrogen gas at atmospheric pressure for 12 h. The mixture is then filtered though celite. The celite is washed with MeOH (50 mL). The filtrated is concentrated to afford 760 mg of amine 4-(4-methoxycarbonyl-butylamino)-cyclohexanecarboxylic acid methyl ester. LC/MS: [M+H]$^+$ 272, R$_t$=0.60 min (method 9).

Step 4:

To a solution of acid 14 (1.29 g, 1.073 mmol) in DMF (25 mL) is added amine amine 4-(4-methoxycarbonyl-butylamino)-cyclohexanecarboxylic acid methyl ester (437 mg, 1.609 mmol), DIPEA (0.573 mL, 3.219 mmol), and HATU (815 mg, 2.146 mmol). The mixture stirs 12 h. The mixture is mounted onto SiO$_2$ and purified by flash chromatography (gradient elution: 0-7.5% MeOH/DCM) which affords 700 mg of the diester. LC/MS: [M+2H]$^+$ 1455, R$_t$=1.45 min (method 13).

Step 5:

To a solution of the diester (400 mg, 0.2750 mmol) in anhydrous DMF (10 mL) is added DIPEA (0.24 mL, 1.348 mmol), DMAP (34 mg, 0.2782 mmol), and CDI (102 mg, 0.6289 mmol). The mixture stirs for 3 h, then 3,4-(2-aminoethyl)morpholine (400 mg, 3.072 mmol) is added and the resulting mixture is stirred 12 h. The reaction mixture is concentrated under reduced pressure to remove DMF and the residue is treated with water (100 mL) and stirred 10 min. The suspension is filtered and the filtercake is purified via preparatory TLC (10% MeOH/DCM) which affords 25 mg of the urethane. LC/MS: [M+3H]$^+$ 1612, R$_t$=1.12 min (method 14).

Step 6:

To a solution of the urethane-diester (25 mg, 0.0155 mmol) in DCM (1 mL) and MeOH (1 mL) is added 4.0N LiOH (aq) (0.4 mL, 0.100 mmol). The reaction stirs at RT for 1 h and the resulting diacid is purified via HPLC (method 1) and treated with 12N HCl (aq) (0.5 mL) to afford compound 122. LC/MS: [M+3H]$^+$ 1584, R$_t$=1.14 min (method 13).

Example 110

Preparation of Diacid (123)

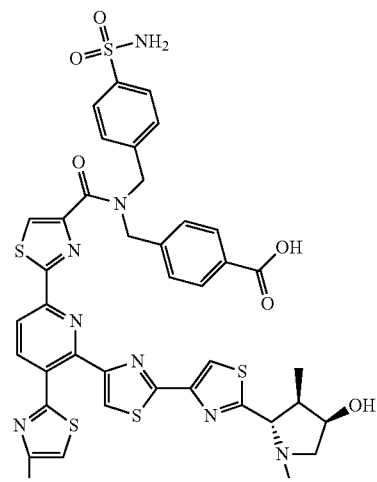

(123)

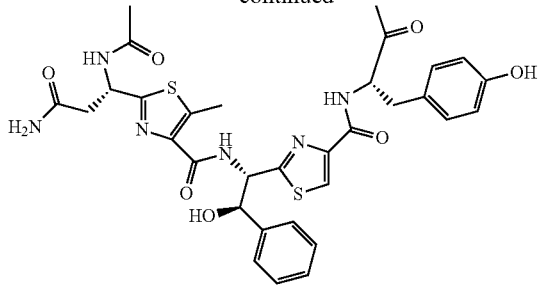

Compound 123 is prepared according to the procedures described in example 96. LC/MS: [M+2H]$^+$ 1461, R$_t$=1.17 min (method 13).

Example 111

Preparation of Acid (124)

(124)

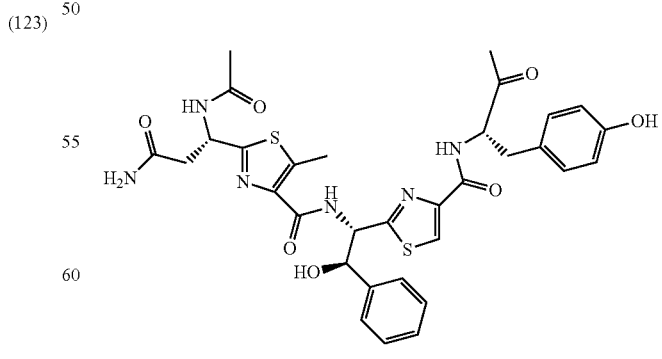

Compound 124 is prepared according to the procedures described in example 96. LC/MS: [M+H]$^+$ 1503, R$_t$=1.24 min (method 13).

Scheme 8:
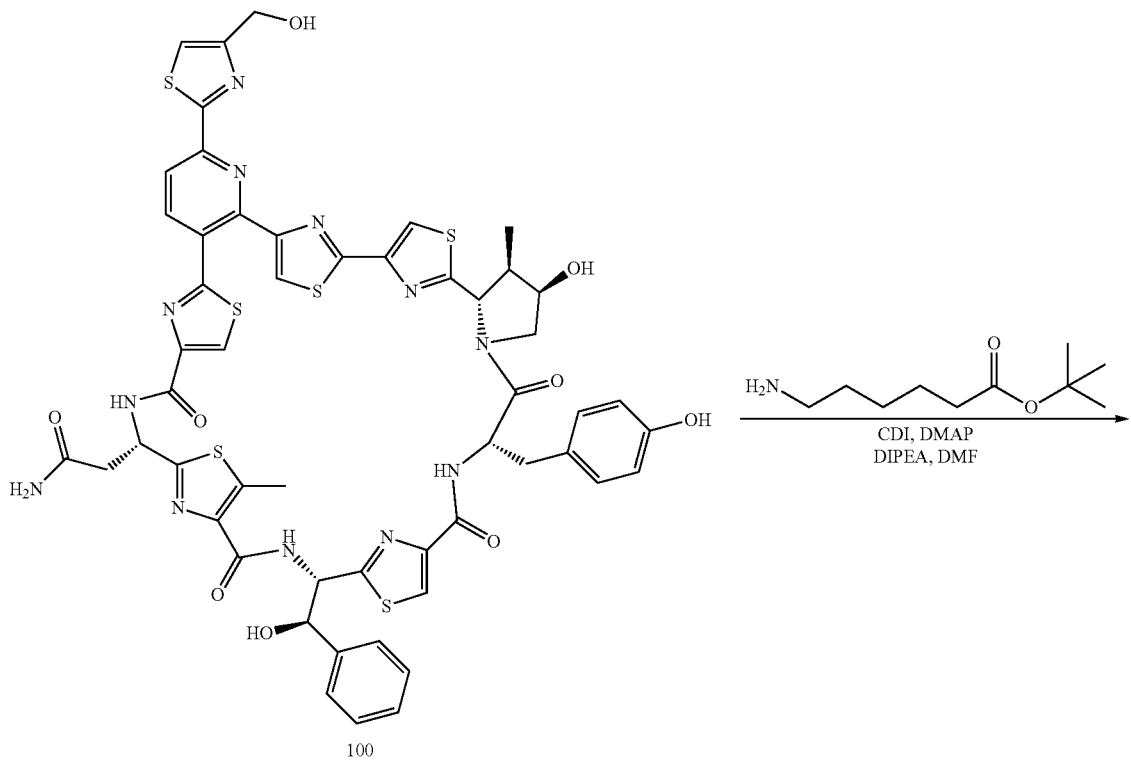
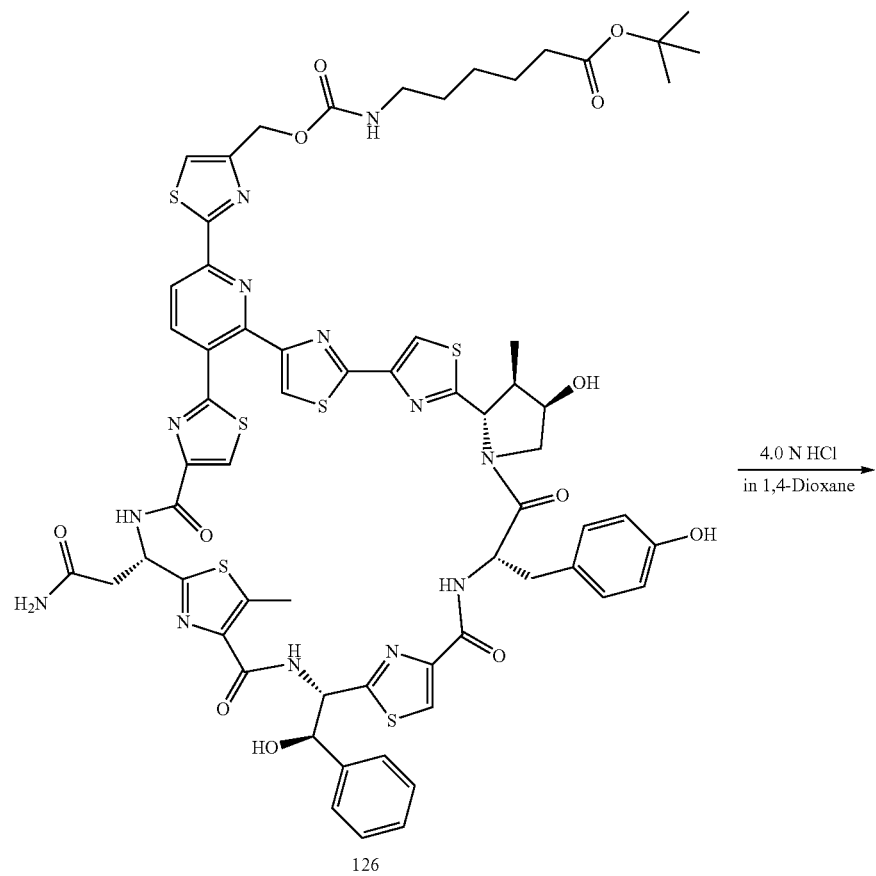

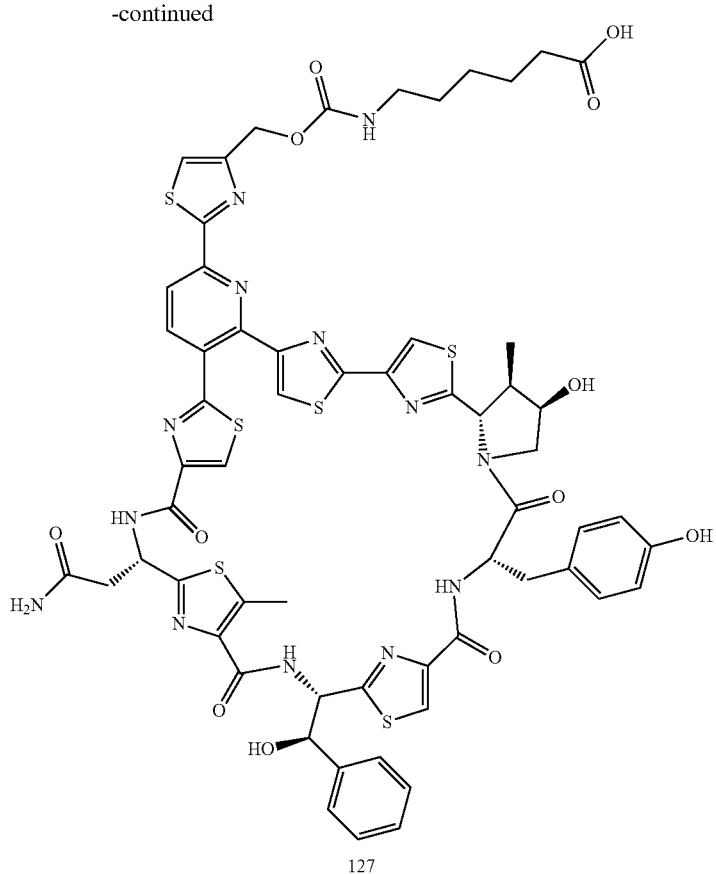
127
Example 112
Preparation of Acid (127)
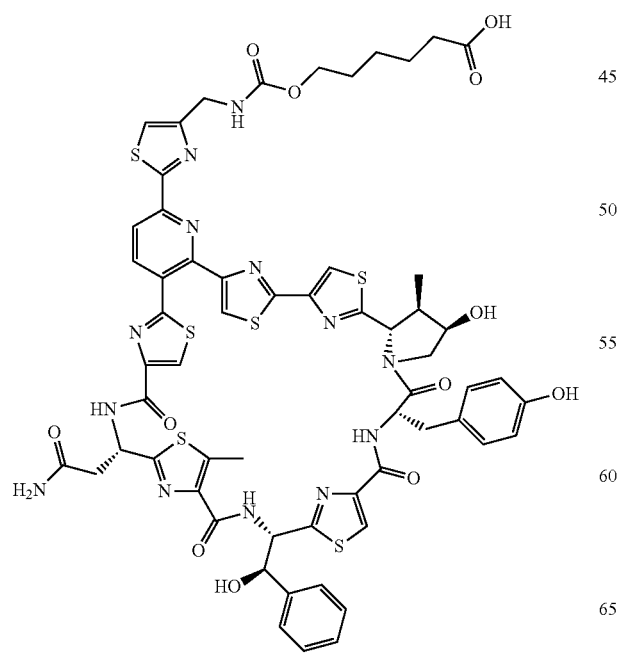
(127)

Step 1:

To a solution of alcohol 100 (260 mg, 0.219 mmol) in DMF (5 mL) is added DIPEA (390 uL, 2.19 mmol), CDI (64 mg, 0.394 mmol) and DMAP (26 mg, 0.219 mmol). The mixture stirs at RT for 2.5 h. Then 6-amino-hexanoic acid tert-butyl ester (410 mg, 0.219 mmol, Syn. Commun. 2004, 34, 2415) is added and the resulting mixture stirs at RT for 18 h. The mixture is then purified via preparatory TLC (10% EtOH/DCM) to yield the ester 126. LC/MS: $[M+H_3O]^+$ 1418, $R_t$=1.52 min (method 13).

Step 2:

To the t-butyl ester (126) is added 4N HCl in 1,4-dioxane (5 mL) and acetic acid (1 mL). The mixture stirs at RT for 1 h and the resulting acid is purified via HPLC (method 1) to afford compound 127. LC/MS: $[M+H_2O]^+$ 1361, $R_t$=1.27 min (method 13).

Scheme 9:

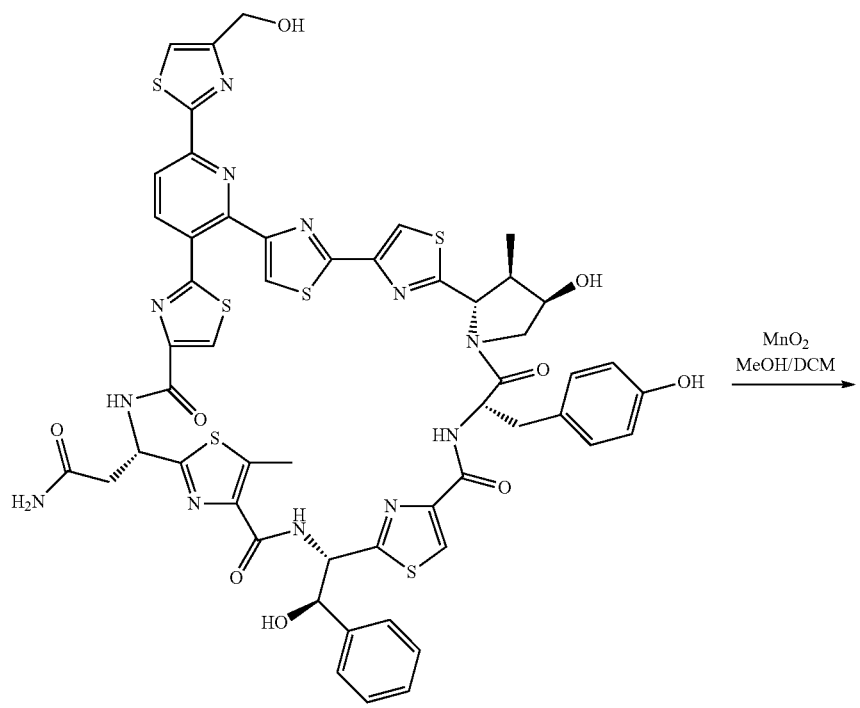

100

-continued
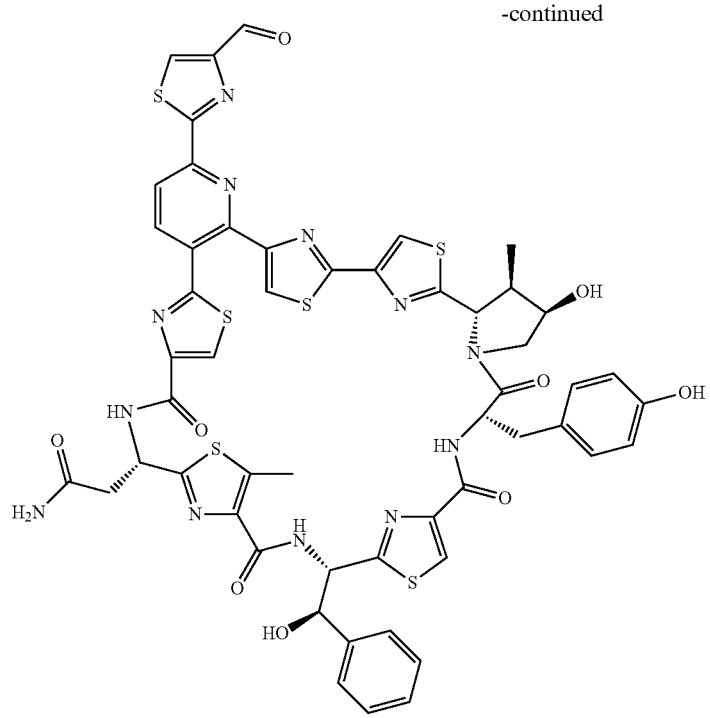
128
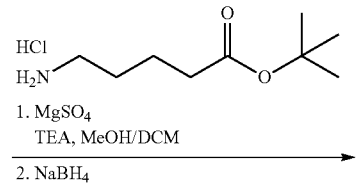
1. MgSO$_4$
   TEA, MeOH/DCM
2. NaBH$_4$
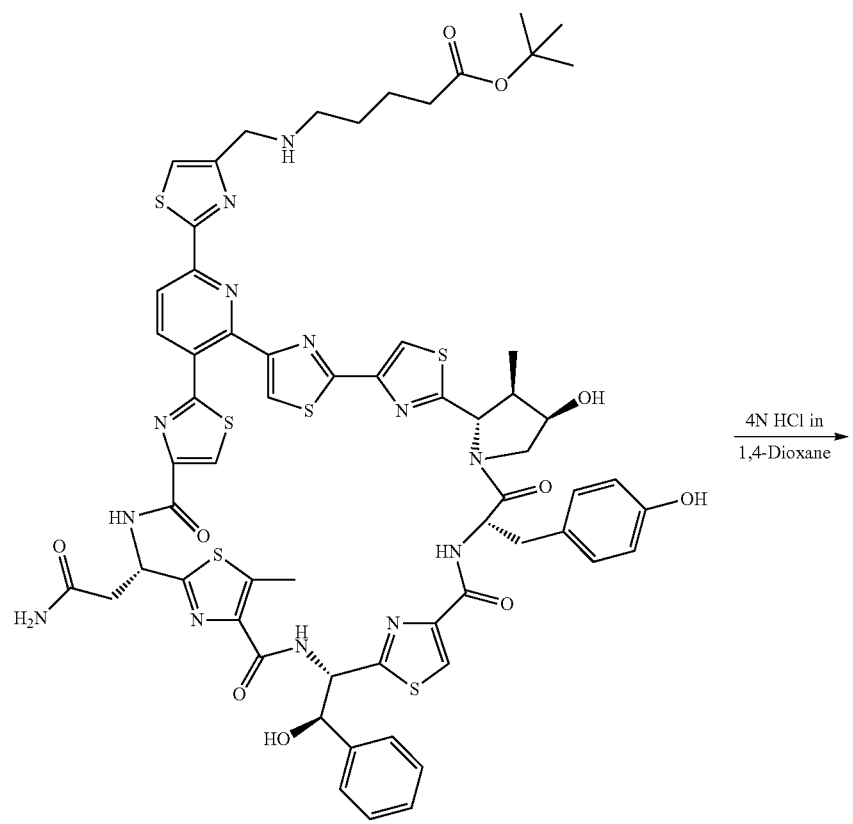
129
4N HCl in
1,4-Dioxane

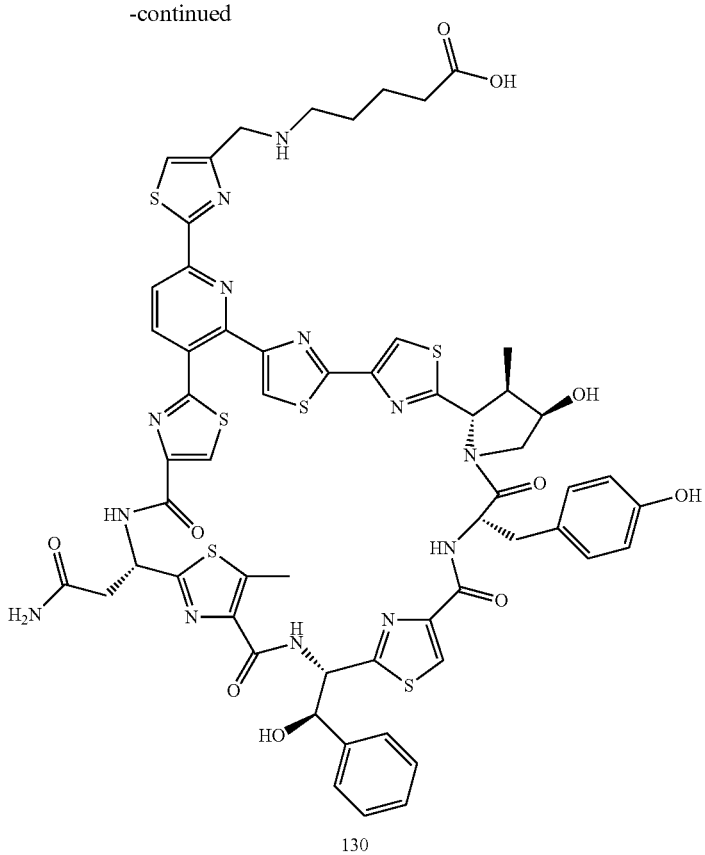

130

Example 113

Preparation of Acid (130)

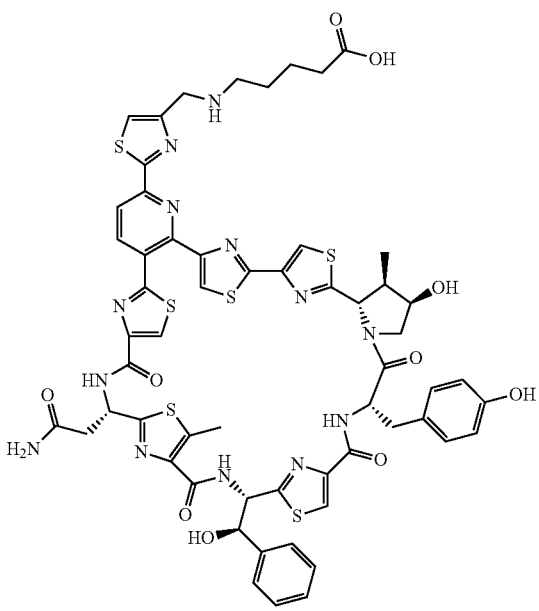

(130)

Step 1:

To a solution alcohol 100 (190 mg, 0.160 mmol) in MeOH (11 mL) and DCM (11 mL) is added $MnO_2$ (696 mg, 8.0 mmol) which has been dried in high vacuum oven at 100° C. for 12 h. The mixture stirs 24 h. The mixture is then adsorbed onto silica gel and purified by flash chromatography (gradient elution: 0-10% MeOH in DCM) which affords the aldehyde 128. LC/MS: $[M+H]^+$ 1185, $R_t$=1.33 min (method 13).

Step 2:

To a solution of aldehyde 128 (72 mg, 0.061 mmol) in MeOH (1.5 mL) and DCM (1.5 mL) is added TEA (8 uL, 0.061 mmol), $MgSO_4$ (12 mg, 0.092 mmol), and 5-aminopentanoic acid tert-butyl ester HCl (12 mL, 0.067 mmol, Syn. Commun. 2004, 34, 2415), is added. The mixture stirs 20 h. The mixture is then cooled to 0° C. and $NaBH_4$ (14 mg, 0.366 mmol) is added. The mixture stirs 18 h at ambient temperature. Then additional $NaBH_4$ (14 mg, 0.366 mmol) is added. The mixture stirs 1 h at ambient temperature. The mixture is then adsorbed onto silica gel and purified by flash chromatography (gradient elution: 0-50% MeOH/DCM+0.1% TEA) which affords the amine 129. LC/MS: $[M+2H]^+$ 1343, $R_t$=1.24 min (method 13).

Step 3:

To the amine 129 is added 4 N HCl in 1,4-dioxane (4 mL). The mixture stirs at RT for 0.5 h and the resulting acid is purified via HPLC (method 1) to afford the amino-acid 130. LC/MS: $[M+H]^+$ 1286, $R_t$=1.06 min (method 13).

Scheme 10:
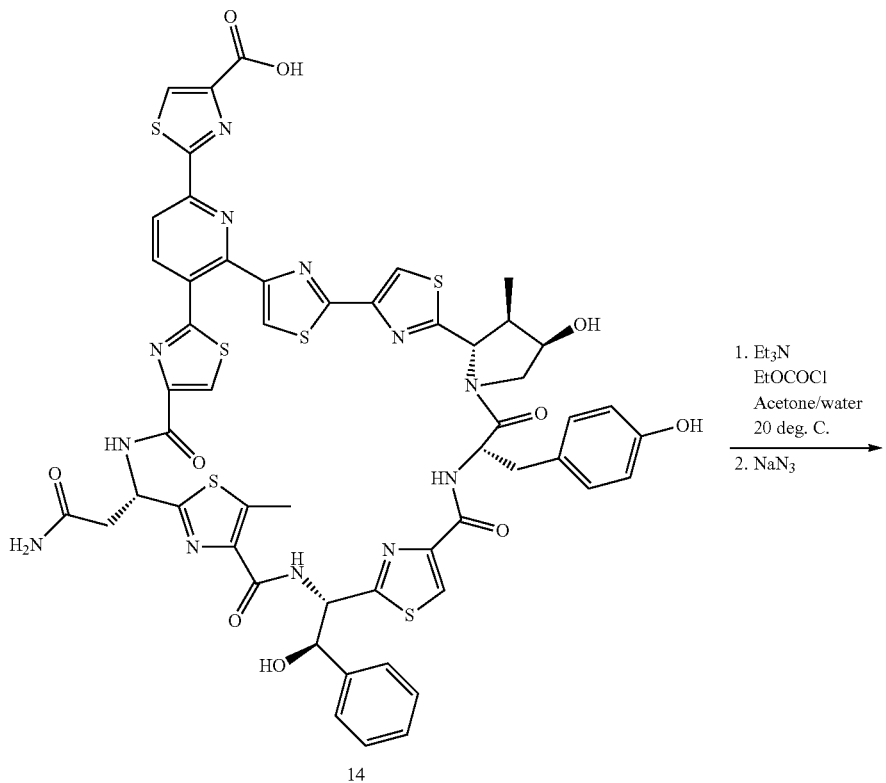
14
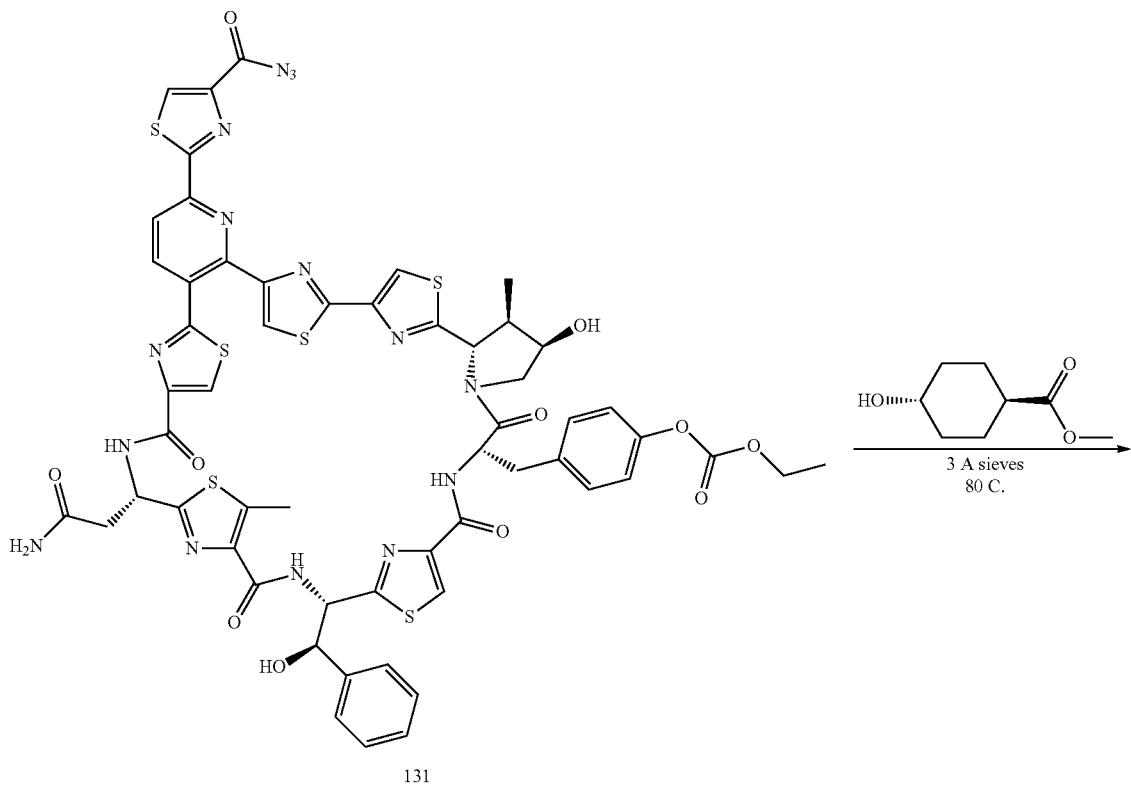
131

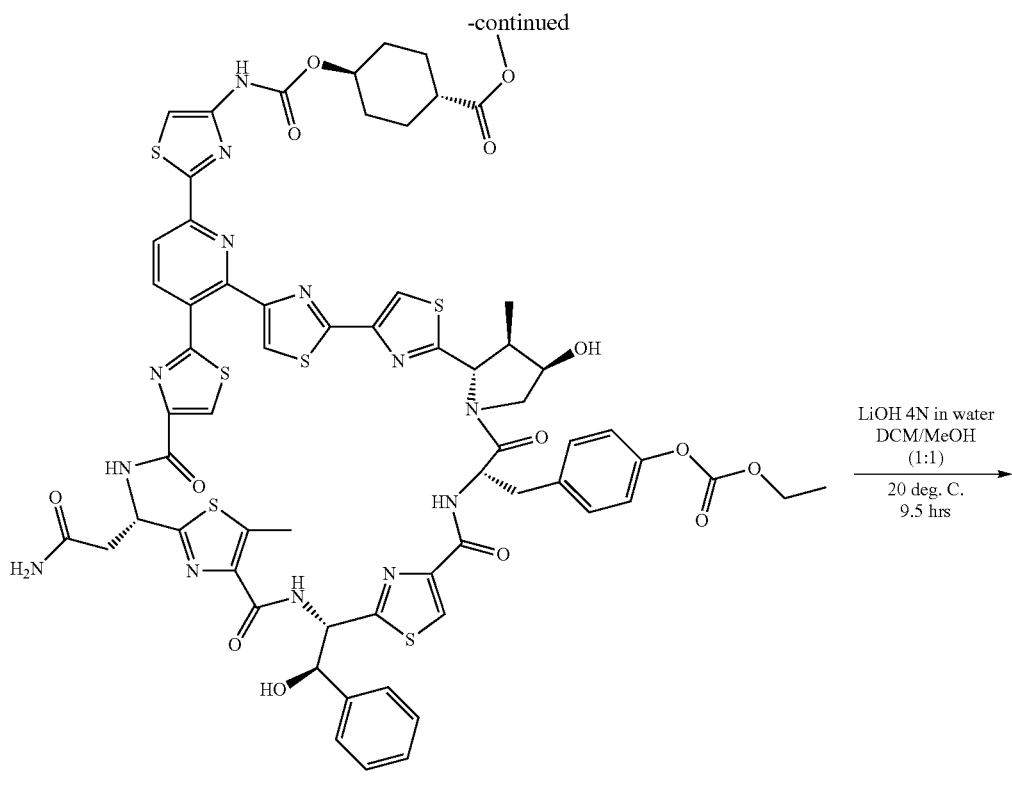
132
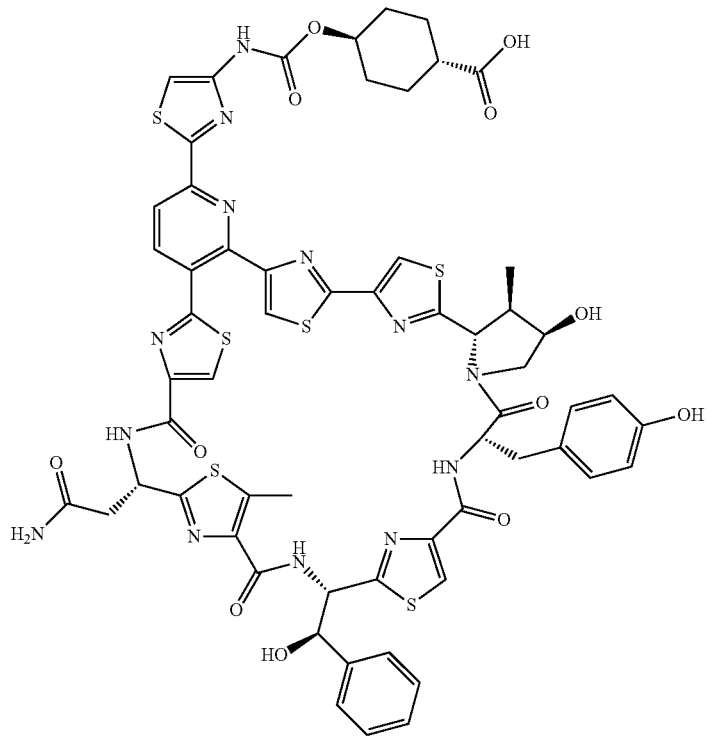
133

Example 114

Preparation of Acid (133)

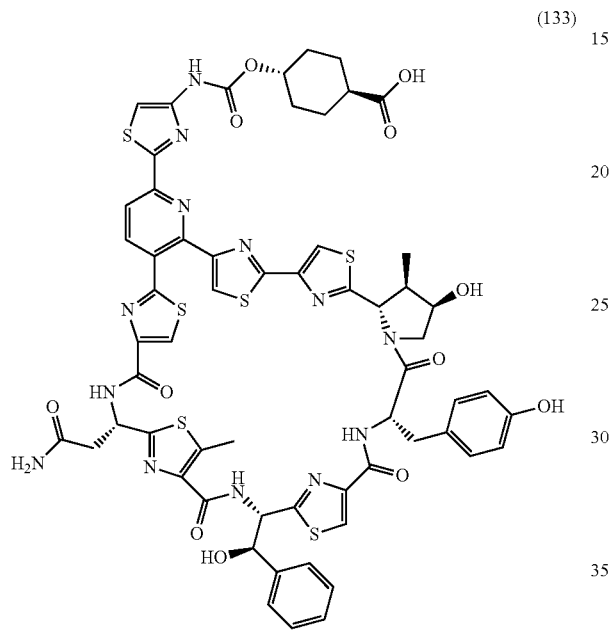

(133)

To a suspension of the acid (14, 392 mg, 0.326 mmol) in 11:1 acetone:water (80.5 mL) is added triethylamine (0.45 mL, 3.26 mmol) and ethyl chloroformate (0.37 mL, 3.91 mmol). The reaction is stirred at room temperature until a solution forms (100 min.). Sodium azide (0.318 g, 4.89 mmol) is added and the reaction is stirred at room temperature until complete. Solvents are evaporated at 20° C. Water is added to the residue to precipitate the azide. The azide is suspended three times in water then once in dichloromethane and isolated by filtration. The azide 131 is dried to a fine white powder. LC/MS: [M+H]$^+$ 1298, R$_t$=1.47 min. (method 13).

Step 2:

The azide 131 (240.8 mg, 0.1854 mmol) is combined with 4-hydroxy-cyclohexanecarboxylic acid methyl ester (88 mg, 0.556 mmol) and oven dried 3 angstrom molecular sieves (240.8 mg) in 1,4-dioxane (6 mL) and stirred at 80° C. for 7 h. Solvent is evaporated and the residue is flashed on silica (gradient elution: 3-100% MeOH/DCM). The product is a pale yellow solid, 132. LC/MS: [M+2H]$^+$ 1429, R$_t$=1.53 min (method 13).

Step 3:

The ester 132 (100 mg, 0.700 mmol) is dissolved in 1:1 dichloromethane:methanol (6 mL). 4N aqueous lithium hydroxide solution (0.3 mL, 1.2 mmol) is gradually added at room temperature with stirring over 7.25 hours. At 9.5 hours 0.5 mL of glacial acetic acid is added. Solvent is evaporated and the residue is purified by HPLC (20 to 100% acetonitrile in water+0.1% TFA) to afford compound 133. LC/MS: [M+H]$^+$ 1342, R$_t$=1.26 min (method 13).

Example 115

Preparation of Acid (134)

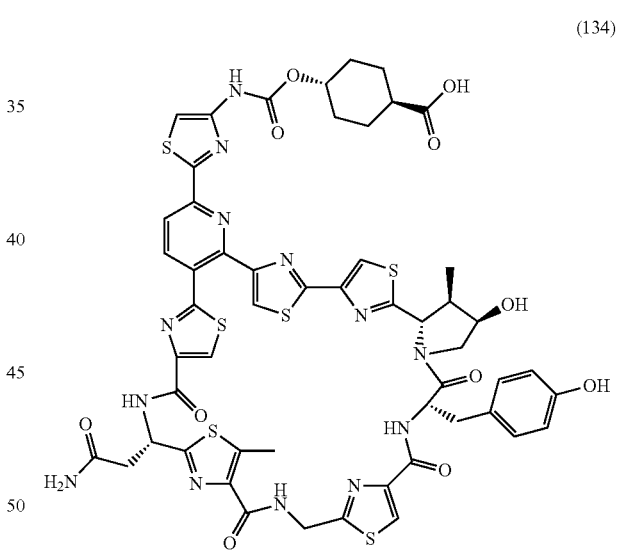

(134)

Compound 134 is prepared according to the procedures in example 114. LC/MS: [M+H]$^+$ 1236, R$_t$=1.17 min (method 13).

Scheme 11:
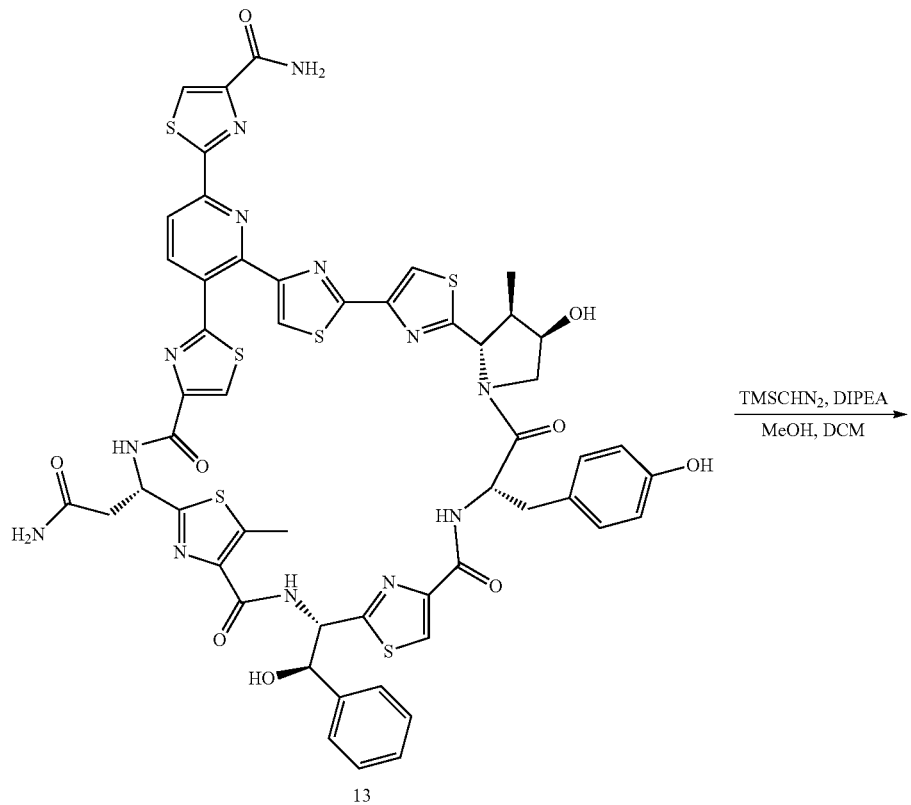
TMSCHN₂, DIPEA
―――――――――→
MeOH, DCM
13
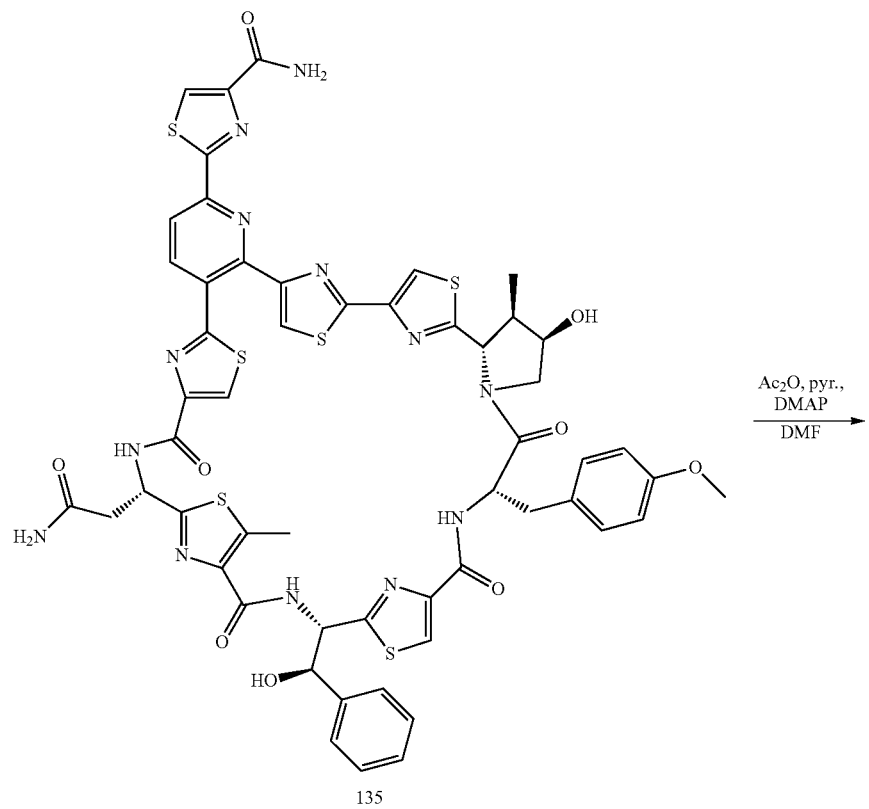
Ac₂O, pyr.,
DMAP
―――――――→
DMF
135

-continued
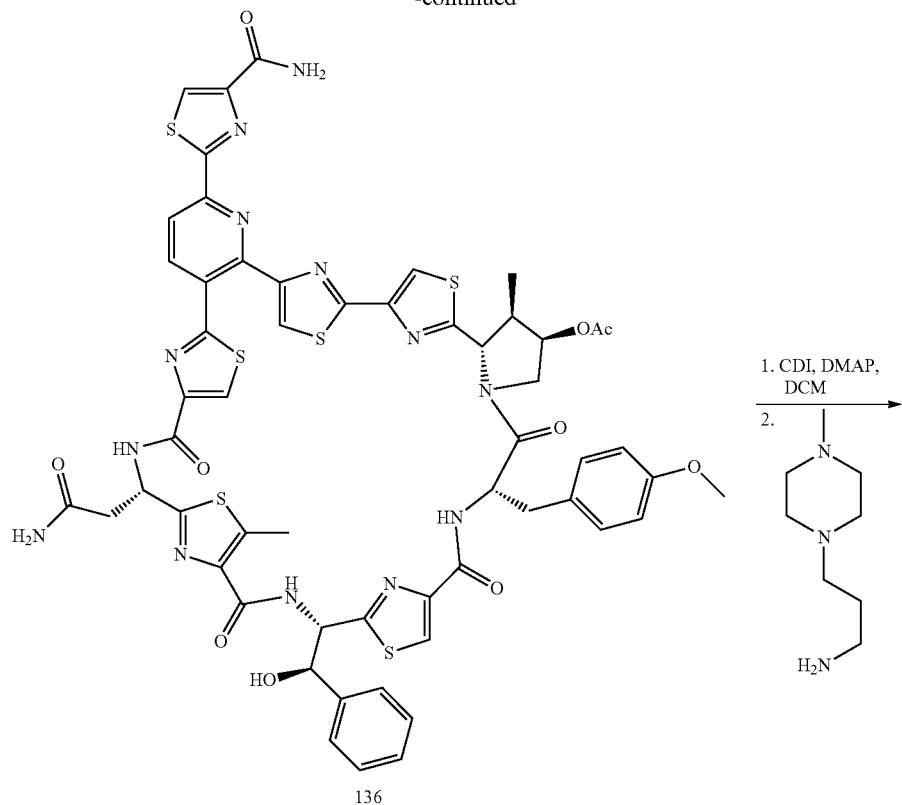
136
1. CDI, DMAP, DCM
2.
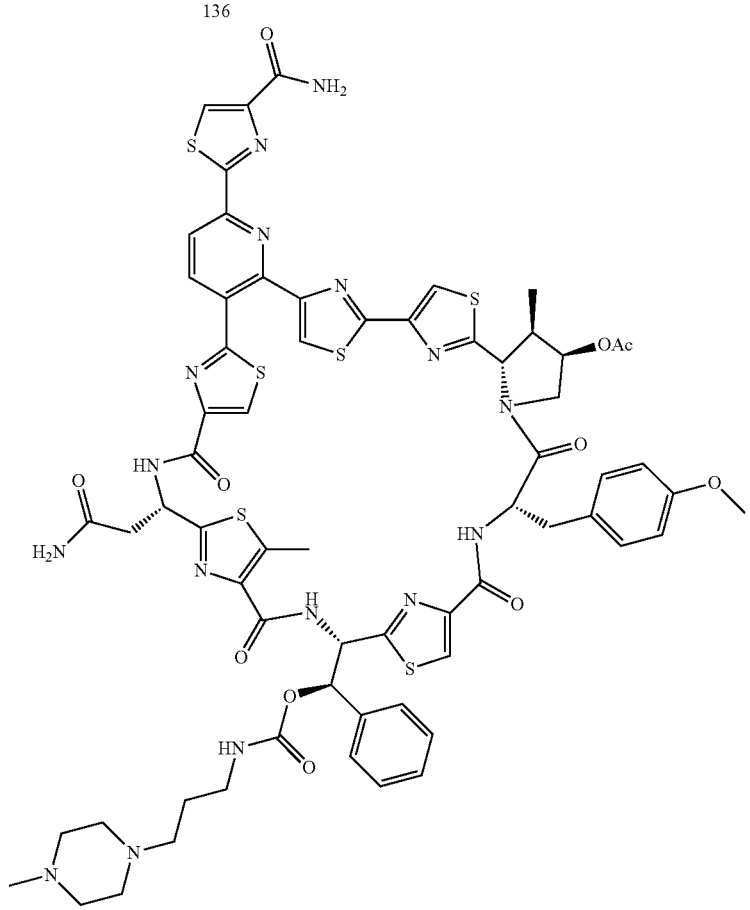
137

Example 116

Preparation of Amine (137)

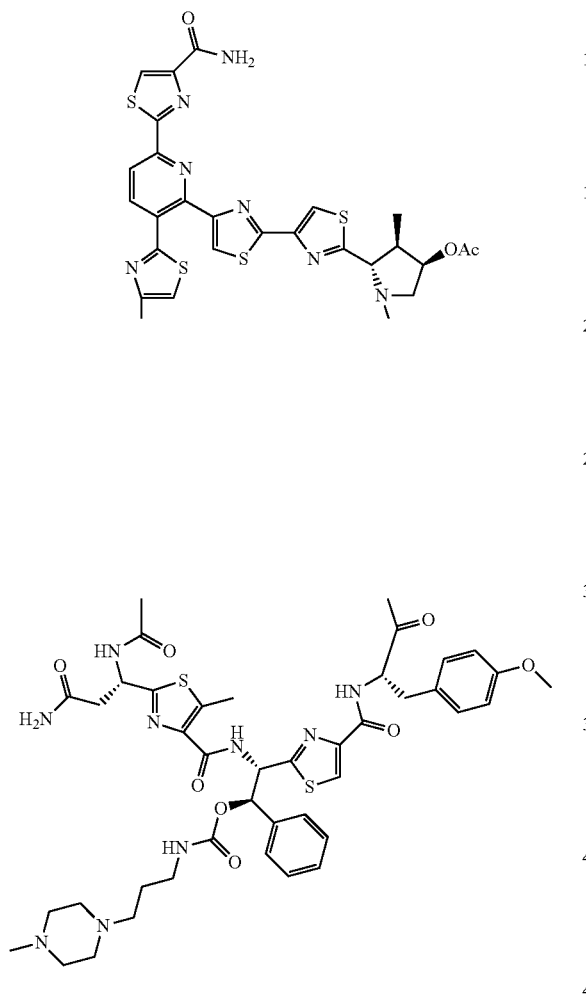

(137)

Step 1:

To a mixture of pyrrolidine 13 (800 mg, 0.666 mmol) and DIPEA (1.16 ml, 6.66 mmol) in DCM (64 mL) and MeOH (6 ml) is added TMSCHN$_2$ dropwise at RT under nitrogen. The reaction is stirred at RT for 2 h, kept at 0° C. for 48 h. The reaction is concentrated in vacuo, the residue is then poured onto H$_2$O (s), filtered to collect the solid, washed with cold water, and dried in vacuo. The dried solid is treated with DCM and filtered to give the methyl ether 135 as a white solid. LC/MS: [M+H]$^+$ 1214, R$_t$=1.24 min (method 14).

Step 2:

To a solution of ether 135 (600 mg, 0.494 mmol) and pyridine (0.4 ml, 4.94 mmol) in DMF (10 mL) is added Ac$_2$O (0.049 mL, 0.52 mmol) at 0° C. followed by DMAP (cat.). The reaction is stirred at RT at 0° C. for 7 h, and more Ac$_2$O (0.049 ml, 0.52 mmol) is added. The reaction is stirred at RT overnight. The mixture is poured onto ice and filtered, washed with cold water and dried in vacuum. The crude mixture is purified by flash chromatography (0-10% MeOH/DCM), and affords acetate 136 as a white solid. LC/MS: [M+H]$^+$ 1256, R$_t$=1.31 min (method 14).

Step 3:

To a suspension of acetate 136 (50 mg, 0.04 mmol) and CDI (19.3 mg, 0.12 mmol) in anhydrous DCM (2 mL) is added DMAP (5 mg, 0.04 mmol) at RT. The reaction is stirred for 3 h and 1-(3-aminopropyl)-4-methylpiperazine (0.02 ml, 0.12 mmol) is added neat and stirred at RT for 3 h. The crude mixture is purified by HPLC (method 1) to afford 137. LC/MS: [M+H]$^+$ 1439, R$_t$=0.41 min (method 14).

Example 117

Preparation of Amine (138)

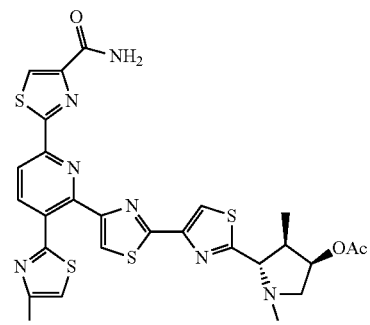

(138)

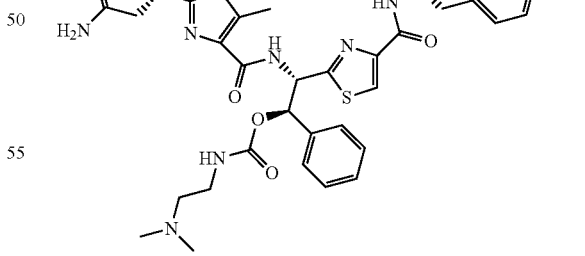

Compound 138 is prepared according to the procedures described in example 116. LC/MS: [M+H]$^+$ 1370, R$_t$=0.46 min (method 13).

Example 118
Preparation of Amine (139)
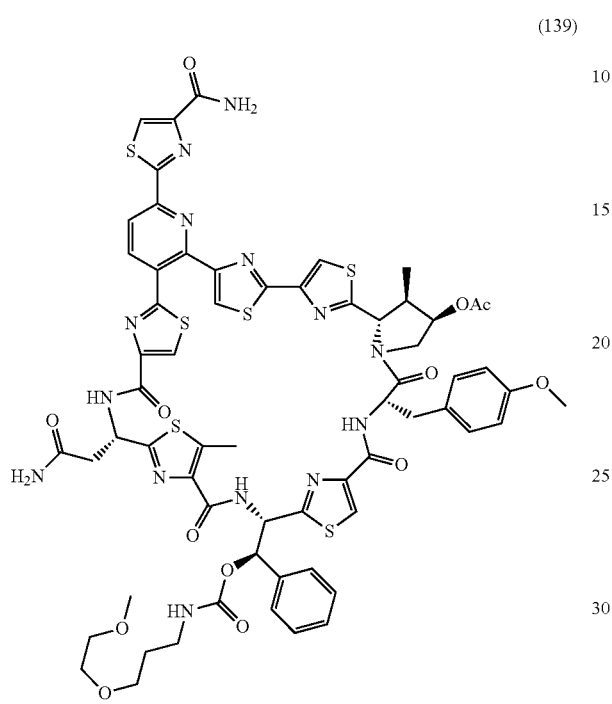
(139)
Compound 139 is prepared according to the procedures described in example 116. LC/MS: [M+H]+ 1415, $R_t$=0.81 min (method 13).
Example 119
Preparation of Amine (140)
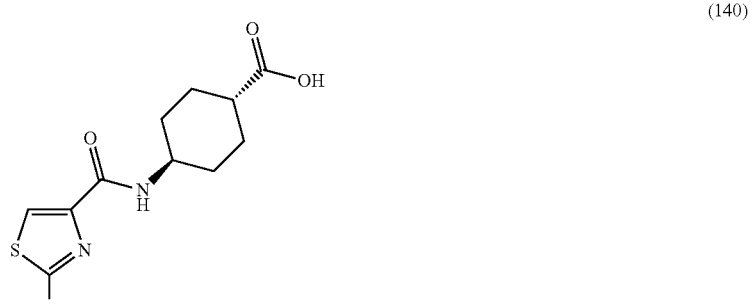
(140)

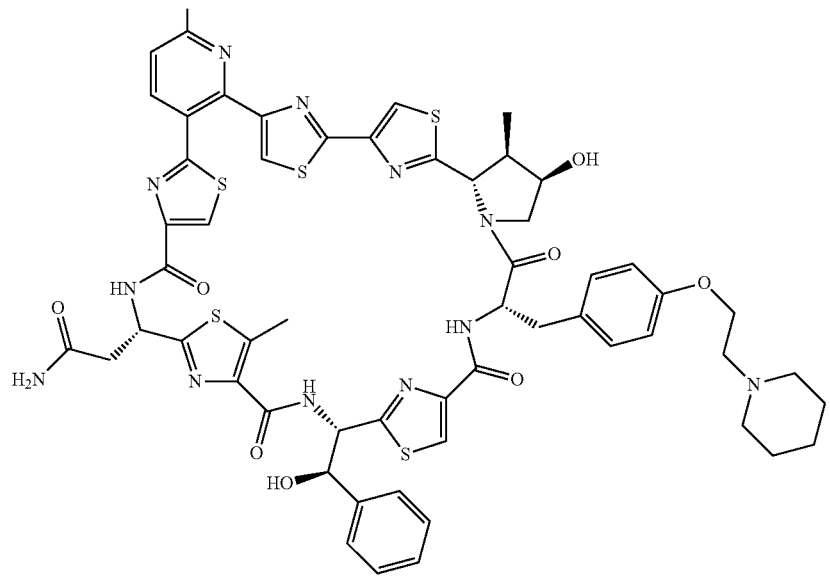
Compound 140 is prepared according to the procedures described in scheme 5 and example 34. LC/MS: [M+2H]$^+$ 1438, R$_t$=1.05 min (method 13).
Example 120
Preparation of Amino-Acid (141)
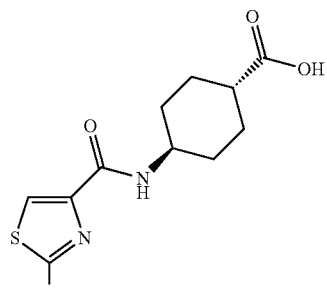
(141)

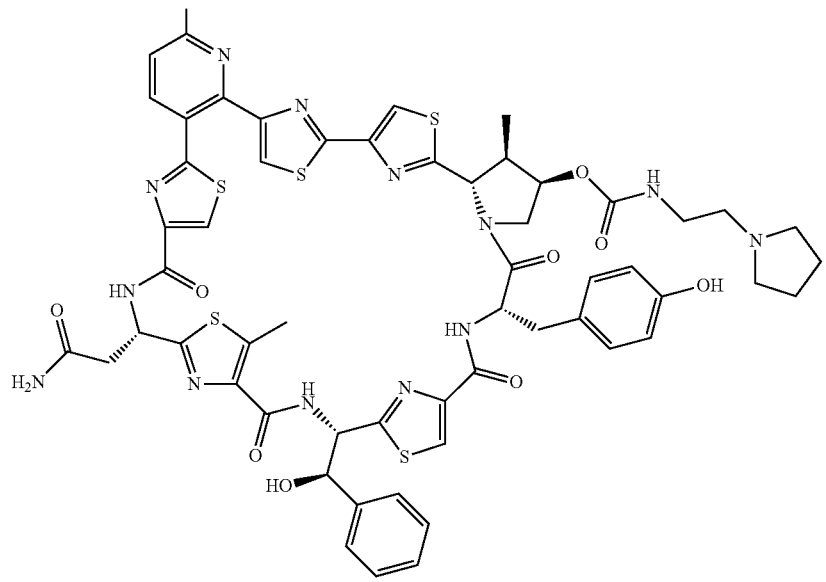
Compound 141 is prepared according to the procedures described in scheme 5 and example 61. LC/MS: [M+H]+ 1466, $R_t$=1.03 min (method 14).
Example 121
Preparation of Amide (142)
(142)
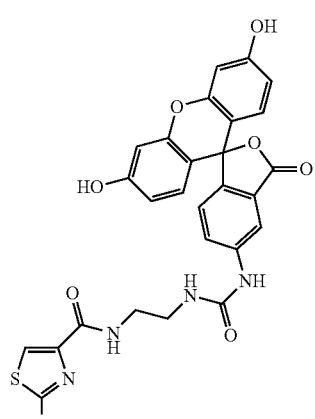
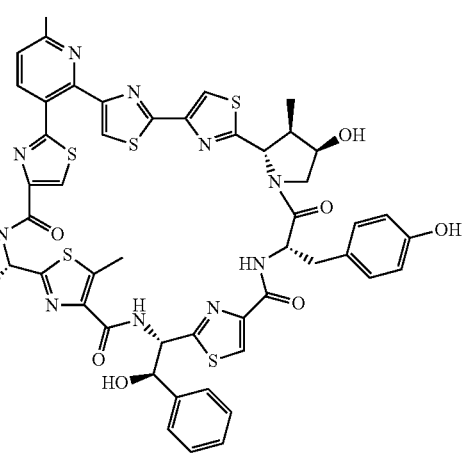
Compound 142 is prepared according to the procedures described in scheme 5. LC/MS: [M+H]+ 1632, $R_t$=1.22 min (method 13).

Scheme 12:
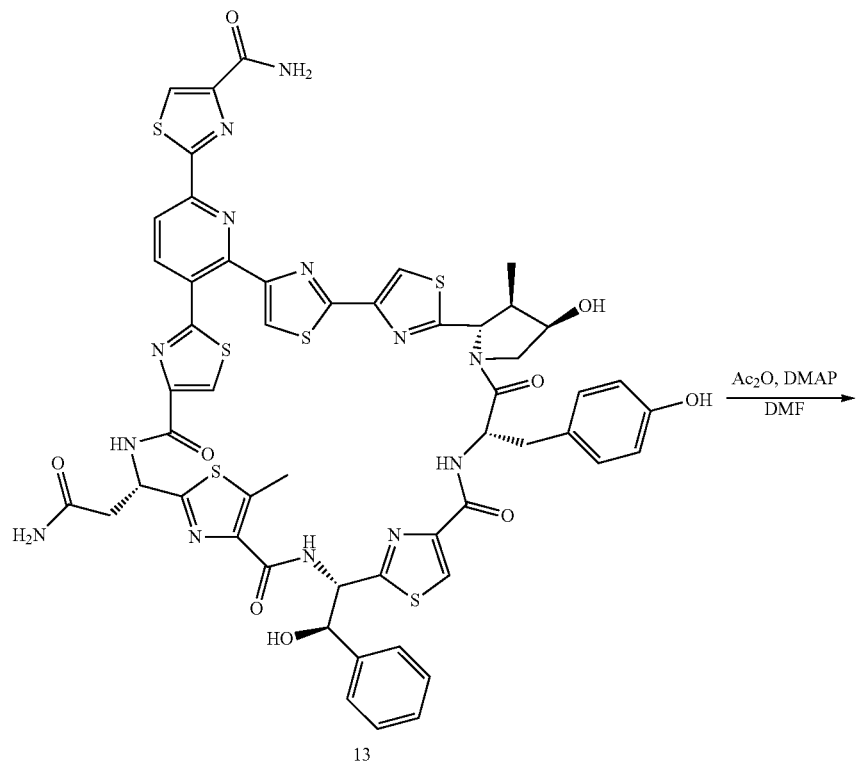
13
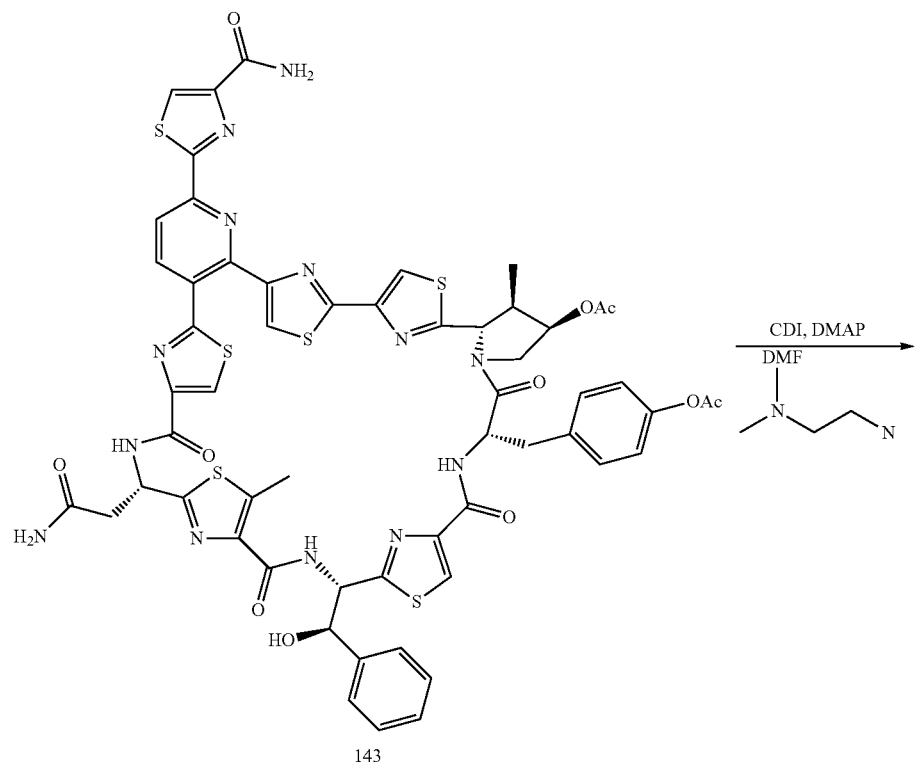
143

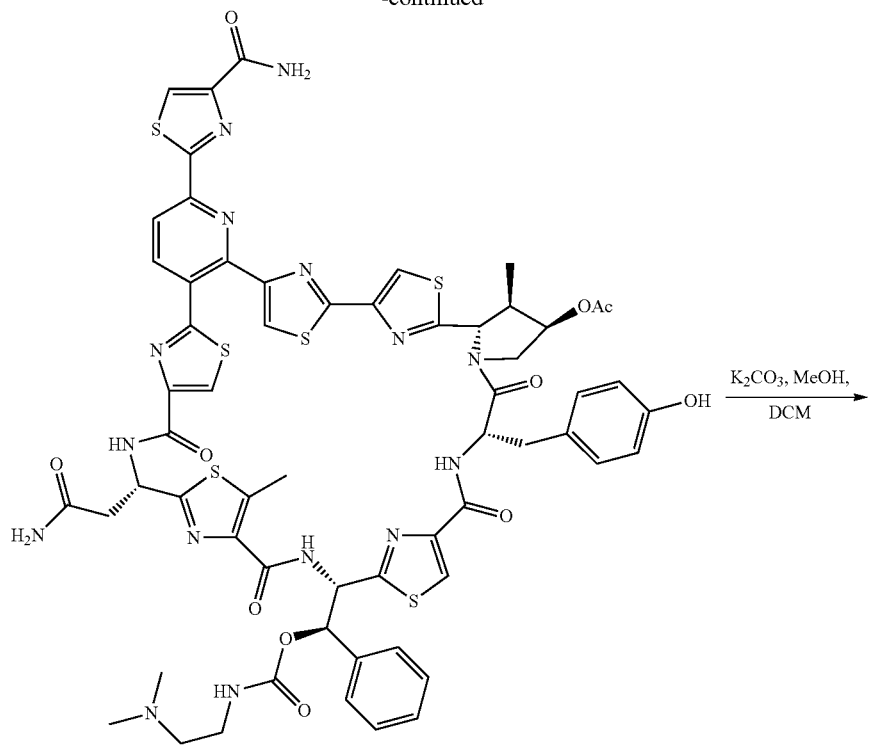
144
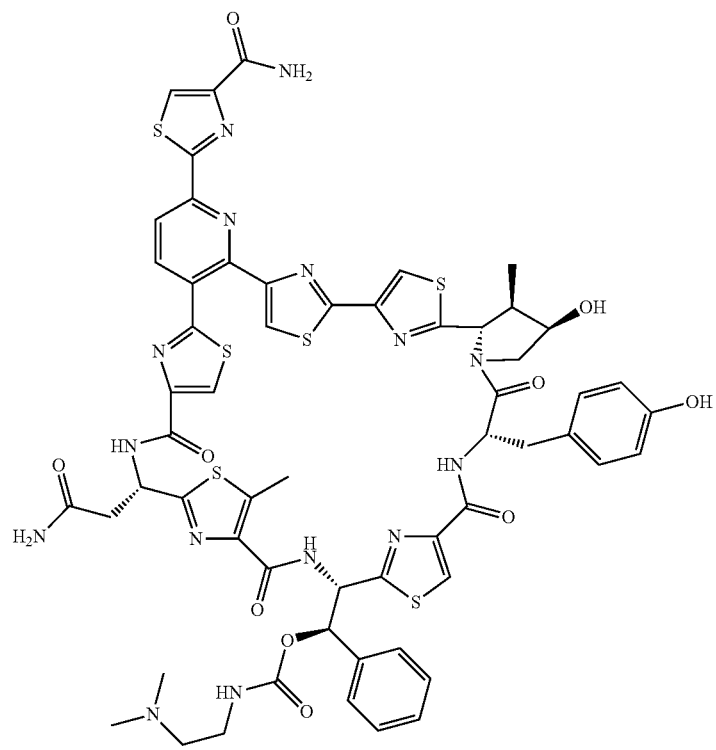
145

Example 122

Preparation of Amine (145)

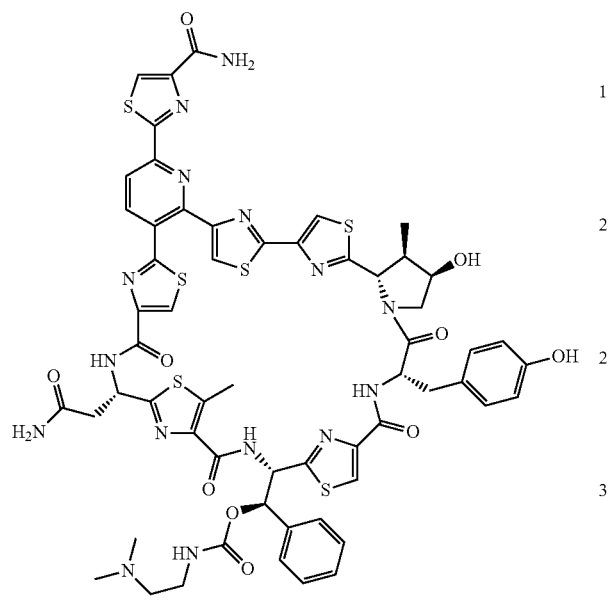
(145)

Step 1:
To a solution of amide 13 (400 mg, 0.333 mmol) and pyridine (0.527 g, 6.66 mmol) in DMF (40 mL) is added acetic anhydride (71.392 mg, 0.699 mmol) at 0° C. under $N_2$, followed by DMAP (cat.). The solution is stirred at 0° C. overnight. Solvent is removed under vacuum. The residue is purified by flash chromatography (gradient elution: 0-10% MeOH/DCM) which affords the diacetate. LC/MS [M+2H]$^+$ 1285, $R_t$=1.38 min (method 13).

Step 2:
To a suspension of the diacetate (128 mg, 0.1 mmol) and CDI (48.5 mg, 0.299 mmol) in anhydrous DCM is added DMAP (12.2 mg, 0.1 mmol) at RT and stirred for 3 h. When the starting material is consumed, N,N-dimethylethyl-diamine is added, and the resulting reaction is stirred overnight. Solvent is removed under vacuum. The residue is purified via HPLC (method 2) to furnish 144. LC/MS: [M+2H]$^+$ 1357, $R_t$=1.14 min (method 13).

Step 3:
A suspension of compound 144 (40 mg, 0.0295 mmol) and potassium carbonate (12 mg, 0.0868 mmol) in DCM/MeOH (1 mL/1 mL) is stirred at RT for 2 h. The reaction mixture is filtered to remove solid. The solvent is removed under vacuum. The residue is purified via HPLC (method 1) which affords compound 145. LC/MS: [M+2H]$^+$ 1315, $R_t$=1.10 min (method 13).

Example 123

Preparation of Amine (146)

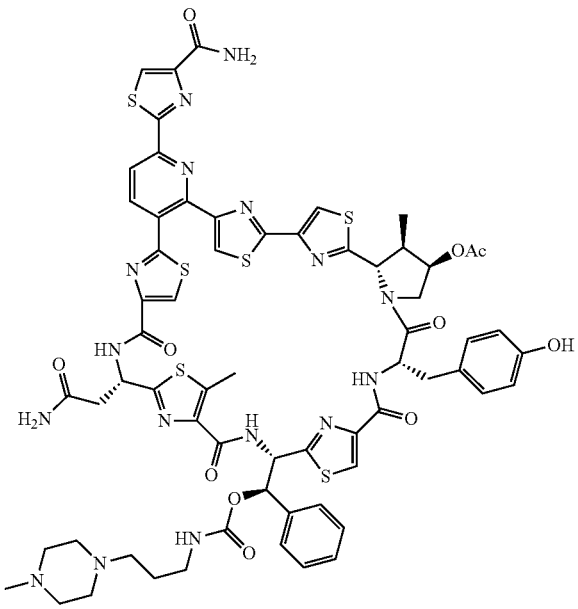
(146)

Compound 146 is prepared according to the procedures described in example 122. LC/MS: [M+4H]$^+$ 1428, $R_t$=0.40 min (method 13).

Example 124

Preparation of Amide (147)

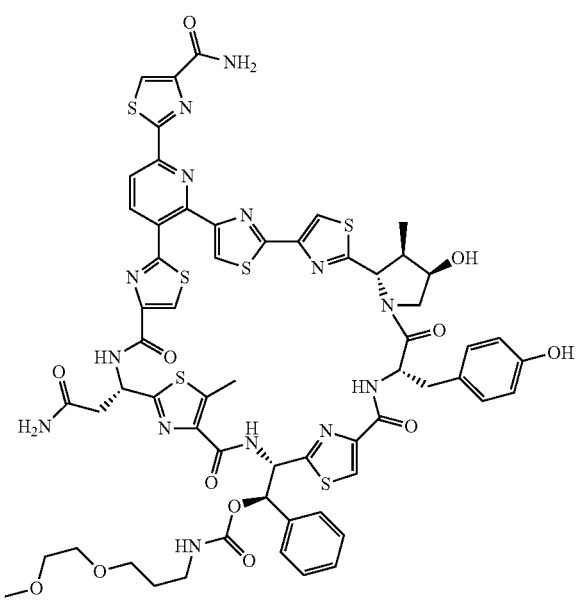
(147)

Compound 147 is prepared according to the procedures described in example 122. LC/MS: [M+2H]+ 1360, R$_t$=1.24 min (method 13).

Example 125

Preparation of Amine (148)

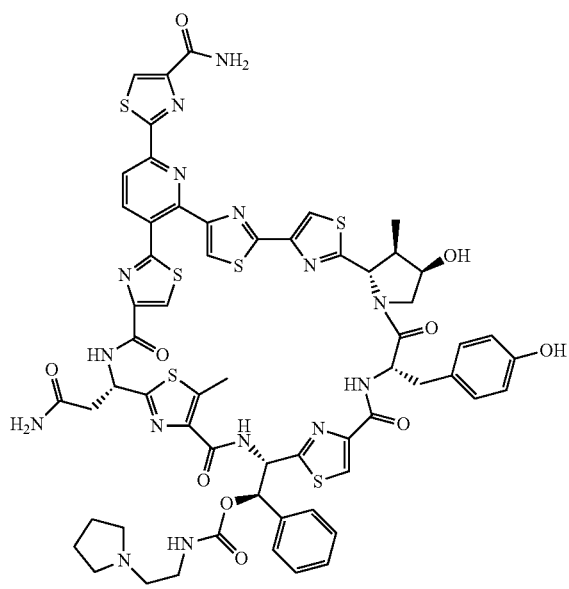
(148)

Compound 148 is prepared according to the procedures described in example 122. LC/MS: [M+3H]+ 1342, R$_t$=1.10 min (method 13).

Example 126

Preparation of Amine (149)

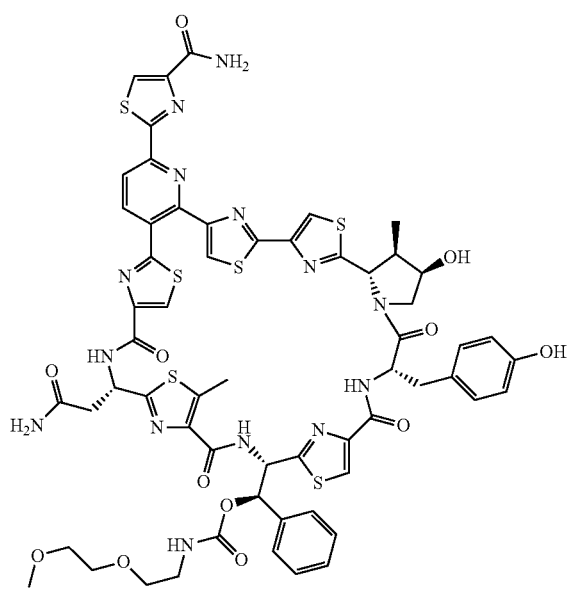
(149)

Compound 149 is prepared according to the procedures described in example 122. LC/MS: [M+2H]+ 1346, R$_t$=1.24 min (method 13).

Example 127

Preparation of Amine (150)

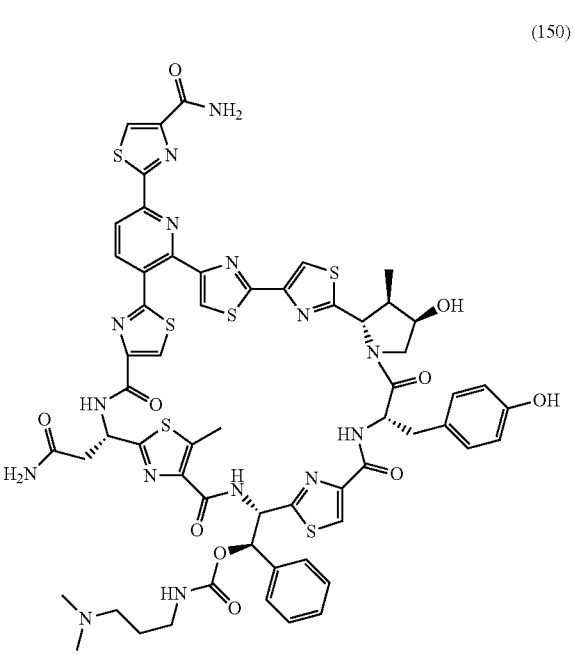 [SMILES: Cc1sc2nc1C(=O)N[C@@H]([C@H](OC(=O)NCCCN(C)C)c1ccccc1)c1nc(cs1)C(=O)N[C@@H](Cc1ccc(O)cc1)C(=O)N1C[C@H](O)[C@H](C)[C@H]1c1nc(cs1)-c1nc(cs1)-c1nc(-c3nc(C(N)=O)cs3)ccc1-c1nc(cs1)C(=O)N[C@H]2CC(N)=O]
(150)

Compound 150 is prepared according to the procedures described in example 122. LC/MS: [M+2H]+ 1329, R$_t$=1.05 min (method 13).

Example 128

Preparation of Imide (151)

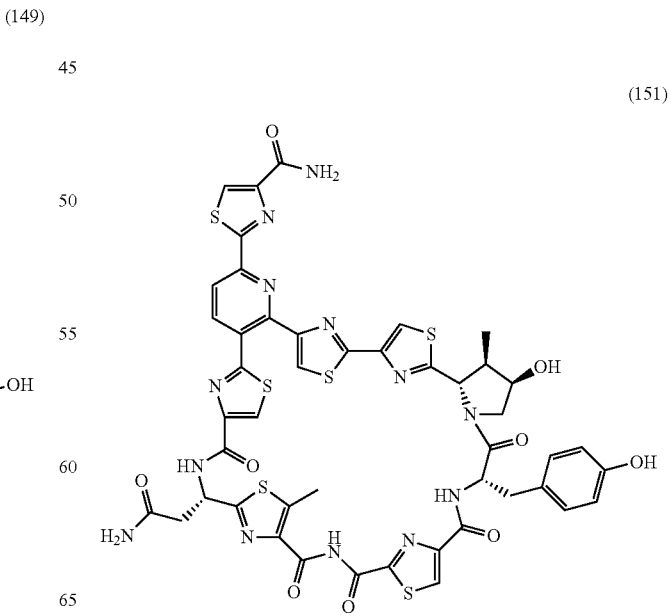
(151)

Step 1:

A suspension of 144 (500 mg, 0.369 mmol) and potassium carbonate (153 mg, 1.107 mmol) in DCM/MeOH (24 mL/24 mL) is stirred at 35° C. for 3 h. The solvent is removed under vacuum. Anhydrous DMSO (1-2 mL) is added to the residue, and the resulting mixture is heated at 45° C. for 2 h. Water (15 mL) is added, and the reaction is stirred at RT. The precipitate is filtered, and washed with water. The solid is dried under vacuum to furnish the intermediate styrene. LC/MS: [M+2H]$^+$ 1183, R$_t$=1.27 min (method 13).

Step 2:

To a mixture of the intermediate styrene (80 mg, 0.0677 mmol) in t-BuOH (2 mL) is added 0.1N HCl (1 mL), osmium tetroxide (2.5% wt in t-BuOH, 85 uL, 0.00678 mmol), and a solution of sodium periodate (27 mg, 0.126 mmol) in H$_2$O (2 mL). The resulting reaction mixture is stirred 12 h at RT. Water (6 mL) is added, and the precipitate is filtered and collected. The solid is redissolved in DMF/MeCN, purified with HPLC (method 1) and further purified by flash chromatography (gradient elution: 0-10% MeOH/DCM) which provides compound 151. LC/MS: [M+2H]$^+$ 1109, R$_t$=1.17 min (method 13).

Scheme 13:

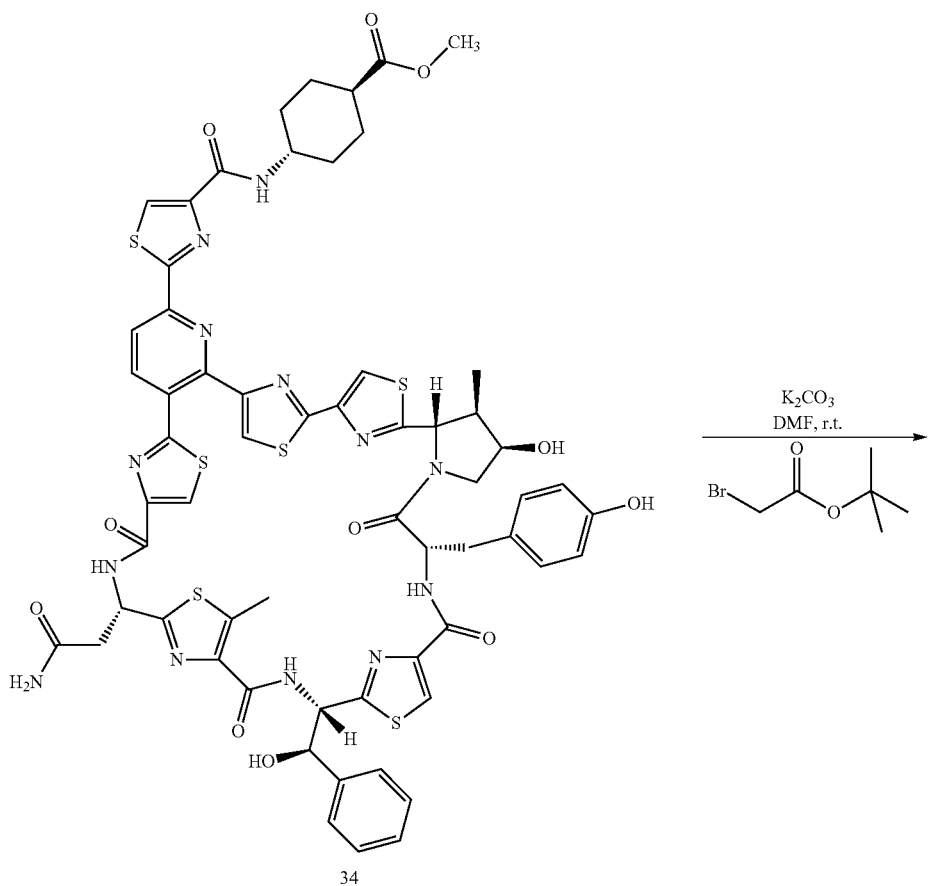

-continued
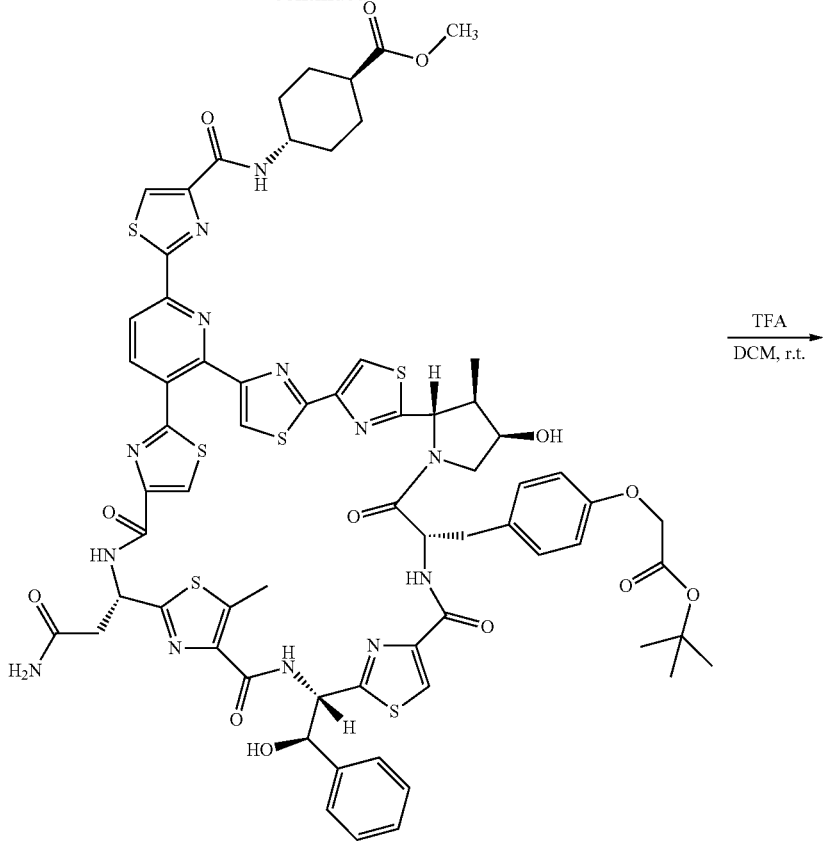
152
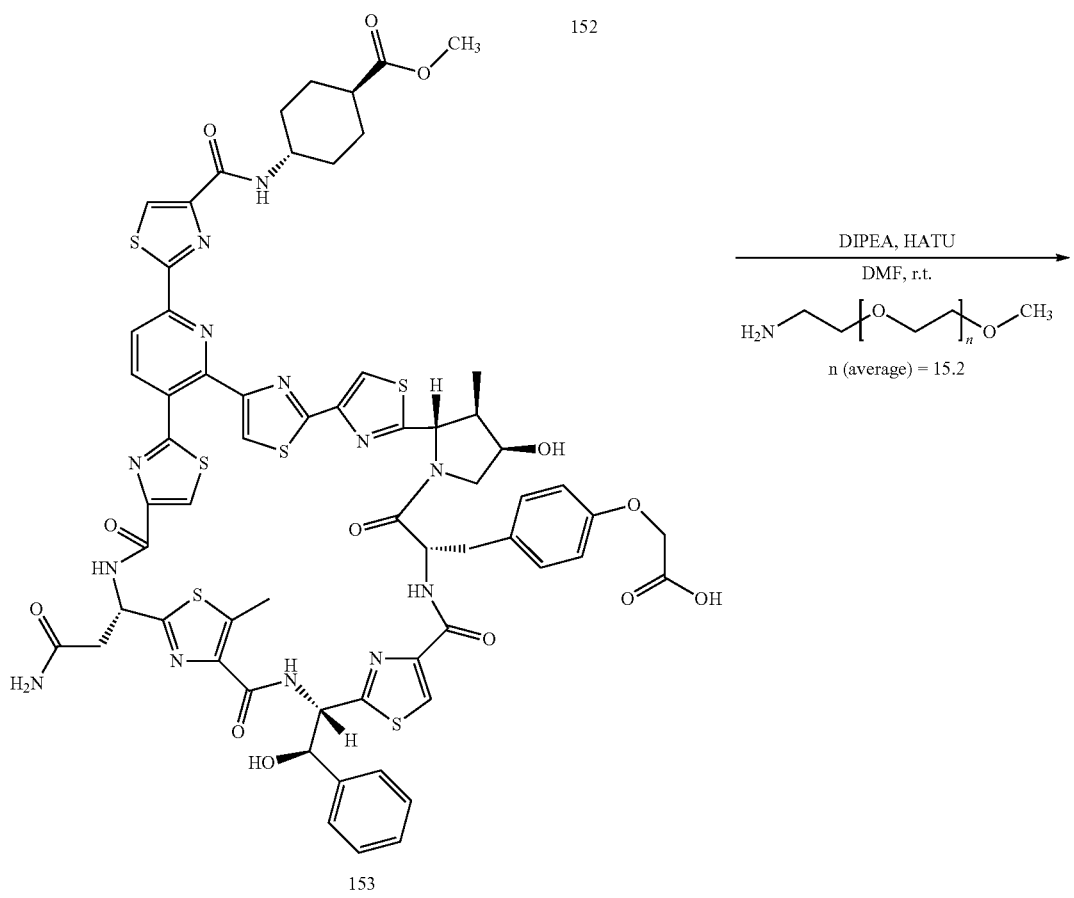
153

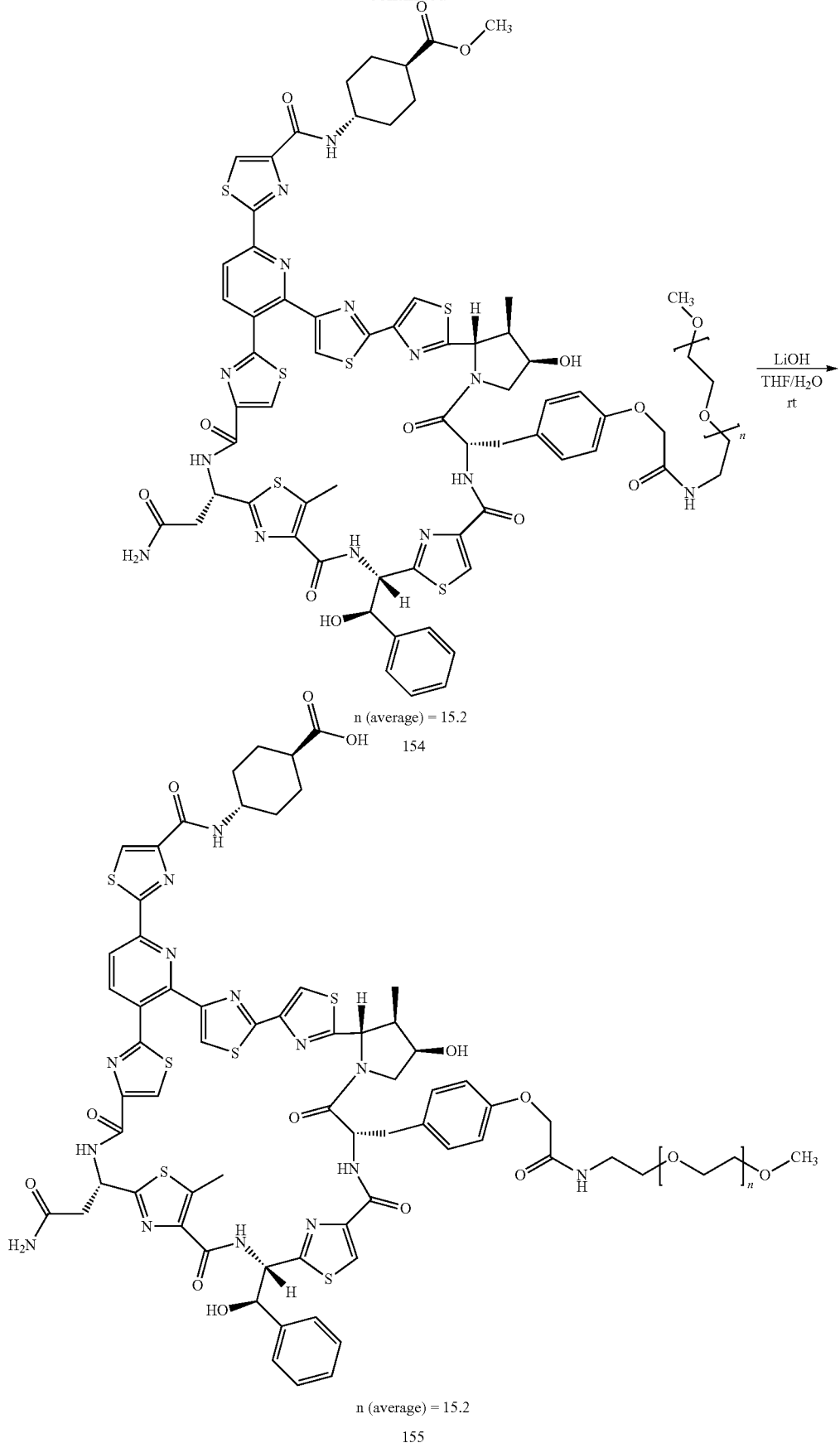

Example 129

Preparation of Acid (155)

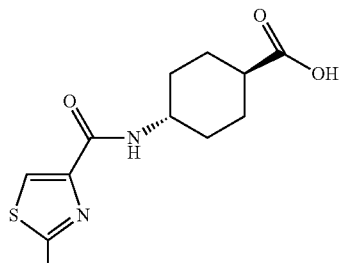

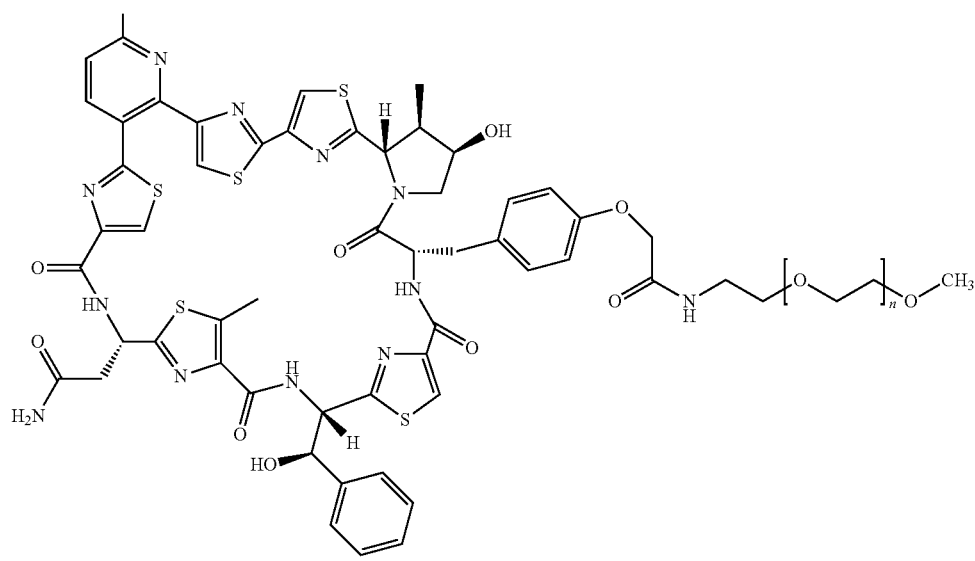

n (average) = 15.2

Step 1:

To a solution of amide 34 (960 mg, 0.72 mmol) in DMF (5 mL) is added tert-butylbromoacetate (221 uL, 1.51 mmol) and $K_2CO_3$ (248 mg, 1.79 mmol). The reaction stirs at RT for overnight. When LC-MS indicates that reaction is finished, 50 mL water is added to the mixture to precipitate product. The mixture is then filtered and washed with water twice to remove $K_2CO_3$ and DMF. Compound 152 is obtained and dried for 12 h in vacuum oven (1.04 g). LC/MS: $[M+2H]^+$ 1455, $R_t$=1.56 min (method 10).

Step 2:

To a solution of tert-butyl ester 152 (1.04 g, 0.72 mmol) in DCM (20 mL) is added TFA (2.7 mL, 36 mmol). The reaction stirs at RT for 5 h and is mounted onto $SiO_2$ and purified by flash chromatography (10% MeOH/DCM) which results in the recovery of 472 mg of acid 153. The impure fractions are combined and purified by RP-HPLC (20-90% ACN/0.015 M ammonium hydroxide in water) which results in the recovery of another 232 mg of acid 153. LC/MS: $[M+2H]^+$ 1399, $R_t$=1.29 min (method 10).

Step 3:

To a solution of acid 153 (135 mg, 0.097 mmol) in DMF (20 mL) is added DIPEA (51 uL, 0.291 mmol), methoxypolyethylene glycol amine 750 (146 mg, 0.194 mmol, n(average)=15.2) and HATU (92 mg, 0.24 mmol). The reaction stirs at RT for 1 h and is quenched by adding water. The aqueous phase is extracted with 5% MeOH/DCM three times, combined organic phases is dried over sodium sulfate, filtered, concentrated in vacuo and purified by flash chromatography (10% MeOH/DCM) which results in the recovery of 230.5 mg of ester 154. LC/MS: $[M+2H+H_2O]^+$ 1068 (n=15), $R_t$=1.34 min (method 10).

Step 4:

To a solution of ester 154 (230.5 mg, 0.108 mmol) in THF (2 mL) is added LiOH (2.7 mL, 0.1M). The reaction stirs at RT for 5 h and is quenched by adding 1N HCl (0.26 mL). The mixture is concentrated in vacuo and purified by HPLC (10-60% ACN/0.015 M ammonium hydroxide in water) affords 155. LC/MS: $[M+2H+H_2O]^+$ 1061 (when n=15), $R_t$=1.17 min (method 10).

Example 130
Preparation of Diacid (156)
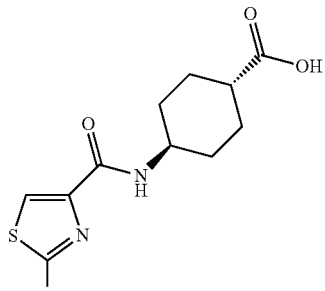
(156)
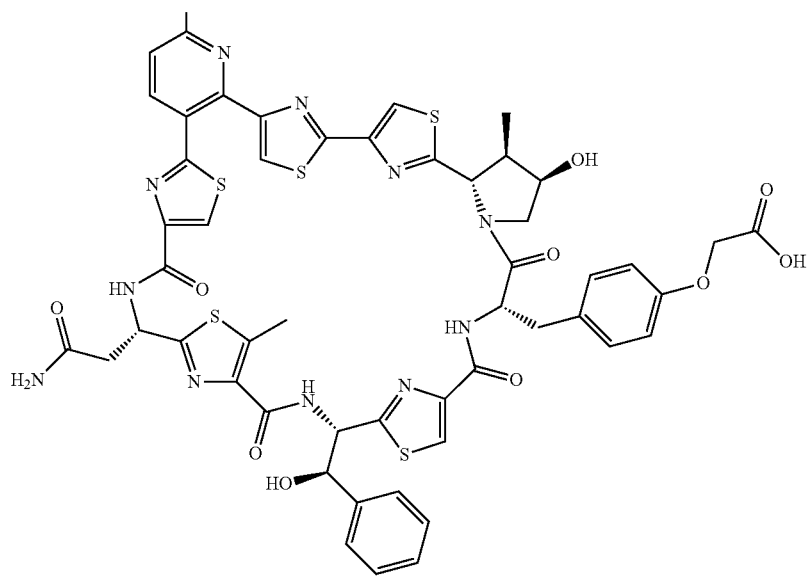
Compound 156 is prepared as described in scheme 13 and in example 129. LC/MS: [M+3H]$^+$ 1386, $R_t$ 1.06 min (method 10).
Example 131
Preparation of Amino-Acid (157)
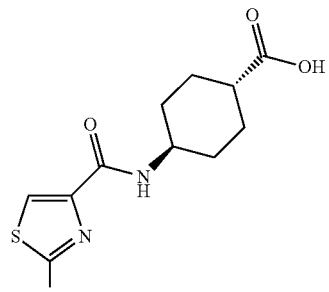
(157)

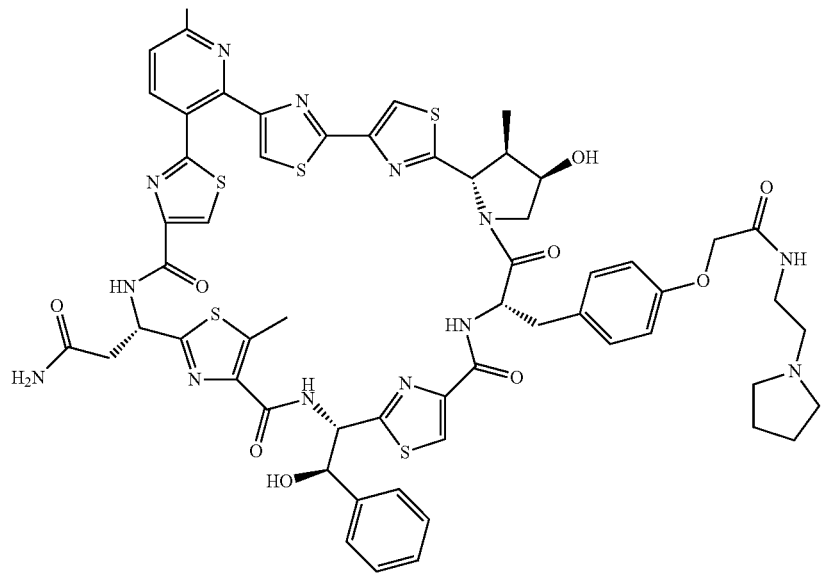
Compound 157 is prepared as described in scheme 13 and in example 129. LC/MS: [M/2+2H]$^+$ 742, R$_t$ 1.06 min (method 10).
Example 132
Preparation of Acid (158)
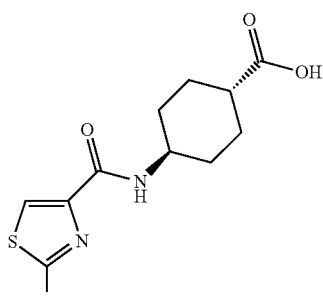
(158)

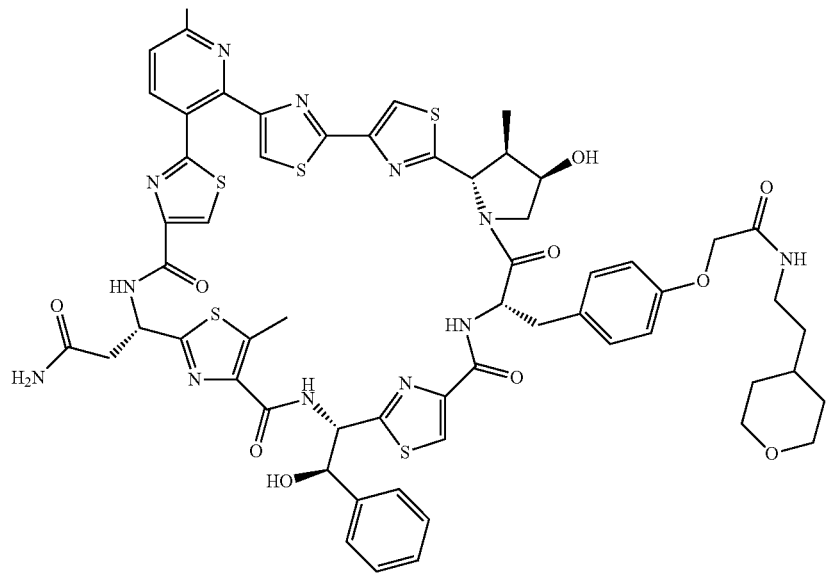
Compound 158 is prepared as described in scheme 13 and in example 129. LC/MS: [M+2H]$^+$ 1496, R$_t$ 1.25 min (method 10).
Example 133
Preparation of Amino-Acid (159)
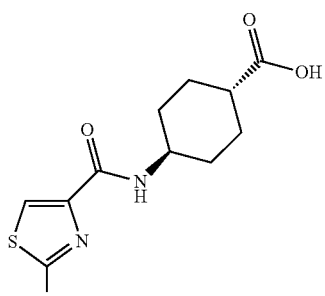
(159)

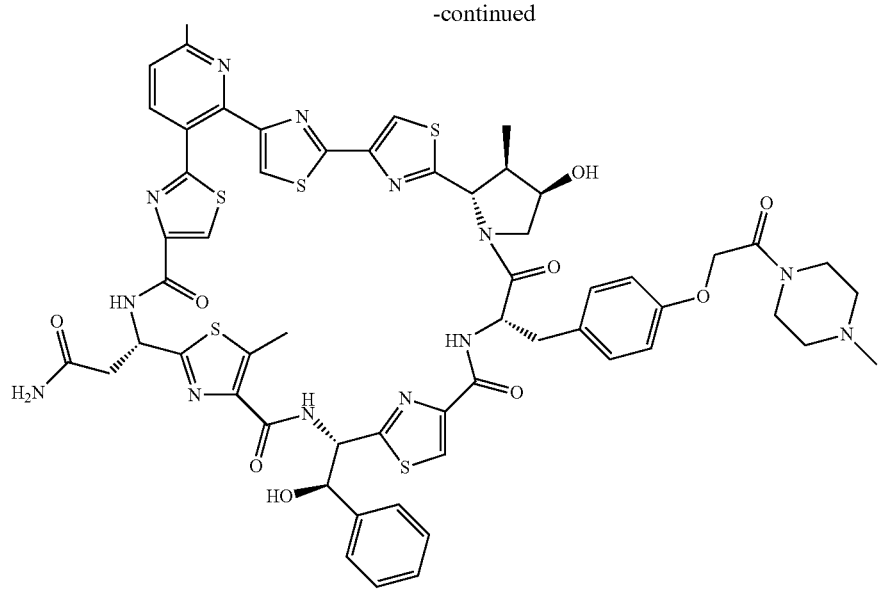
Compound 159 is prepared as described in scheme 13 and in example 129. LC/MS: [M+2H]⁺ 1467, R_t 1.09 min (method 10).
Example 134
Preparation of Acid (160)
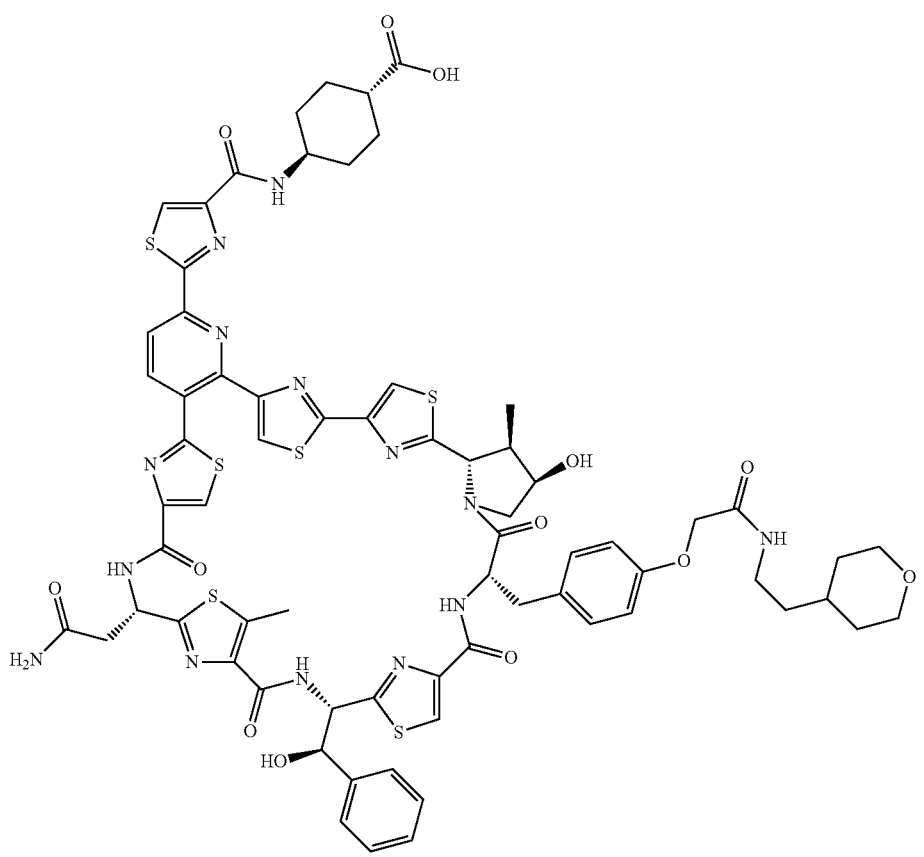

Compound 160 is prepared as described in scheme 13 and in example 129. LC/MS: [M+2H]⁺ 1496, R$_t$ 1.10 min (method 10).
Example 135
Preparation of Diacid (161)
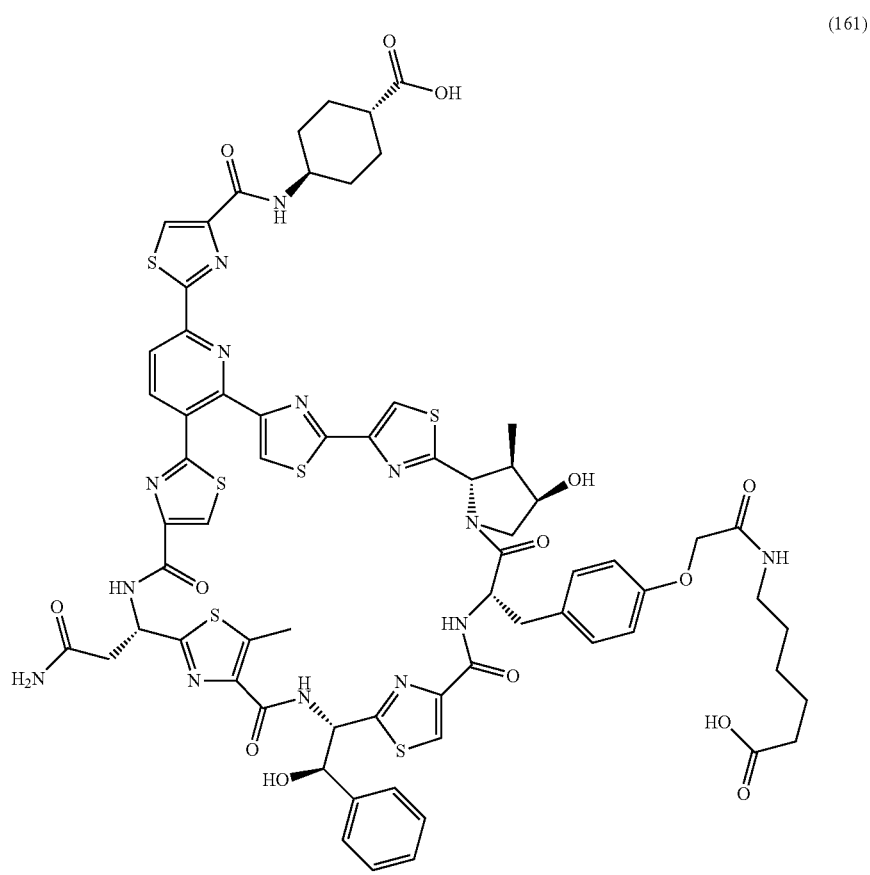 [SMILES: Cc1sc2nc1C(=O)N[C@@H]([C@H](O)c1ccccc1)c1nc(cs1)C(=O)N[C@@H](Cc1ccc(OCC(=O)NCCCCCC(=O)O)cc1)C(=O)N1C[C@H](O)[C@H](C)[C@H]1c1nc(cs1)-c1nc(cs1)-c1nc(-c3nc(C(=O)N[C@H]4CC[C@H](C(=O)O)CC4)cs3)ccc1-c1nc(cs1)C(=O)N[C@H]2CC(N)=O]
(161)
Compound 161 is prepared as described in scheme 13 and in example 129. LC/MS: [M+3H]⁺ 1499, R$_t$ 1.12 min (method 10).

Example 136
Preparation of Acid (162)
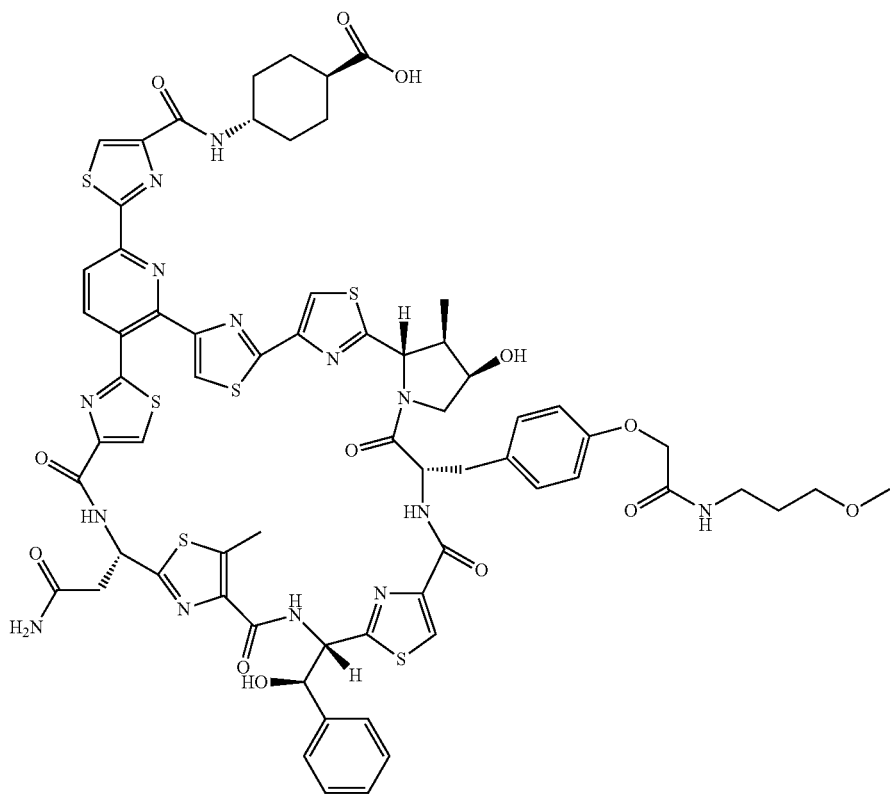
(162)
Compound 162 is prepared as described in scheme 13 and in example 129. LC/MS: [M/2+2H]$^+$ 729, R$_t$ 1.21 min (method 10).

Example 137
Preparation of Acid (163)
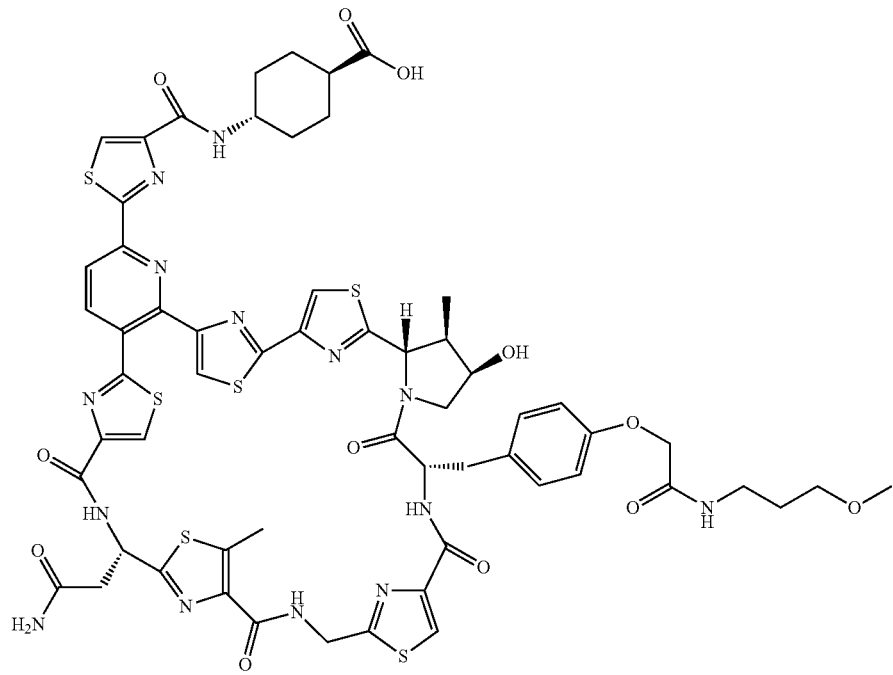
Compound 163 is prepared as described in scheme 13 and in example 129. LC/MS: $[M+2H]^+$ 1350, $R_t$ 1.13 min (method 10).
Example 138
Preparation of Diacid (164)

Compound 164 is prepared as described in scheme 5.
LC/MS: [M+H]$^+$ 1224, $R_t$=1.04 min (method 10).
Scheme 14:
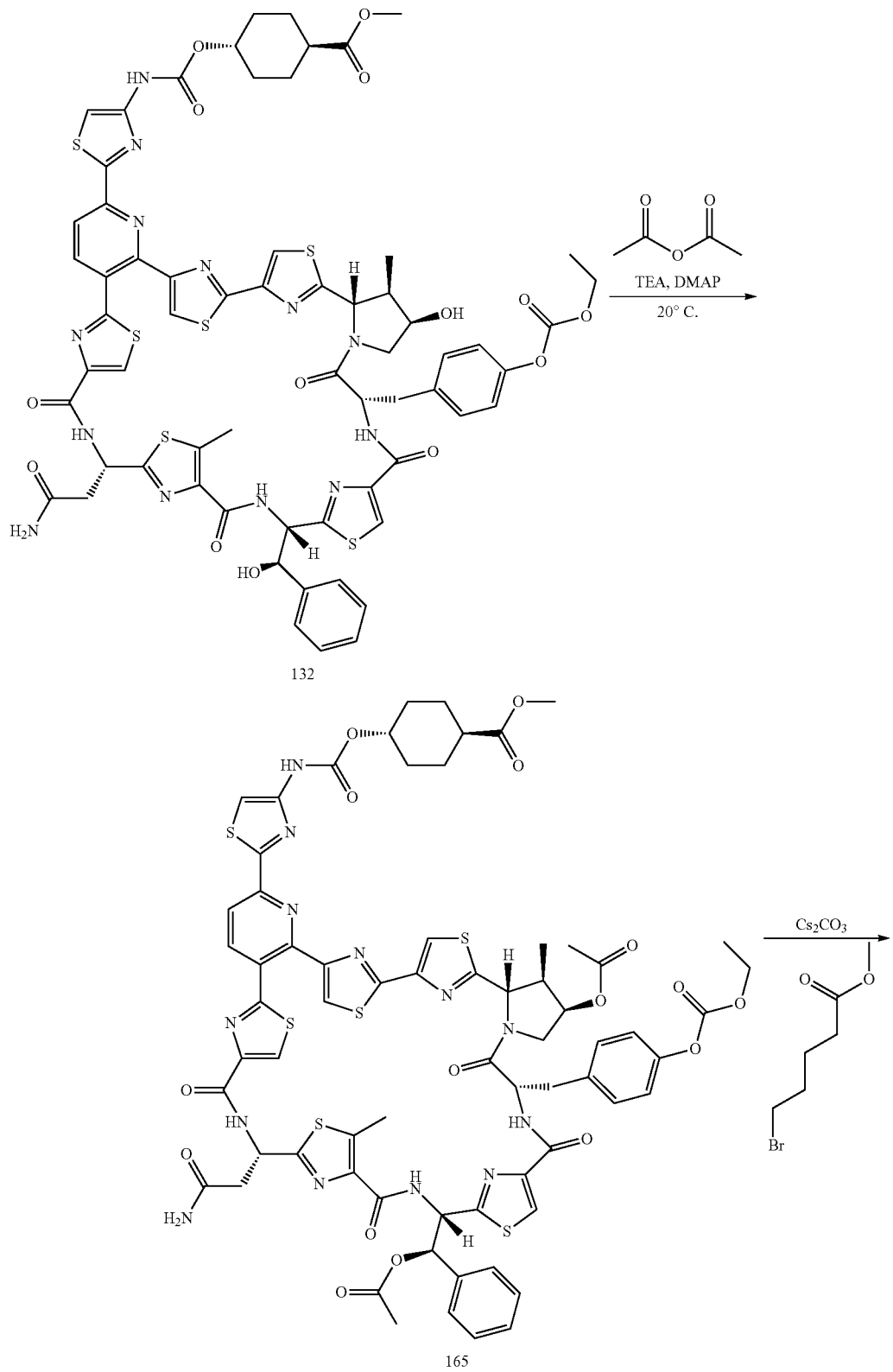

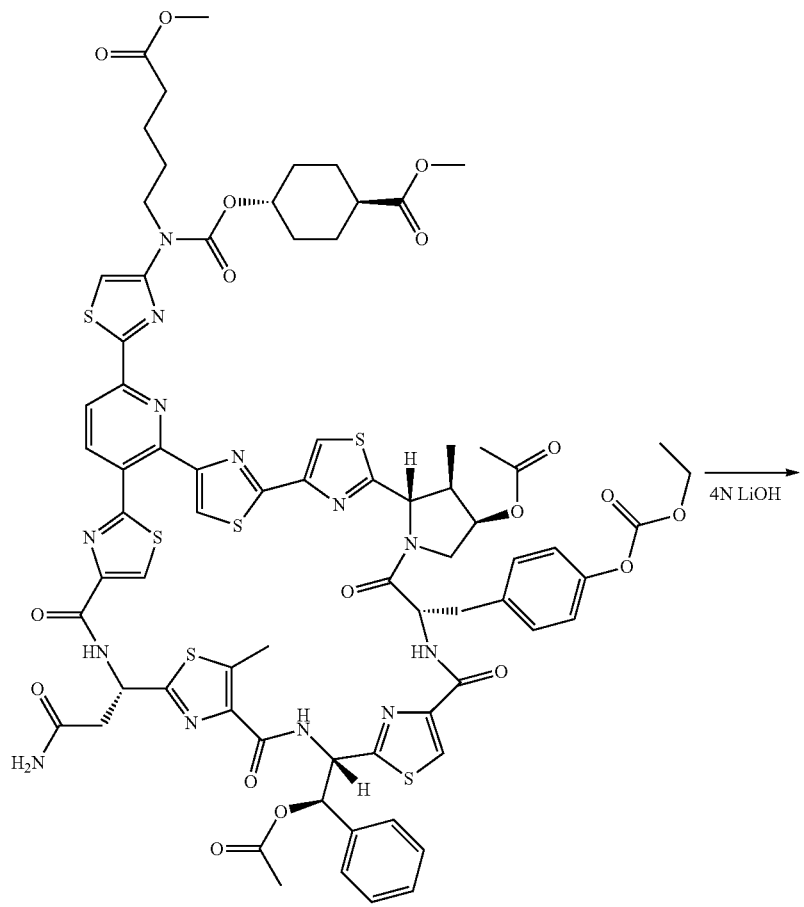
166
4N LiOH

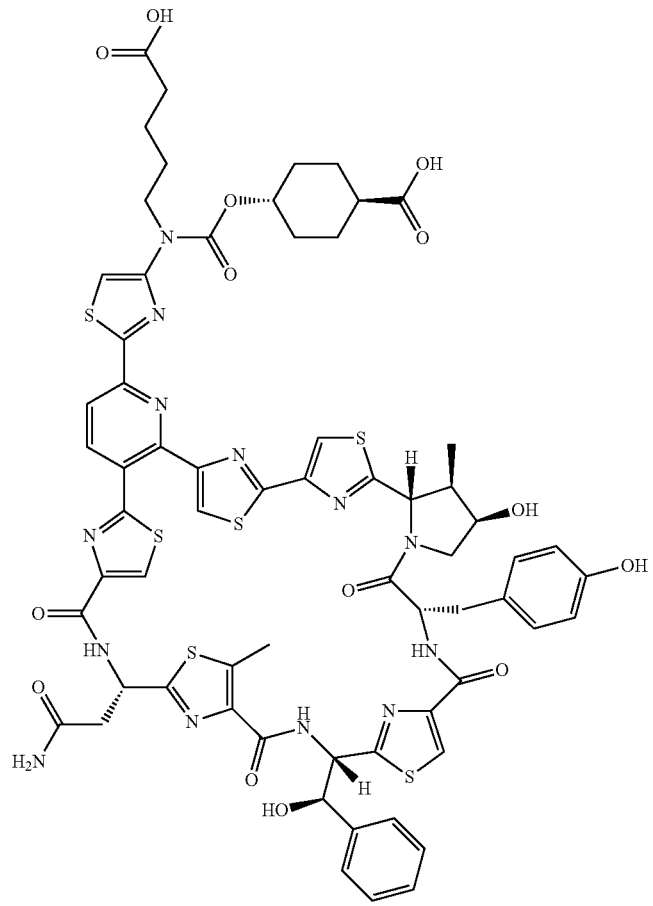
167

Example 139

Preparation of Diacid (167)

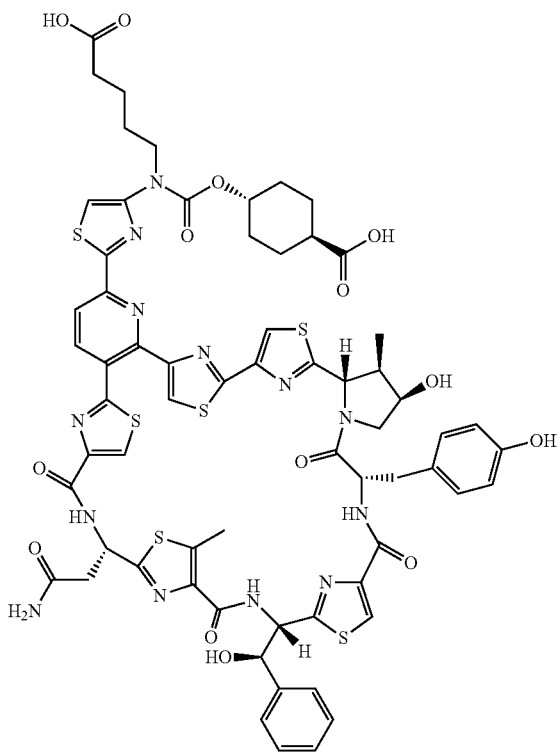
(167)

Step 1:

To a solution of compound 132 (scheme 10, 680 mg) in dichloromethane (57 mL) are added triethylamine (0.6 mL), acetic anhydride (0.44 mL) and 4-di(methylamino)pyridine (57 mg) at 20° C. The reaction is stirred at room temperature for 1 hour. The solvents are evaporated and the residue is flashed on silica (gradient elution 0-10% i-PrOH/DCM) to afford 600 mg of the diacetate 165. LC/MS: $[M+H_3O]^+$ 1531, $R_t$=1.65 min (method 13).

Step 2:

To a solution of the diacetate (165) (600 mg in 18 mL N,N-dimethylformamide) are added oven dried 4 angstrom molecular sieves (1.15 g), methyl-5-bromovalerate (1.13 mL) and cesium carbonate (1.29 g). The reaction is stirred at room temperature until complete. Acetic acid (5 mL) and silica (6 g) are added and the mixture is evaporated to dryness. Flash chromatography (gradient elution: 0-10% i-PrOH/DCM) provides 522 mg yellow solid 166. LC/MS: $[M+H]^+$ 1627, $R_t$=1.74 min (method 14).

Step 3:

Compound 166 (505 mg) is dissolved in 1:1 dichloromethane:methanol (30 mL) and chilled to 0° C. Saturated lithium hydroxide solution (5 mL) is added slowly. The reaction is stirred at 0° C. until complete, then quenched with 10 mL acetic acid. The solvent is evaporated and the residue purified by HPLC to produce compound 167, 240 mg. LC/MS: $[M+2H]^+$ 1443, $R_t$=1.39 min (method 9).

Scheme 15:

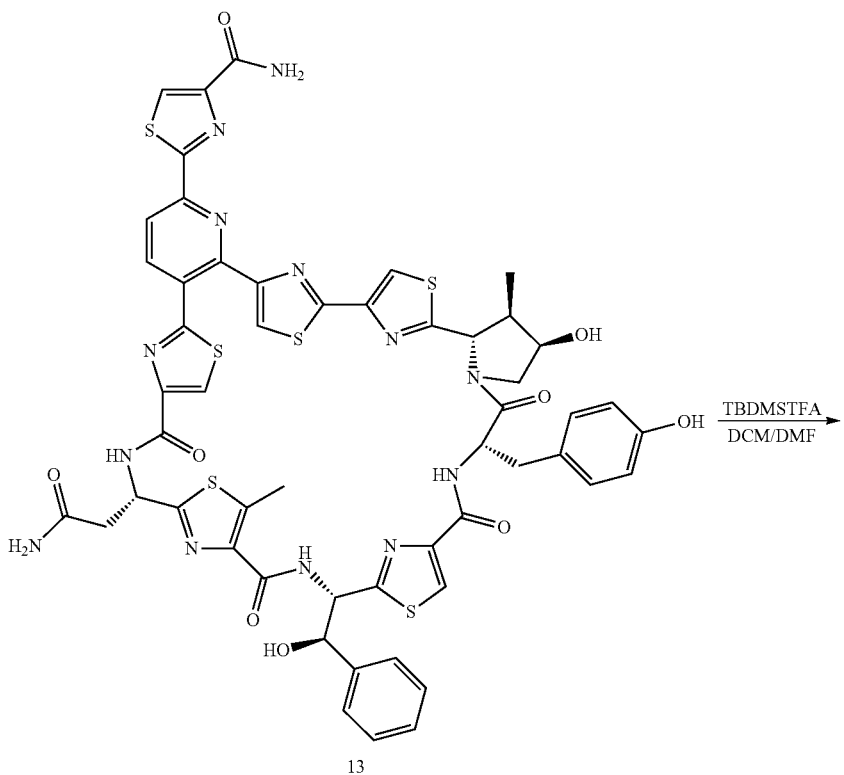

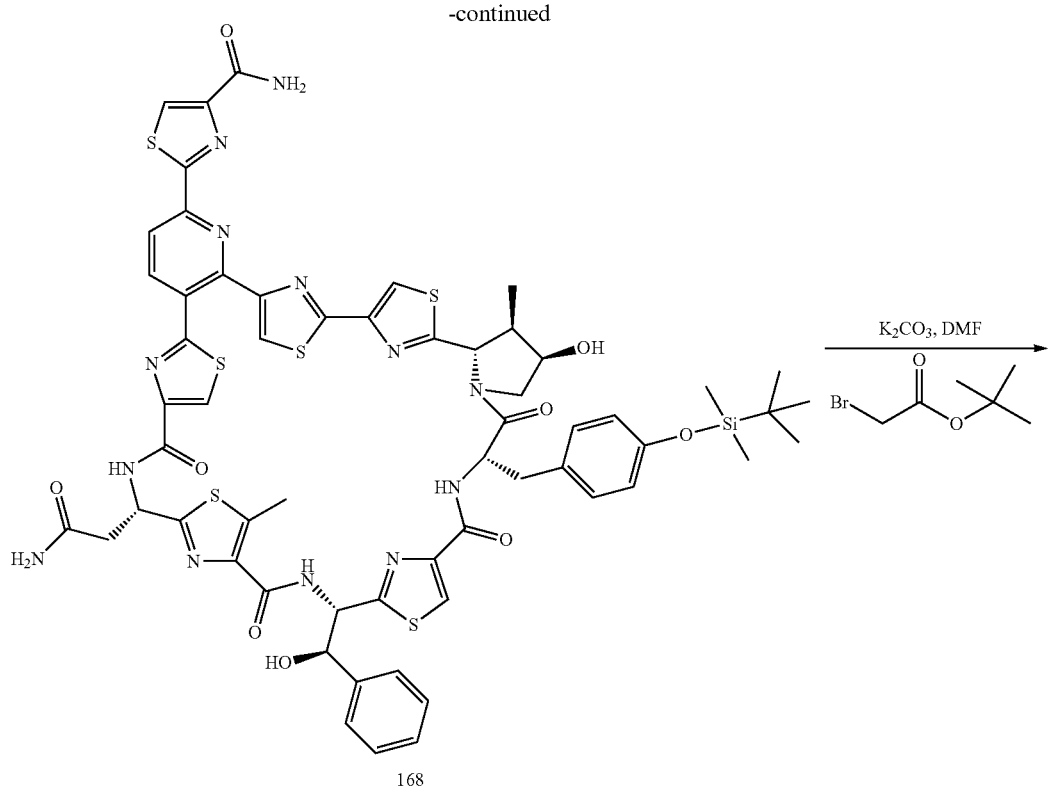
168
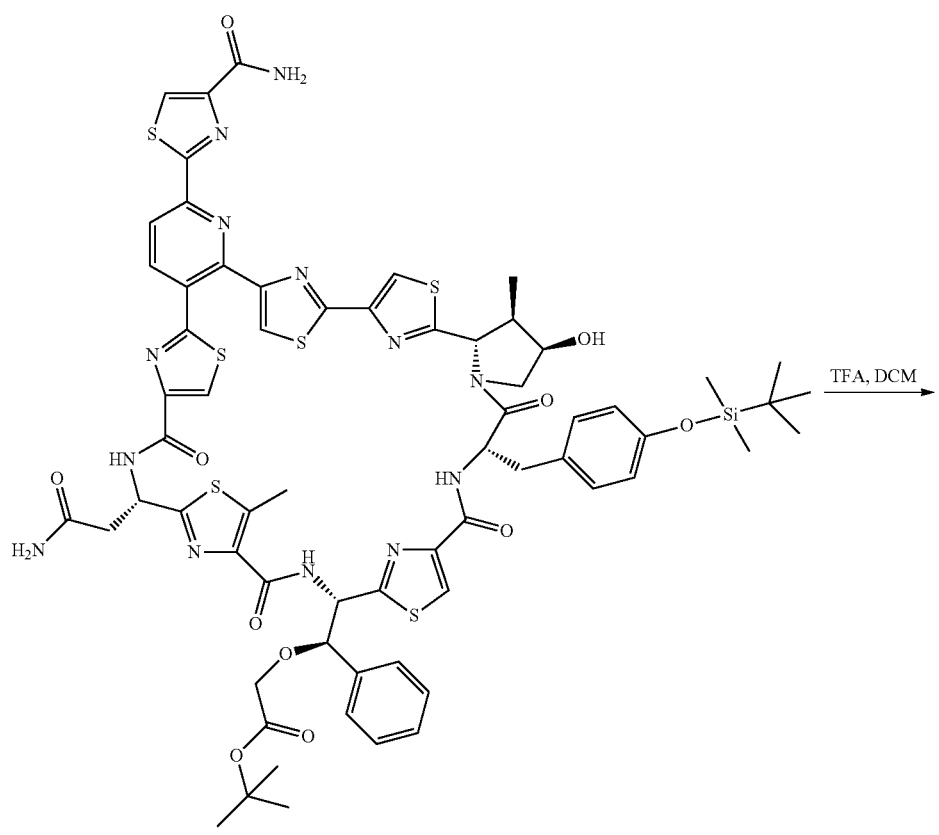
169

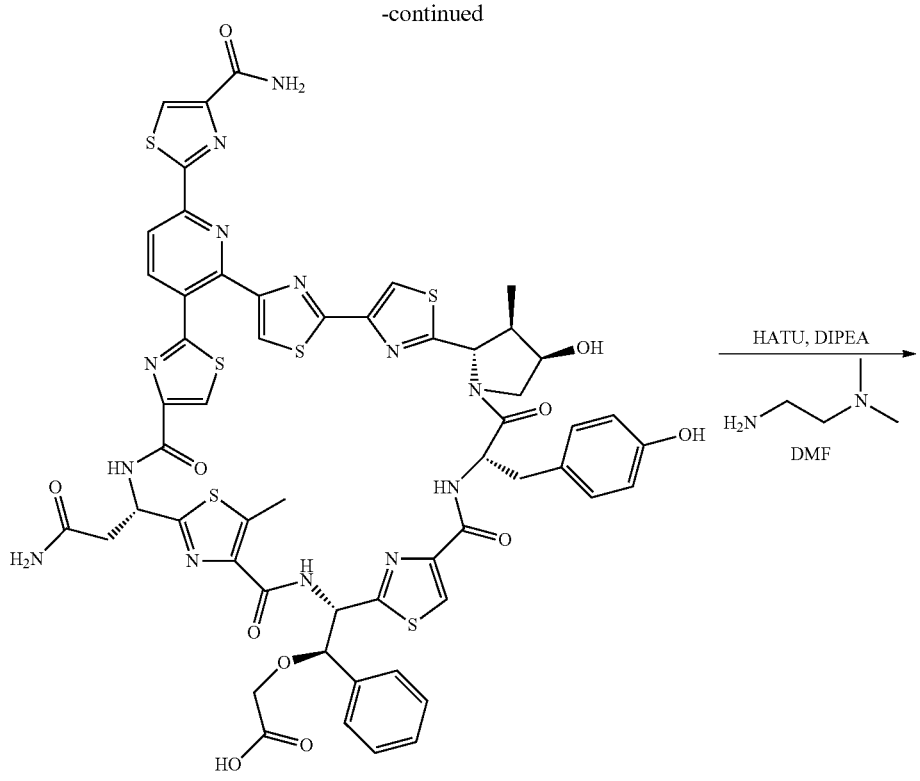
170
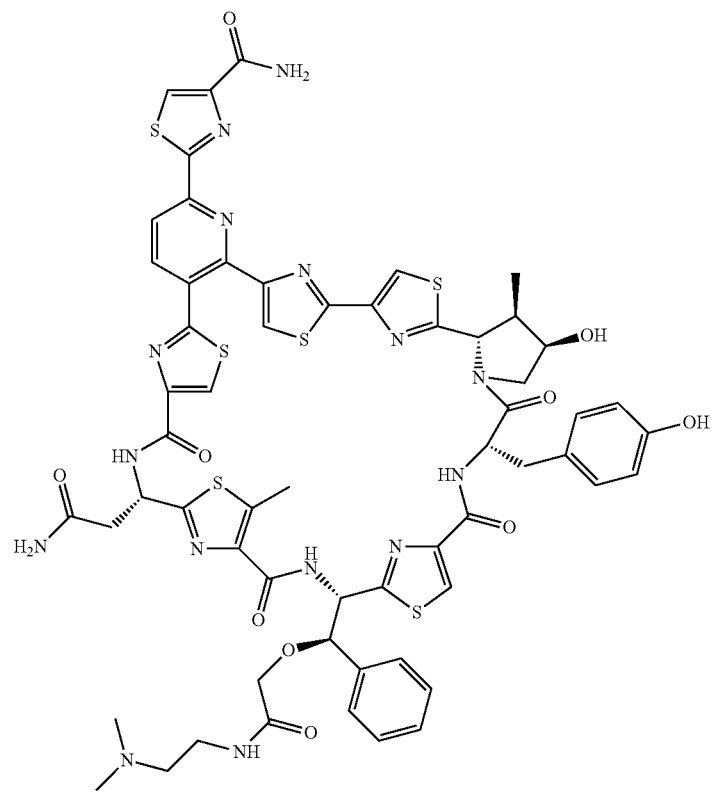
171

Example 140

Preparation of Amine (170, 171)

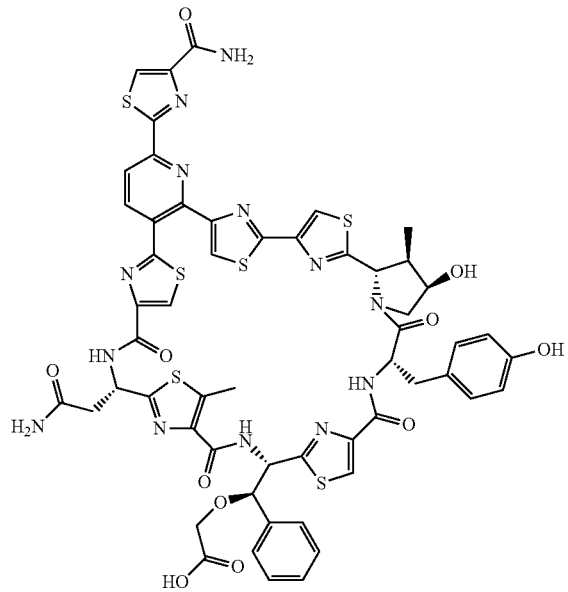

(170)

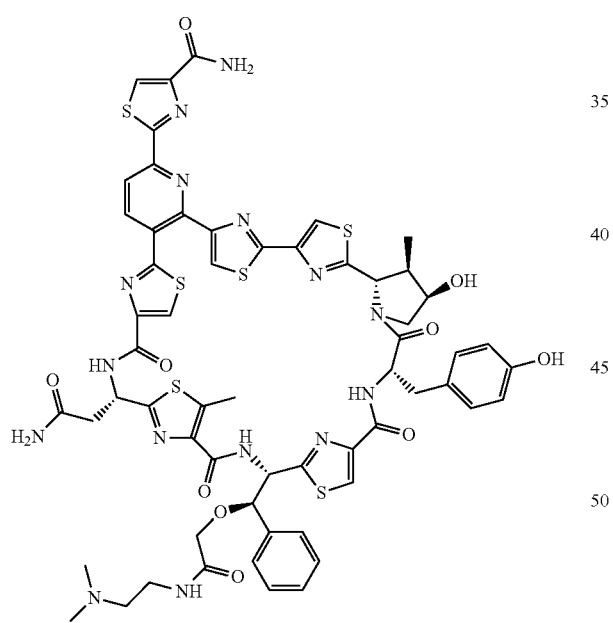

(171)

Step 1:

A mixture of 13 (2 g, 1.667 mmol), TBDMSTFA (N-tert-butyldimethylsilyl-N-methyltrifluoroacetamide, 2.642 g, 10.948 mmol) and DMF/DCM (10 mL/20 mL) is stirred at RT for 4 h. The solvent is removed under reduced pressure at 40° C. The residue is purified by flash chromatography (gradient elution: 0-10% MeOH/DCM) which affords 1 g of 168. LC/MS: [M+2H]$^+$ 1315, R$_t$=1.56 min (method 13).

Step 2:

To a suspension of 168 (560 mg, 0.426 mmol) and potassium carbonate (924 mg, 6.686 mmol) in anhydrous DMF (10 ml) is added t-butyl bromoacetate (1.305 g, 6.690 mmol). The resulting reaction is stirred at RT under N$_2$ overnight. The solid is filtered, and the solvent is removed under reduced vacuum. The residue is purified by flash chromatography (gradient elution: 1-6% MeOH/DCM) which affords 250 mg of 169. LC/MS: [M+4H]$^+$ 1431, R$_t$=1.75 min (method 13).

Step 3:

A solution of 169 (500 mg, 0.350 mmol), TFA (3.5 mL) and thioanisole (2 mL) in DCM (12 mL) is stirred at RT overnight. Additional TFA is added until the starting material disappears. The solvent is removed under reduced vacuum, and the residue is purified by flash chromatography (gradient elution: 5-20% MeOH/DCM) which affords 240 mg of 170. LC/MS: [M+3H]$^+$ 1260, R$_t$ 1.14 min (method 13).

Step 4:

A solution of 170 (50 mg, 0.0397 mmol), N,N-dimethylethyldiamine (3.50 mg, 0.0397 mmol), HATU (20 mg, 0.0526 mmol), DIPEA (51.213 mg, 0.397 mmol) in DMF (1 mL) is stirred at RT overnight. The solvent is removed under reduced pressure. The residue is purified by flash chromatography (gradient elution: 10-20% MeOH/DCM) which affords 15 mg of 171. LC/MS: [M+2H]$^+$ 1329, R$_t$ 1.06 min (method 13).

Example 141

Preparation of Amine (172)

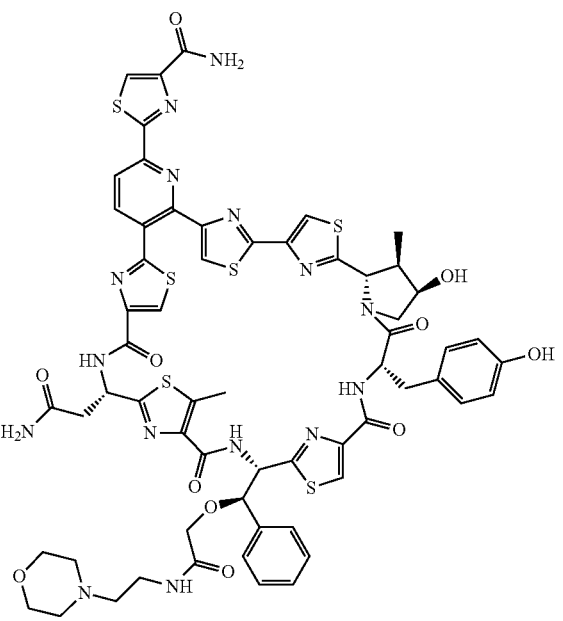

(172)

Compound 172 is prepared according to the procedures described in example 140. LC/MS: [M+2H]$^+$ 1371, R$_t$=1.17 min (method 13).

Example 142

Preparation of Acid (173)

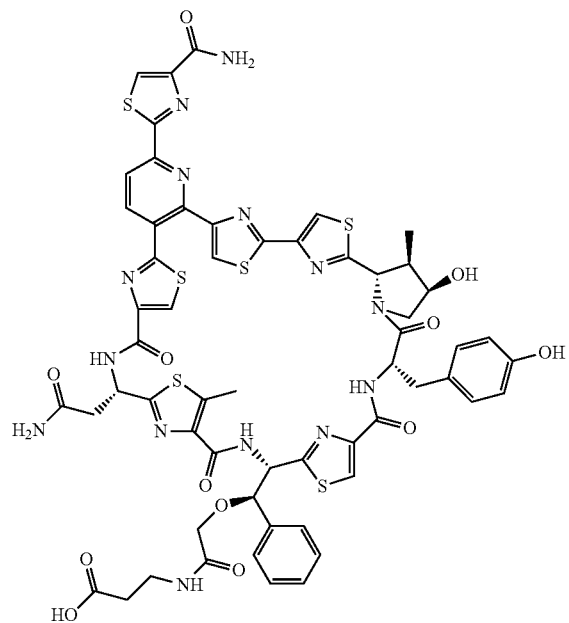

(173)

Compound 173 is prepared according to the procedures described in example 140. LC/MS: [M+2H]$^+$ 1330, R$_t$=1.13 min (method 13).

Example 143

Preparation of Diacid (174)

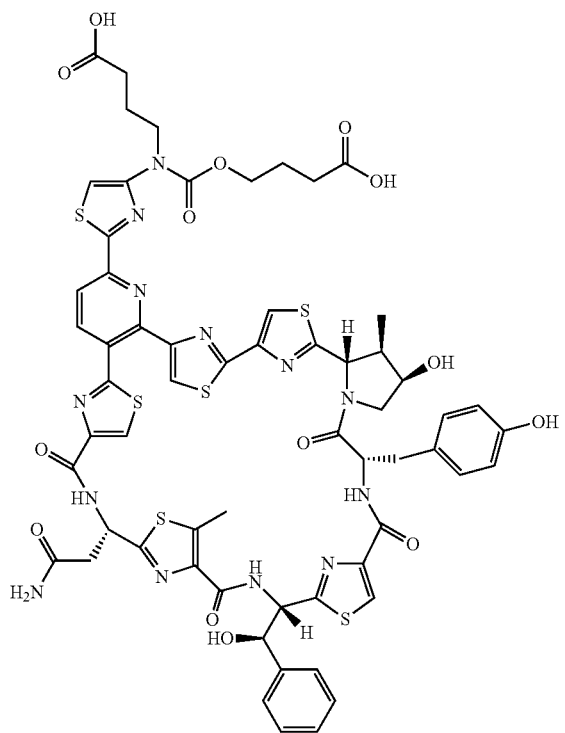

(174)

Compound 174 is prepared according to the procedures described in example 139.

LC/MS: [M+H]$^+$ 1388, R$_t$=1.27 min (method 14).

Biological Activity

Using standard MIC test described above with the bacteria *Enterococcus faecalis, Enterococcus faecium, Staphylococcus aureus,* or *Streptomyces pyogenes*, compounds 1-17, 20-24, 26, 29-37, 39, 40, 42-66, 69-98, 100-115, 117-124, 127, 130, 133, 134, 137-142, 145-151, 155-164, 167, 170-174 demonstrate a minimum inhibitory concentration of <32 mg/mL.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A method of treating a bacterial infection, comprising:
administering to a subject in need thereof a pharmaceutically acceptable amount of a compound of Formula III:

III

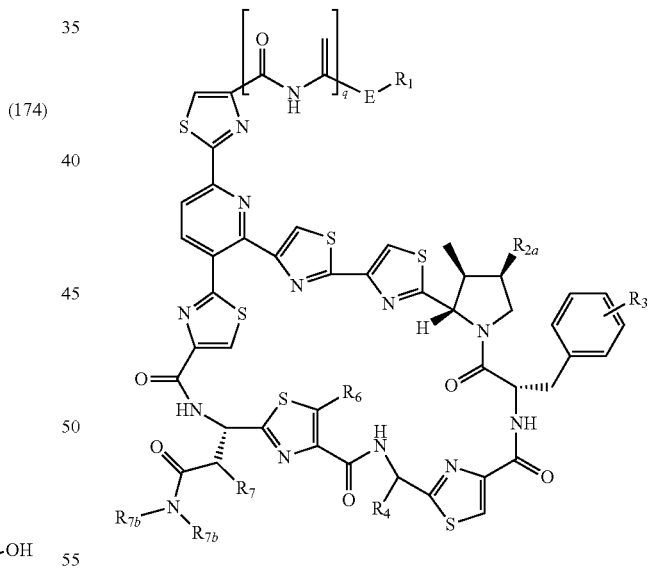

or pharmaceutically acceptable salts thereof; wherein
q is 1, or 2 and the fragment

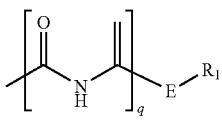

is selected from the group consisting of:
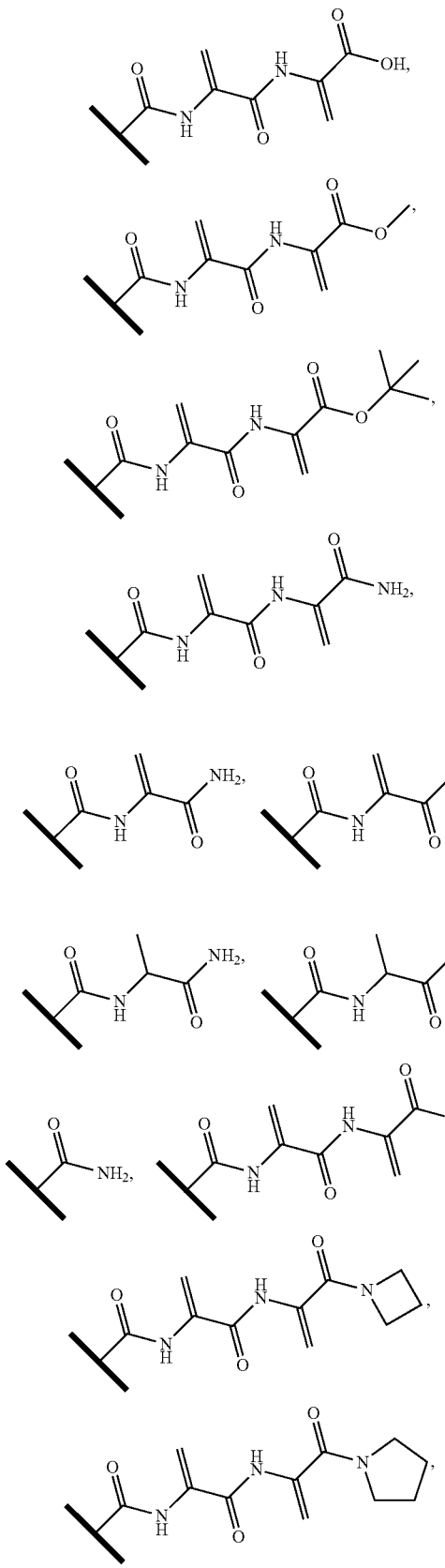
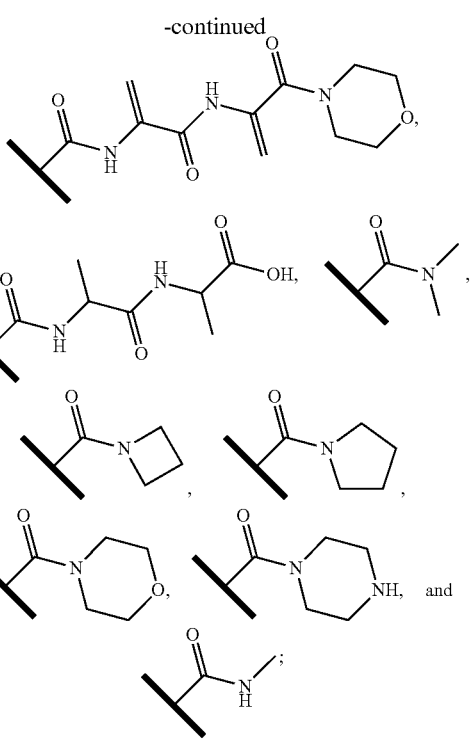
or
q is 0 and E-R₁ is selected from the group consisting of:
NR₁R₁₂,
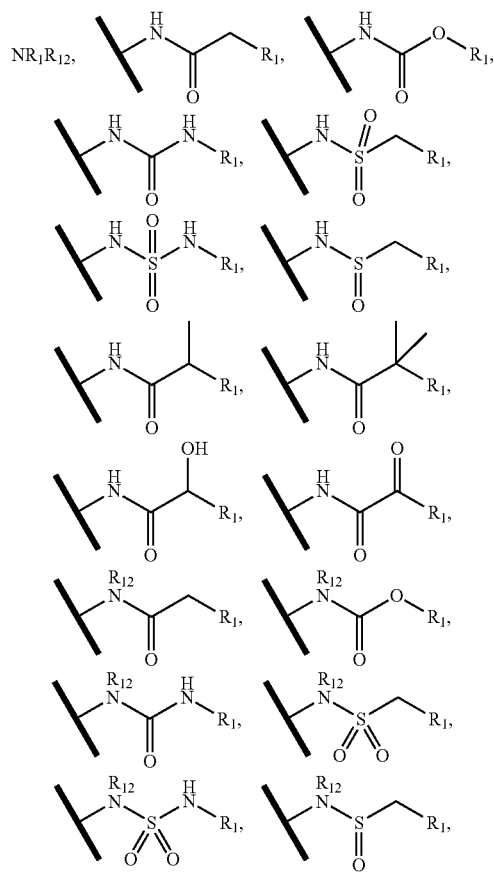
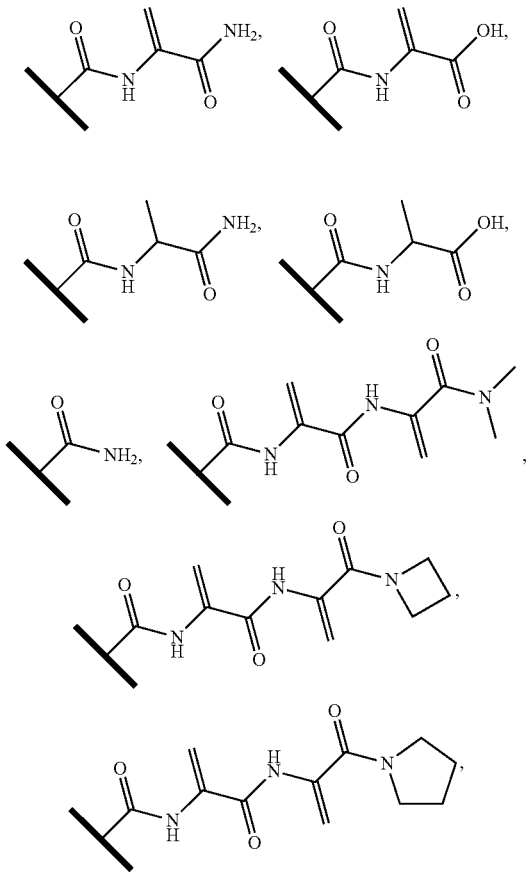

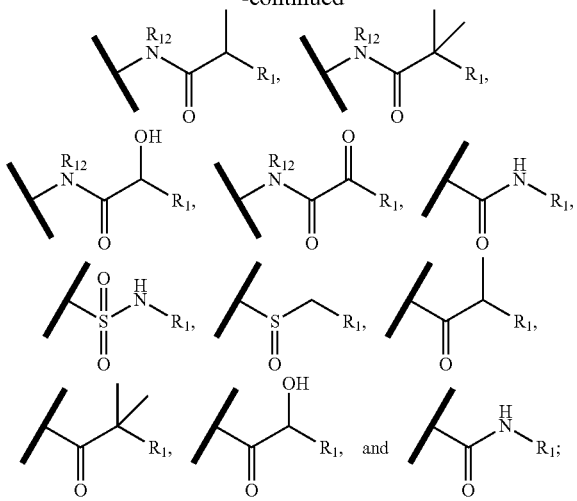

and

R₁ is selected from the group consisting of hydrogen, hydroxymethyl, and aminomethyl and R₁₂;

R$_{2a}$ is hydrogen, hydroxy or amino, or is selected from the group consisting of $C_{1-8}$alkoxy, amino, mono- and di-$C_{1-8}$alkylamino, $C_{3-7}$cycloalkyl$C_{0-6}$alkoxy, each of which is substituted with hydroxy, oxo, halo, $C_{1-8}$alkyl, halo$C_{1-8}$alkyl, $C_{1-8}$alkoxy, halo$C_{1-8}$alkoxy, $C_{3-7}$cycloalkyl$C_{0-6}$alkyl, COOH, NH₂, mono- and di-$C_{1-8}$alkylamino, tri-$C_{1-8}$alkylammonium, heterocycle$C_{0-6}$alkyl, heteroaryl$C_{0-6}$alkyl, or —(CH₂—CH₂—O—)$_n$—R₈;

R₃ is selected from R₁₂, OR₁₂, N(R₁₂)₂ or R₁₃;

R₄ is selected from hydrogen, CO₂R$_{4a}$, C(O)N(R$_{4a}$)₂, OR$_{3a}$, N(R$_{3a}$)₂, or C(R₁₀)(R₁₁)phenyl;

R$_{4a}$ is independently selected at each occurrence from hydrogen, hydroxymethyl, aminomethyl or R₁₂;

R₆ is hydrogen or $C_{1-4}$alkyl;

R₇ is selected from the group consisting of H, OH, NH₂, $C_{1-8}$alkyl, $C_{1-8}$alkoxy, and mono- and di-$C_{1-8}$alkylamino;

R$_{7b}$ is independently selected at each occurrence from the group consisting of H, $C_{1-8}$alkyl and —(CH₂—CH₂—O—)$_n$—R₈;

R₈ is independently selected at each occurrence from the group consisting of H, $C_{1-8}$alkyl and CH₂CO₂H;

R₁₀ is absent or hydrogen;

R₁₁ is oxo, OR$_{4a}$, N(R$_{4a}$)₂, or =NR$_{4a}$;

R₁₂ is independently selected at each occurrence from the group consisting of

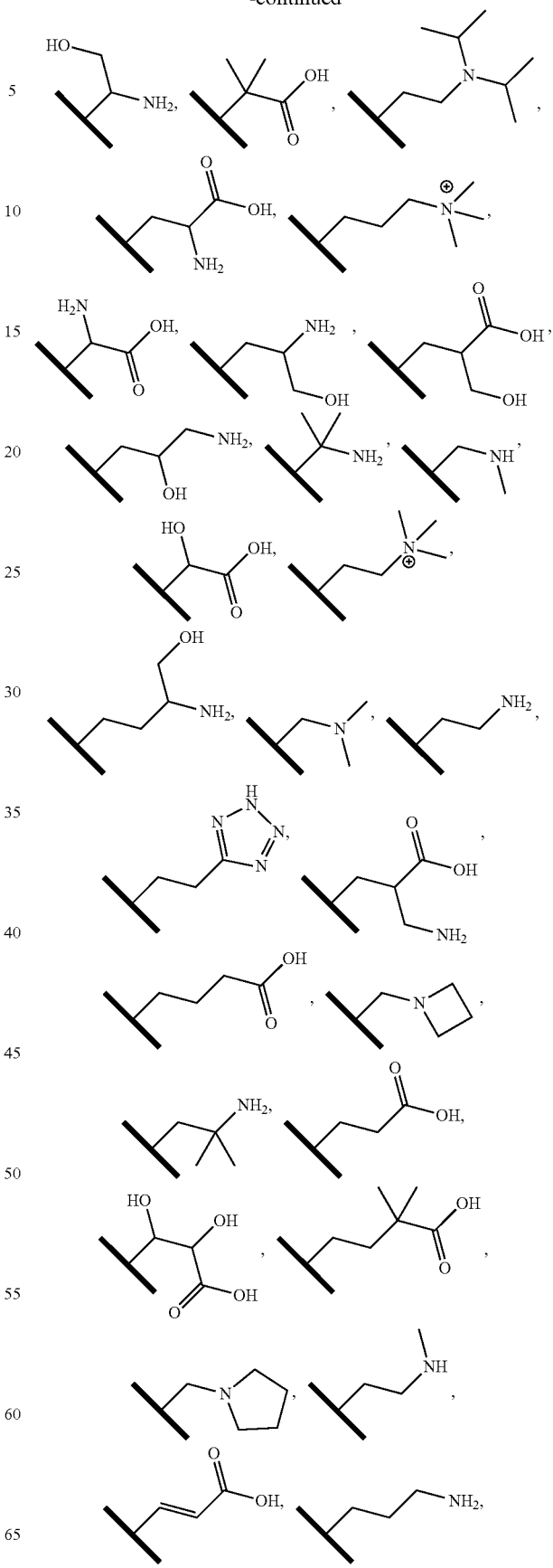

275
-continued
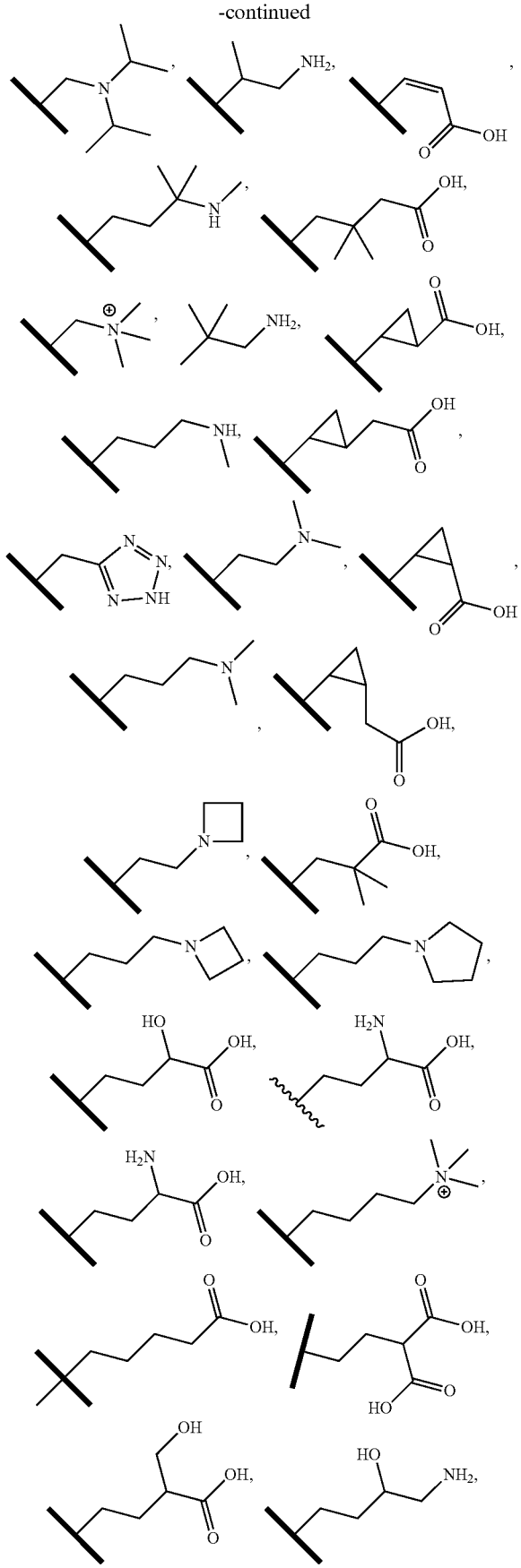
276
-continued
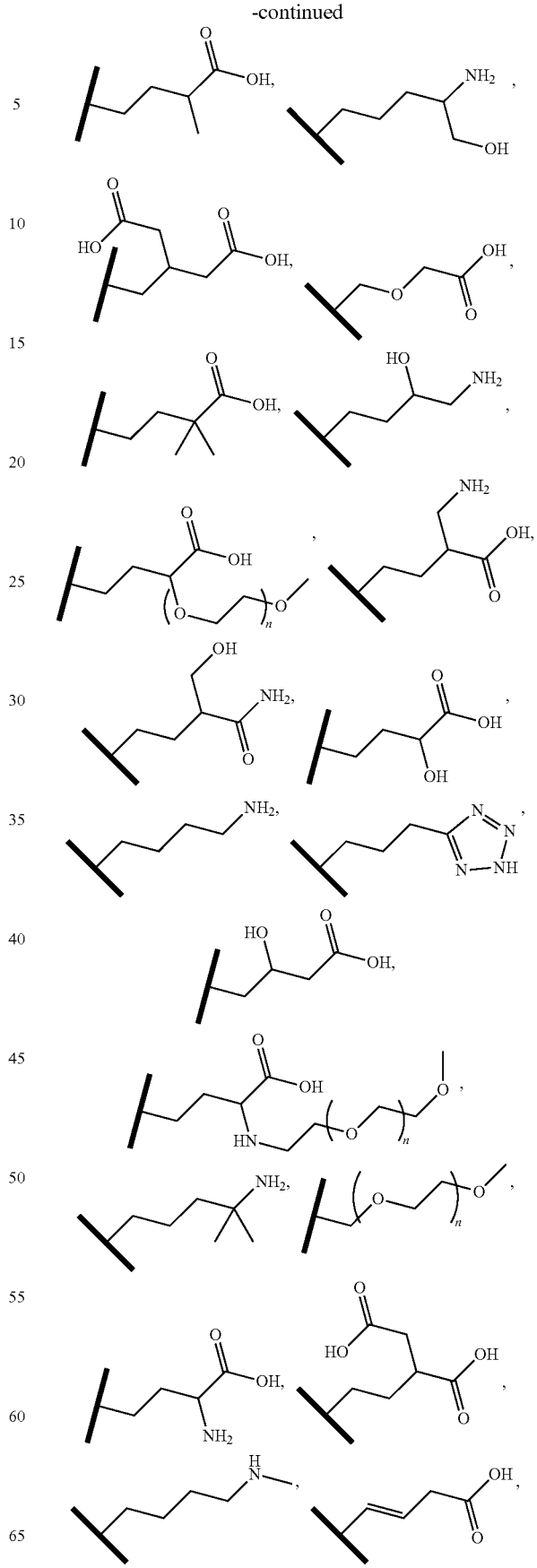

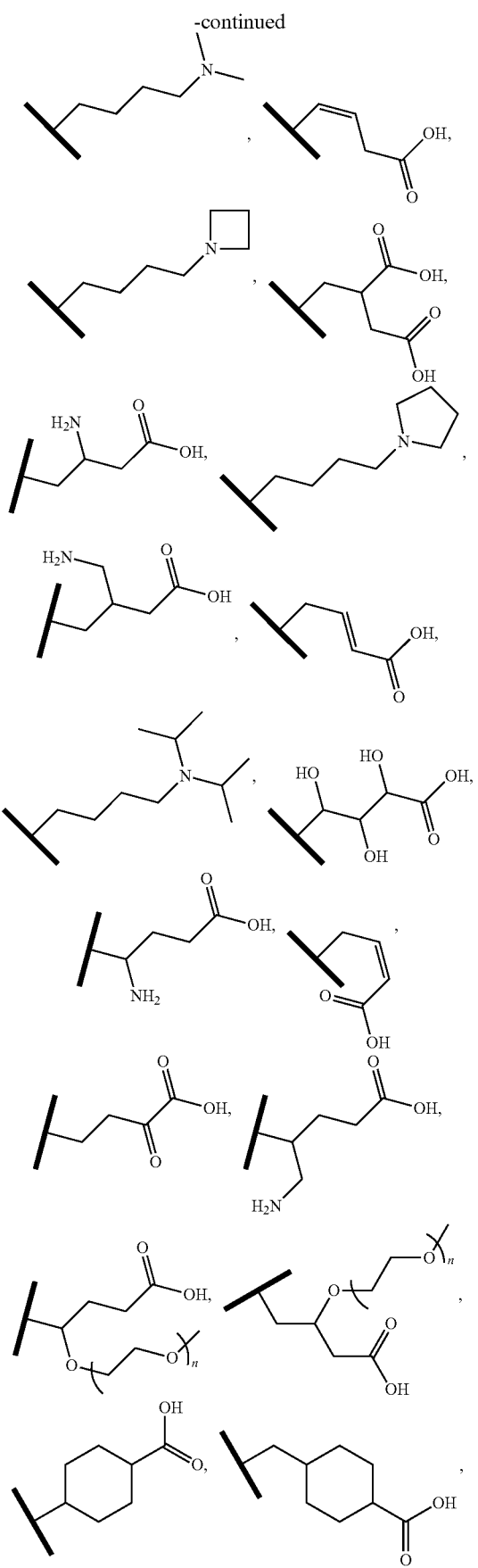
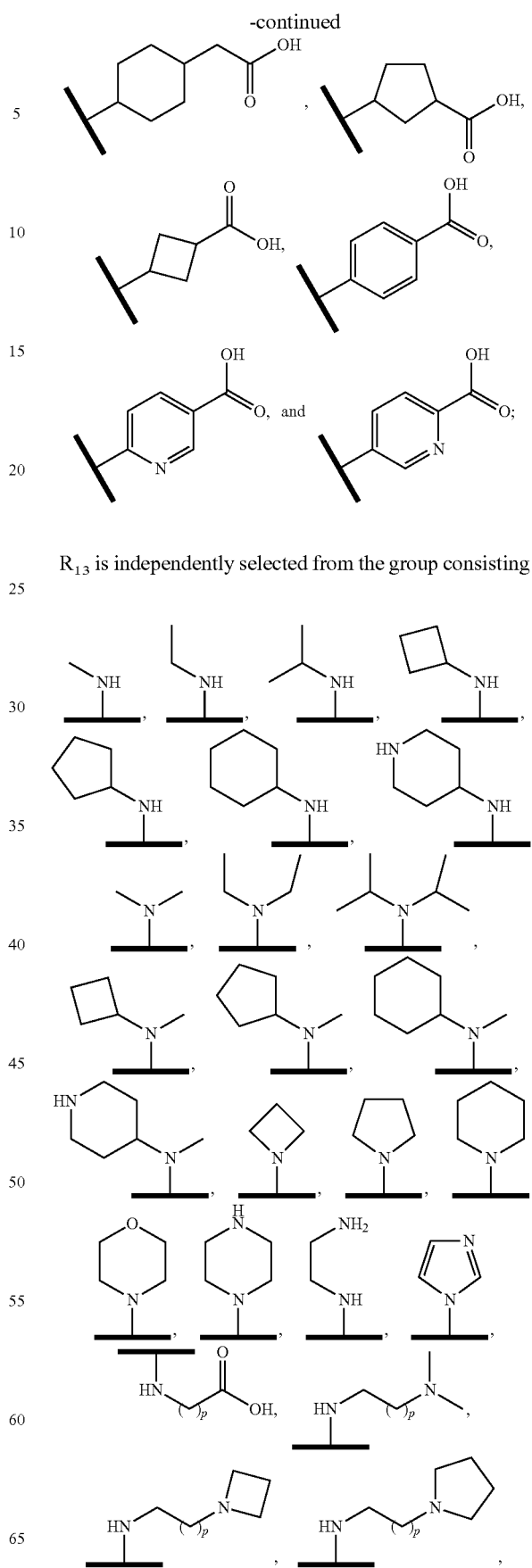
$R_{13}$ is independently selected from the group consisting of -continued

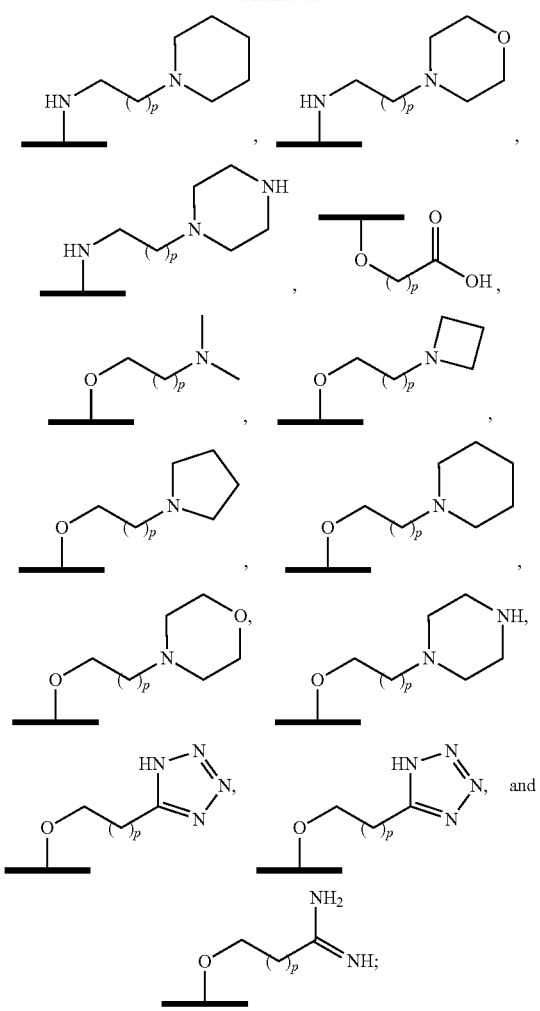

n is an integer of between 1-60,000 or is a mean of a plurality of integers having a value of between 1-60,000; and p is 0, 1, 2, 3, or 4.

2. The method of claim 1, wherein $R_7$ and each occurrence of $R_{7b}$ are hydrogen.

3. The method of claim 1, wherein q is 0; E-$R_1$ is selected from the group consisting of

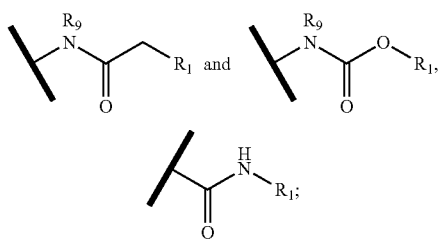

$R_1$ and $R_9$ are independently selected from the group consisting of hydrogen, hydroxymethyl, aminomethyl and $R_{12}$;

$R_{12}$ is independently selected at each occurrence from the group consisting of:

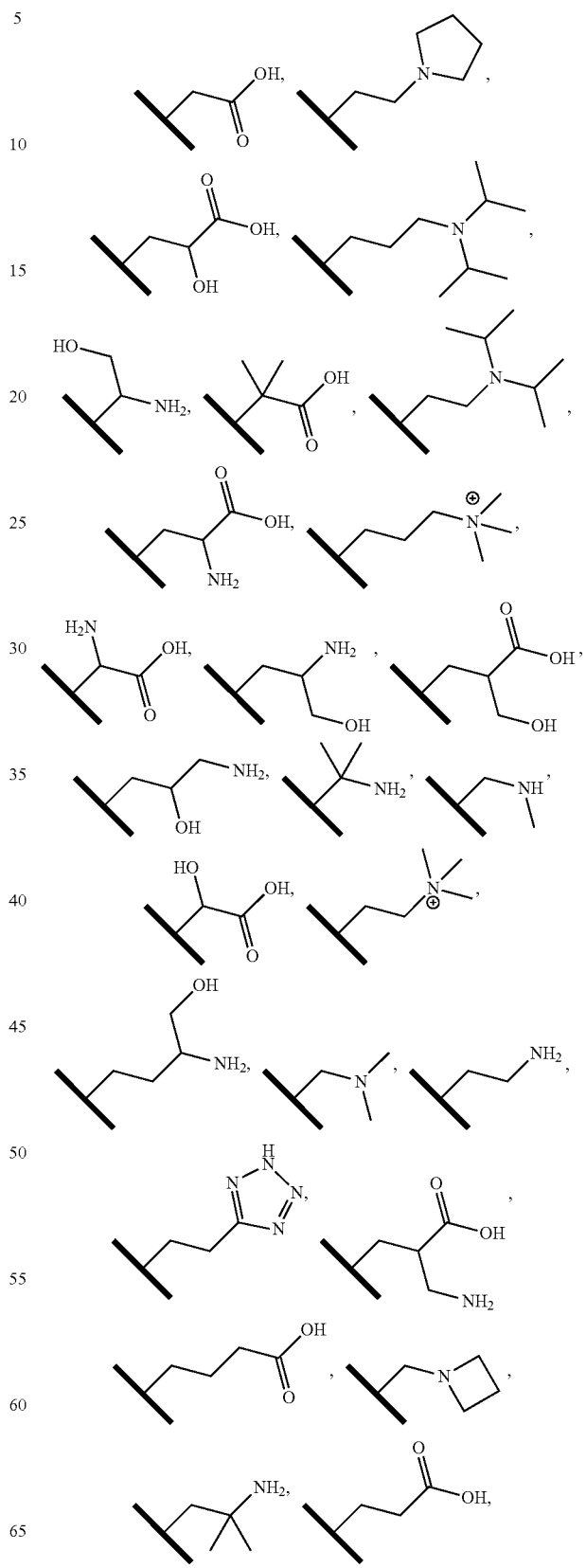

281
-continued
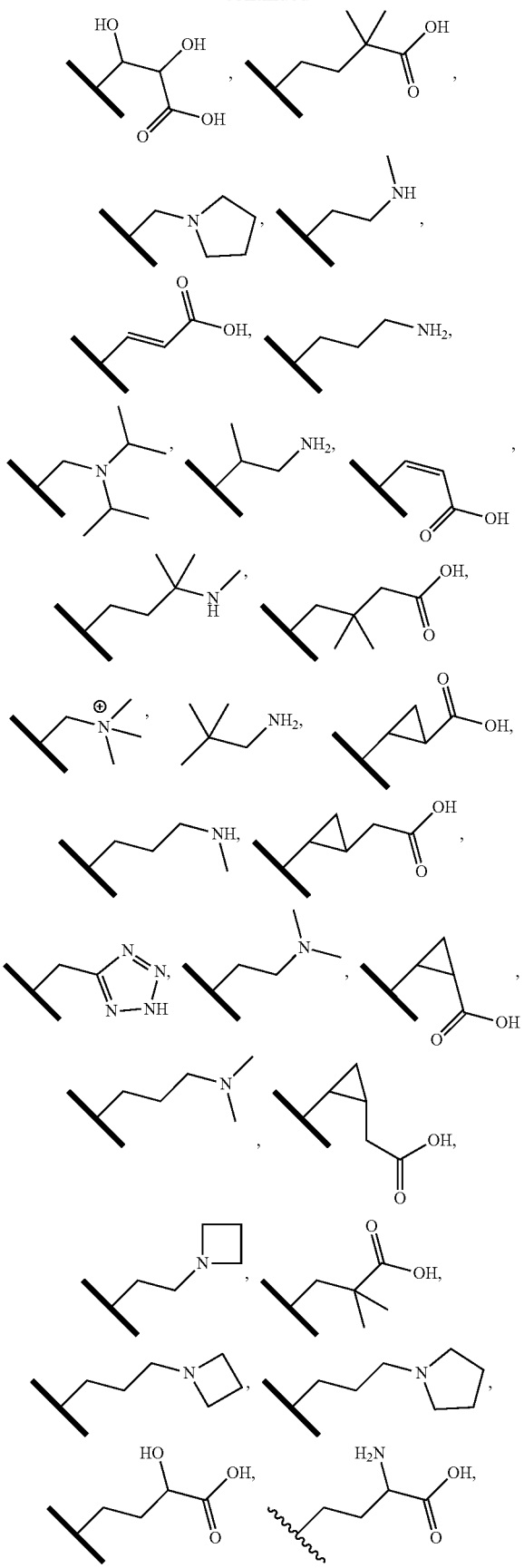
282
-continued
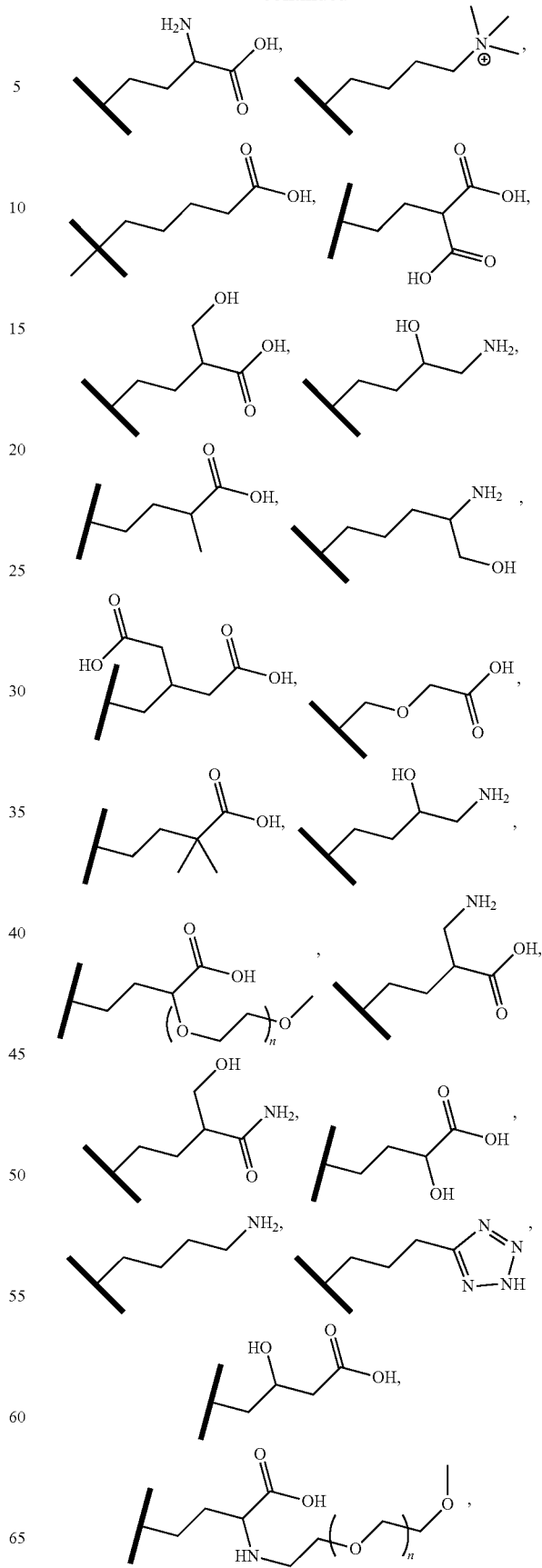

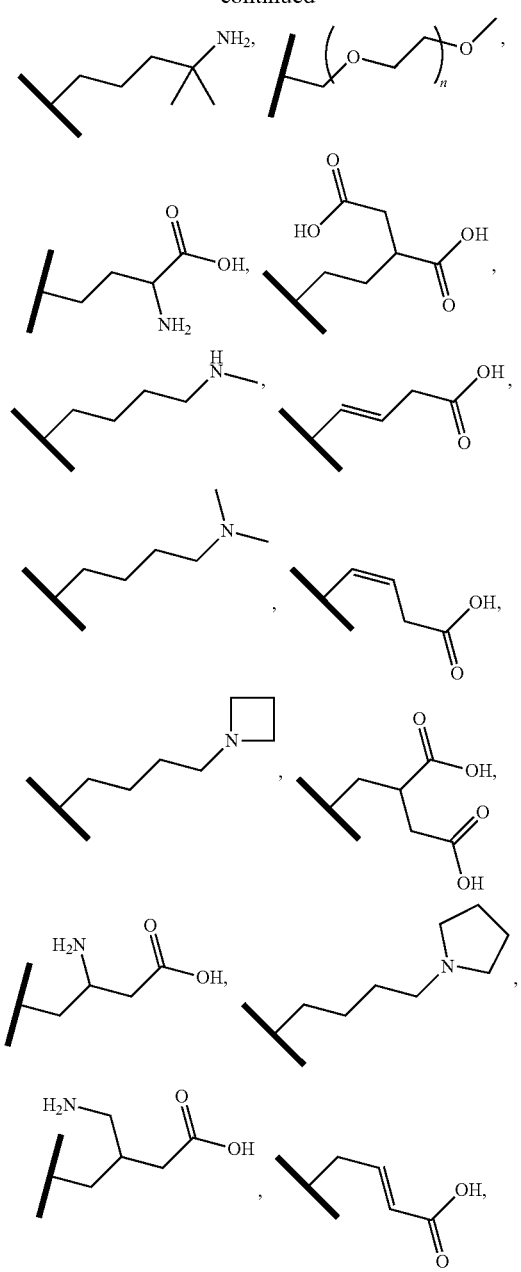
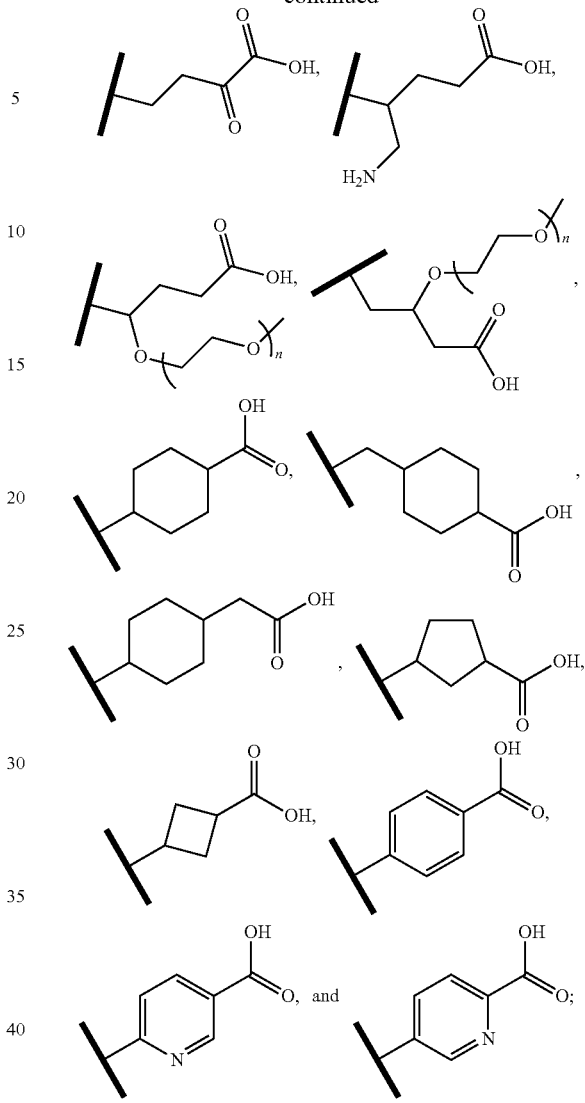
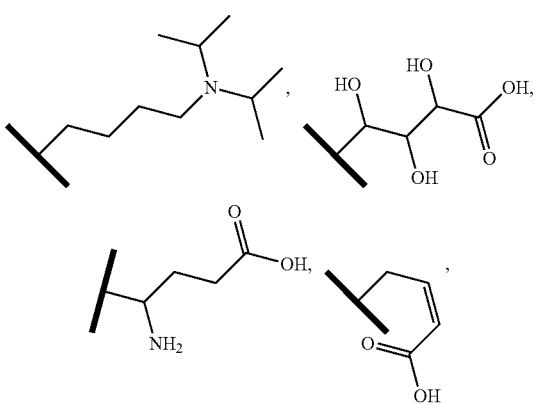
and pharmaceutically acceptable salts thereof.
4. The method of claim 1, wherein $R_{2a}$ is selected from hydrogen, amino, hydroxy, halogen, or is selected from the group consisting of
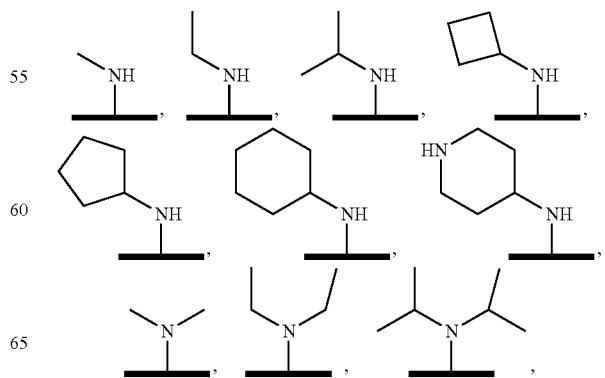

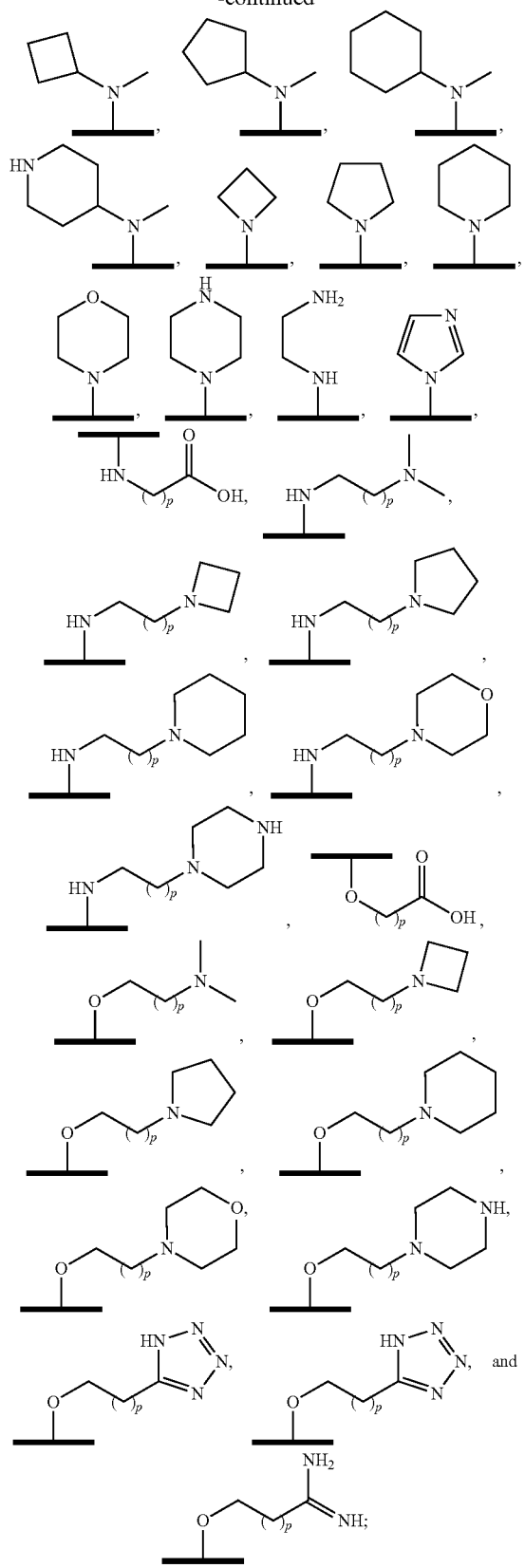
and
p is 0, 1, 2, 3, or 4.
5. The method of claim 1, wherein $R_3$ is selected from $R_{3a}$, $OR_{3a}$ or $N(R_{3a})_2$; or
$R_3$ is selected from the group consisting of
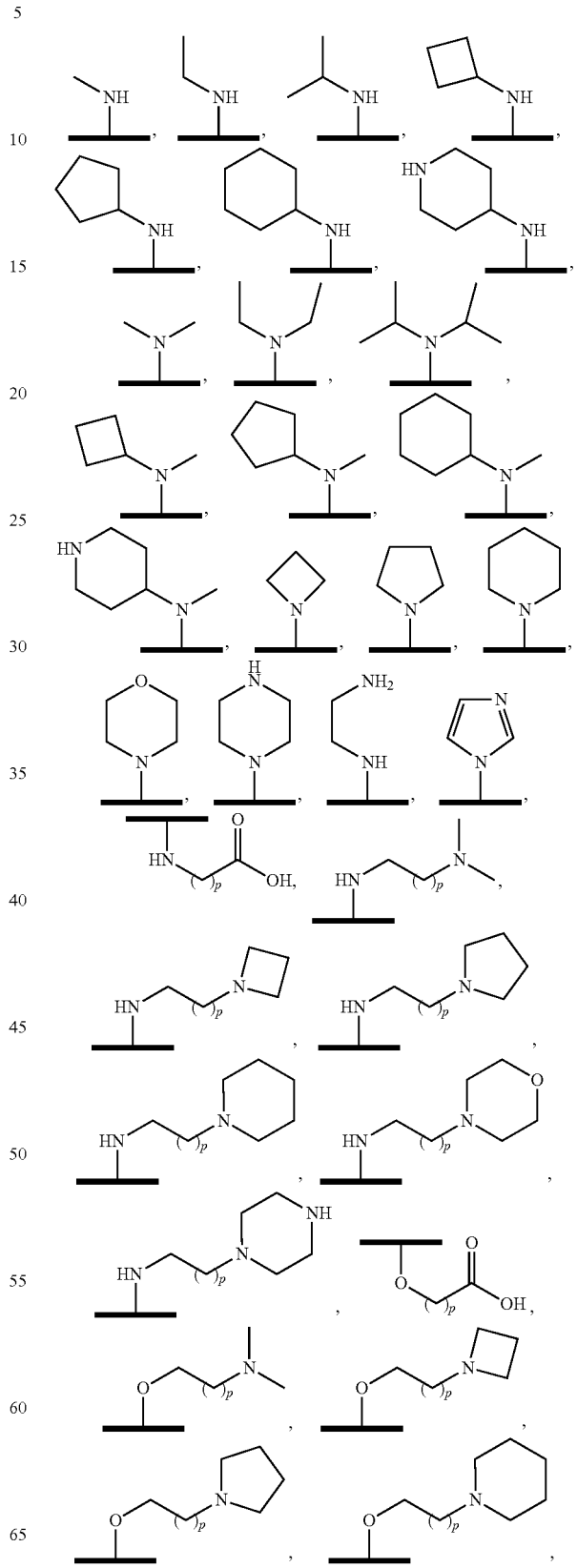

-continued
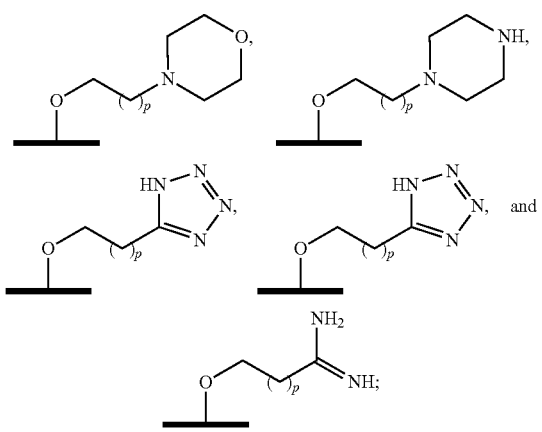
p is 0, 1, 2, 3, or 4; and
$R_{3a}$ is independently selected, at each occurrence from hydrogen, hydroxymethyl, and aminomethyl or from the group consisting of:
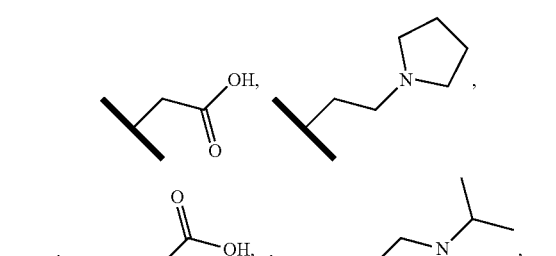
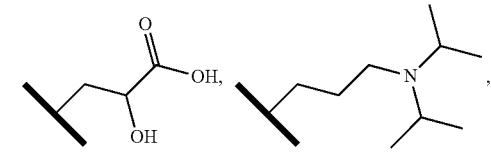
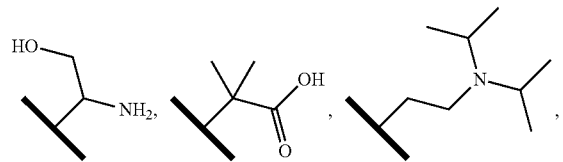
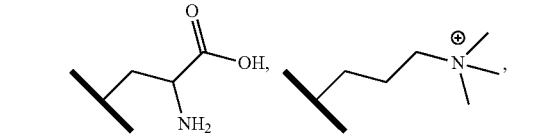
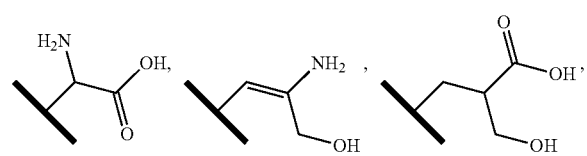
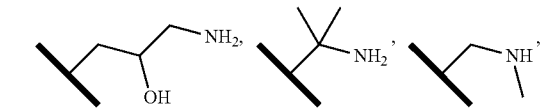
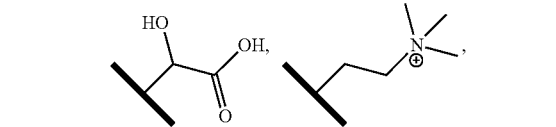
-continued
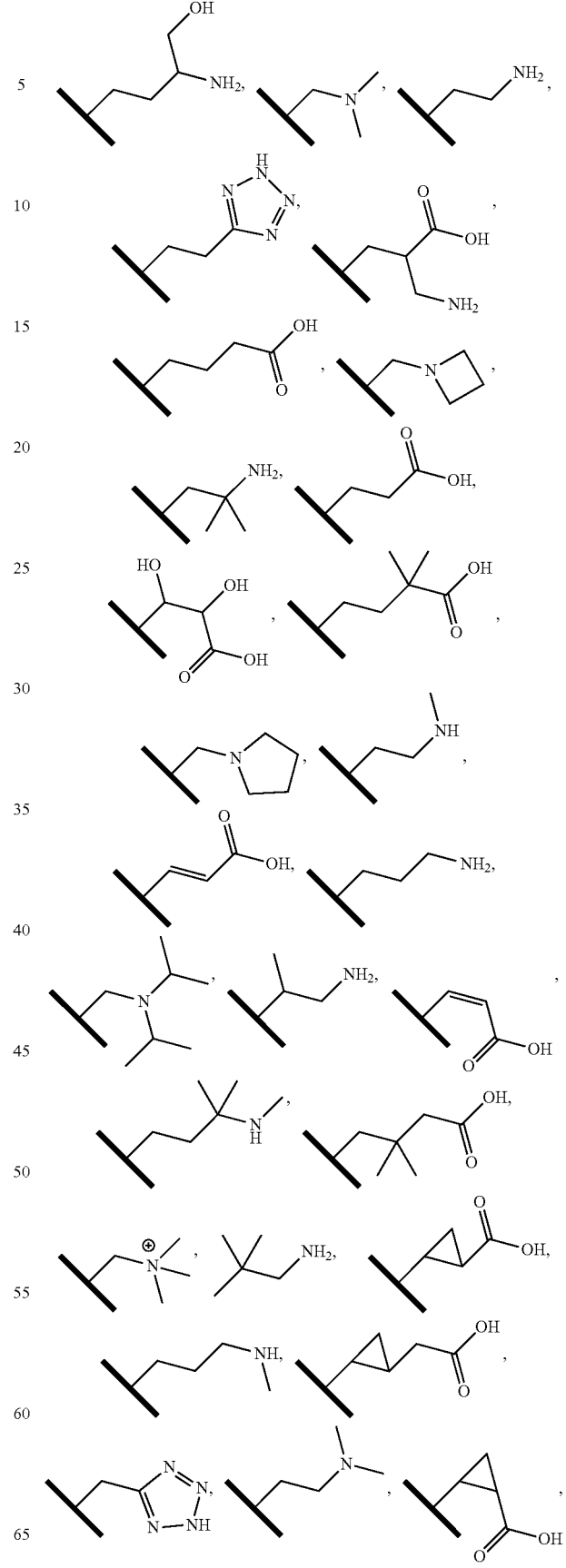

289
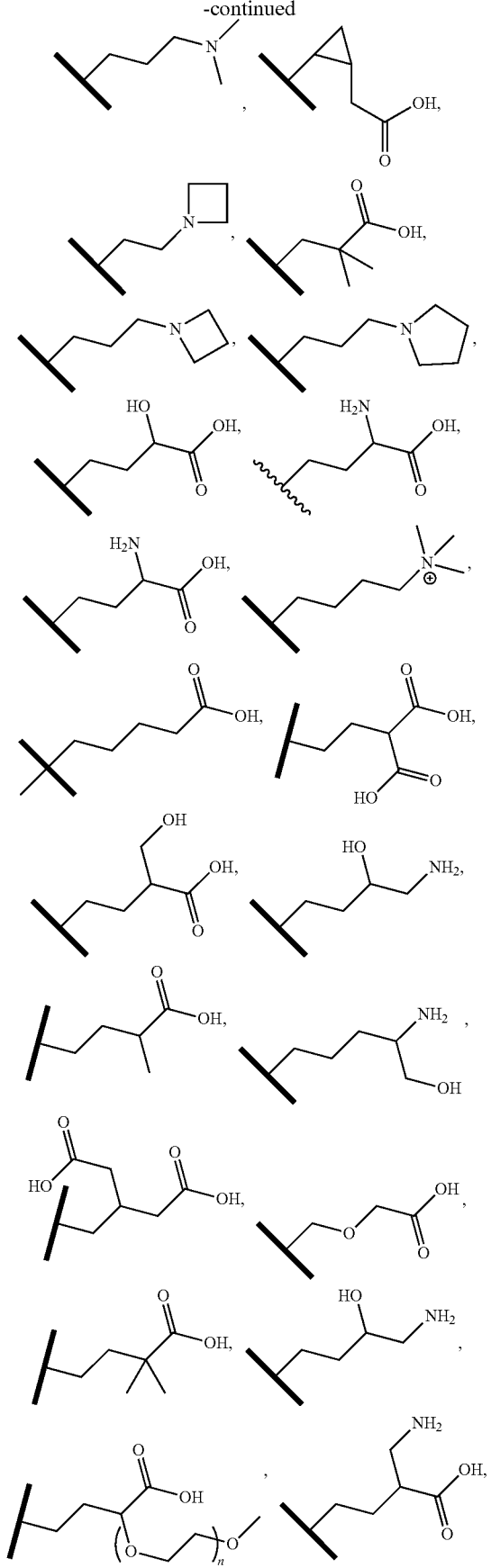
290
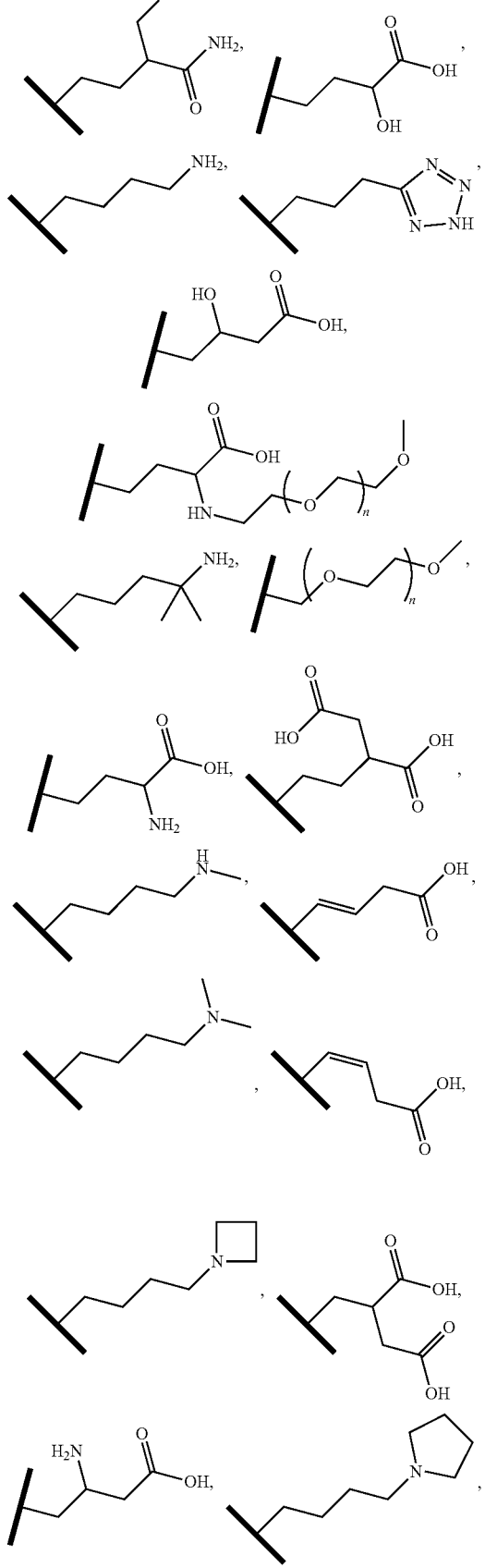

-continued

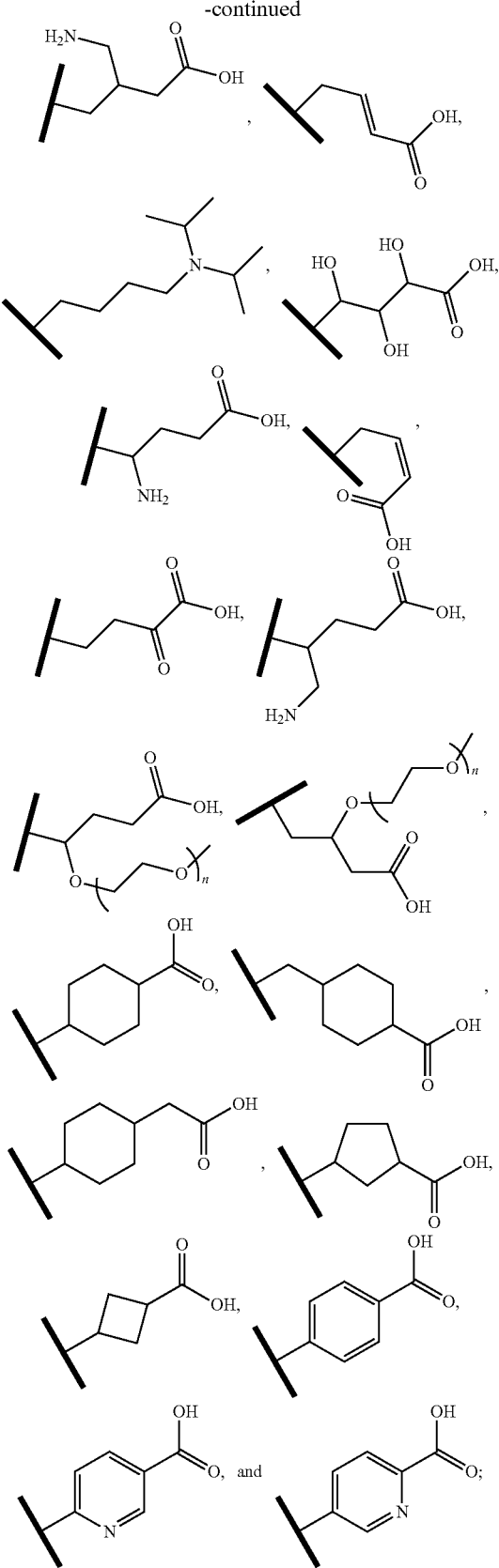

and
pharmaceutically acceptable salts thereof.

6. The method of claim 1, wherein $R_4$ is selected from hydrogen, $CO_2R_{4a}$, $C(O)N(R_{4a})_2$, $N(R_{4a})_2$, or $C(R_{10})(R_{11})$ phenyl;

$R_{10}$ is absent or hydrogen;

$R_{11}$ is oxo, $OR_{4a}$, $C(O)R_{4a}$, $C(O)OR_{4a}$, $C(O)N(R_{4a})_2$, $OC(O)N(R_{4a})_2$, $N(R_{4a})_2$, or $=NR_{4a}$;

$R_{4a}$ is independently selected at each occurrence from hydrogen, hydroxymethyl, and aminomethyl or from the group consisting of:

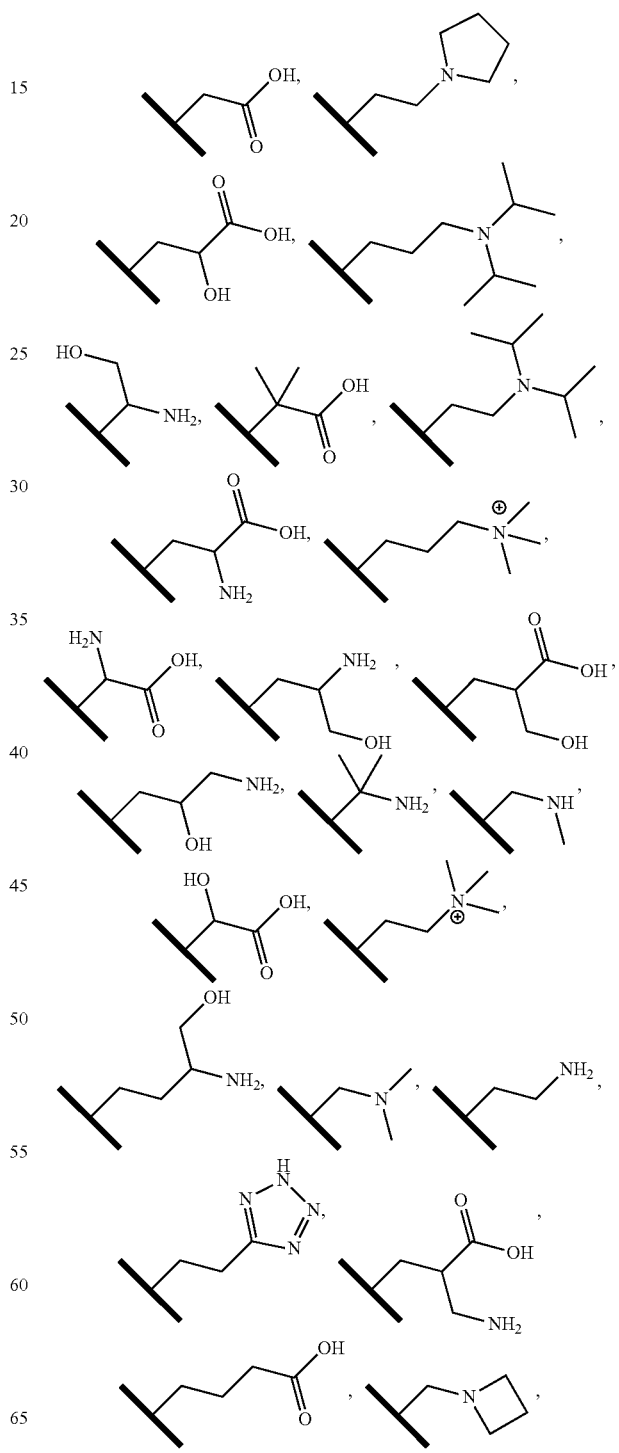

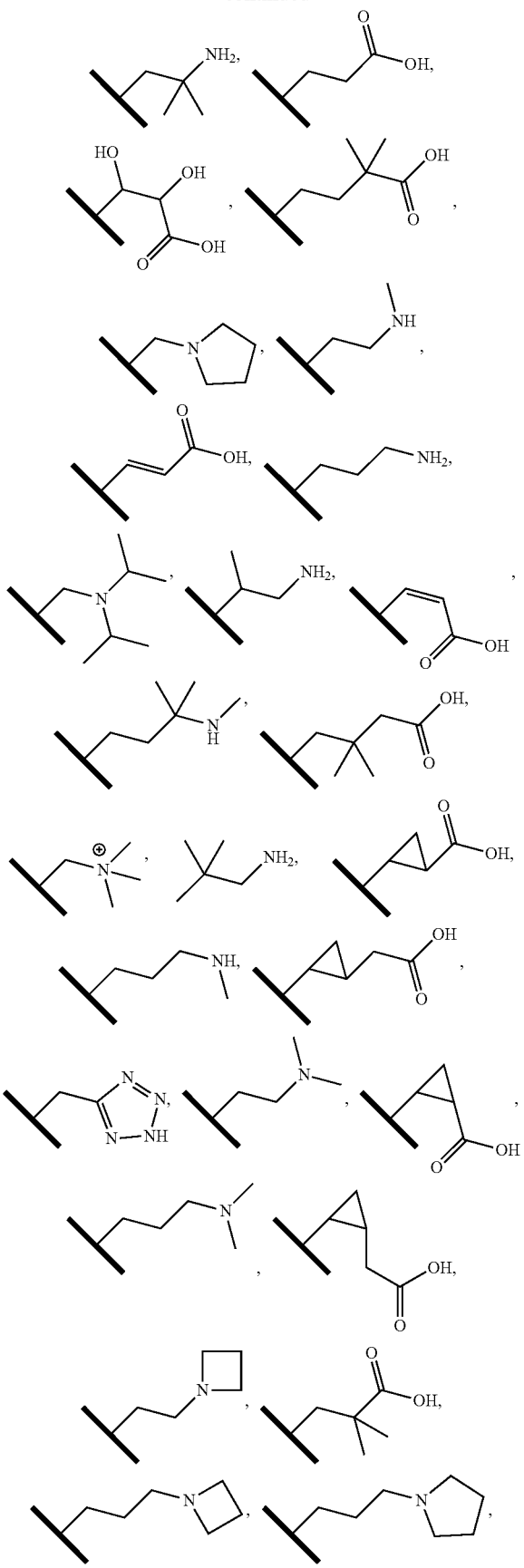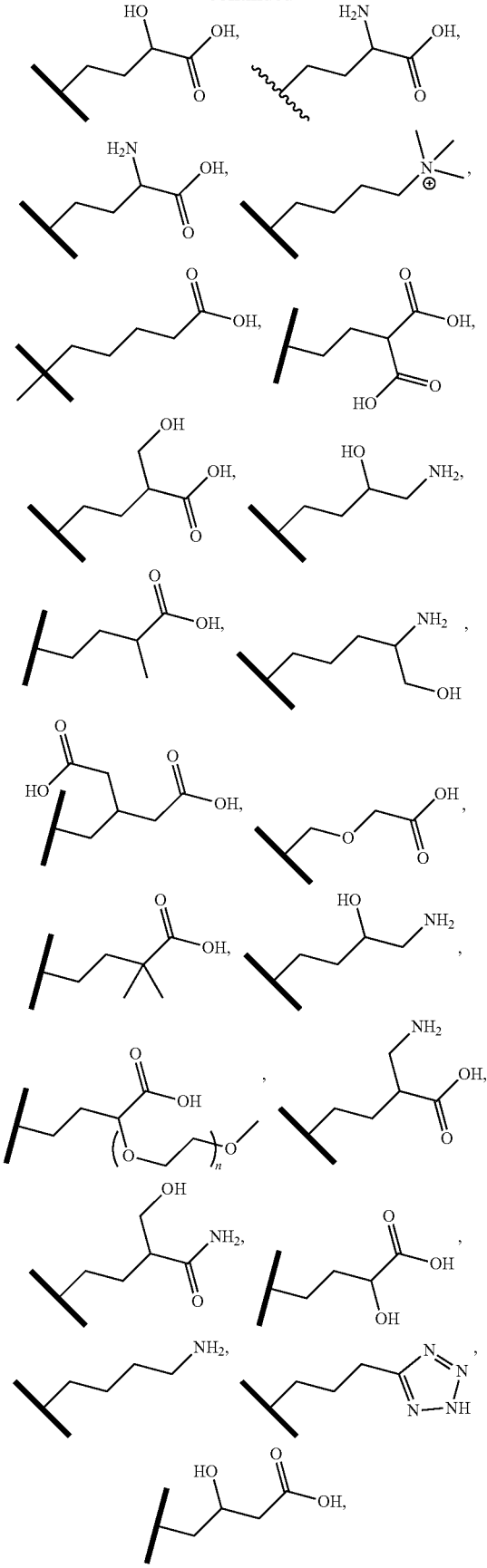

-continued

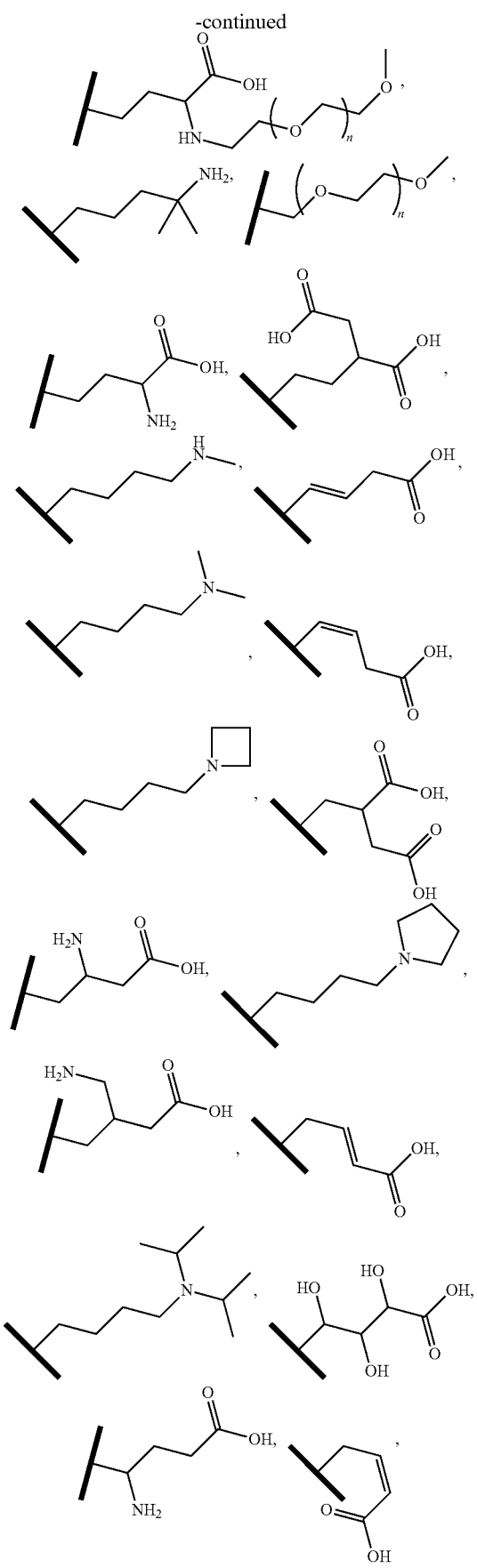

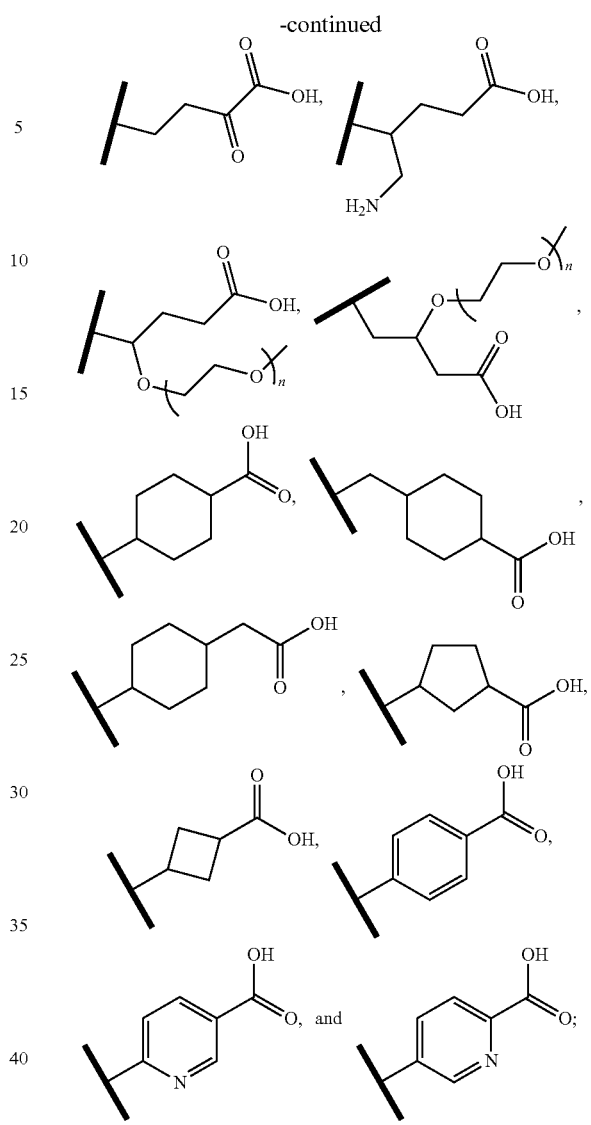

and pharmaceutically acceptable salts thereof.

7. The method of claim 1, wherein the bacterial infection is selected from *Staphyloccocus aureus, Streptococcus pneumoniae, Mycobacterium tuberculosis, Enterococci, Clostridium difficile, Propionibacterium acnes, Bacteroides fagiles, Neisseria gonorrhoeae, Branhamella catarrhalis, Haemophilus influenzae, E. coli, Pseudomonas aeruginosa, Proteus vulgaris, Klebsiella pneumonia*, and *Chlamydia trachomatis*.

8. The method of claim 7, wherein the bacterial infection is *Clostridium difficile*.

9. A method of treating a bacterial infection according to claim 1, further comprising:

administering to a subject in need thereof a pharmaceutically effective amount of an additional therapeutic agent.

10. A method of treating a bacterial infection, comprising:

administering to a subject in need thereof a pharmaceutically acceptable amount of a compound of Formula IV:

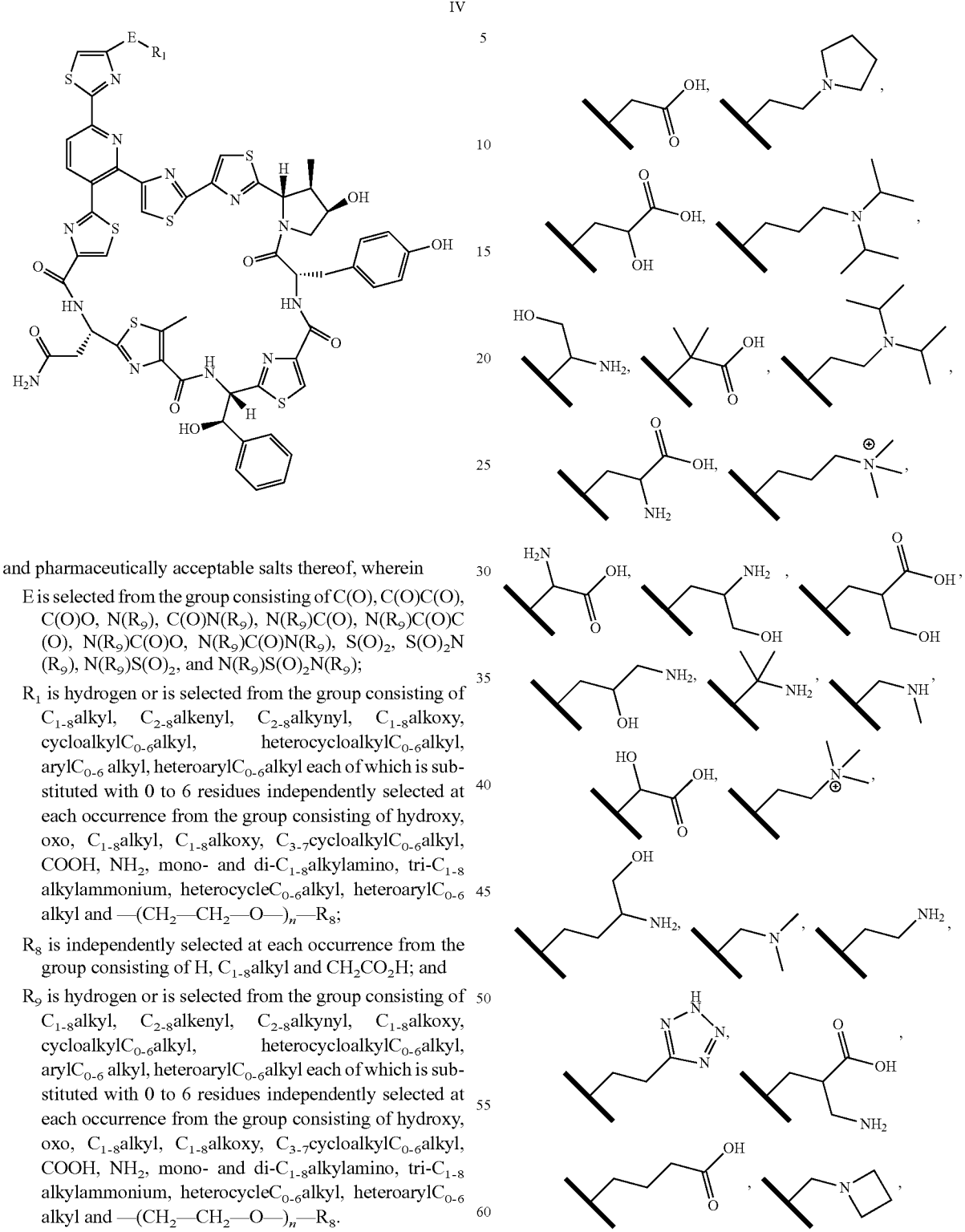

and pharmaceutically acceptable salts thereof, wherein

E is selected from the group consisting of C(O), C(O)C(O), C(O)O, N($R_9$), C(O)N($R_9$), N($R_9$)C(O), N($R_9$)C(O)C(O), N($R_9$)C(O)O, N($R_9$)C(O)N($R_9$), S(O)$_2$, S(O)$_2$N($R_9$), N($R_9$)S(O)$_2$, and N($R_9$)S(O)$_2$N($R_9$);

$R_1$ is hydrogen or is selected from the group consisting of $C_{1-8}$alkyl, $C_{2-8}$alkenyl, $C_{2-8}$alkynyl, $C_{1-8}$alkoxy, cycloalkyl$C_{0-6}$alkyl, heterocycloalkyl$C_{0-6}$alkyl, aryl$C_{0-6}$alkyl, heteroaryl$C_{0-6}$alkyl each of which is substituted with 0 to 6 residues independently selected at each occurrence from the group consisting of hydroxy, oxo, $C_{1-8}$alkyl, $C_{1-8}$alkoxy, $C_{3-7}$cycloalkyl$C_{0-6}$alkyl, COOH, NH$_2$, mono- and di-$C_{1-8}$alkylamino, tri-$C_{1-8}$alkylammonium, heterocycle$C_{0-6}$alkyl, heteroaryl$C_{0-6}$alkyl and —(CH$_2$—CH$_2$—O—)$_n$—$R_8$;

$R_8$ is independently selected at each occurrence from the group consisting of H, $C_{1-8}$alkyl and CH$_2$CO$_2$H; and $R_9$ is hydrogen or is selected from the group consisting of $C_{1-8}$alkyl, $C_{2-8}$alkenyl, $C_{2-8}$alkynyl, $C_{1-8}$alkoxy, cycloalkyl$C_{0-6}$alkyl, heterocycloalkyl$C_{0-6}$alkyl, aryl$C_{0-6}$alkyl, heteroaryl$C_{0-6}$alkyl each of which is substituted with 0 to 6 residues independently selected at each occurrence from the group consisting of hydroxy, oxo, $C_{1-8}$alkyl, $C_{1-8}$alkoxy, $C_{3-7}$cycloalkyl$C_{0-6}$alkyl, COOH, NH$_2$, mono- and di-$C_{1-8}$alkylamino, tri-$C_{1-8}$alkylammonium, heterocycle$C_{0-6}$alkyl, heteroaryl$C_{0-6}$alkyl and —(CH$_2$—CH$_2$—O—)$_n$—$R_8$.

11. The method of claim 10, wherein $R_1$ and $R_9$ are independently selected at each occurrence from the group consisting of H, $C_{1-8}$alkyl, $C_{3-8}$cycloalkyl, and $R_{12}$, wherein the $C_{1-8}$alkyl and $C_{3-8}$cycloalkyl groups are unsubstituted or substituted with 1 or 2 groups selected from halogen, hydroxyl, or COOH;

$R_{12}$ is independently selected at each occurrence from the group consisting of 299
-continued
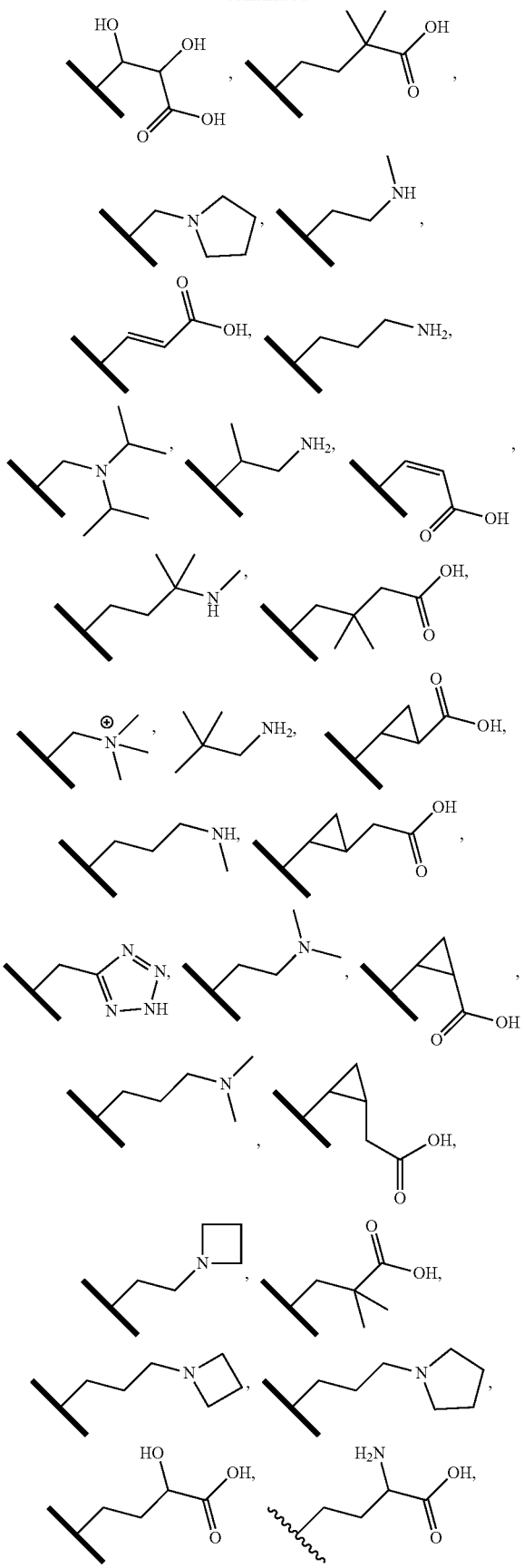
300
-continued
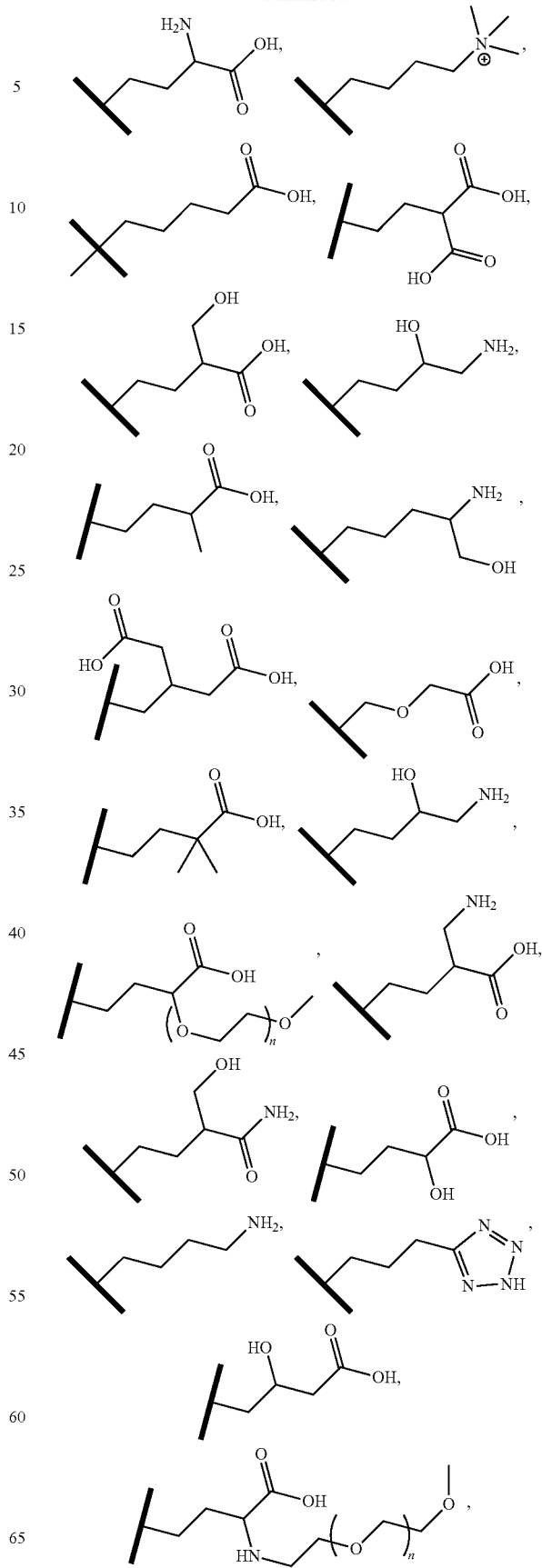

301
-continued

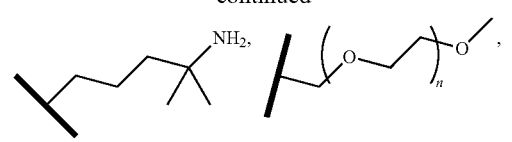

302
-continued

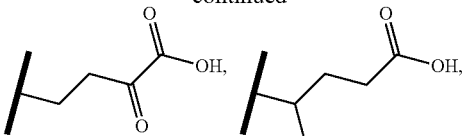

and n is an integer of between 1-60,000 or is a mean of a plurality of integers having a value of between 1-60,000.

12. The method of claim 10, wherein E-R$_1$ is selected from the group consisting of

and R$_1$ and R$_9$ are independently selected from the group consisting of hydrogen, hydroxymethyl, aminomethyl and R$_{12}$; and pharmaceutically acceptable salts thereof.

13. The method of claim 10, wherein the bacterial infection is selected from *Staphyloccocus aureus, Streptococcus pneumoniae, Mycobacterium tuberculosis, Enterococci, Clostridium difficile, Propionibacterium acnes, Bacteroides* fagiles, Neisseria gonorrhoeae, Branhamella catarrhalis, Haemophilus influenzae, E. coli, Pseudomonas aeruginosa, Proteus vulgaris, Klebsiella pneumonia, and Chlamydia trachomatis.

14. The method of claim 13, wherein the bacterial infection is Clostridium difficile.

15. A method of treating a bacterial infection according to claim 10, further comprising:

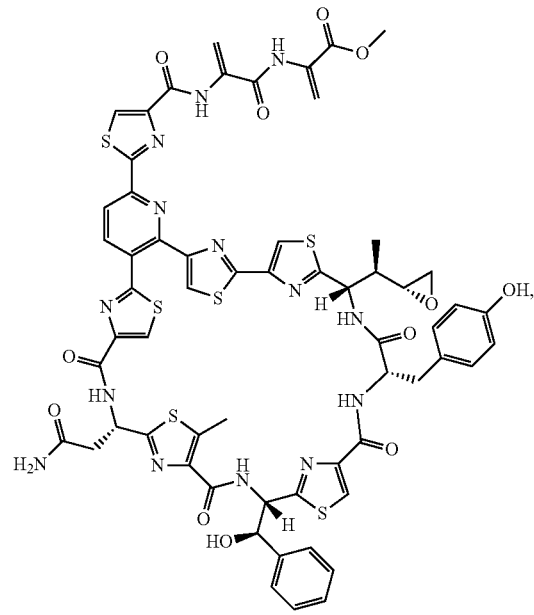

administering to a subject in need thereof a pharmaceutically effective amount of an additional therapeutic agent.

16. A method of treating a bacterial infection, comprising:

administering to a subject in need thereof a therapeutically effective amount of a compound selected from the group consisting of:

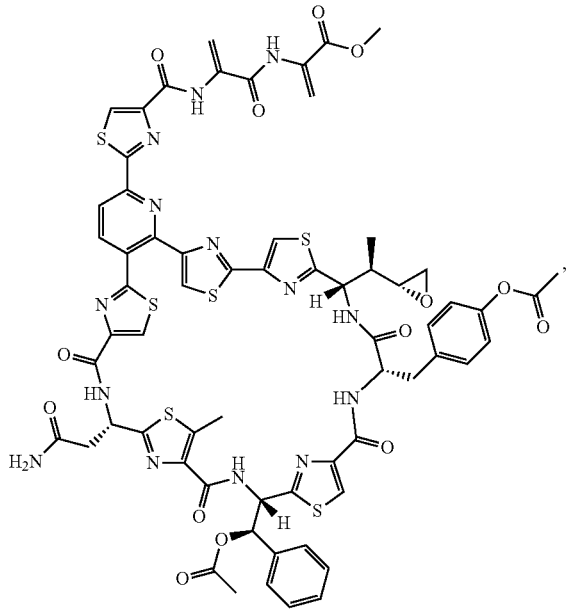

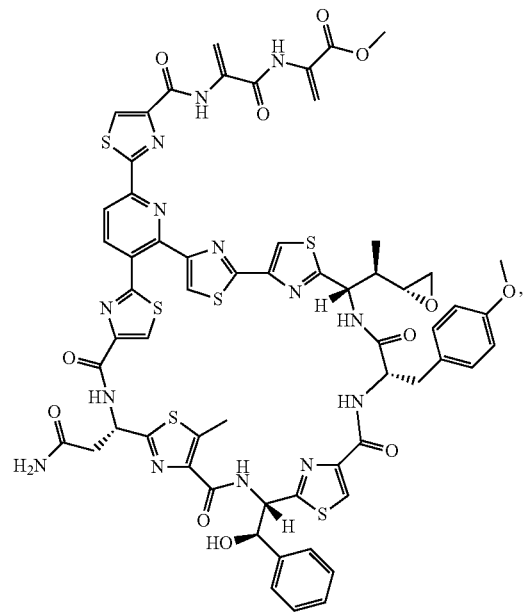

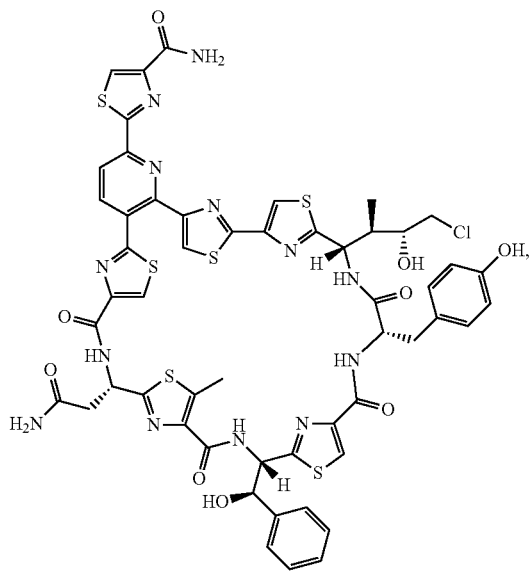

305
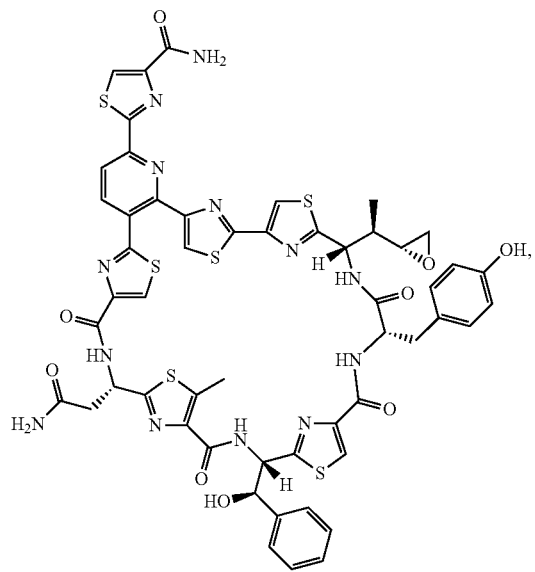
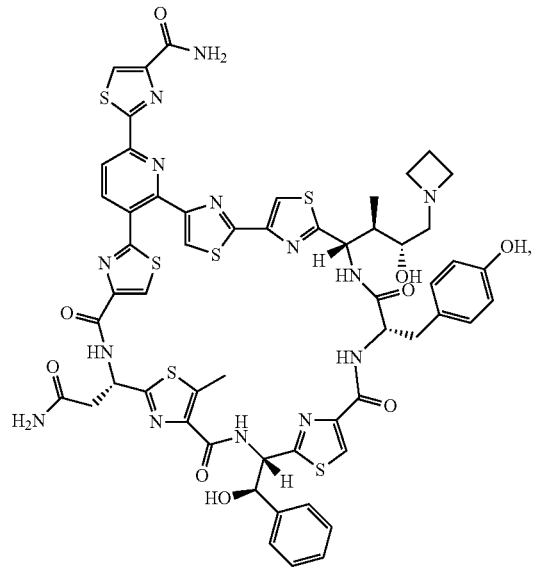
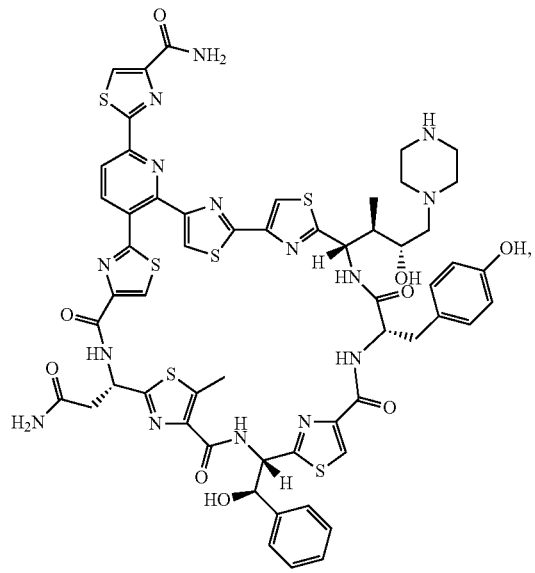
306
-continued
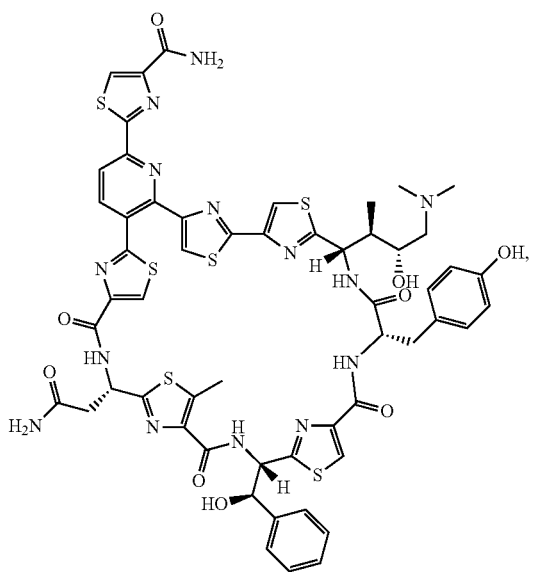
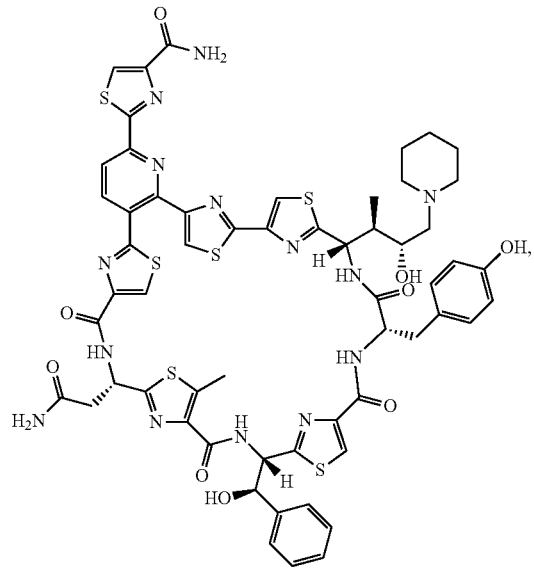
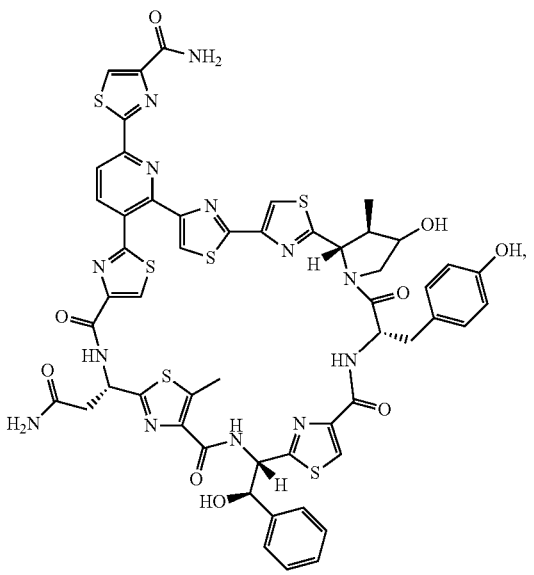

307
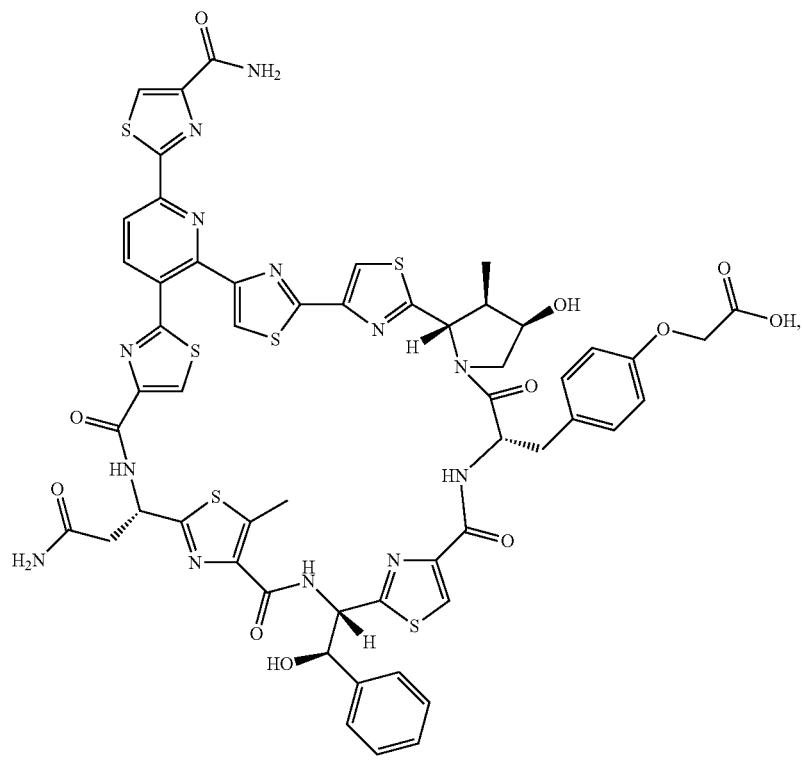
308
-continued
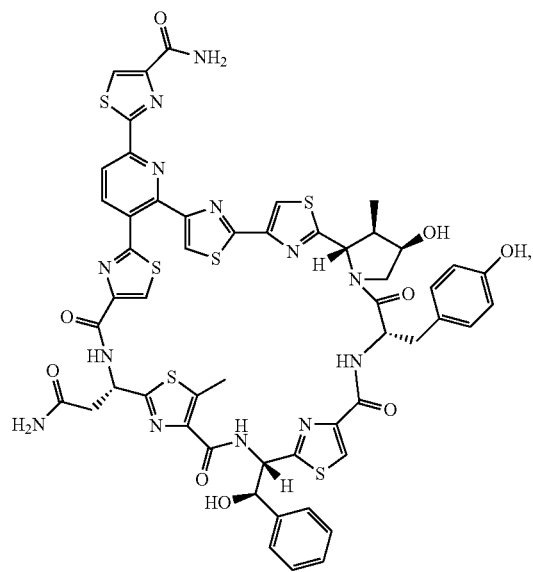
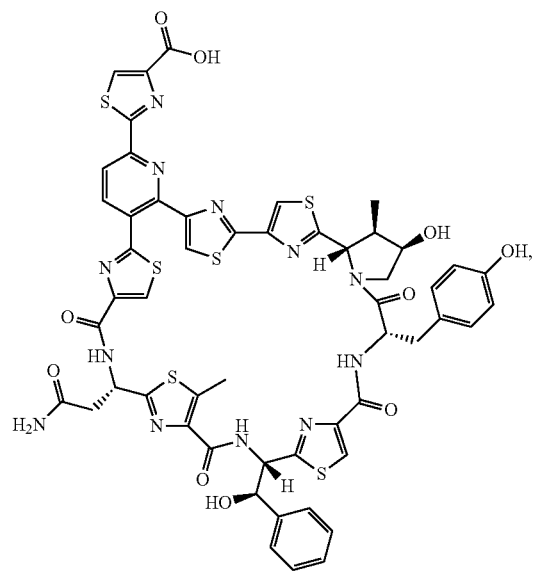

309
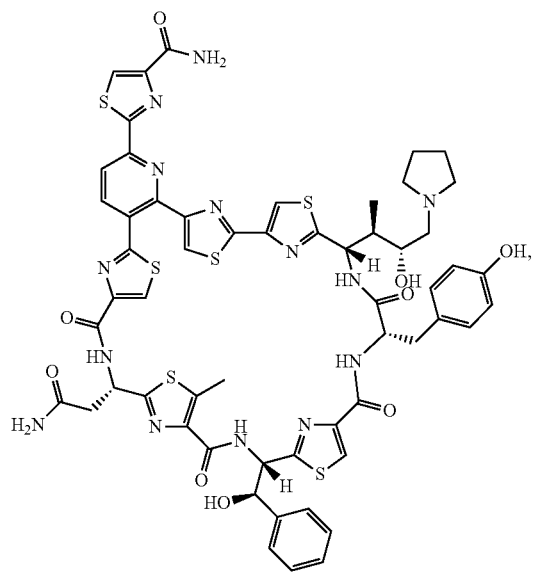
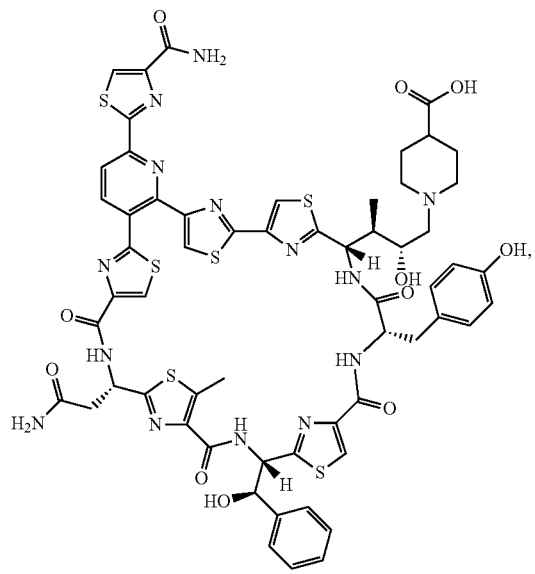
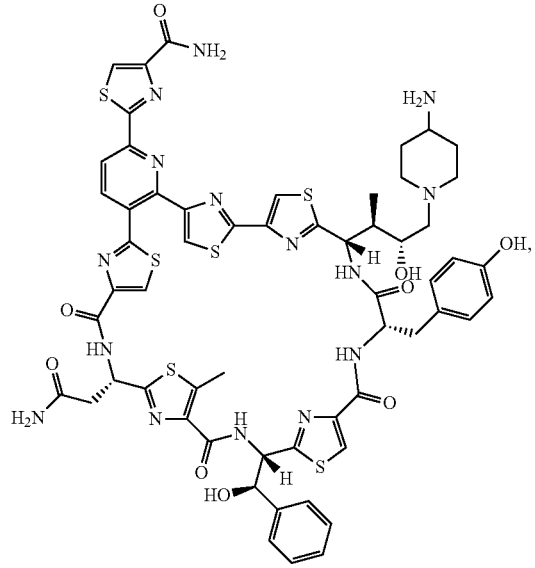
-continued
310
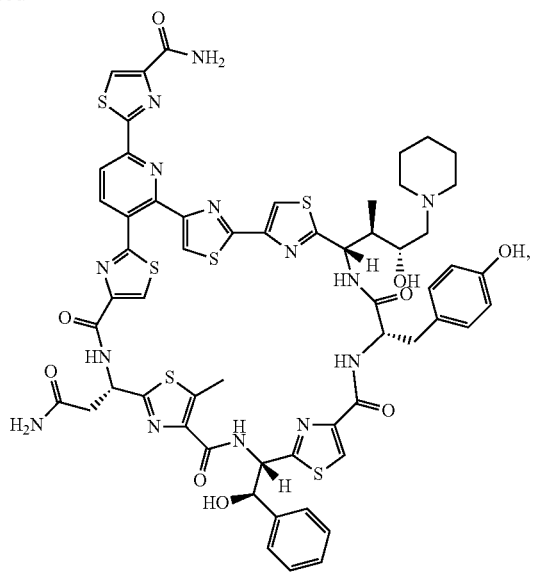
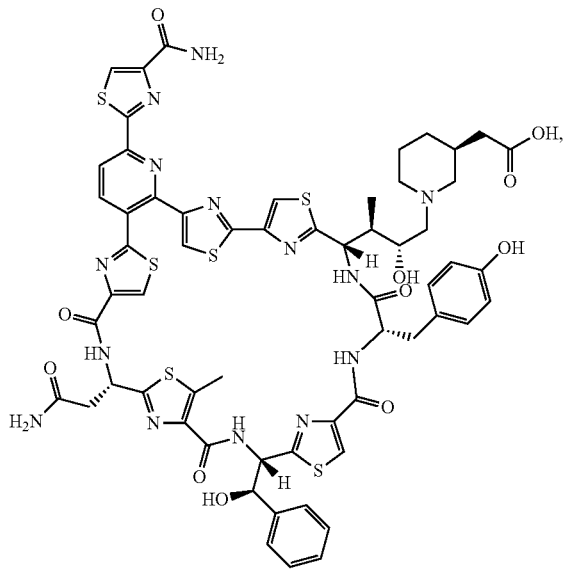
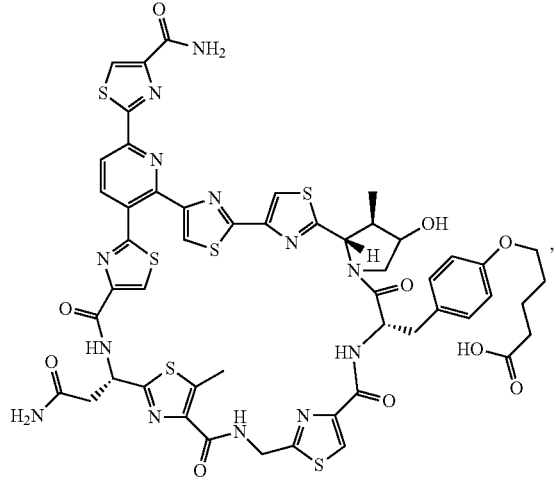

-continued
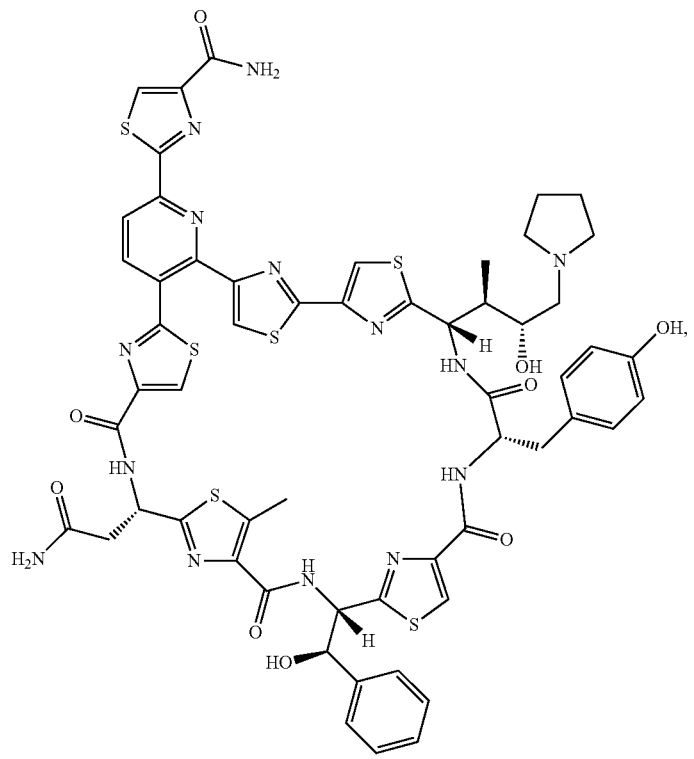
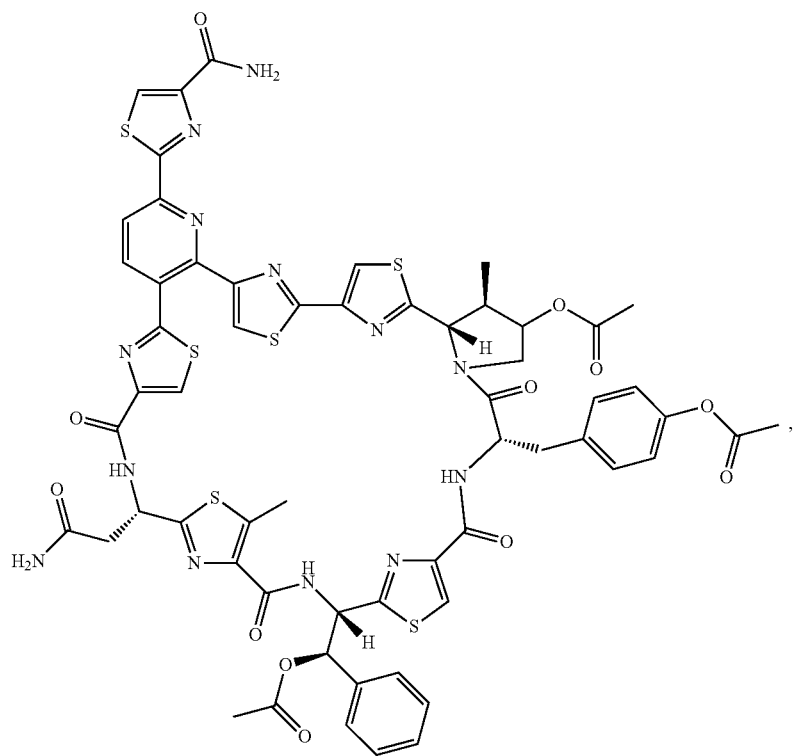

313
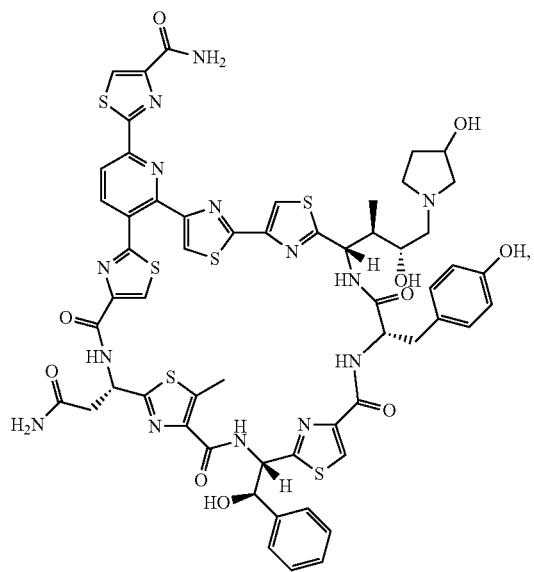
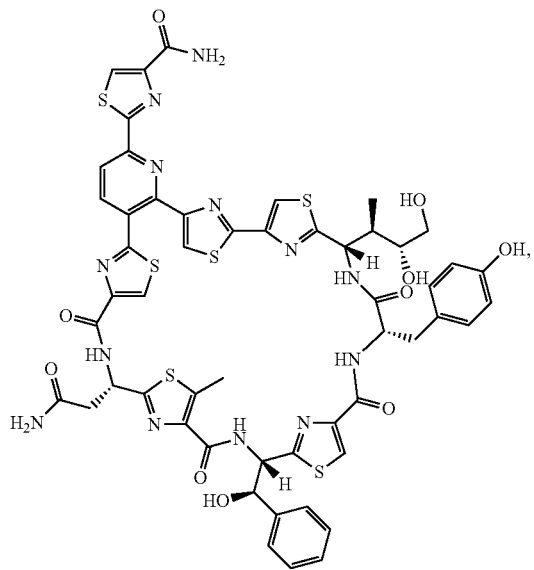
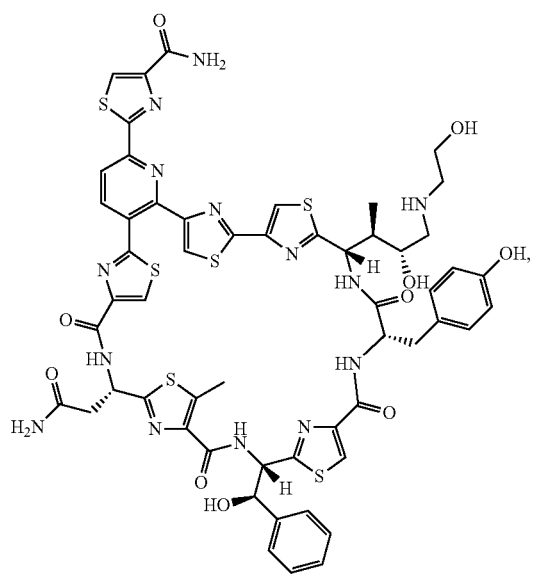
-continued
314
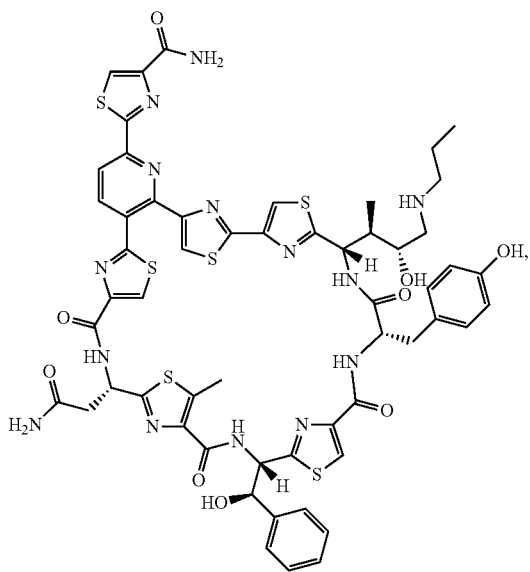
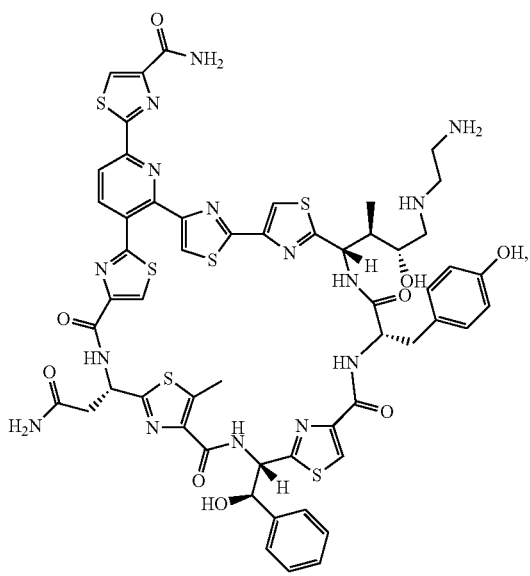
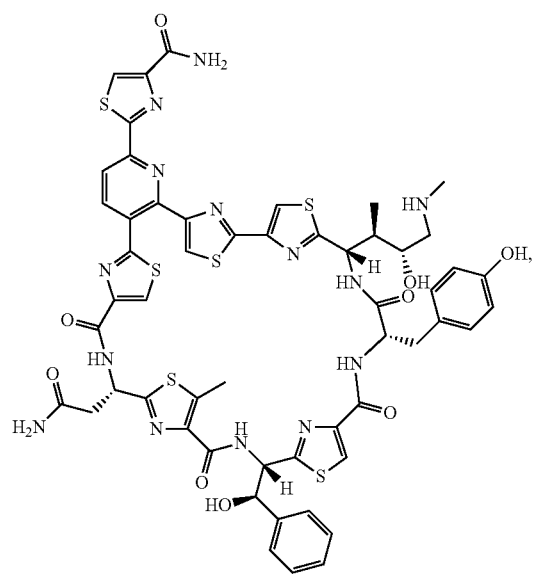

315
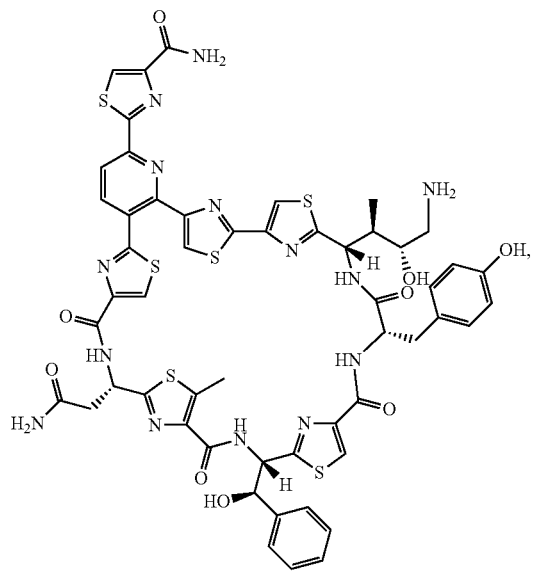
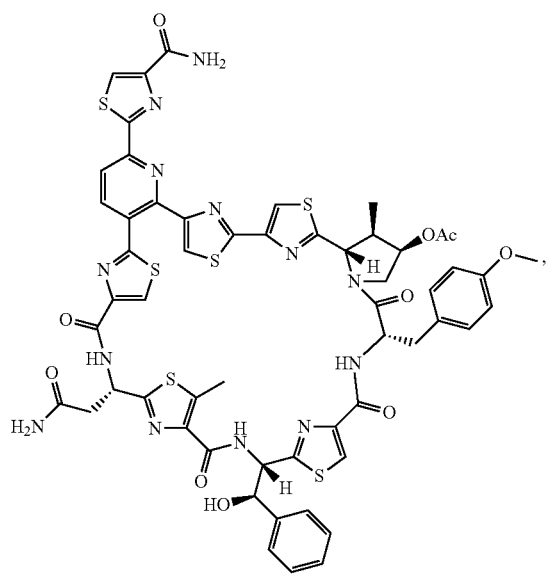
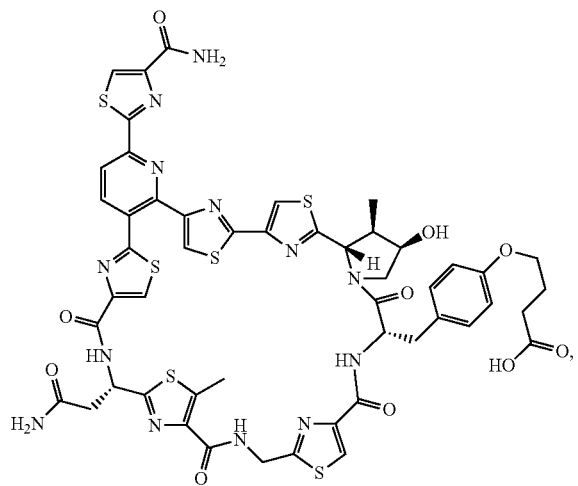
-continued
316
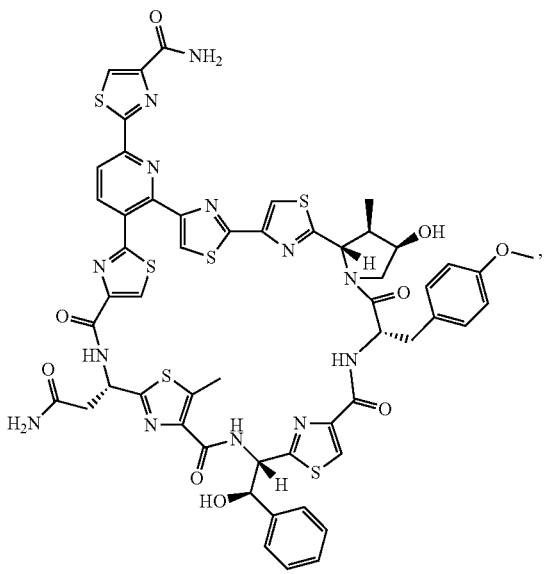
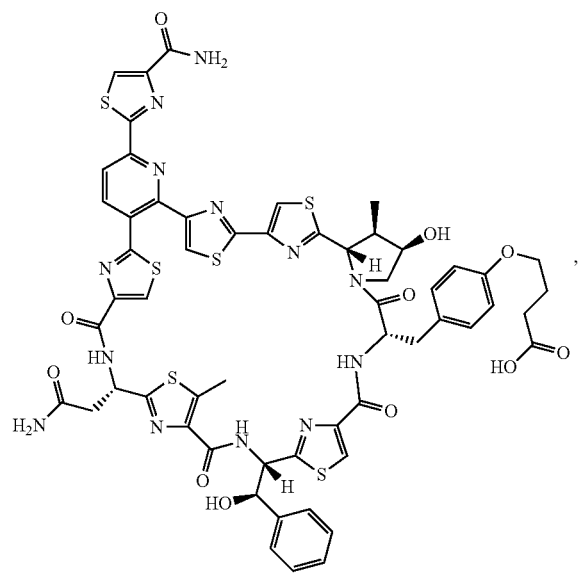
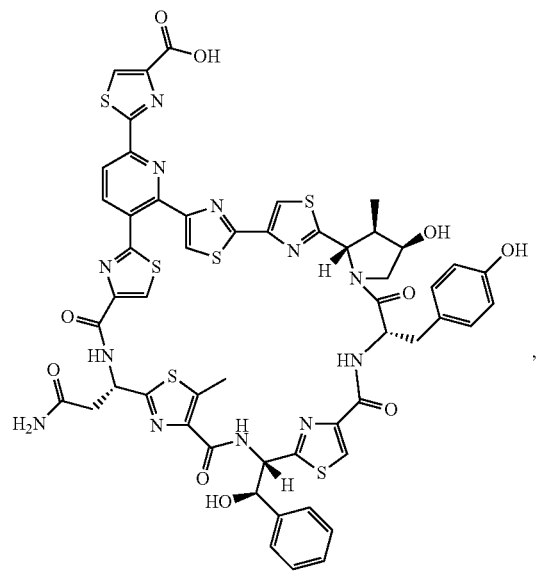

-continued
317
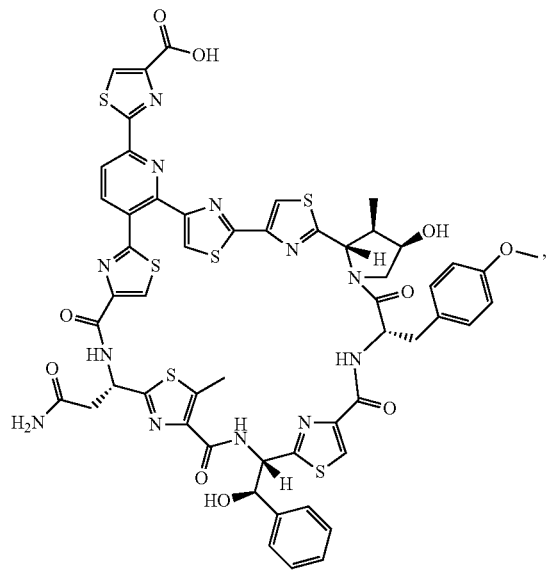
318
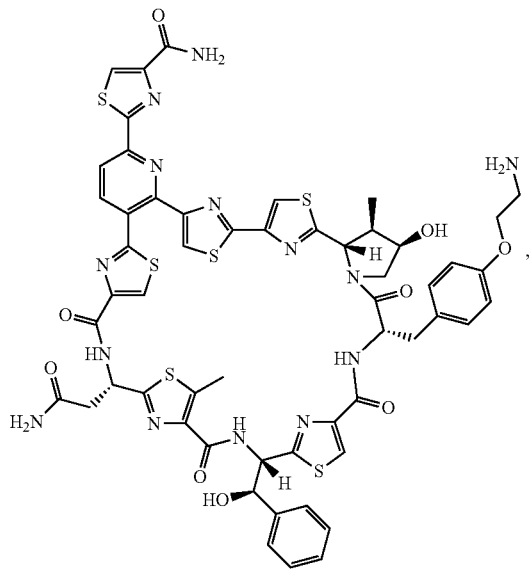
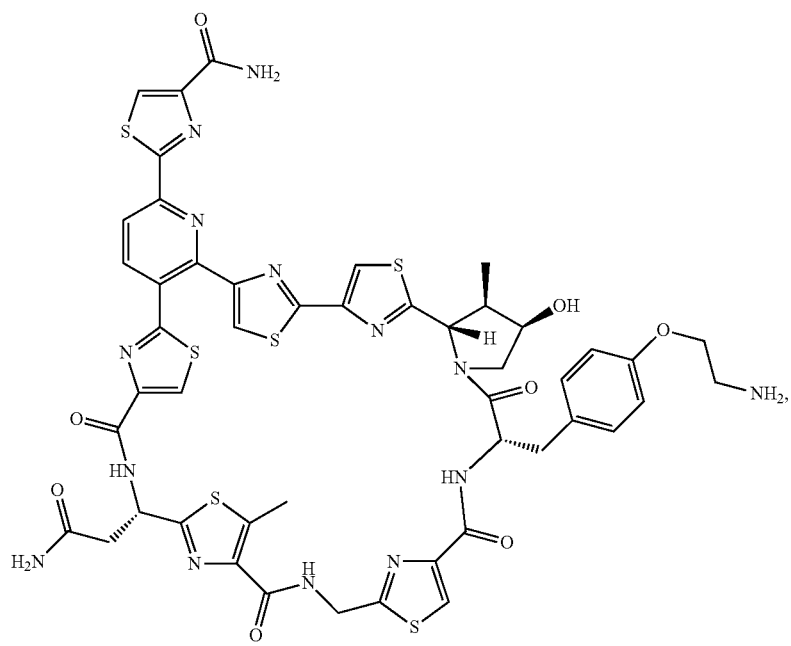

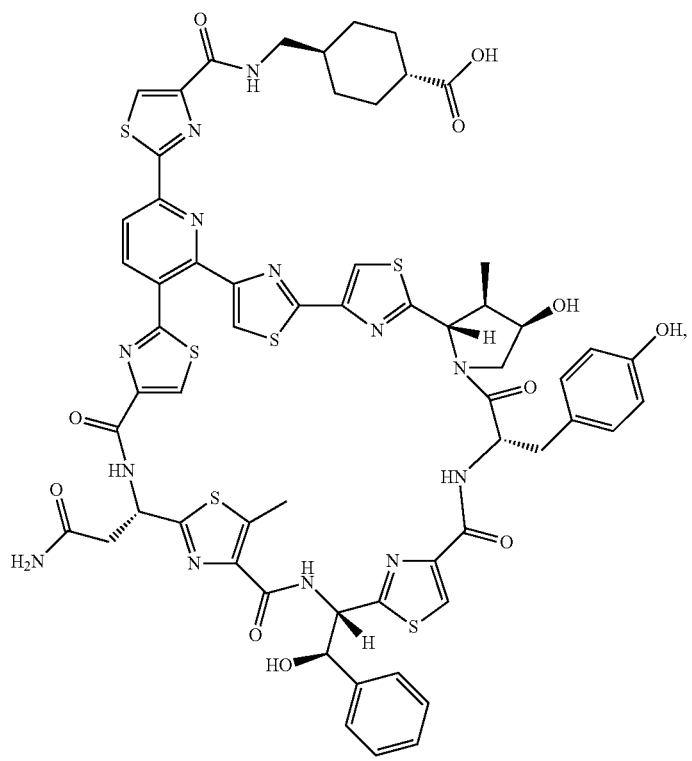
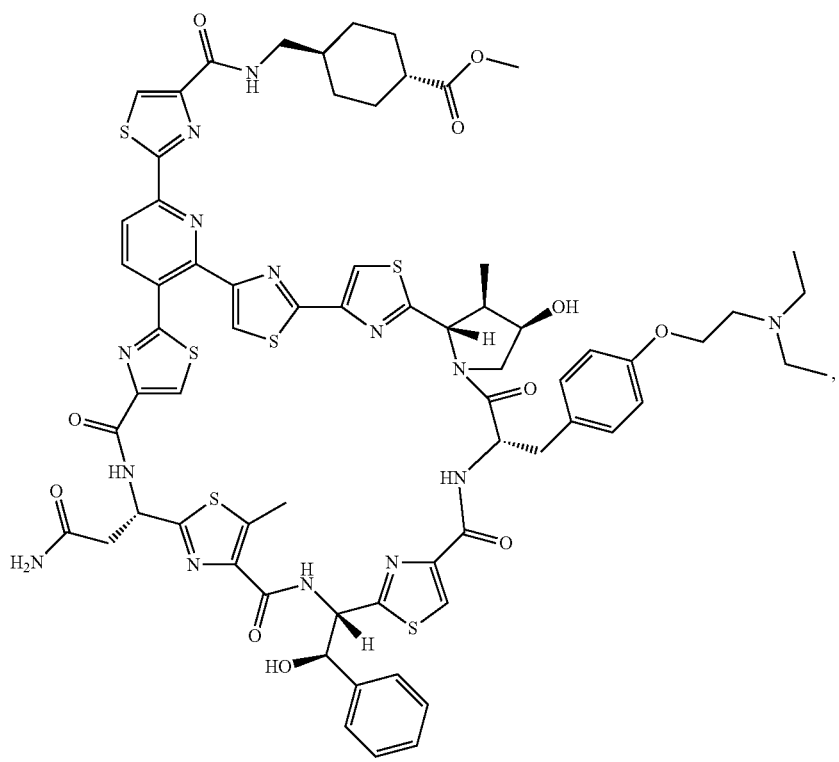

321
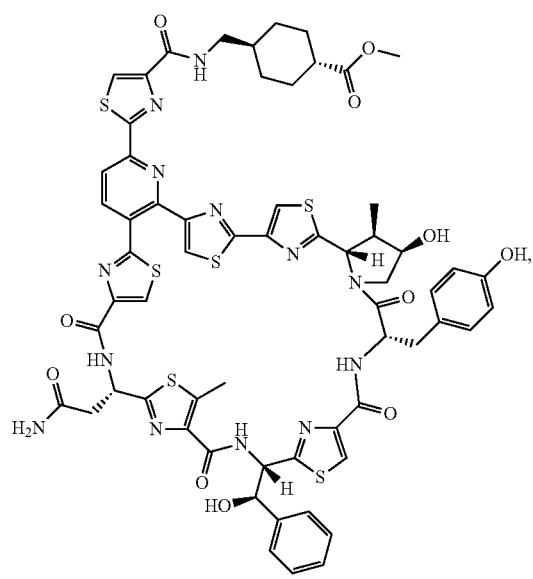
322
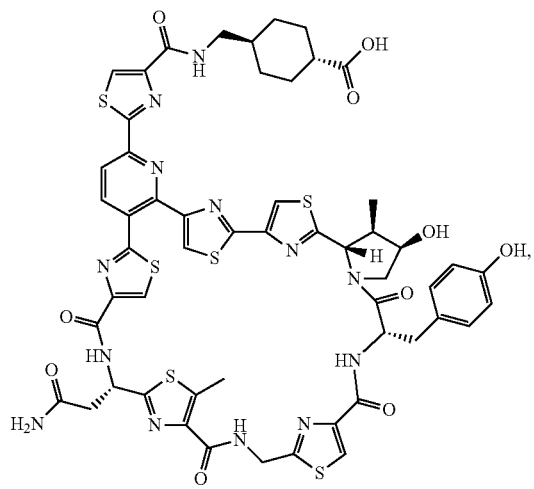
-continued
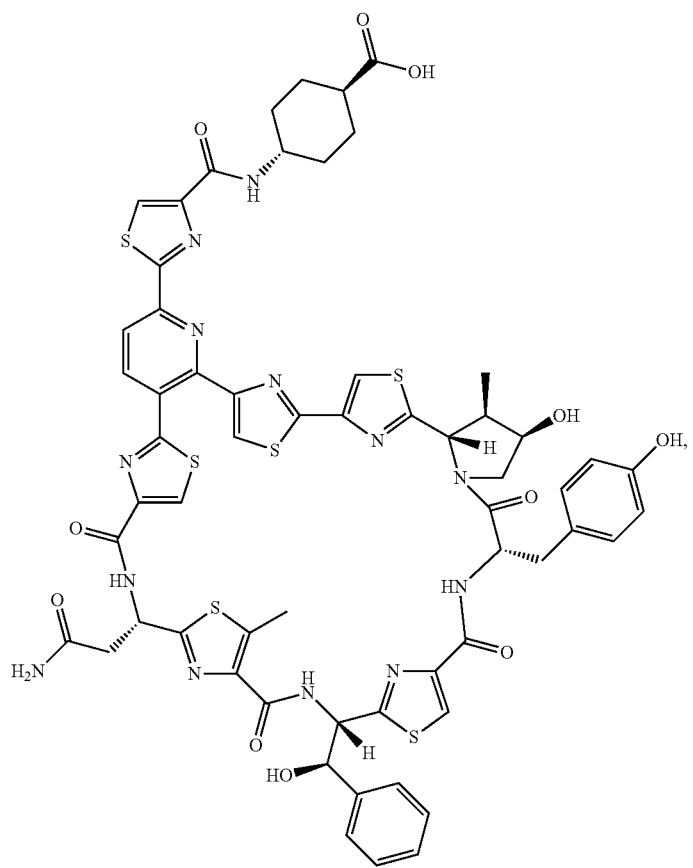

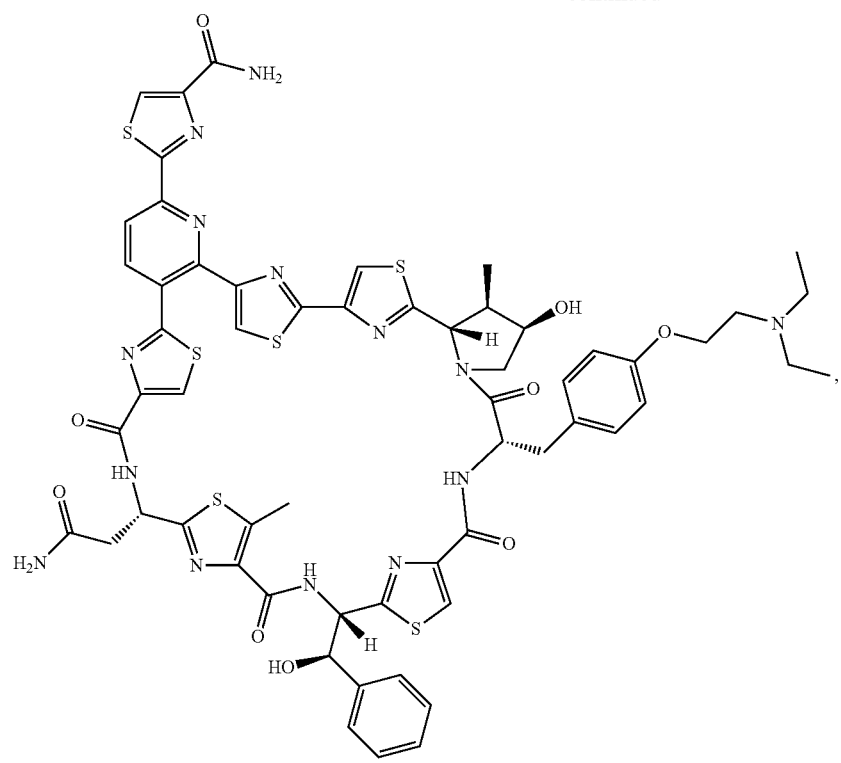
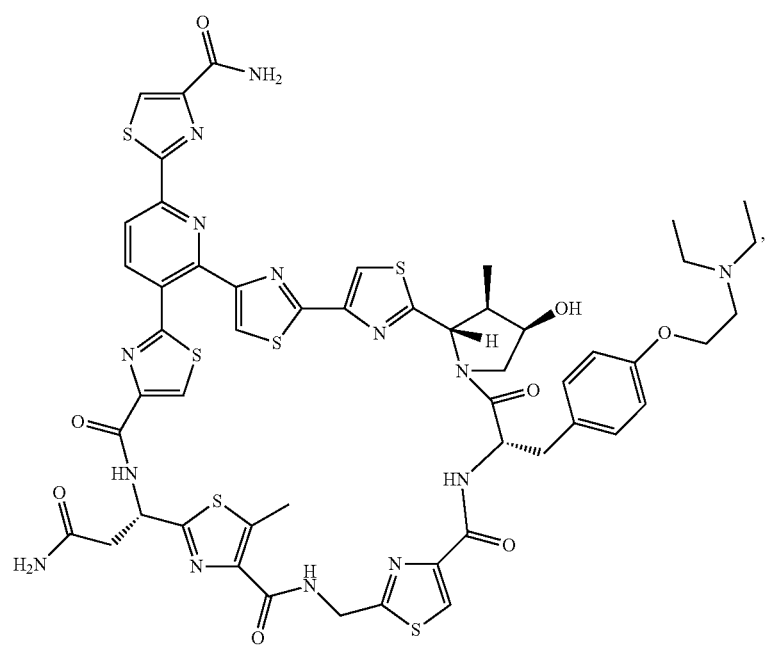

325
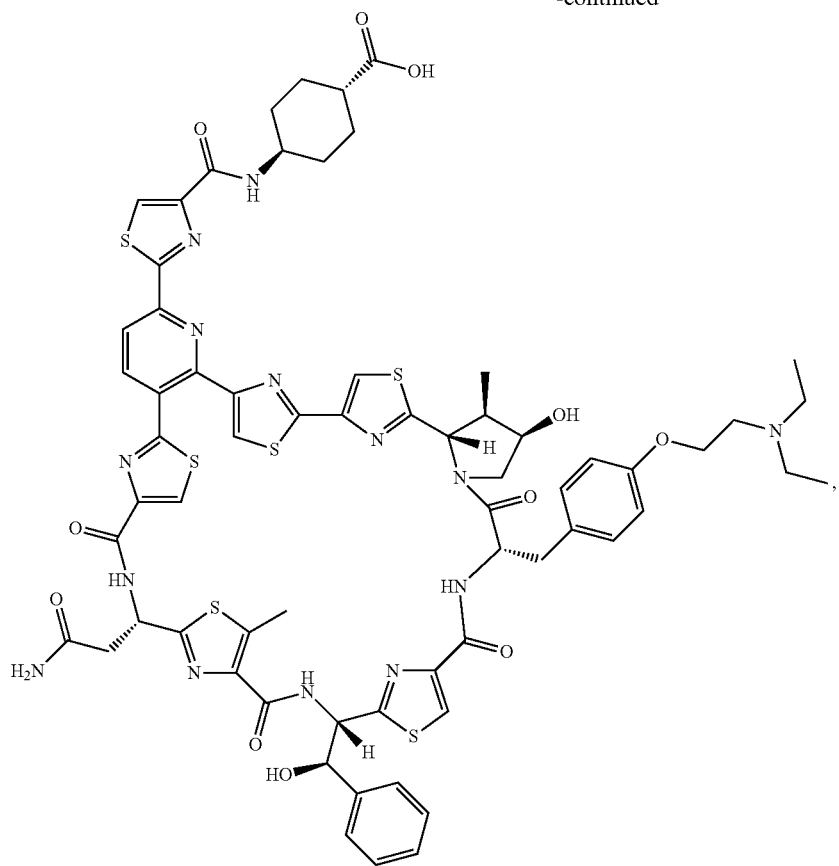
326
-continued
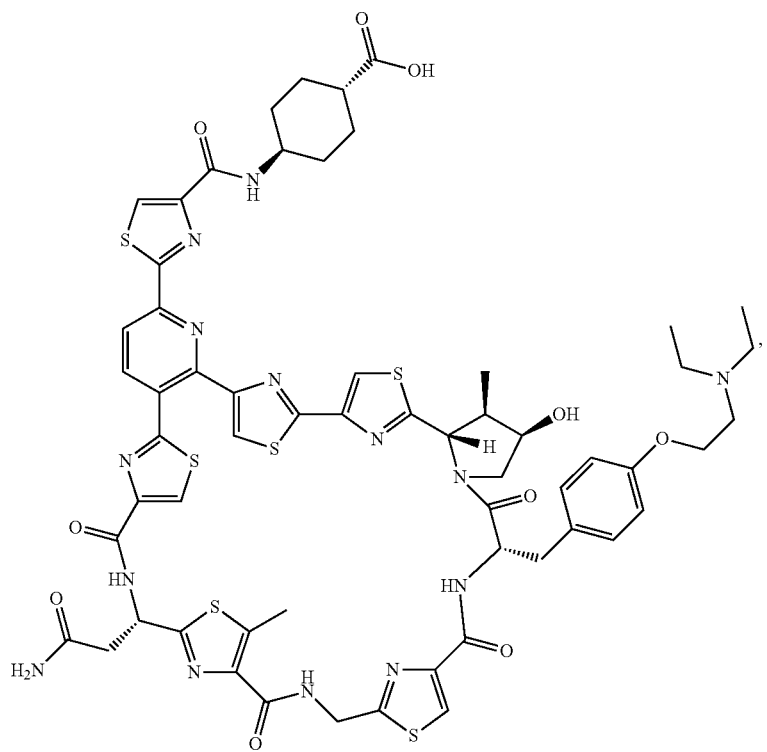

327 328
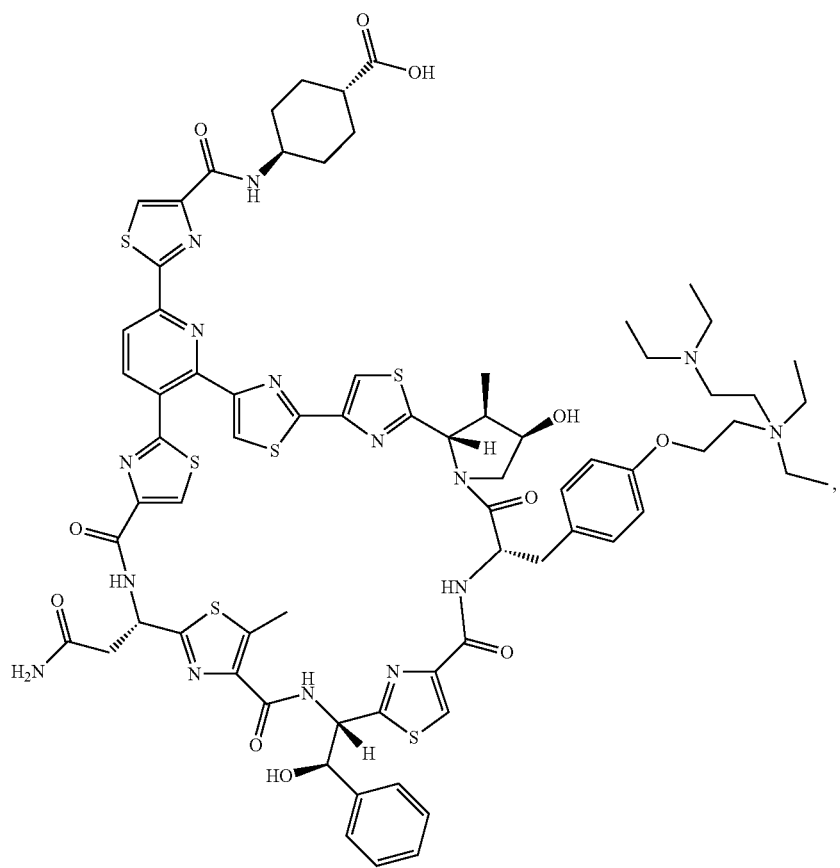
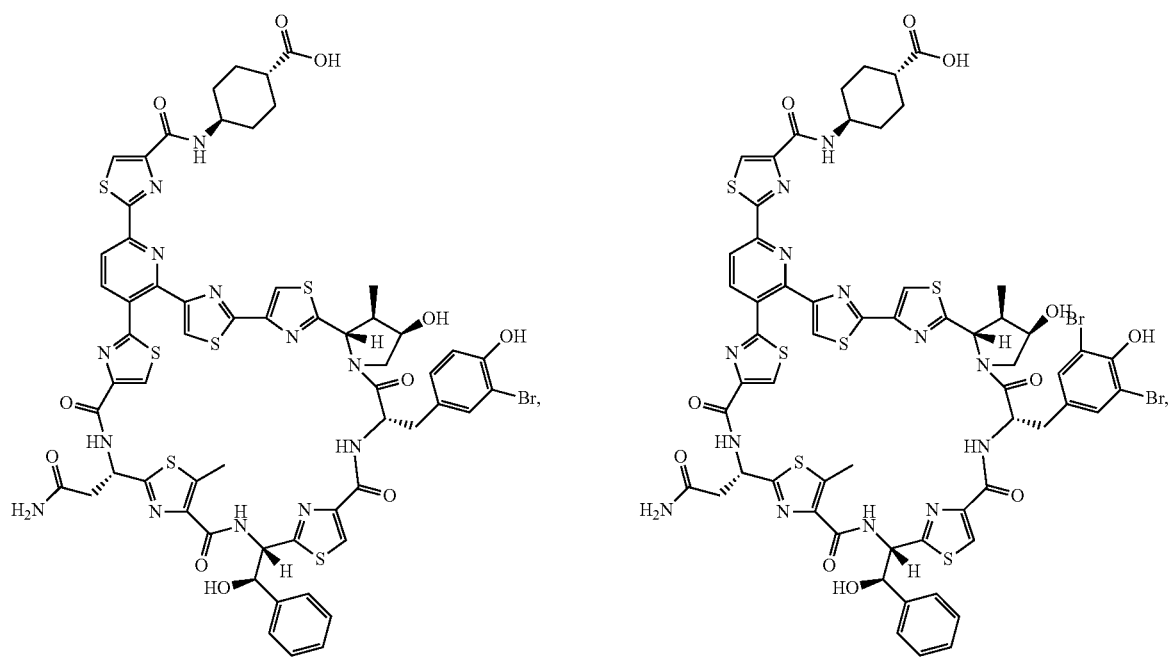

329
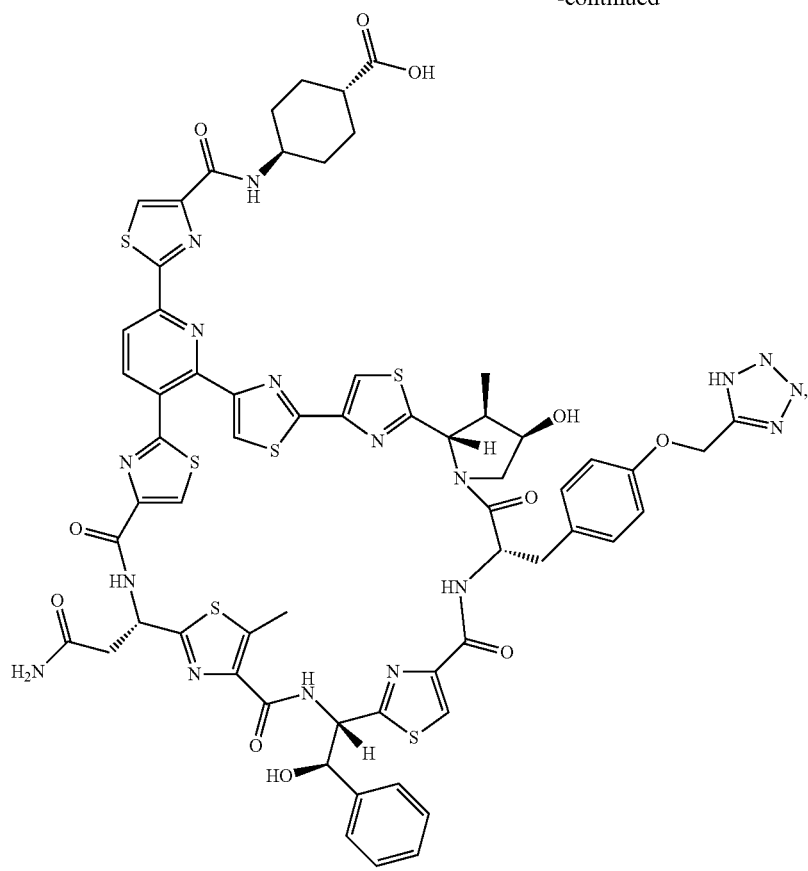
330
-continued
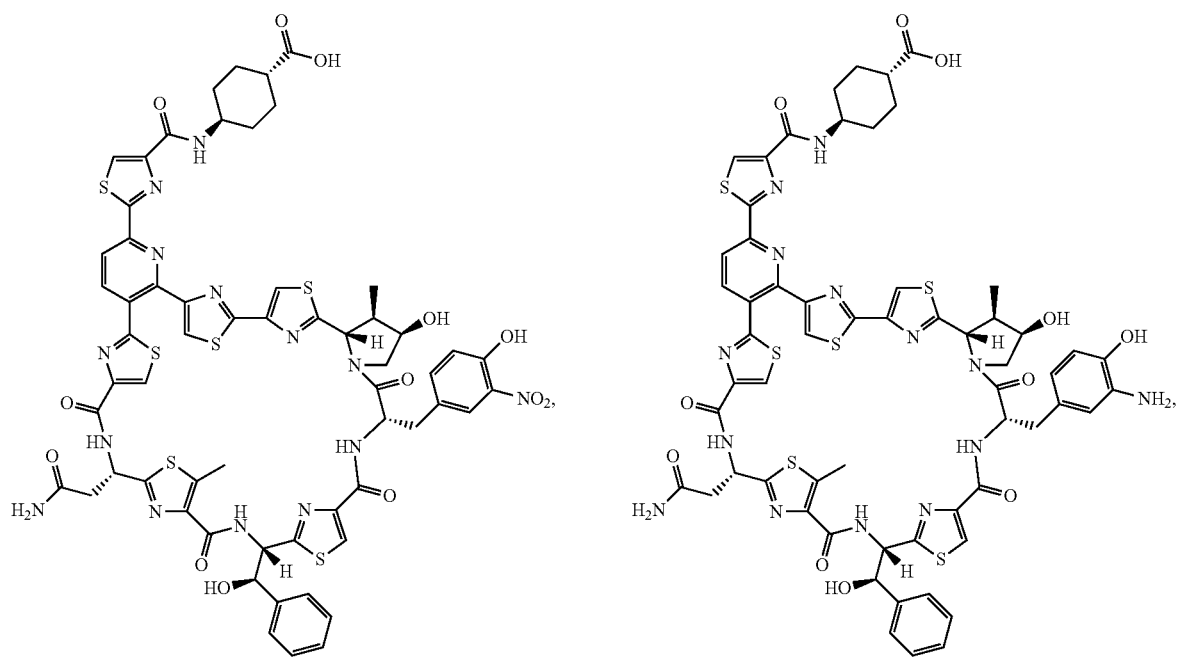

331
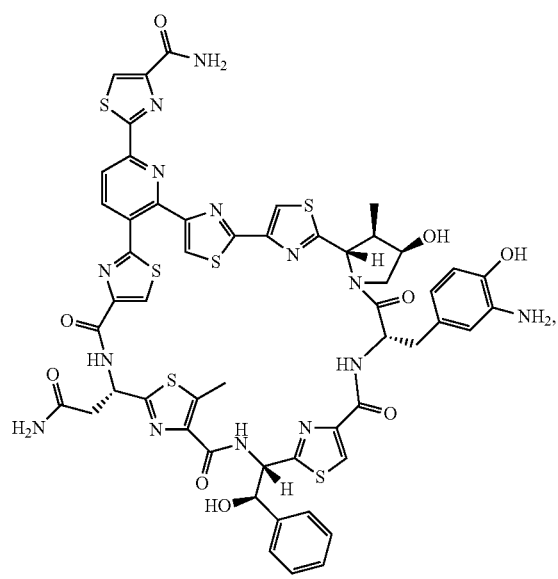
332
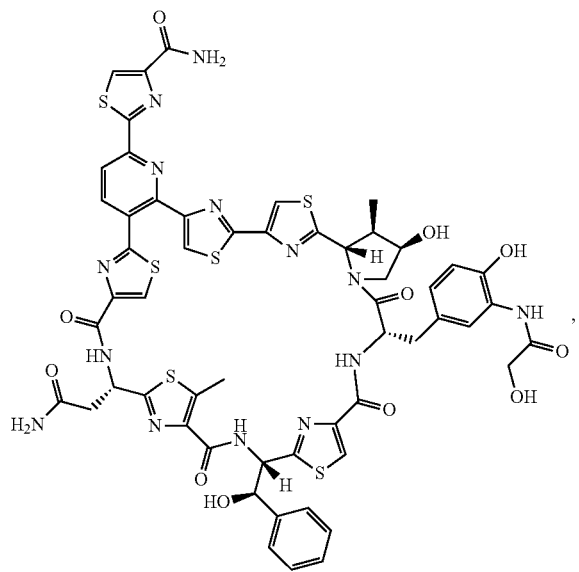
-continued
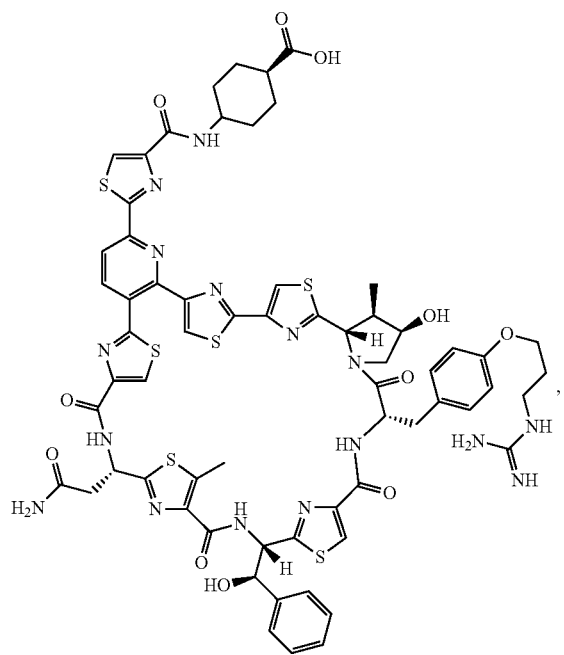
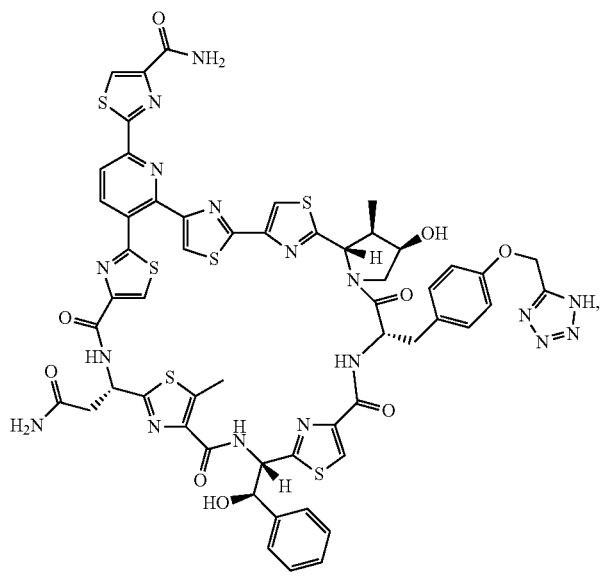

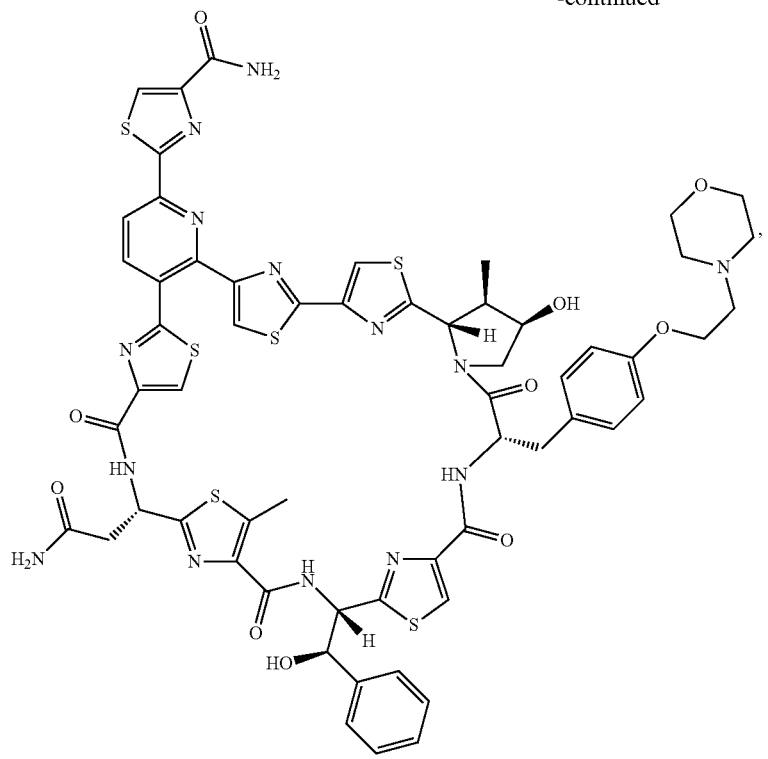
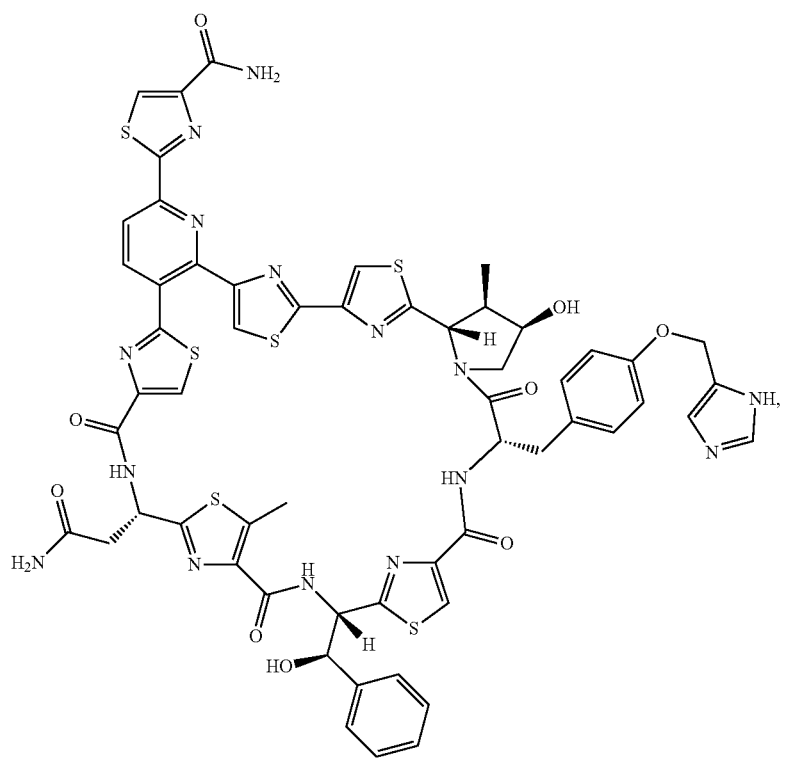

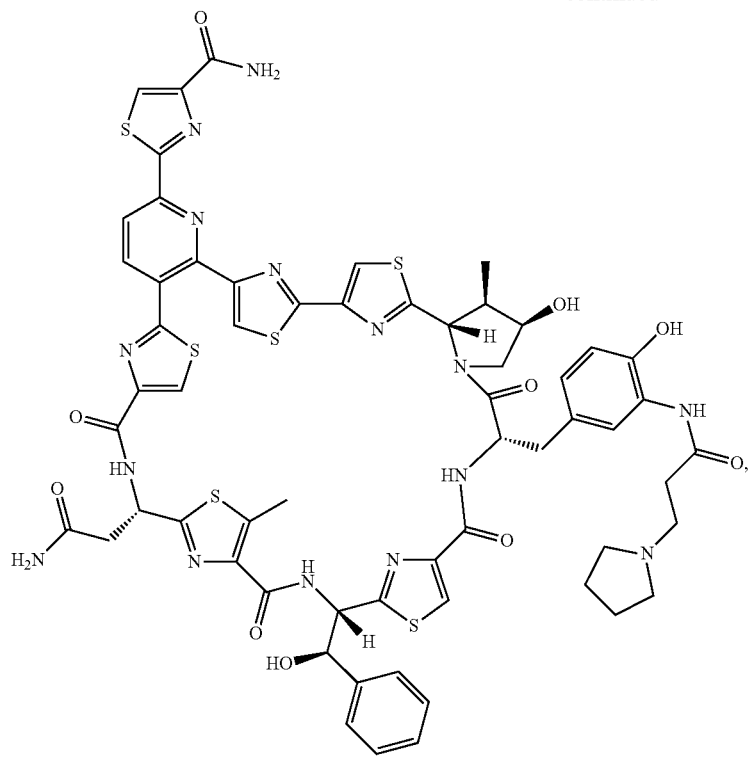
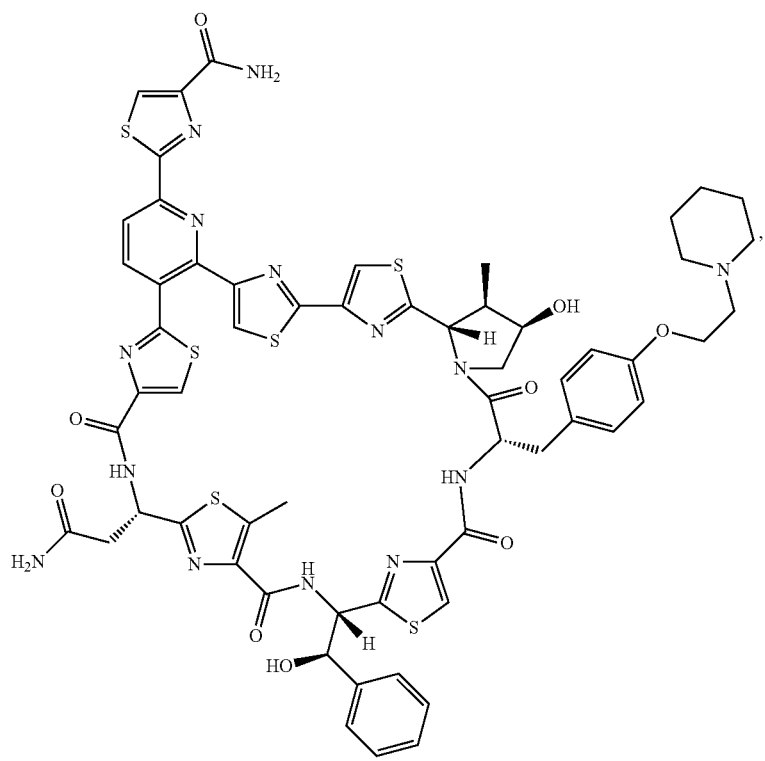

337
338
-continued
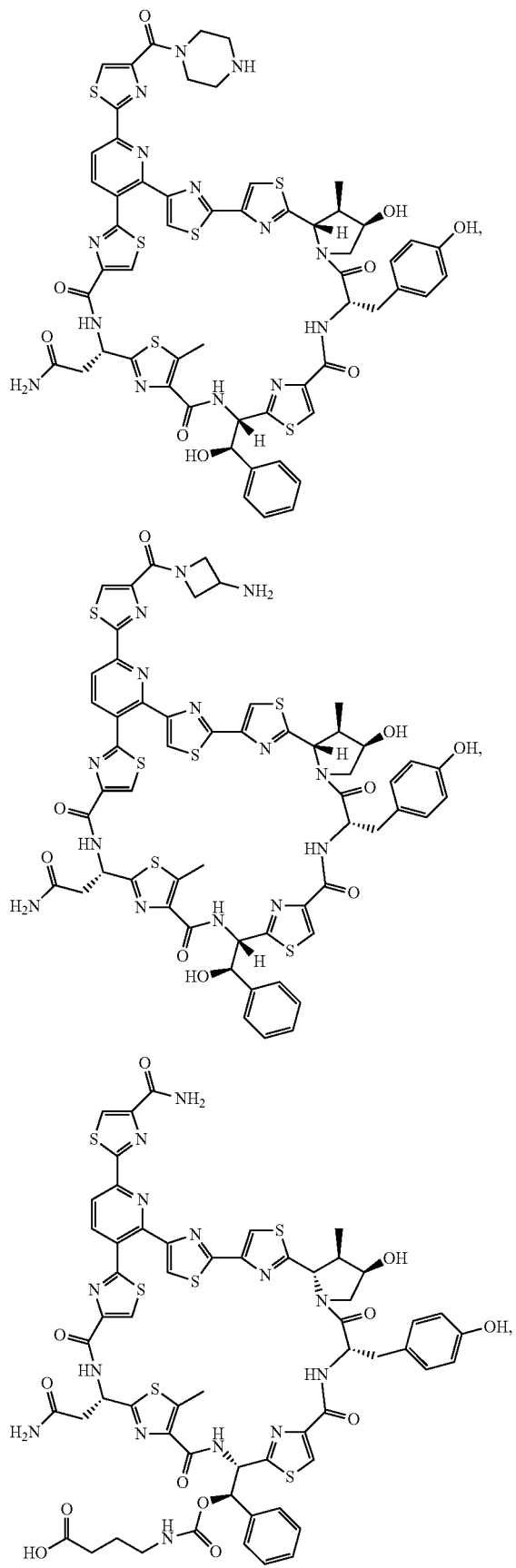
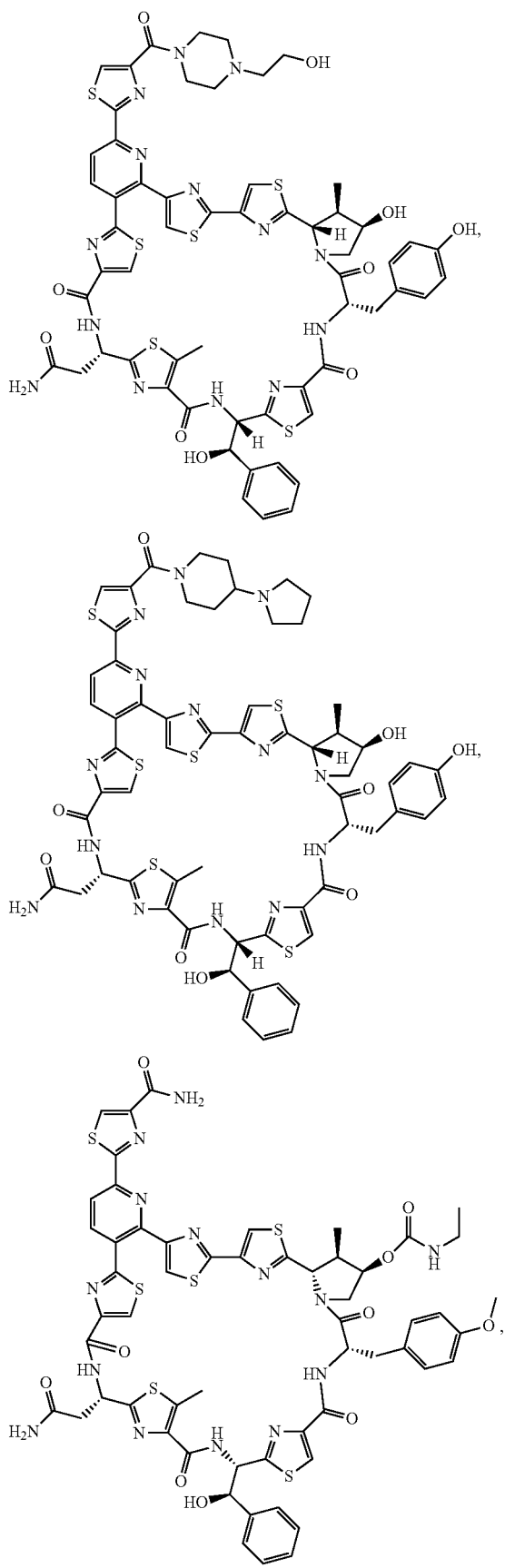

339
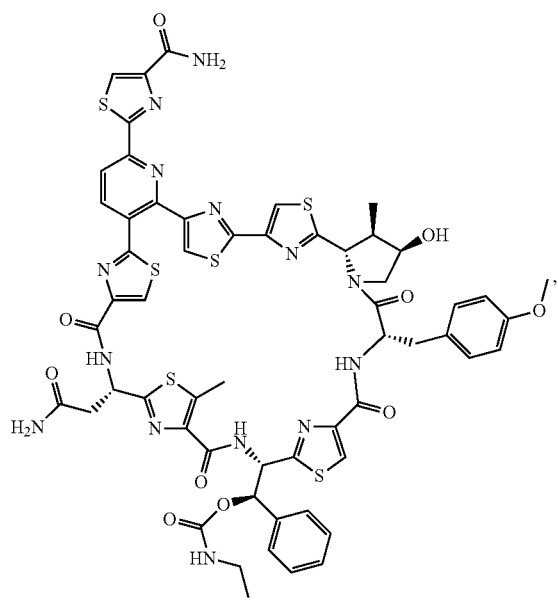
340
-continued
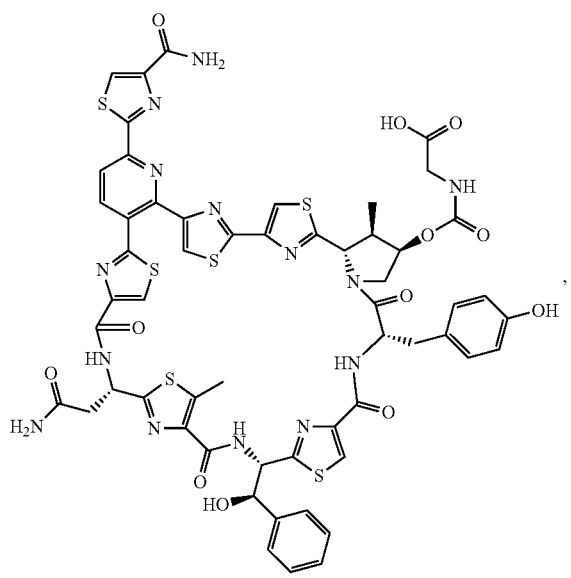
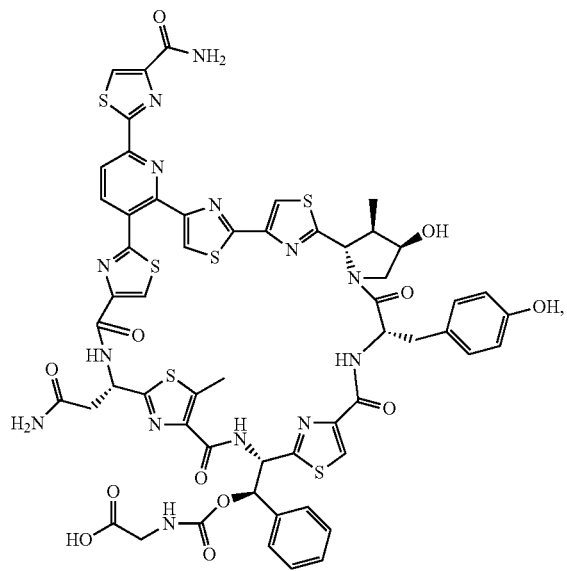
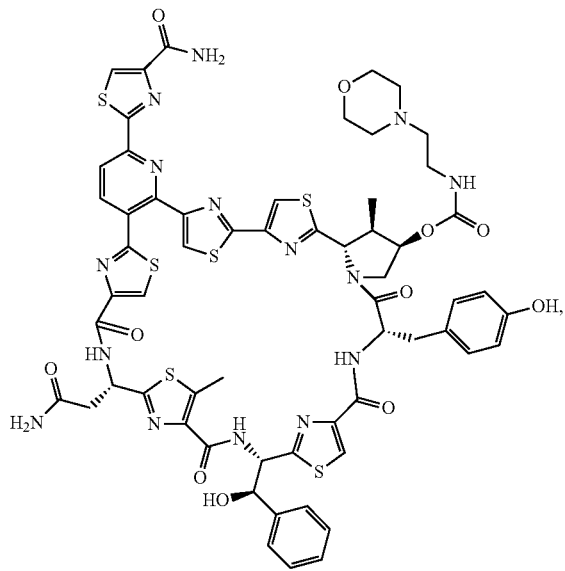

341
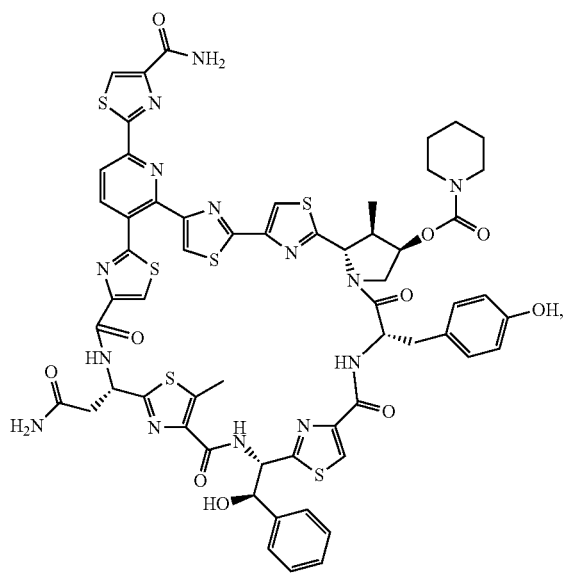
342
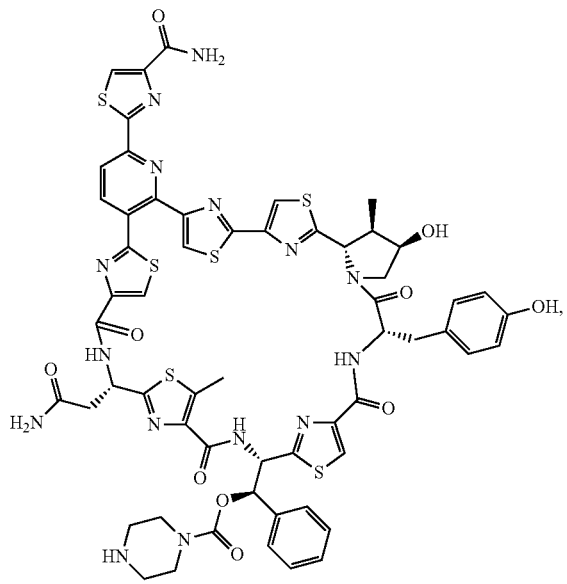
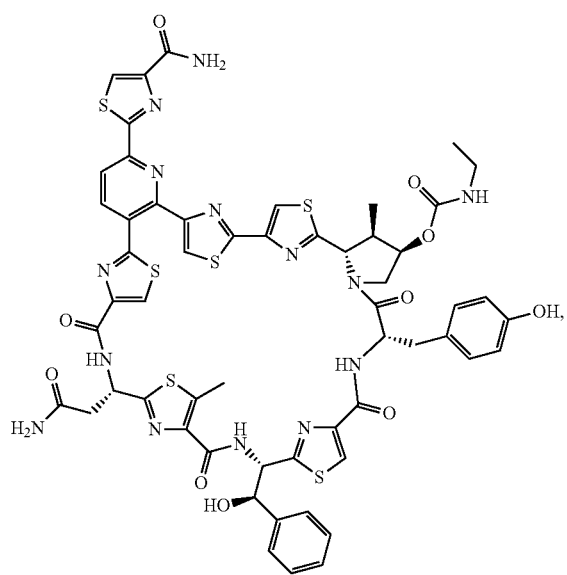
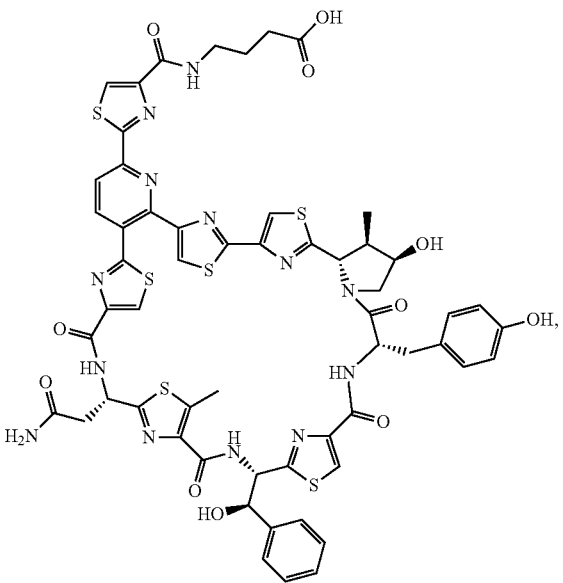

343
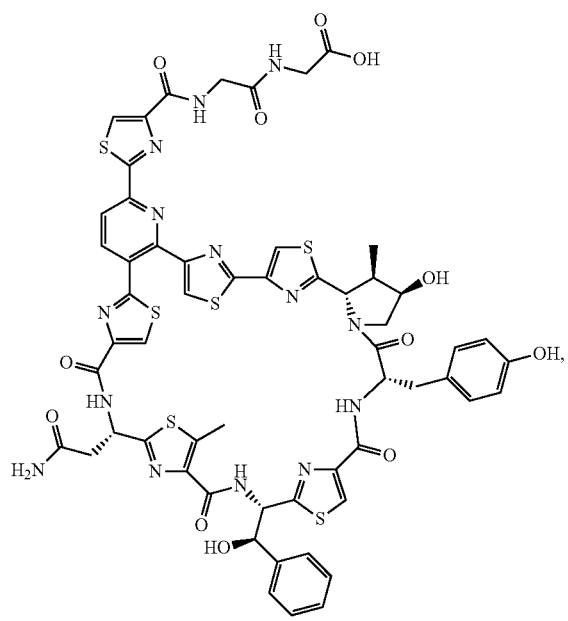
344
-continued
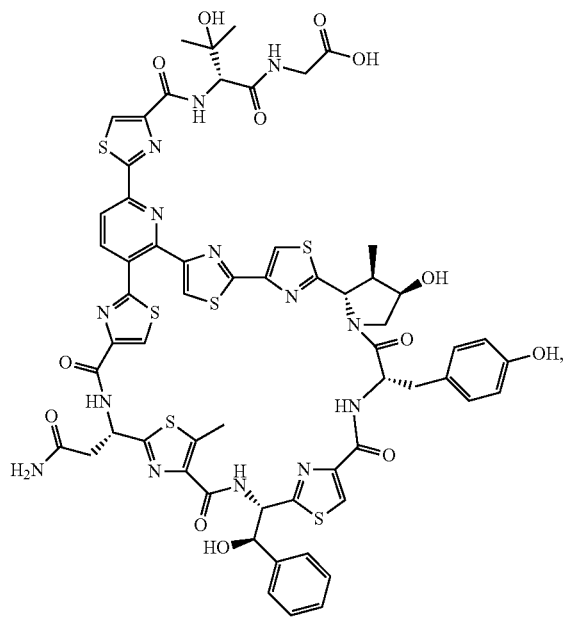
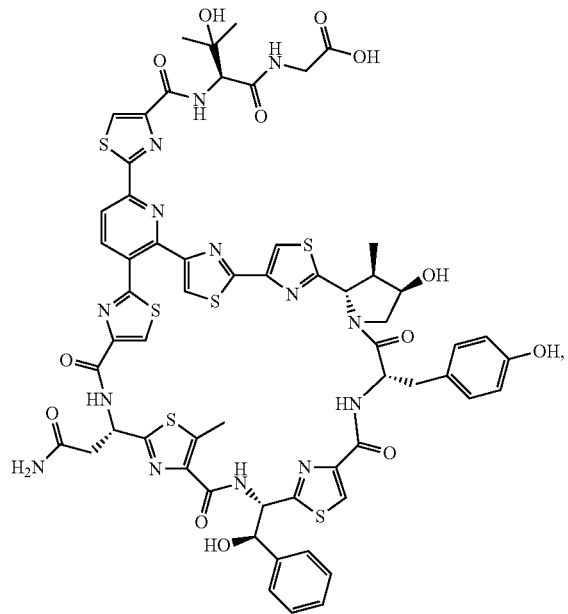
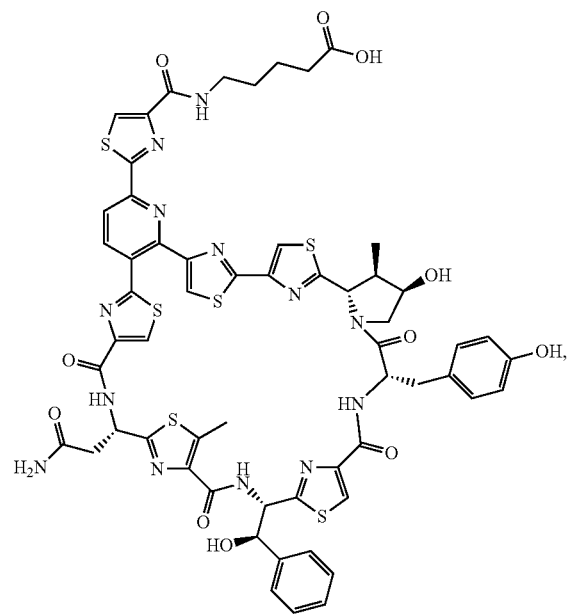

345
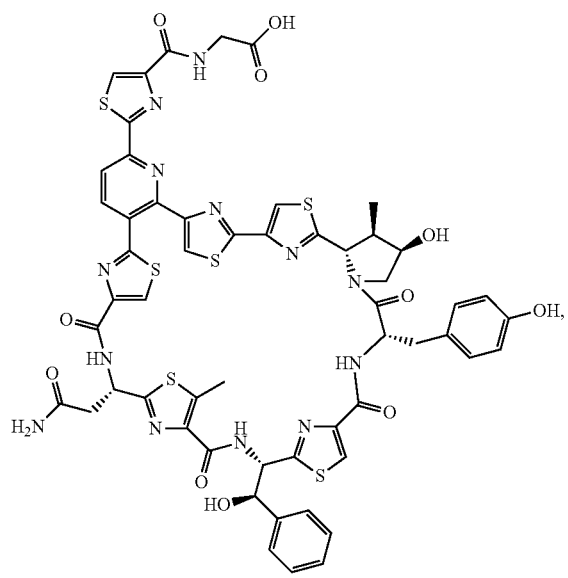
346
-continued
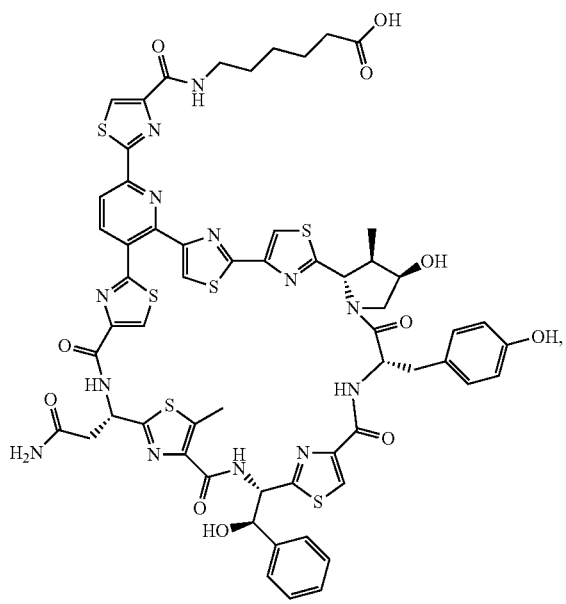
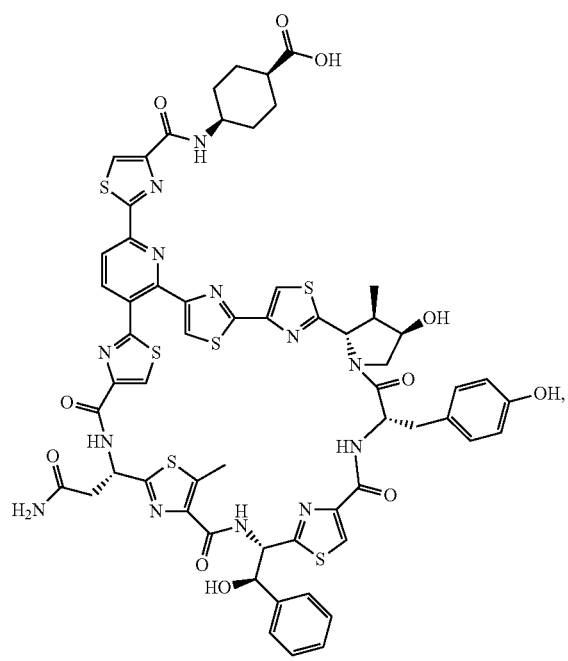
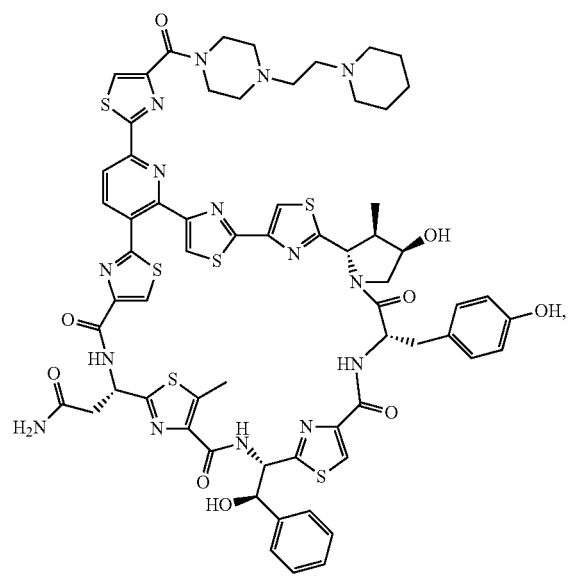

-continued
347
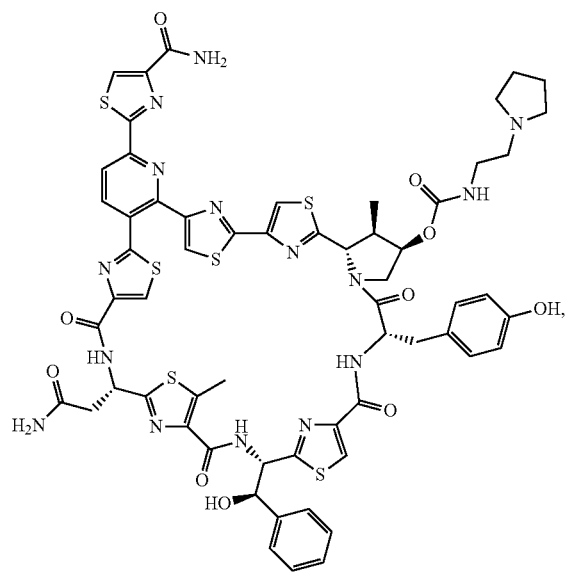
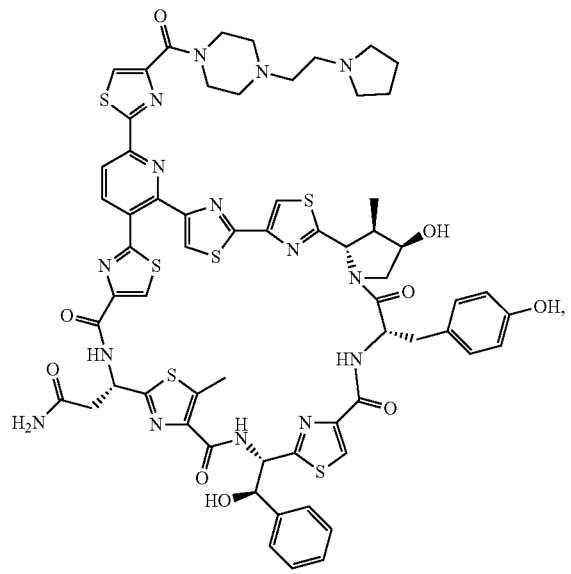
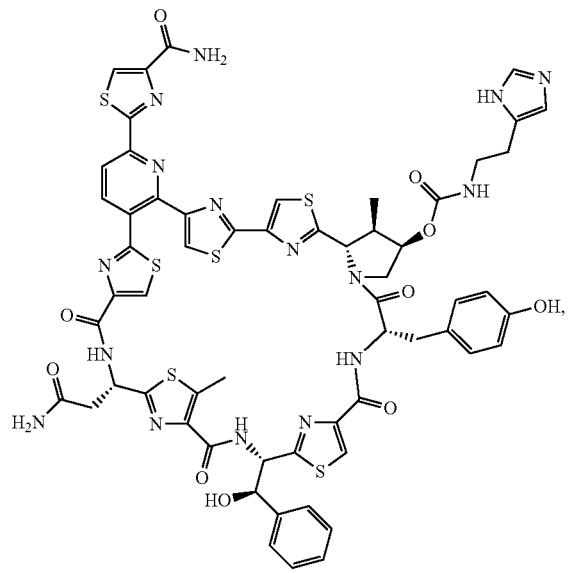
348
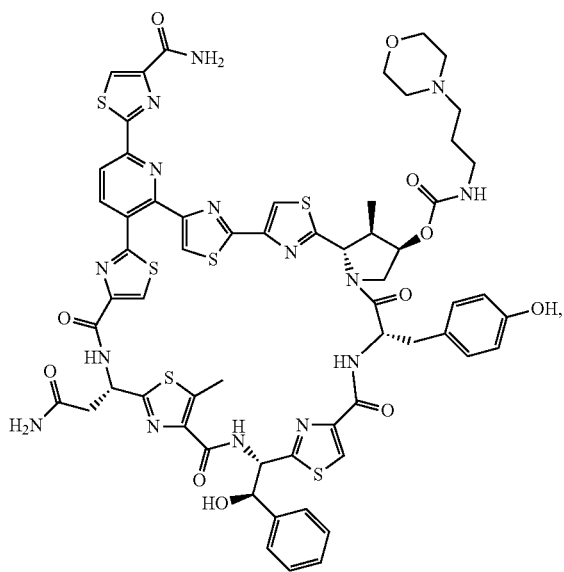
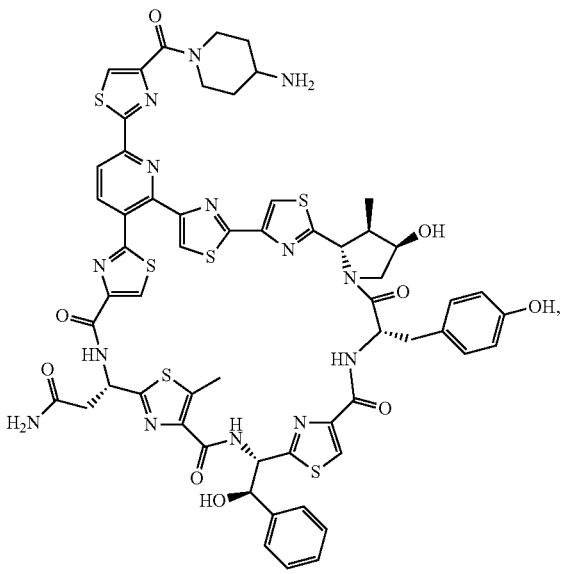
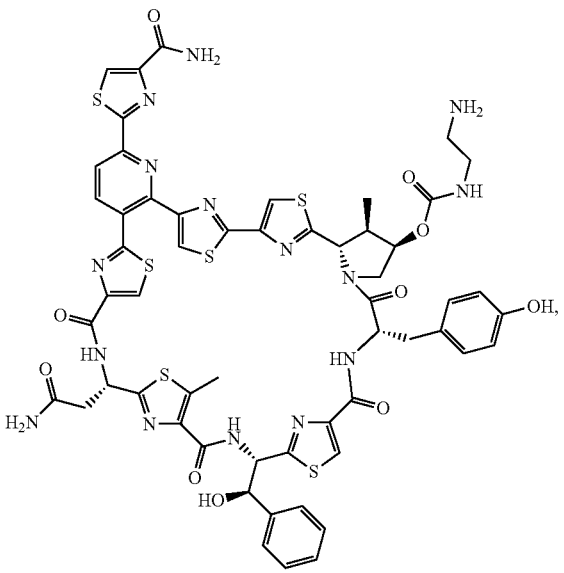

349
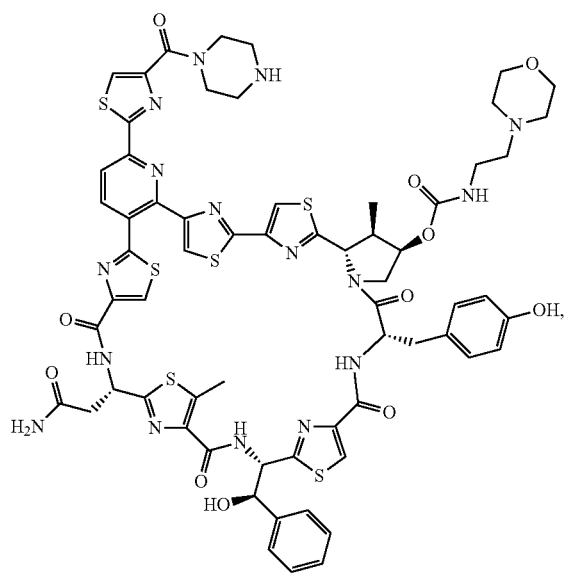
350
-continued
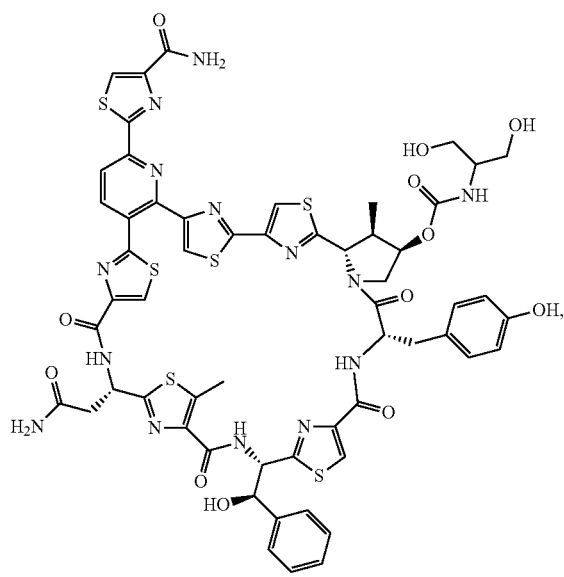
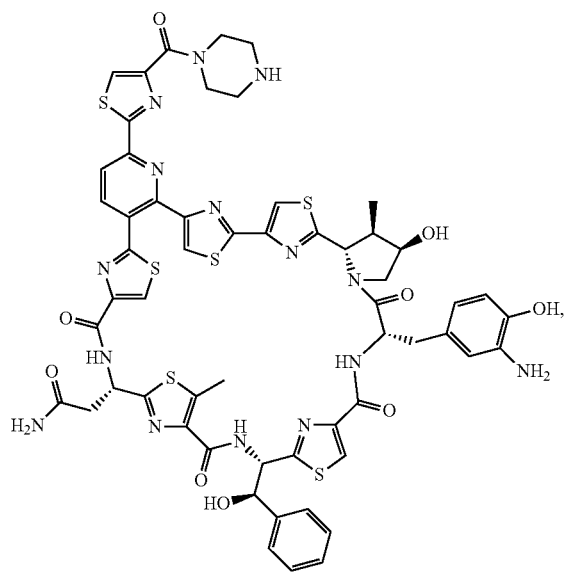
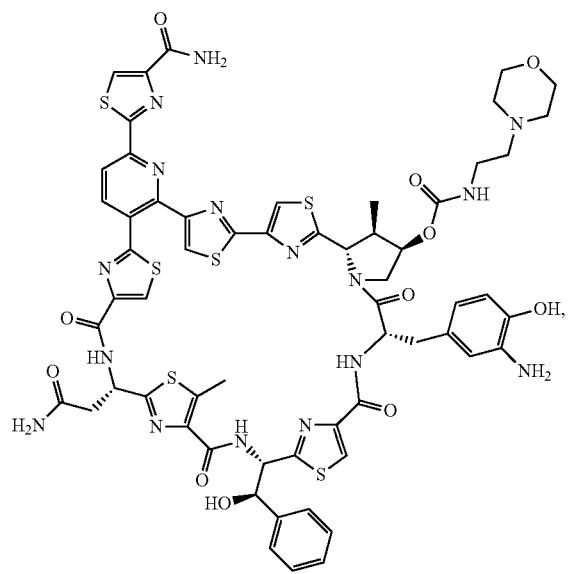

351
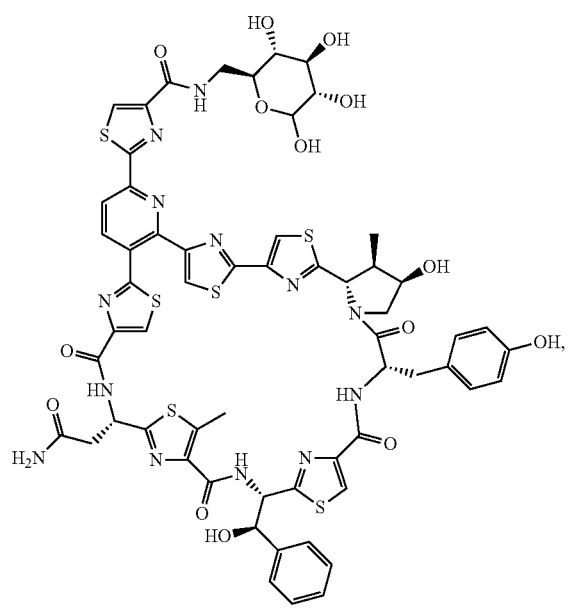
352
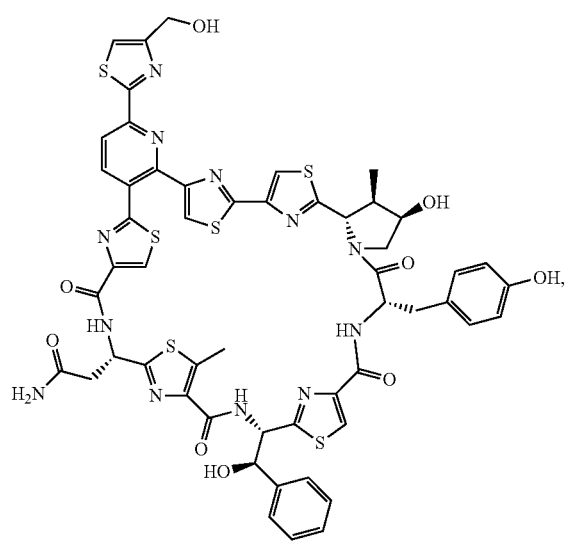
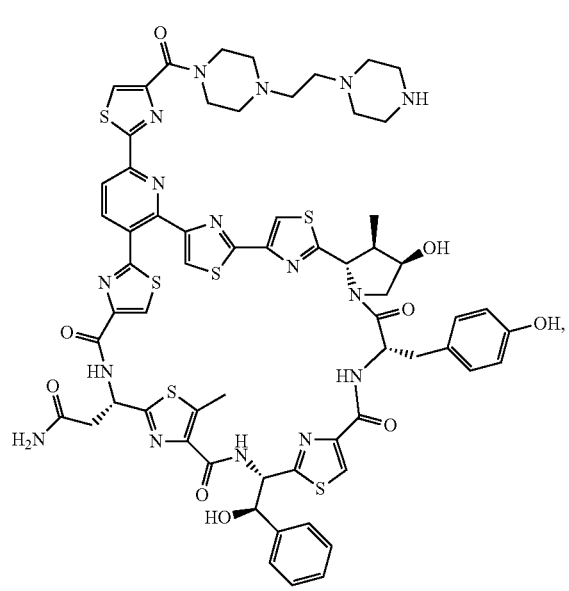
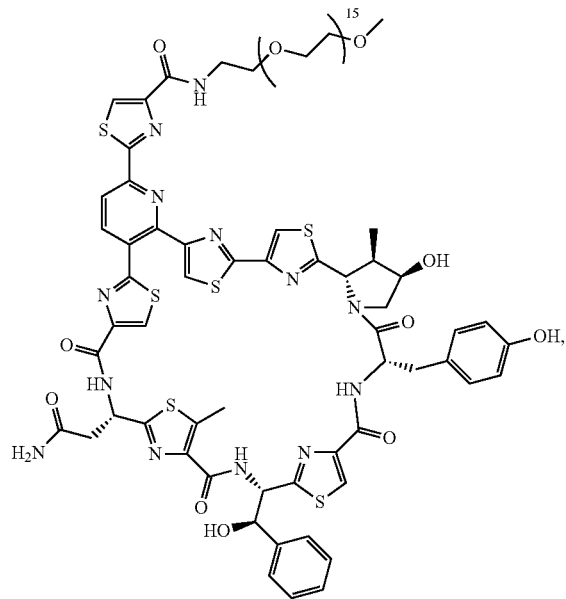

353
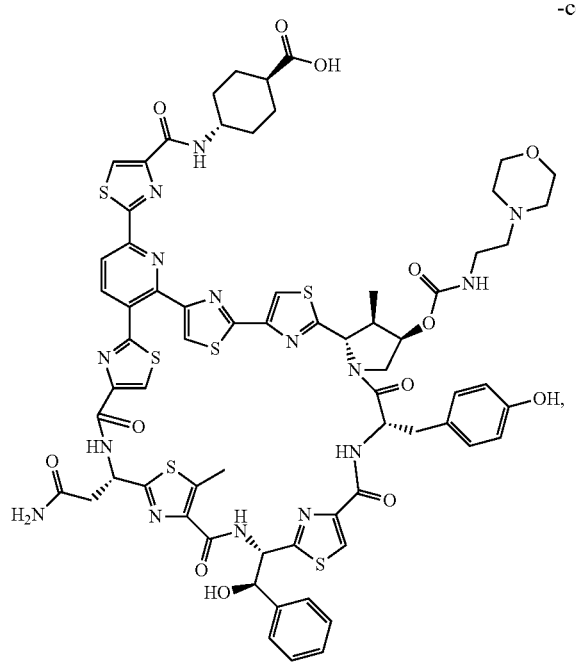
354
-continued
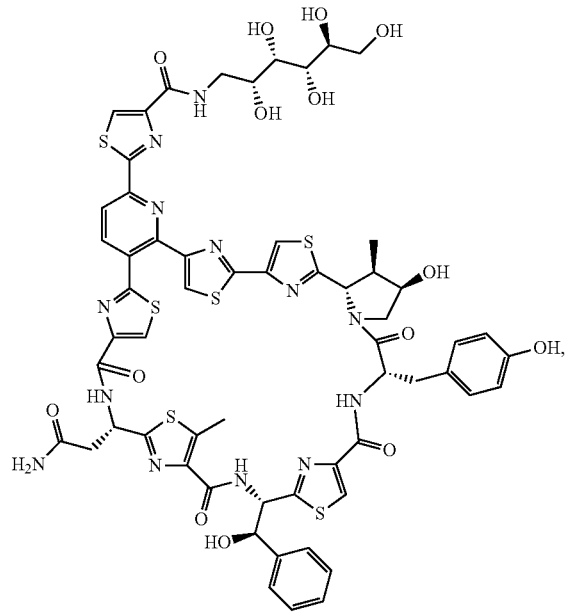
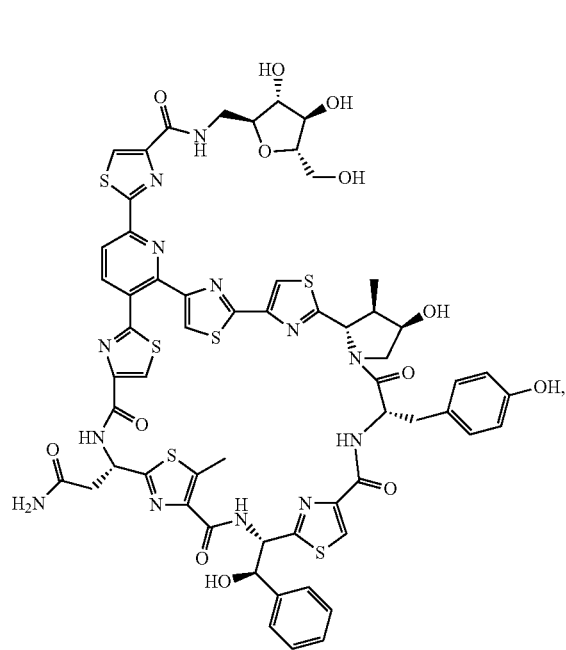
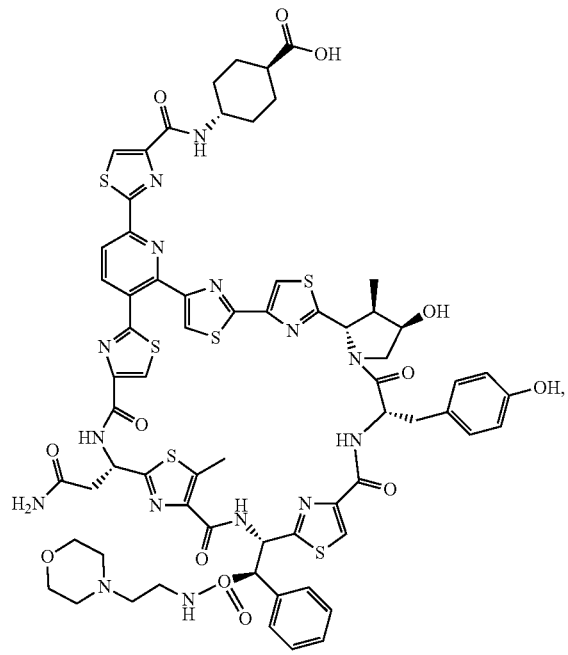

355
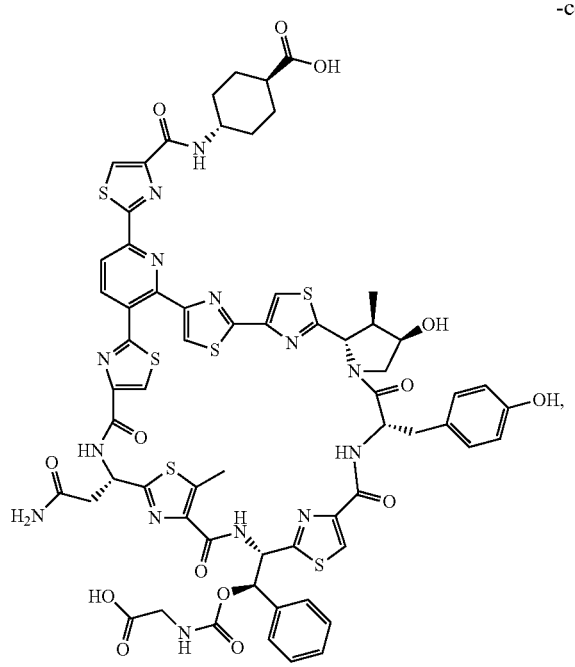
356
-continued
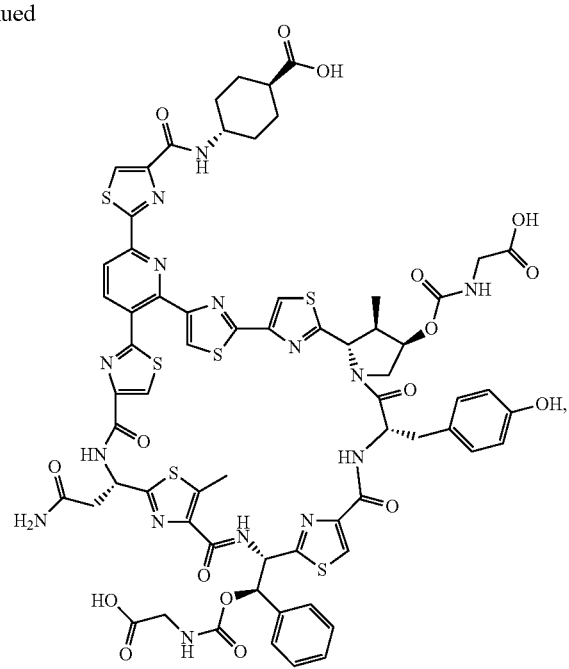
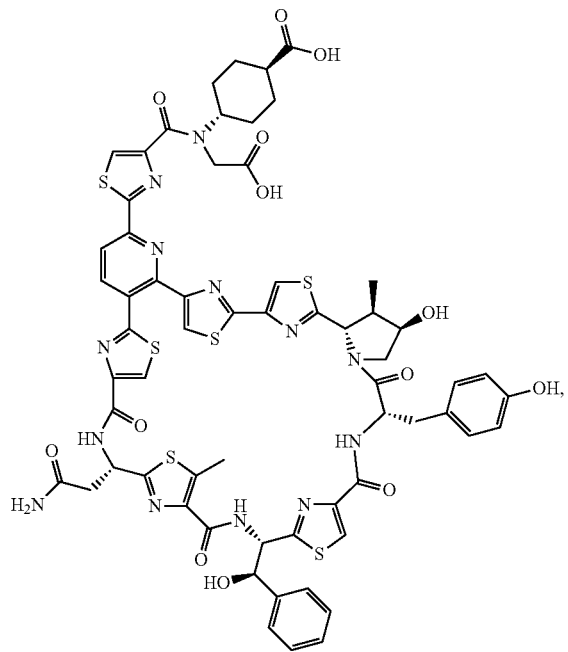
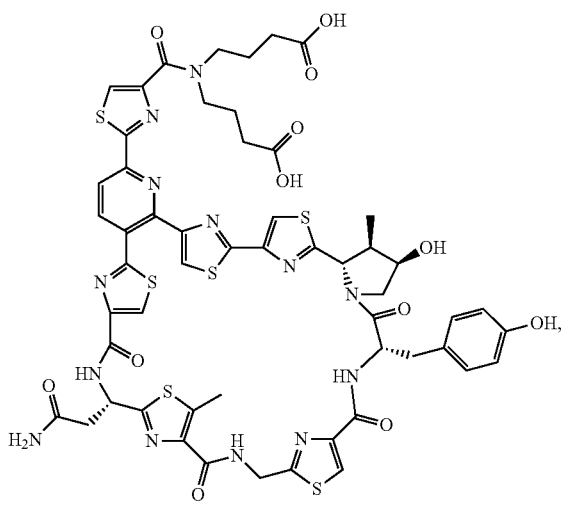

357
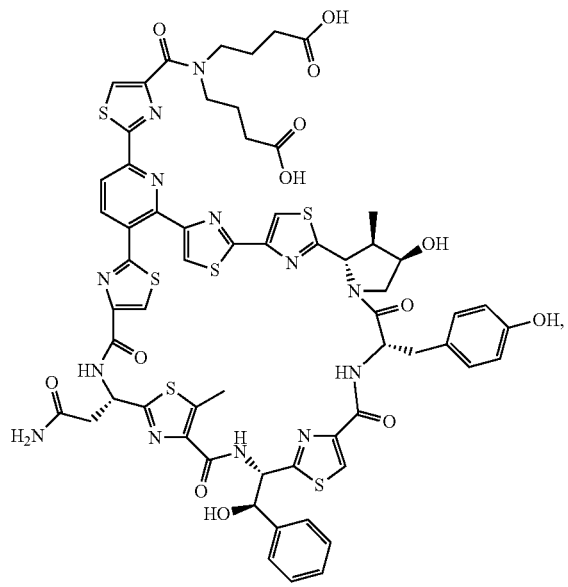
358
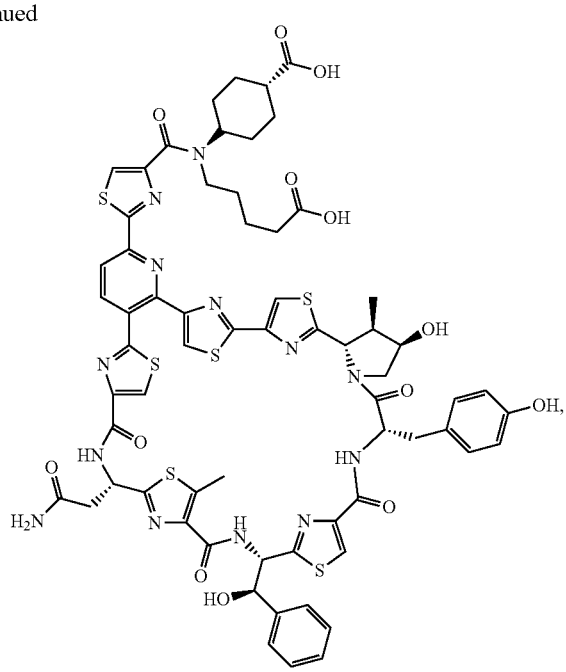
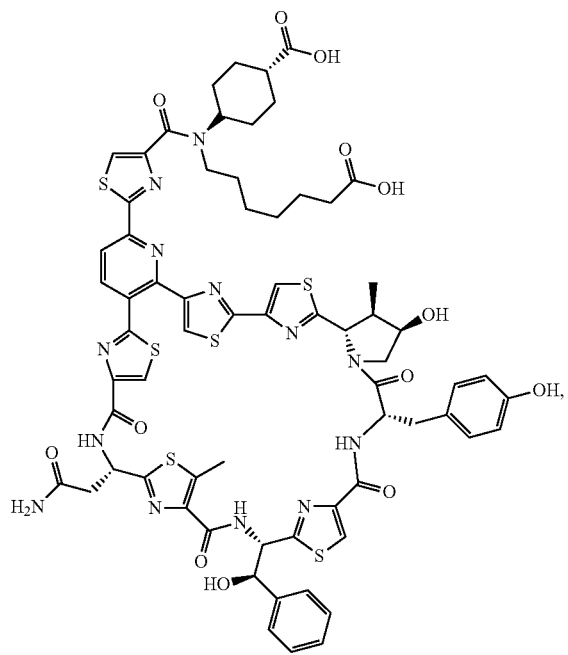
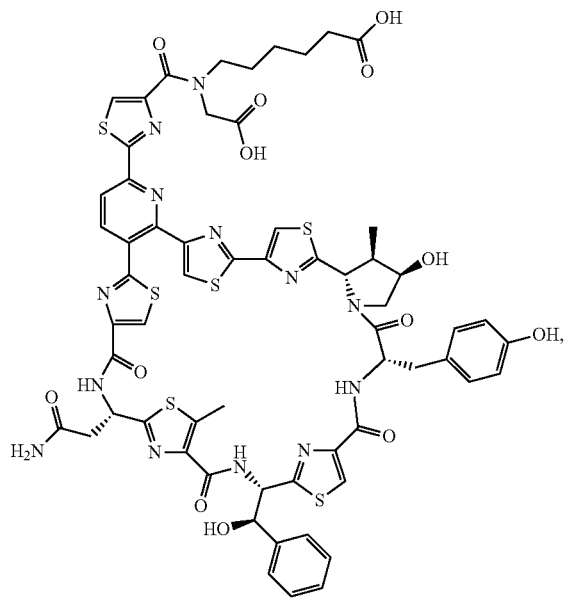

359
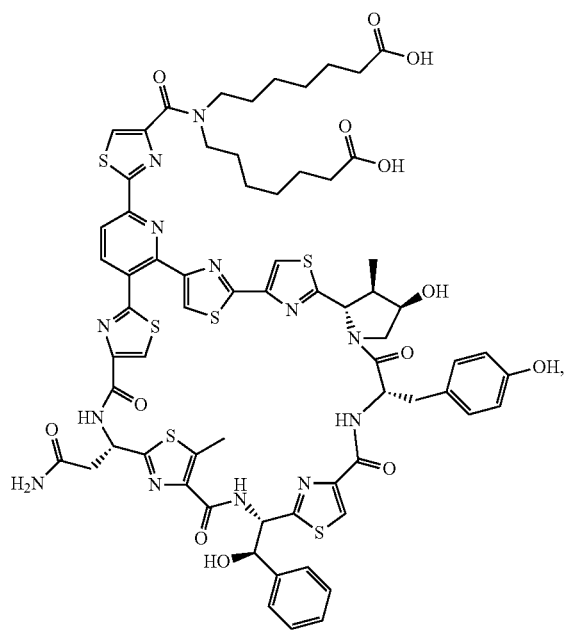
360
-continued
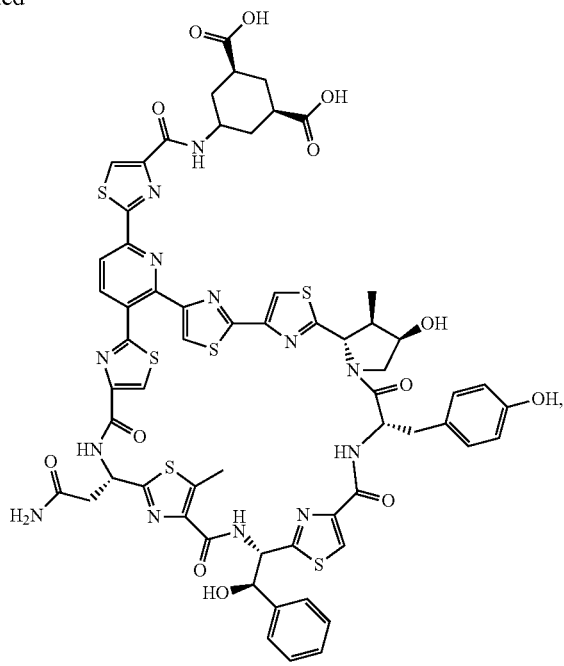
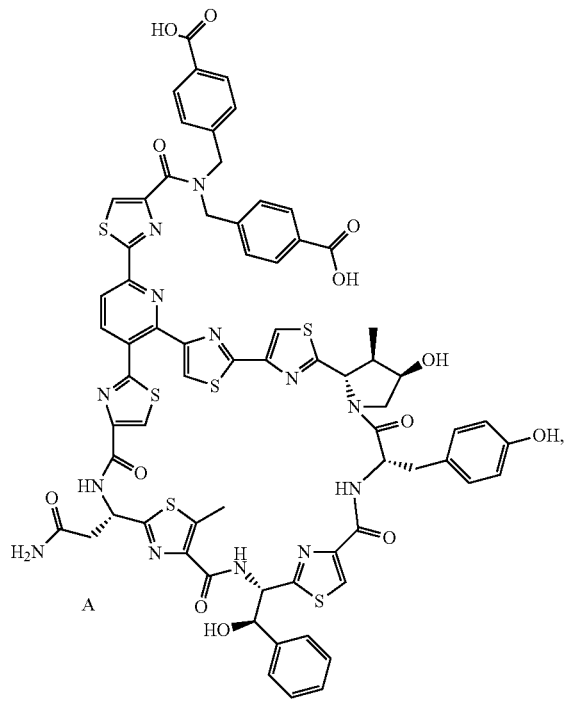
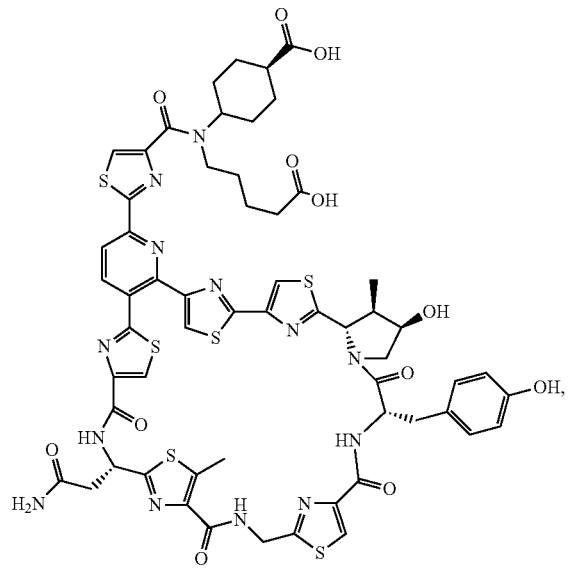

361
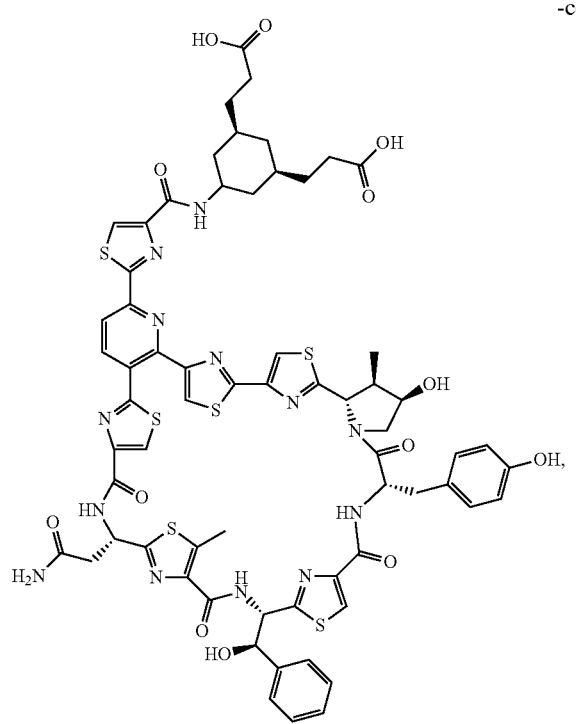
362
-continued
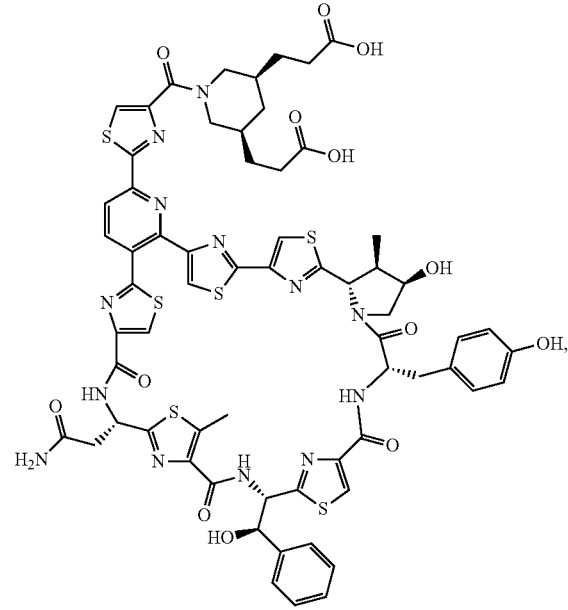
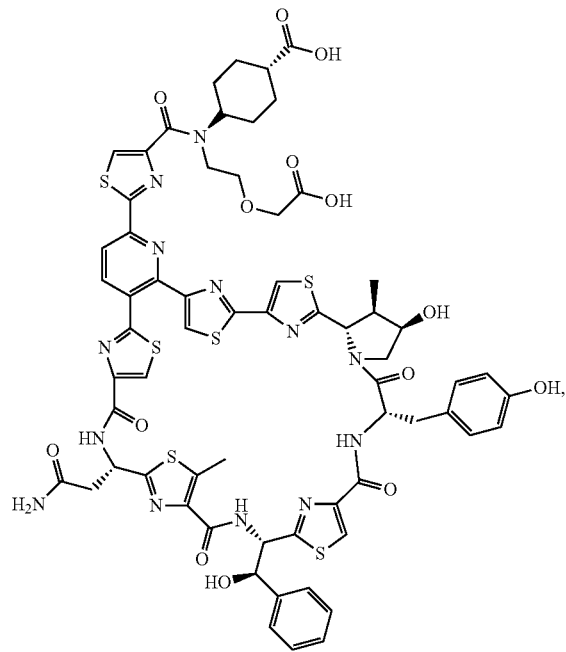
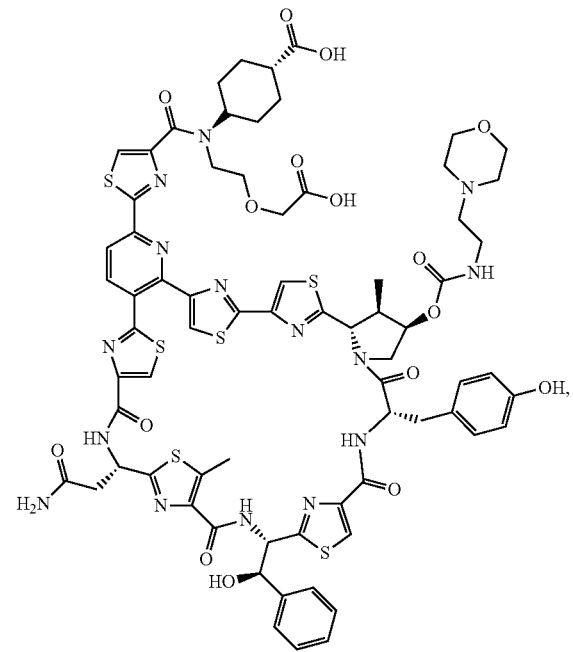

363
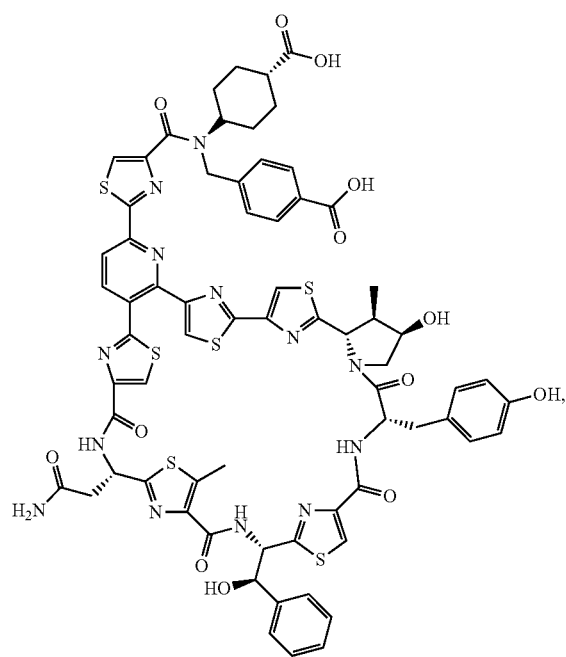
364
-continued
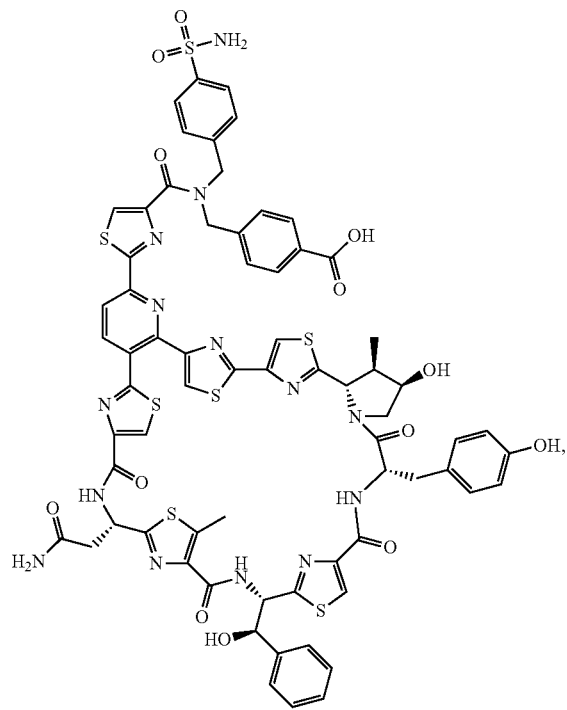
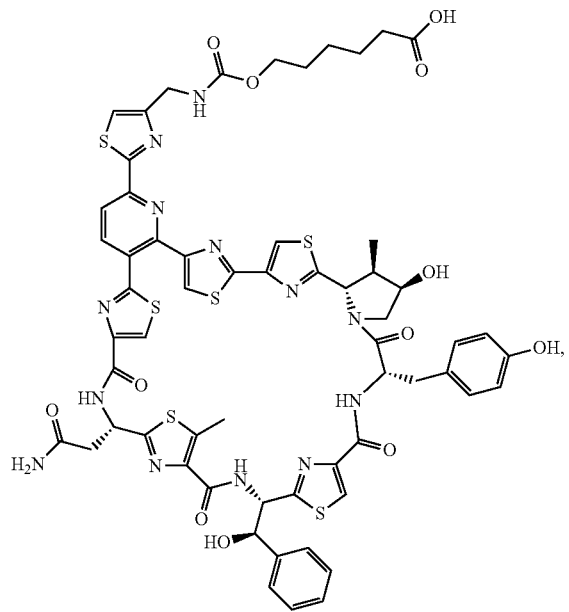
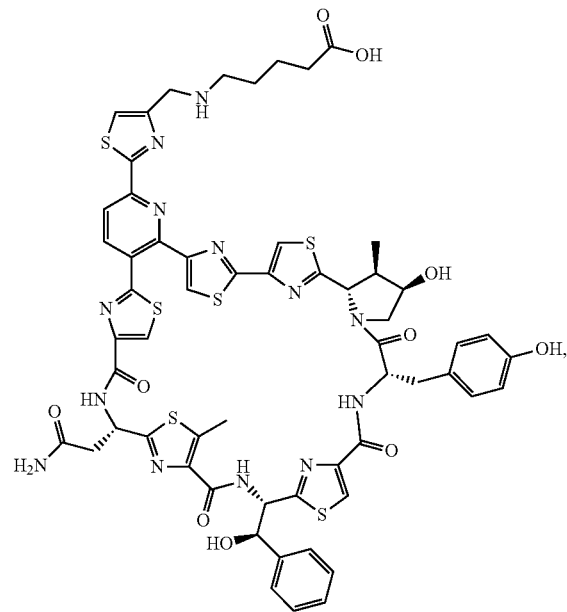

365
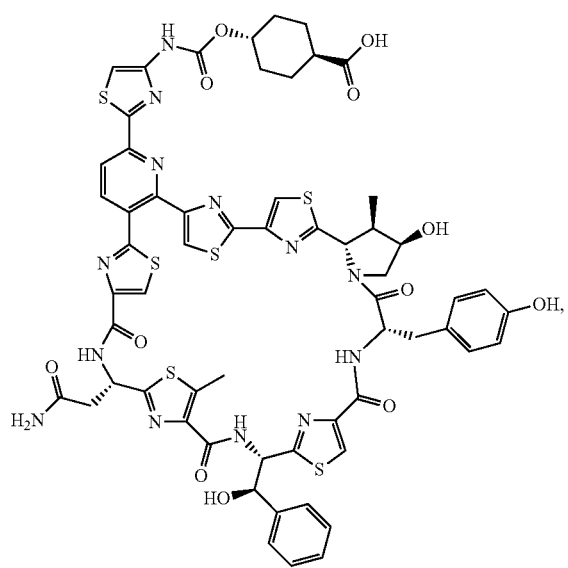
366
-continued
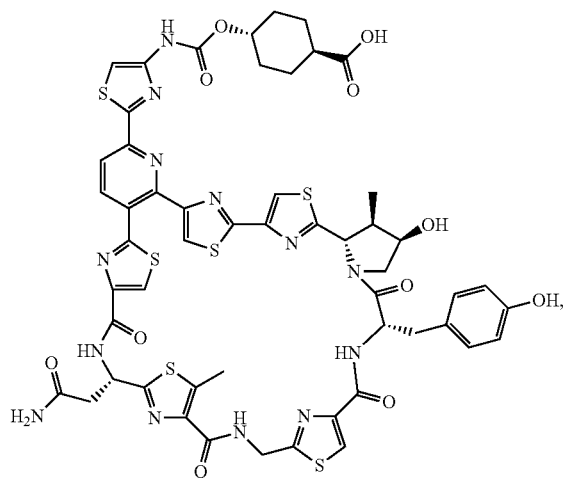
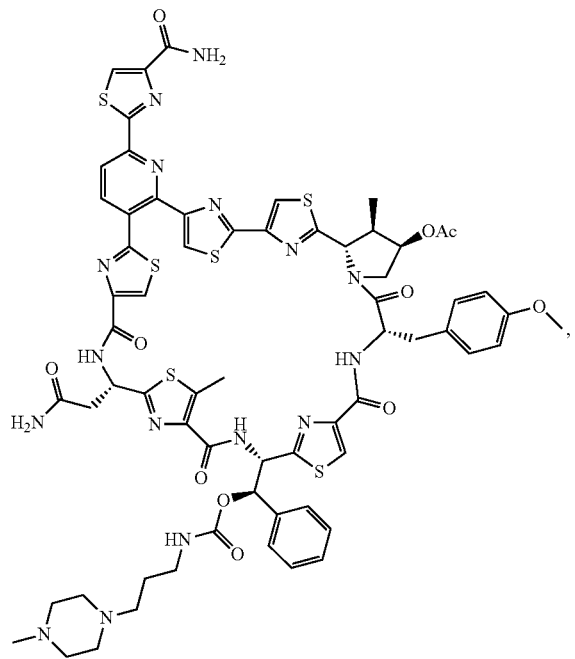
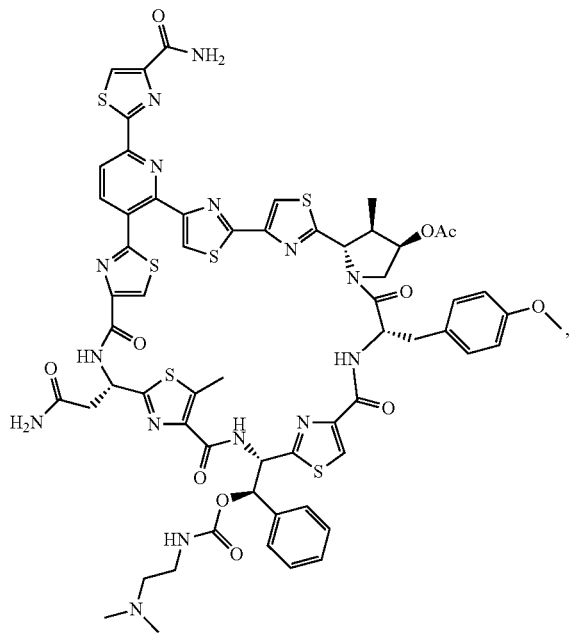

367
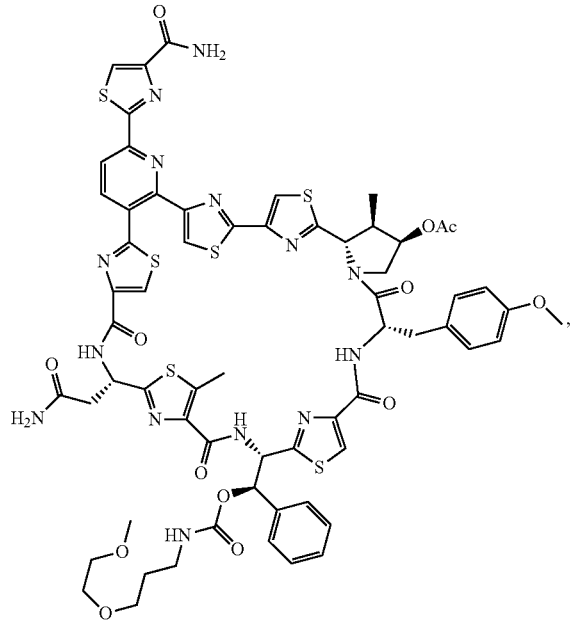
368
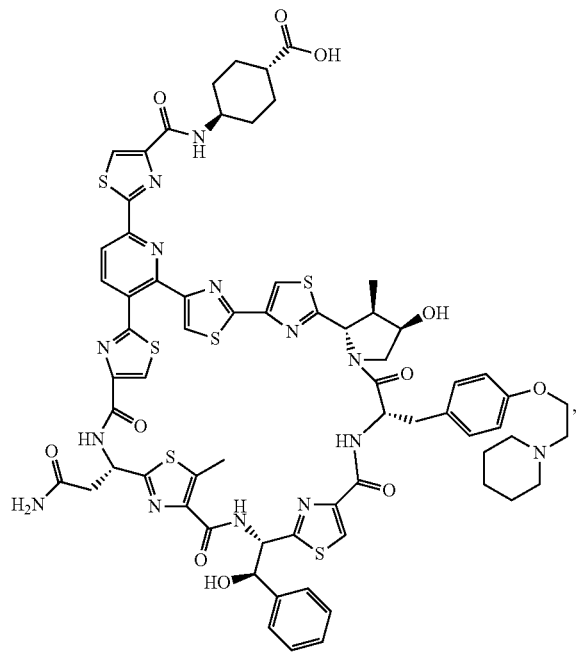
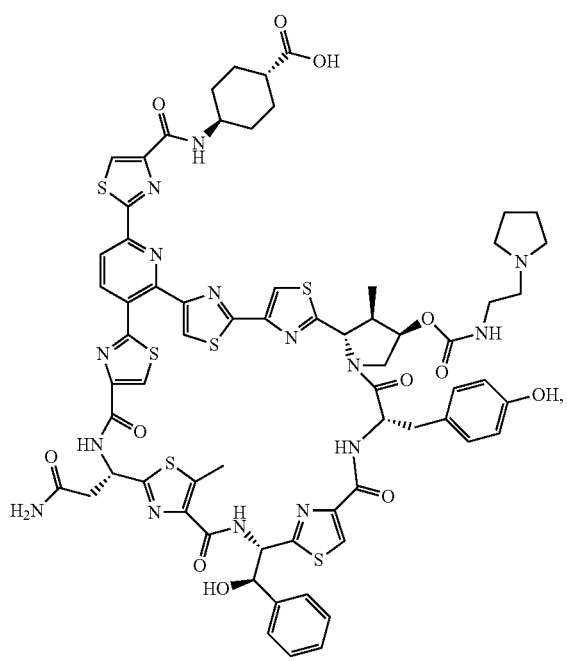
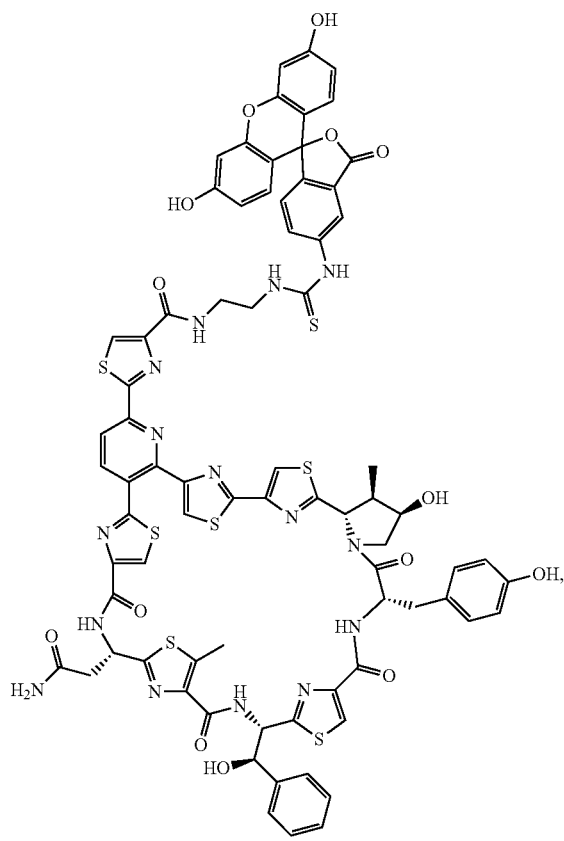

369
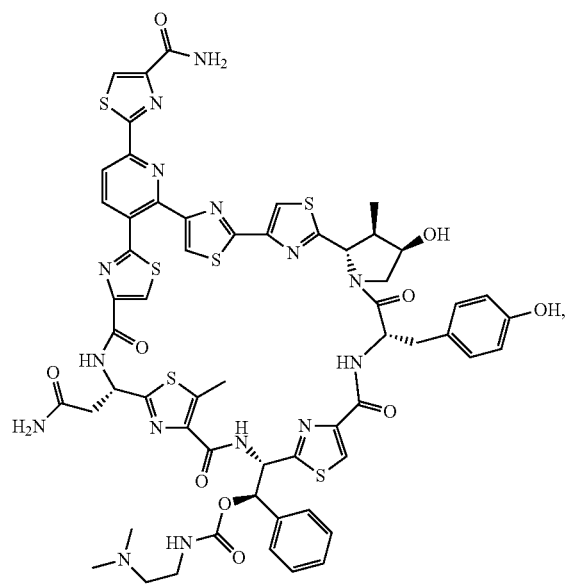
370
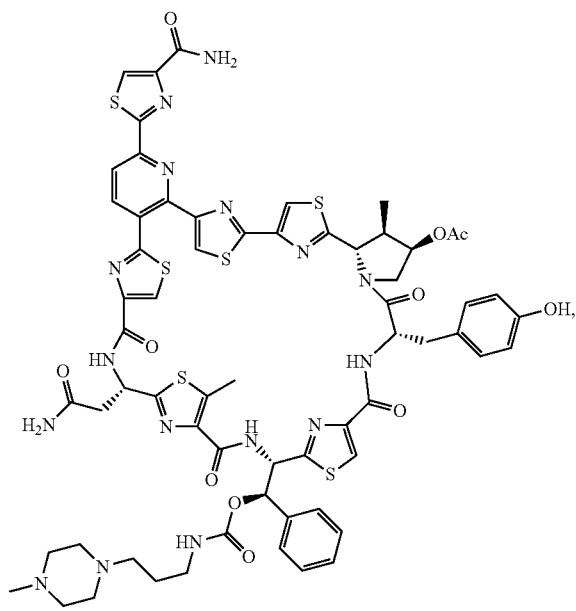
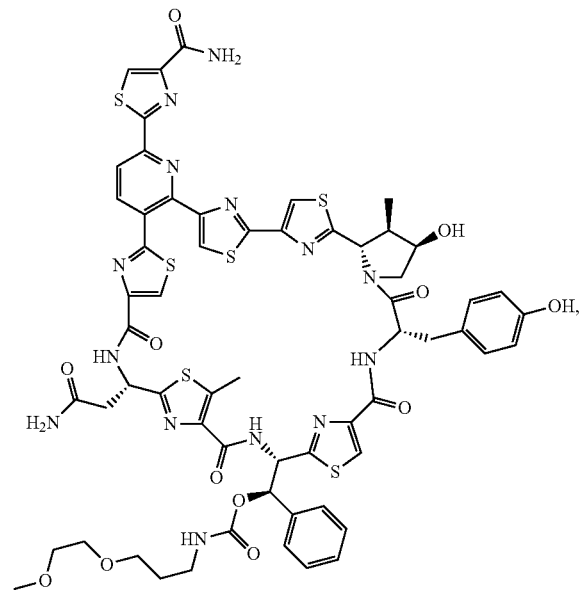
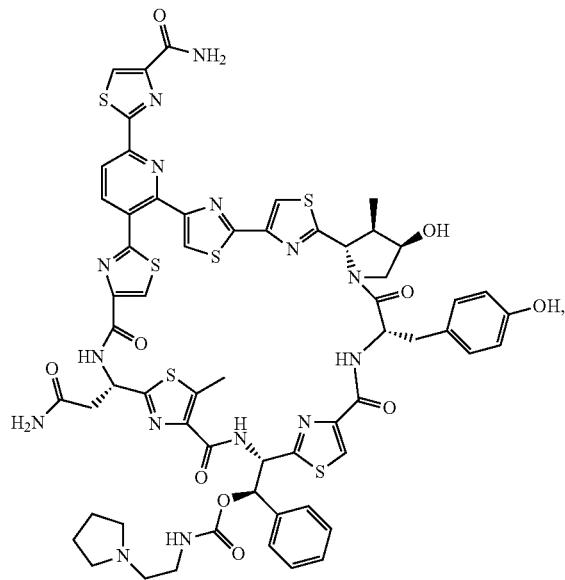

-continued
371
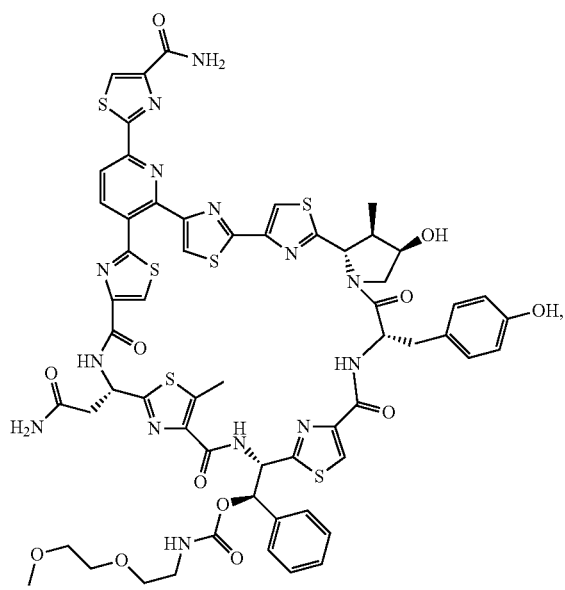
372
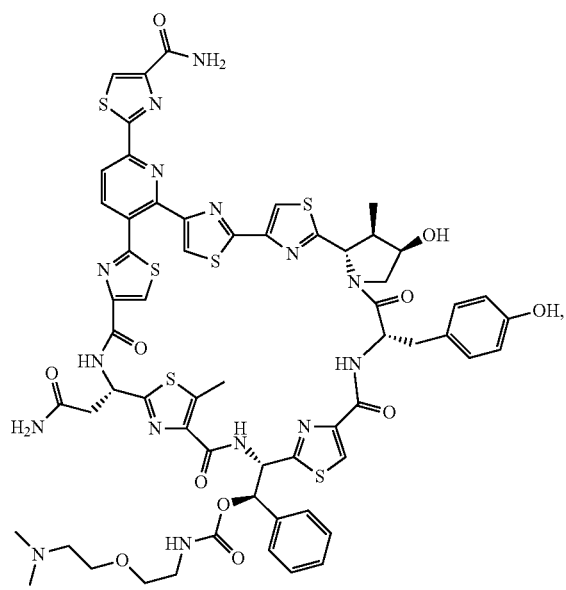
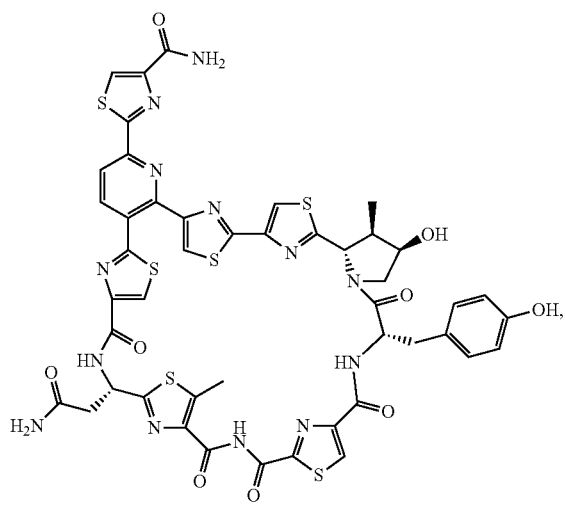
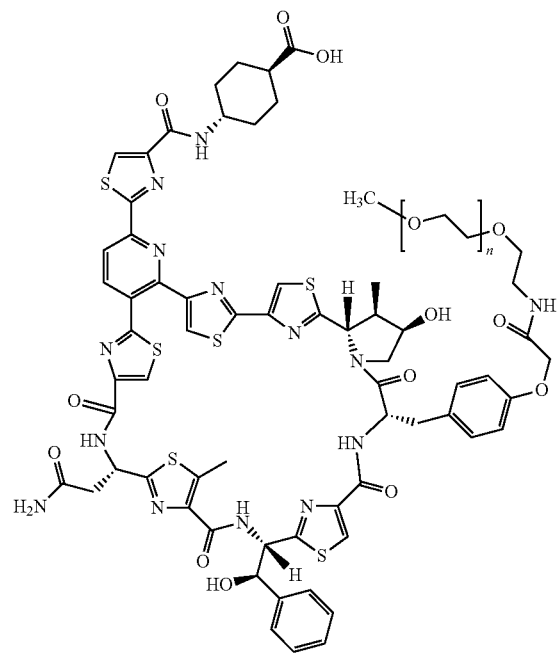
n (average) = 15.2

-continued
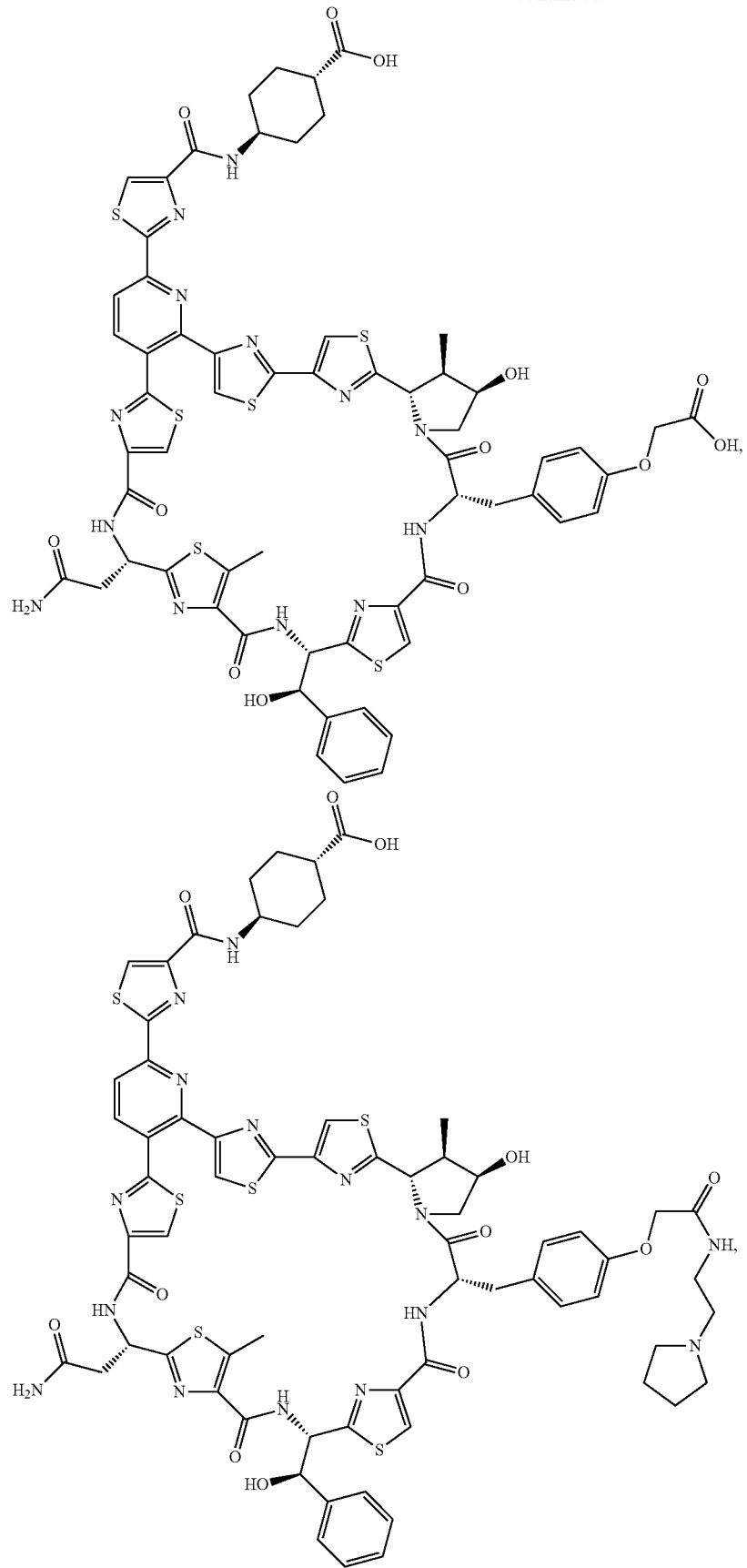

-continued
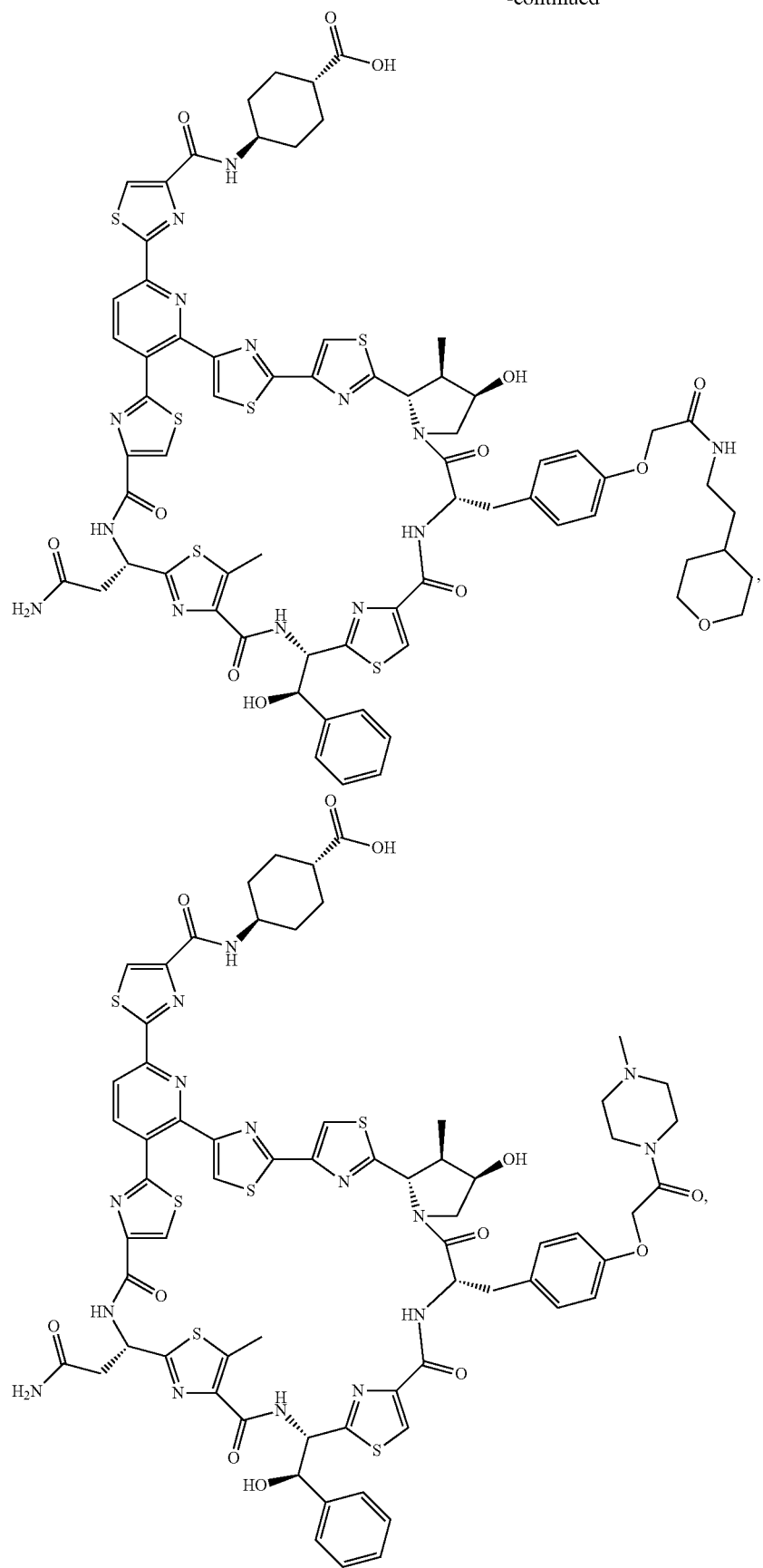

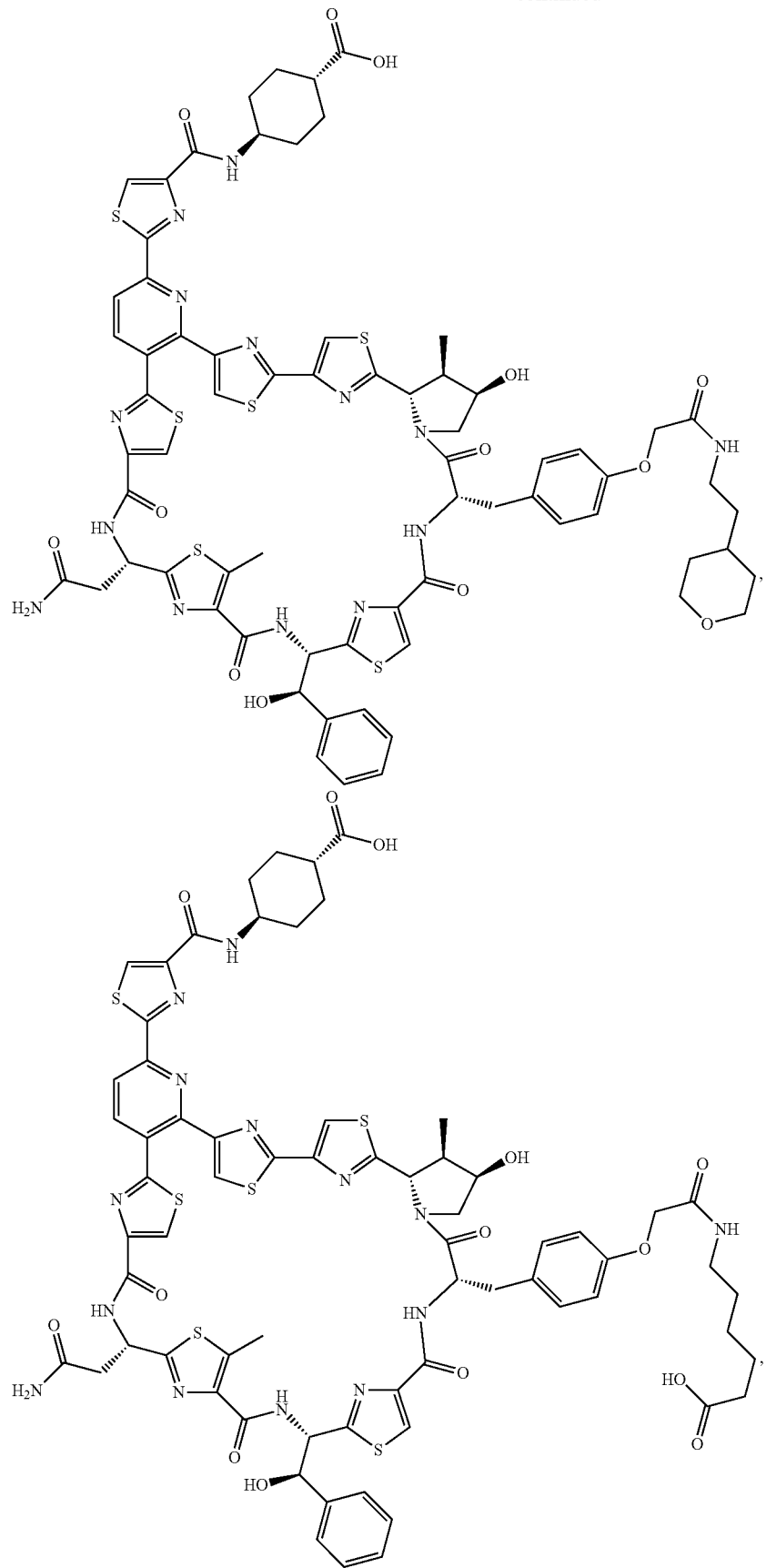

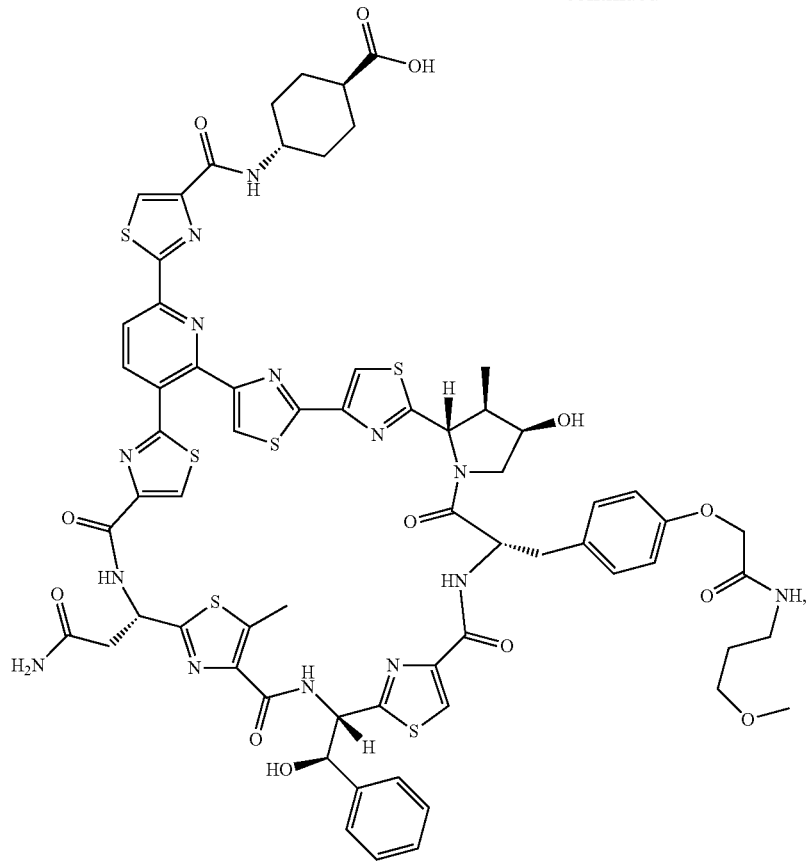
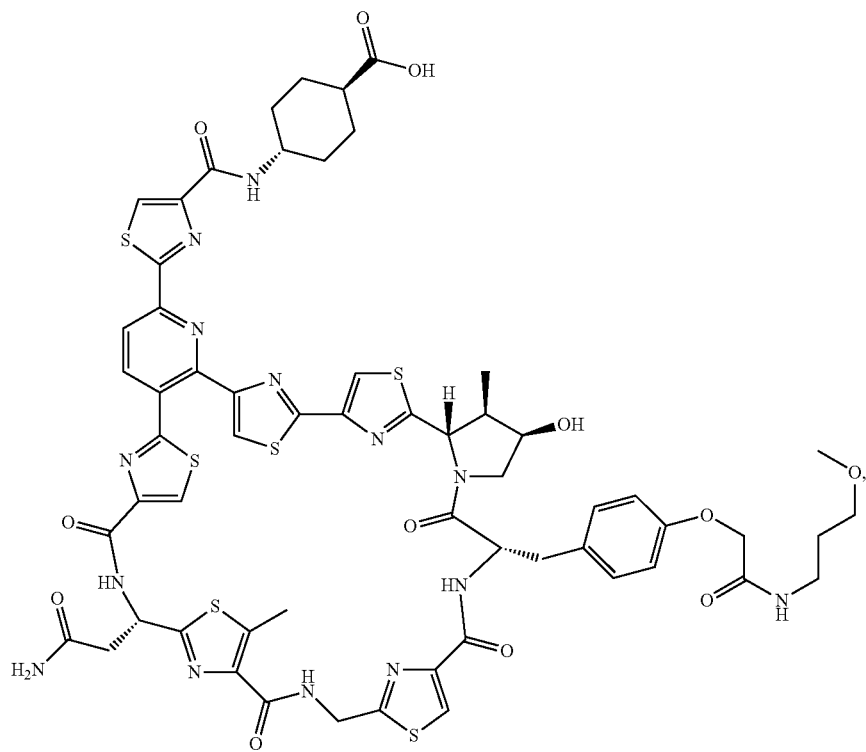

-continued
381
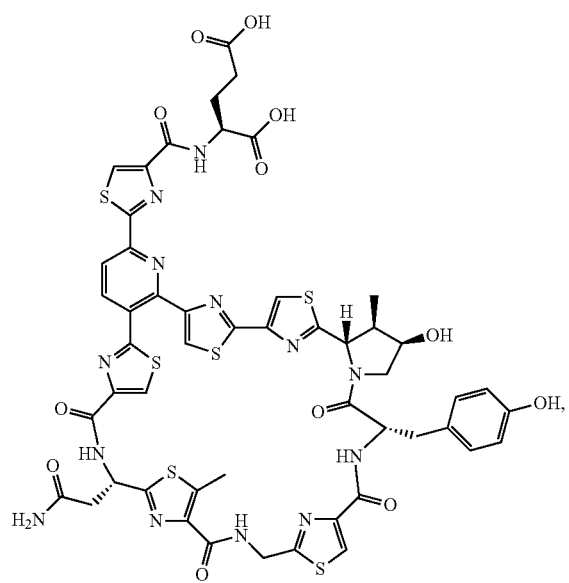
382
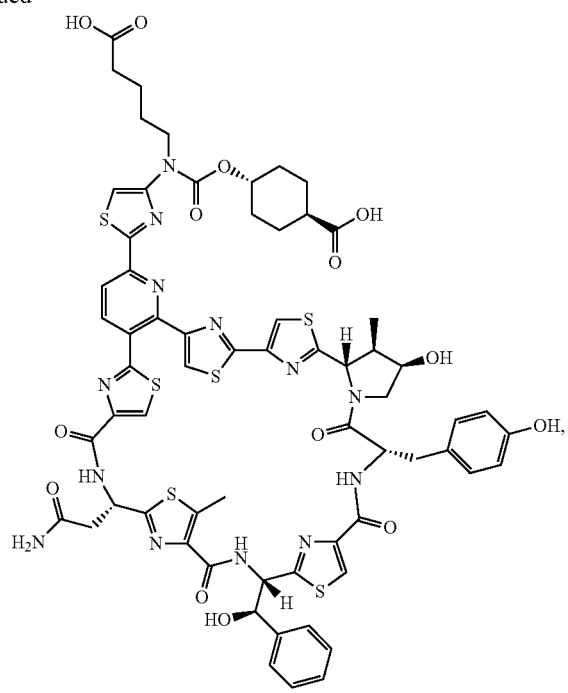
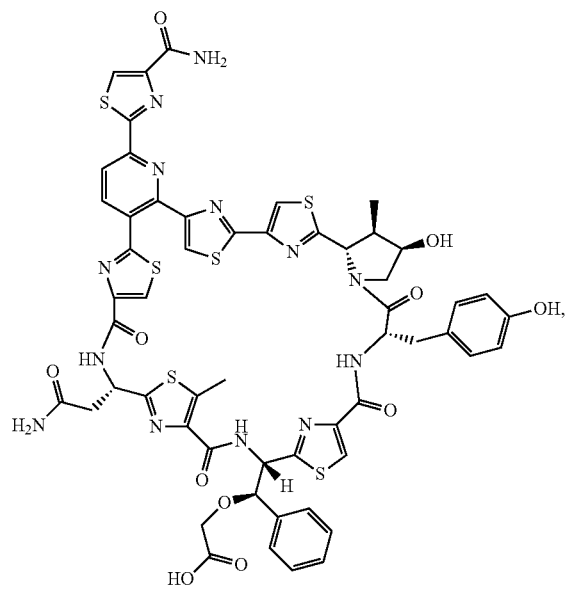
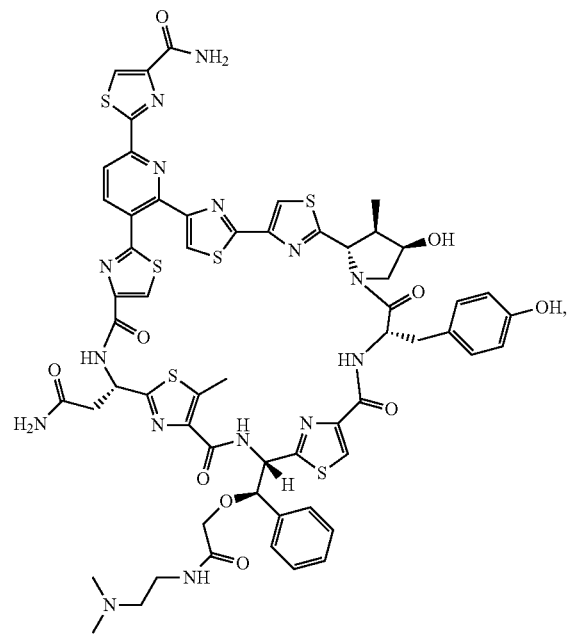

383
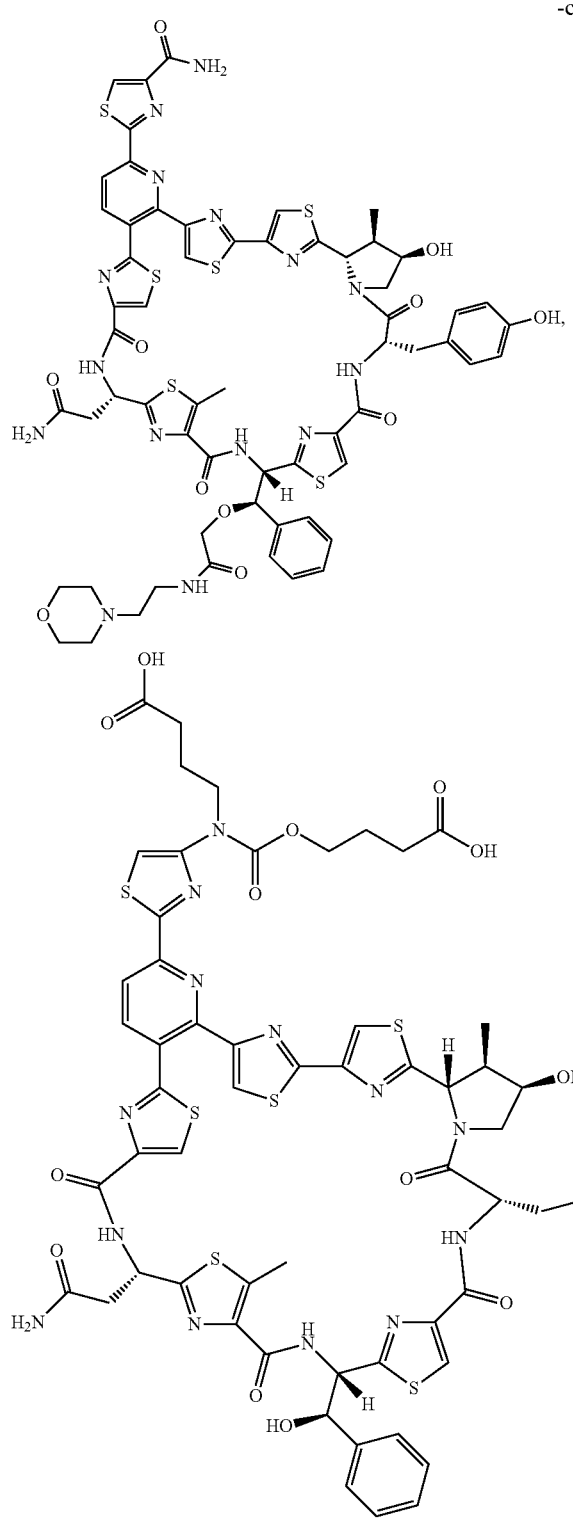
384
-continued
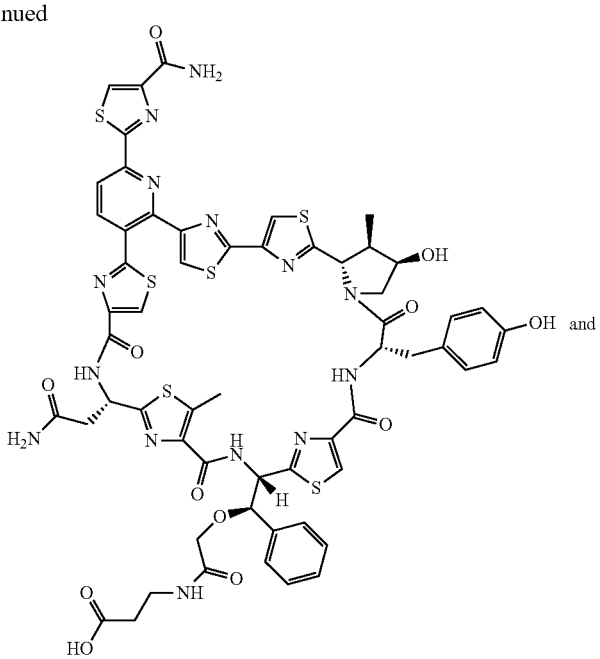
and
* * * * *